(12) United States Patent
Varadhachary et al.

(10) Patent No.: US 7,420,033 B2
(45) Date of Patent: Sep. 2, 2008

(54) COMPOSITION OF LACTOFERRIN RELATED PEPTIDES AND USES THEREOF

(75) Inventors: Atul Varadhachary, Houston, TX (US); Peter Glynn, Houston, TX (US); Karel Petrak, Houston, TX (US); Jose Engelmayer, Houston, TX (US)

(73) Assignee: Agennix, Inc., Houston, TX (US)

( * ) Notice: Subject to any disclaimer, the term of this patent is extended or adjusted under 35 U.S.C. 154(b) by 0 days.

(21) Appl. No.: 11/677,796

(22) Filed: Feb. 22, 2007

(65) Prior Publication Data

US 2007/0142292 A1 Jun. 21, 2007

Related U.S. Application Data

(63) Continuation of application No. 11/258,767, filed on Oct. 26, 2005, now Pat. No. 7,183,381.

(60) Provisional application No. 60/622,176, filed on Oct. 26, 2004.

(51) Int. Cl.
*A61K 38/00* (2006.01)

(52) U.S. Cl. .................................... 530/324

(58) Field of Classification Search ........................ None
See application file for complete search history.

(56) References Cited

U.S. PATENT DOCUMENTS

| | | | |
|---|---|---|---|
| 4,200,435 A | 4/1980 | Stroupe et al. |
| 4,977,137 A | 12/1990 | Nichols et al. |
| 5,006,333 A | 4/1991 | Saifer et al. |
| 5,198,419 A | 3/1993 | Ando et al. |
| 5,240,909 A | 8/1993 | Nitsche |
| 5,304,633 A | 4/1994 | Tomita et al. |
| 5,317,084 A | 5/1994 | Tomita et al. |
| 5,322,286 A | 6/1994 | Frost |
| 5,322,836 A | 6/1994 | Tomita et al. |
| 5,457,093 A | 10/1995 | Cini et al. |
| 5,466,669 A | 11/1995 | Konig et al. |
| 5,571,691 A | 11/1996 | Conneely et al. |
| 5,571,697 A | 11/1996 | Conneely et al. |
| 5,571,896 A | 11/1996 | Conneely et al. |
| 5,576,299 A | 11/1996 | Ando et al. |
| 5,656,591 A | 8/1997 | Tomita et al. |
| 5,712,247 A | 1/1998 | Wu et al. |
| 5,766,939 A | 6/1998 | Conneely et al. |
| 5,789,542 A | 8/1998 | McLaughlin et al. |
| 5,834,424 A | 11/1998 | Valenti et al. |
| 5,849,881 A | 12/1998 | Conneely et al. |
| 5,849,885 A | 12/1998 | Nuyens et al. |
| 5,919,913 A | 7/1999 | Nuyens et al. |
| 5,955,316 A | 9/1999 | Conneely et al. |
| 6,066,469 A | 5/2000 | Kruzel et al. |
| 6,080,559 A | 6/2000 | Conneely et al. |
| 6,100,054 A | 8/2000 | Conneely et al. |
| 6,111,081 A | 8/2000 | Conneely et al. |
| 6,228,614 B1 | 5/2001 | Conneely et al. |
| 6,277,817 B1 | 8/2001 | Kruzel et al. |
| 6,333,311 B1 | 12/2001 | Nuijens et al. |
| 6,399,570 B1 | 6/2002 | Mann et al. |
| 6,440,690 B1 | 8/2002 | Mor et al. |
| 6,455,687 B1 | 9/2002 | Kruzel et al. |
| 6,613,741 B2 | 9/2003 | Kruzel et al. |
| 6,635,447 B1 | 10/2003 | Conneely et al. |
| 6,890,902 B2 | 5/2005 | Svendsen et al. |
| 2002/0016289 A1 | 2/2002 | Conneely |
| 2002/0064524 A1 | 5/2002 | Cevc |
| 2002/0072596 A1 | 6/2002 | Ruben et al. |
| 2002/0107283 A1 | 8/2002 | Codd et al. |
| 2002/0111295 A1 | 8/2002 | Yajima et al. |
| 2002/0119928 A1 | 8/2002 | McAnalley |
| 2003/0039651 A1 | 2/2003 | Olmarker |
| 2003/0060425 A1 | 3/2003 | Ahlem et al. |
| 2003/0077641 A1 | 4/2003 | Laskowitz et al. |
| 2003/0096736 A1 | 5/2003 | Kruzel et al. |
| 2003/0096763 A1 | 5/2003 | Kruzel et al. |
| 2003/0105006 A1 | 6/2003 | Mann |
| 2003/0186854 A1 | 10/2003 | Daffre et al. |
| 2003/0190303 A1 | 10/2003 | Kimber et al. |
| 2004/0009895 A1 | 1/2004 | Varadhachary et al. |
| 2004/0009896 A1 | 1/2004 | Glynn et al. |
| 2004/0023334 A1 | 2/2004 | Prior |
| 2004/0082504 A1 | 4/2004 | Varadhachary et al. |
| 2004/0142037 A1 | 7/2004 | Engelmayer et al. |
| 2004/0151784 A1 | 8/2004 | Varadhachary et al. |
| 2004/0152623 A1 | 8/2004 | Varadhachary et al. |

(Continued)

FOREIGN PATENT DOCUMENTS

EP 0426924 5/1991

(Continued)

OTHER PUBLICATIONS

Vogel et al., Towrads a structure-function analysis of bovine lactoferricin and related tryptophan- and arginine-containing peptides, Biochem. cell Biol. 80: 49-63 (2002).*

(Continued)

*Primary Examiner*—Kathleen Kerr Bragdon
*Assistant Examiner*—Agnes B. Rooke
(74) *Attorney, Agent, or Firm*—Fulbright & Jaworski LLP

(57) ABSTRACT

The present invention is directed to a composition consisting of a series of novel biologically active 33-mer peptides.

6 Claims, 9 Drawing Sheets

U.S. PATENT DOCUMENTS

| | | |
|---|---|---|
| 2004/0152624 A1 | 8/2004 | Varadhachary et al. |
| 2004/0176276 A1* | 9/2004 | Varadhachary et al. ......... 514/6 |
| 2005/0004006 A1 | 1/2005 | Engelmayer et al. |
| 2005/0019342 A1 | 1/2005 | Varadhachary et al. |
| 2005/0064546 A1 | 3/2005 | Conneely et al. |
| 2005/0075277 A1 | 4/2005 | Varadhachary et al. |

FOREIGN PATENT DOCUMENTS

| | | |
|---|---|---|
| EP | 0478101 | 1/1992 |
| EP | 0730868 A1 | 9/1996 |
| JP | 07233086 A | 9/1995 |
| JP | 07316069 | 12/1995 |
| JP | 8165248 A2 | 6/1996 |
| WO | WO-9113982 | 9/1991 |
| WO | WO-9806425 A1 | 2/1998 |
| WO | WO-9844940 A1 | 10/1998 |
| WO | WO-0001730 | 1/2000 |
| WO | WO-0049040 | 8/2000 |
| WO | WO-0172322 | 10/2001 |
| WO | WO-0203910 A2 | 1/2002 |
| WO | WO-0211772 | 2/2002 |
| WO | WO-0241912 | 5/2002 |
| WO | WO-02080891 | 10/2002 |
| WO | WO-02100445 | 12/2002 |
| WO | WO-03061688 | 7/2003 |
| WO | WO-2004024180 | 3/2004 |

OTHER PUBLICATIONS

P4663 Poly-L-arginine hydrochloride, CAS No. 26982-20-7, Sigma-Aldrich Co., 2007, p. 1 of 1.*

Amouric et al, "Effect of Lactoferrin on the Growth of a Human Colon Adenocarcinoma Cell Line—Comparison with Transferrin," In Vitro vol. 20 No. 7, Jul. 1984, pp. 543-548.

Baraniuk et al., "Hypertonic saline nasal provocation stimulates nociceptive nerves, substance P release, and glandular mucous exocytosis in normal humans," Am. J. Respir. Crit. Care Med., 160: 655-662, 1999.

Barresi et al, "Lactoferrin in Benign Hypertrophy and Carcinomas of the Prostatic Gland," Virchows Archiv (Pathol Anat) 403; 1984, pp. 59-66.

Bellamy et al., "Antifungal properties of lactoferricin B, a peptide derived from the N-terminal region of bovine lactoferrin," Lett. Appl. Microbiol., 18: 230-233, 1994.

Bellamy et al., "Identification of the bactericidal domain of lactoferrin," Biochim. Biophys. Acta, 1121: 130-136, 1992.

Benezra et al., "A synthetic heparin-mimicking polyanionic compound binds to the LDL receptor-related protein and inhibits vascular smooth muscle cell proliferation," J. Cell. Biochem., 81(1): 114-27, 2001.

Bezault et al, "Human Lactoferrin Inhibits Growth of Solid Tumors and Development of Experimental Metastases in Mice," Cancer Research 54, May 1, 1994, pp. 2310-2312.

Birgisdottir et al., "Variation in consumption of cow milk proteins and lower incidence of Type 1 diabetes in Iceland vs the other 4 Nordic countries," DNM, 15(4): 240-245, 2002.

Butte et al, "Milk Composition on Insulin Dependent Diabetic Women," Journal of Pediatric Gastroenterology and Nutrition vol. 6, 1987, pp. 936-941.

Chan et al, "Autoantibody Formation aster Allogeneic Bone Marrow Transplantation: Correlation with the Reconstitution of CD5+ B Cells and Occurence of Graft-verus-host Disease," Pathology vol. 29 No. 2, May 1997, pp. 184-188.

Cianflone et al., "Inhibition of lipoprotein lipase induced-cholesterol ester accumulation in human hepatoma HepG2 cells," Atherosclerosis, 120: 101-114, 1996.

Clare et al., "Bioactive milk peptides: a prospectus," J. Diary Sci., 83: 1187-1195, 2000.

Clarke et al, "Evaluation of Bovine Lactoferrin as a Topical Therapy for Chemotherapy-induced Mucositis in the Golden Syrian Hamster," Oral Oncology 35, 1999, pp. 197-202.

Croy et al., "All three LDL receptor homology regions of the LDL receptor-related protein bind multiple ligands," Biochemistry, 42(44): 13049-13057, 2003.

Cumberbatch et al, "IL-I B-induced Langerhans' cell Migration and TNF-A production in Human Skin: Regulation by Lactoferrin," Clin Exp. Immunol 132, 2003, pp. 352-359.

Cumberbatch et al, "Regulation of Epidermal Langerhans Cell Migration by Lactoferrin," Immunology 2000, 100, pp. 21-28.

Damiens et al, "Effects of Human Lactoferrin on NK Cell Cytotoxicity Against Haematopoietic and Epithelial Tumour Cells," Biochimica et Biophysica Acta 1402, 1998, pp. 277-287.

Damiens et al, "Lactoferrin Inhibits G1 Cyclin-Dependent Kinases During Growth Arrest of Human Breast Carcinoma Cells," Journal of Cellular Biochemistry 72, 1999, pp. 486-498.

Eckmann, "Mucosal defences against Giardia," Parasite Immunol., 25(5): 259-270, 2003.

Edde et al, "Lactoferrin Protects Neonatal Rats from Gut-related Systemic Infection," Am J Physiol Gastrointest Liver Phsyiol 281: G1140-G1150, 2001.

Fujihara et al, "Lactoferrin Protects Against UV-B Irradiation-Induced Corneal Epithelial Damage in Rats," Cornea 19(2); 2000, pp. 207-211.

Fujita et al, "Down-Regulation of 2-Amino-3, 8-dimethylimidazo [4,5-f] Quinoxaline (MelQx)-induced CYP1A2 Expression is Associated with Bovine Lactoferrin Inhibition of MelQx-induced Liver and Colon Carcinogenesis in Rats," Jpn. J. Cancer Res. 93, Jun. 2002, pp. 616-625.

Hayashida et al., "Bovine lactoferrin has a nitric oxide-dependent hypotensive effect in rats," Am. J. Physiol. Regul. Integr. Comp. Physiol., 286(2): R359-65, 2004.

Hayashida et al., "Lactoferrin enhances opioid-mediated analgesia via nitric oxide in the rat spinal cord," Am. J. Physiol. Regul. Integr. Comp. Physiol., 285: R306-R312, 2003.

Hayashida et al., "Novel function of bovine milk-derived lactoferrin on antinociception mediated by mu-opioid receptor in the rat spinal cord," Brain Res., 965: 239-245, 2003.

He et al, "The Inhibition of Mast Cell Activation by Neutrophil Lactoferrin: Uptake by Mast Cells and Interaction with Tryptase, Chymase and Cathepsin G," Biochemical Pharmacology 65, 2003, pp. 1007-1015.

Hoek et al., "Antibacterial activity in bovine lactoferrin-derived peptides," Antimicrob. Agents Chemother., 41: 54-59, 1997.

Huettinger et al., "Characteristics of chylomicron remnant uptake into rat liver," Clin. Biochem., 21(2): 87-92, 1988.

Huettinger et al., "The LDL-receptor family. Lactoferrin and lipid metabolism," Adv. Exp. Med. Biol., 443: 107-11, 1998.

Iigo et al, "Inhibitory Effects of Bovine Lactoferrin on Colon Carcinoma 26 Lung Metastasis in Mice," Clinical & experimental Metastasis 17, 1999, pp. 35-40.

Inoue et al, "Lactoferrin for gut GVHD," Bone Marrow Transplant vol. 28 No. 11, Dec. 2001, pp. 1091-1092.

Jurado, "Iron, infections, and anemia of inflammation," Clin. Infect. Dis., 25: 888-895, 1997.

Kajikawa et al., "Lactoferrin inhibits cholesterol accumulation in macrophages mediated by acetylated or oxidized low-density lipoproteins," Biochim. Biophys. Acta., 1213(1): 82-90, 1994.

Kimber et al, "Lactoferrin: Influence on Langerhans Cells, Epidermal Cytokines, and Cutaneous Inflammation," Biochem Cell Biol. 80, 2002, pp. 103-107.

Kruzel et al, "Lactoferrin and insult induced metabolic imbalance in humans and other animals," International Congress Series 2000, 1195, pp. 301-310.

Kuby et al., Immunology, 4th Ed., Freeman and Co., 517-537, 2000.

Kuhara et al, "Orally Administered Lactoferrin Exerts an Antimetastatic Effect and Enhances Production of IL-18 in the Intestinal Epithelium," Nutrition and Cancer, vol. 28 No. 2, 2000, pp. 192-199.

Kuzendorf, "The Th1-Th2 paradigm in 1998: law of nature or rule with exception," Nephrology Dialysis Transplantation, 13: 2445-2448, 1998.

Lee et al, "The Protective Effects of Lactoferrin Feeding against Endotoxin Lethal Shock in Germfree Piglets," Infection and Immunity vol. 66 No. 4, 1998, pp. 1421-1426.

Legrand et al, "The N-terminal Arg2, Arg3, Arg4 of Human Lactoferrin Interact with Sulphated Molecules but Not with the Receptor Present on Jurkat Human Lymphoblastic T-Cells," Biochem J vol. 327, pp. 841-846 (1997).

Legrand et al., "Molecular interactions between human lactotransferrin and the phytohemagglutinin-activated human lymphocyte lactotransferrin receptor lie in two loop-containing regions of the N-terminal domain I of human lactotransferrin," *Biochemistry*, 31: 9243-9251, 1992.

Li et al, "Antibacterial Activity of Lysozyme and Lactoferrin is Inhibited by Binding of Advanced Glycation-modified Proteins to a Conserved Motif," Nature Medicine vol. 1 No. 10, Oct. 1995, pp. 1057-1061.

Li, "Glycation ligand binding motif in lactoferrin. Implications in diabetic infection," *Adv. Exp. Med. Biol.*, 443: 57-63, 1998.

Llirbat et al., "Normal and inhibited cholesterol synthesis in the cultured rat embryo," *J. Lipid Res.*, 38: 22-34, 1997.

Masuda et al, "Chemopreventive Effects of Bovine Lactoferrin on N-Butyl-N (4-hydroxybutyl) Nitrosamine-Induced Rat Bladder Carcinogenesis," Jpn. J. Cancer Res. 91, Jun. 2000, pp. 582-588.

Mazoyer et al., "KRDS, a new peptide derived from human lactotransferrin, inhibits platelet aggregation and release reaction," *Eur. J. Biochem.*, 194: 43-49, 1990.

McClead et al, "Oral Lactoferrin and Lactoperoxidase decrease Mortality of Enterotoxigenic *E coli*. Infenction," Pediatric Research 1987, vol. 21, No. 4 Part 2, pp. 417A.

Mencucci et al, "Ophthalmological Aspects in Allogenic Bone Marrow Transplantation: Sjogren-like Syndrome in Graft-versus-Host Disease," Eur. J. Ophthalmol vol. 7, No. 1 Jan.-Mar. 1997, pp. 13-18.

Nakajima et al, "Lactoferrin as a Suppressor of Cell Migration of Gastrointestinal Cell Lines," Journal of Cellular Physiology 170, 1997, pp. 101-105.

Nicolic, "The Th1 and Th2 mediate acute graft-versus-host disease, each with distinct end-organ targets," *The Journal of Clinical Investigation*, 15(9): 1289-1298, 2000.

Nikolic et al., "Th1 and Th2 mediate acute graft-versus-host disease, each with distinct end-organ targets," *J. Clin. Invest*., 105: 1289-1298, 2000.

Norby et al,"Orally Administered Bovine Lactoferrin Systemically Inhibits VEGF 165—Mediated Angiogenesis in the Rat," Int. j. Cancer 91, 2001, pp. 236-240.

Perico et al., "Delayed graft function in kidney transplantation," *Lancet*, 364: 1814-1827, 2004.

Saito et al., "Potent bactericidal activity of bovine lactoferrin hydrolysate produced by heat treatment at acidic pH," *J. Dairy Sci*., 74(11): 3724-30, 1991.

Sakamoto, N., "Antitumor Effect of Human Lactoferrin against Newly Establishes Human Pancreatic Cancer Cell Line SPA," Gan To Kagaku Ryoho, Aug. 1998 25(10), pp. 1557-1563.

Schmidt et al, "Cellular Receptors for Advanced Glycation End Products," Arterioscler Thromb vol. 14, 1994, pp. 1521-1528.

Schmidt et al, "The Dark Side of Glucose," Nature Medicine vol. 1 No. 10, Oct. 1995, p. 1002-1004.

Sekine et al, "Inhibition of Azoxymethane-initiated Colon Tumor by Bovine Lactoferrin Administration in F344 Rats," Jpn. J. Cancer Res. 88, Jun. 1997, pp. 523-526.

Shau et al, "Modulation of Natural Killer and Lymphokine-activated Killer Cell Cytotoxicity by Lactoferrin," Journal of Leukocyte Biology vol. 51, Apr. 1992, pp. 343-349.

Skolnick et al., "From genes to protein structure and function: novel applications of computational approaches in the genomic era," *Trends in Biotech*., 18: 34-39, 2000.

Sugita et al., "Induction of macrophage-inflammatory protein-3alpha gene expression by TNF-dependent NF-kappaB activation," *J. Immunol*., 168(11): 5621-8, 2002.

Tabak et al, "Alterations in Lactoferrin in Salivary Gland Disease," J Dent Res 57(1), Jan. 1978; pp. 43-47.

Takayama et al, "Effects of Lactoferrin on Collagen Gel Contractile Activity and Myosin Light Chain Phosphorylation in Human Fibroblasts," FEBS Letter 508, 2001, pp. 111-116.

Takayama et al, "The Bovine Lactoferrin Region Responsible for Promoting the Collagen Gel Contractile activity of Human Fibroblasts," Biochemical and Biophysical Research Communications 299 (2002), pp. 813-817.

Tanaka et al, "Bovine Lactoferrin Inhibits Rat Tongue Carcinogenesis," Elsevier Sciences B.V. Lactoferrin: Structure, Function and Applications 2000, pp. 401-411.

Teng et al, "Lactoferrin Gene: Methylation, Expression and Cancer," Elseiver Science B.V.—Lactoferrin: Structure, Function and Application, 2000, pp. 247-255.

Teschemacher, "Lactoferrin elicits opioid-mediated antinociception without development of tolerance: central nNOS-1 set off duty?" *Am. J. Physiol. Regul. Integr. Comp. Physiol*., 285: R302-R305, 2003.

Thornalley, "Cell activation by glycated proteins. AGE receptors, receptor recognition factors and functional classification of AGEs," *Cell. Mol. Biol*., 44(7): 1013-23, 1998.

Tomita et al., "Bovine lactoferrin and lactoferricin derived from milk: production and applications," *Biochem. Cell. Biol*., 80(1): 109-12, 2002.

Tomita et al., "Potent antibacterial peptides generated by pepsin digestion of bovine lactoferrin," *J. Dairy Sci*., 74: 4137-4142, 1991.

Tsuda et al, "Cancer Prevention by Bovine Lactoferrin and Underlying Mechanisms—a Review of Experimental and Clinical Studies," Biochem. Cell Biol. 80, 2002, pp. 131-136.

Tsuda et al, "Milk and Dairy Products in Cancer Prevention: Focus on Bovine Lactoferrin," Elsevier Science B.V.—Mutation Research 462, 2000, pp. 227-233.

Tsuda et al, "Prevention of Carcinogenesis and Metastasis by Dietary Bovine Lactoferrin," Elsevier Sciences B.V.—Lactoferrin: Structure, Function and Applications, 2000, pp. 389-399.

Tsuda et al, "Prevention of Colon Carcinogenesis and Carcinoma Metastasis by Orally Administered Bovine Lactoferrin in animals," BioFactors 12, 2000, pp. 83-88.

Tsuda et al, Inhibition of Azoxymethane Initiated Colon Tumor and Aberrant Crypt FOCI Development by Bovine Lactoferrin Administration in F344 Rats, Advances in Lactoferrin research, edited by Spik et al, Plenum Press, New York, 1998, pp. 273-283.

Ushida et al, "Inhibitory Effects of Bovine Lactoferrin on Intestinal Polyposis in the Apc Mouse," Cancer Letters 134, 1998, pp. 141-145.

Ushida et al, "Possible Chemopreventive Effects of Bovine Lactoferrin on Esophagus and Lung Carcinogenesis in the Rat," Jpn. J. Cancer Res. 90, Mar. 1999, pp. 262-267.

Van Belzen, nico, "The Role of Lactoferrin in Cancer Prevention," Sciences Des Aliments, 22, 2002, pp. 461-468.

Van Berkel et al, "N-terminal Stretch Arg2, Arg3, and Arg5 of Human Lactoferrin is Essential for Binding to Heparin, Bacterial Lipopolysaccharide, Human Lysozyme and DNA," Biochem J. vol. 328, pp. 145-151 (1997).

Van Dijk et al., "Recognition of chylomicron remnants and beta-migrating very-low-density lipoproteins by the remnant receptor of parenchymal liver cells is distinct from the liver alpha 2-macroglobulin-recognition site," *Biochem. J*., 279(Pt 3): 863-70, 1991.

Varadhachary et al, "Recombinant Human Lactoferrin, a novel oral Anti-Cancer Drug," www.asco.org, Abstract No. 934, 2003.

Varadhachary et al., "Intratumoral Injection of human Recombinant Lactoferrin Inhibits the Growth of Human Tumors Implanted in Athymic Nude Mice," www.asco.org, Abstract No. 1875, 2002.

Vogel et al., "Towards a structure-function analysis of bovine lactoferricin and related tryptophan- and arginine-containing peptides," *Biochem. Cell. Biol*., 80(1): 49-63, 2002.

Wang et al, "Activation of Intestinal Mucosal Immunity in Tumor-bearing Mice by Lactoferrin," Jpn. J. Cancer Res. 91, Oct. 2000, pp. 1022-1027.

Ward et al, "Lactoferrin and Host Defense," Biochem Cell Biol. 80, 2002, pp. 95-102.

Weinberg, Eugene, "The Therapeutic Potential of Lactoferrin," Expert Opinion Investig. Drugs, 12(5), 2003, pp. 841-851.

Wu et al., "Inhibition effects of KRDS, a peptide derived from lactotransferrin, on platelet function and arterial thrombus formation in dogs," *Haemostasis*, 22: 1-6, 1992.

Yamauchi et al., "Antibacterial activity of lactoferrin and a pepsin-derived lactoferrin peptide fragment," *Infect. Immun.*, 61: 719-728, 1993.

Yamauchi et al., "Increased serum levels of macrophage inflammatory protein-3α in chronic viral hepatitis: prognostic importance of macrophage inflammatory protein-3α during interferon therapy in chronic hepatitis C", Journal of Viral Hepatitis; 2002; 213-220; vol. 9 (3).

Yan et al, "Enhanced Cellular Oxidant Stress by the Interaction of Advanced Glycation End Products with Their Receptors/Binding Proteins," The Journal of Biomedical Chemistry vol. 269, No. 13, Apr. 1, 1994, pp. 9889-9897.

Yang et al, "Antitumor Activity and Specificity as a Function of Substitutions in the Lipophilic Sector of Helical Lactoferrin-derived Peptide," Journal of Peptide Science 9, 2003, pp. 300-311.

Yang et al., "Enhanced Antitumor Activity and Selectivity of Lactoferrin-derived peptides," J. Peptide Res. 60, 2002, pp. 187-197.

Yoo et al, "Bovine Lactoferrin and Lactoferricin Inhibit Tumor Metastasis in Mice," Advances in Lactoferrin Research, Chapter 35, Plenum Press, New York, 1998, pp. 285-291.

Yoo et al, "Bovine Lactoferrin and Lactoferricin, a Peptide Derived from Bovine Lactoferrin, Inhibit Tumor Metastasis in mice," Jpn. J. Cancer Res. 88, Feb. 1997, pp. 184-190.

Zagulski et al., "Lactoferrin stimulates killing and clearance of bacteria but does not prevent mortality of diabetic mice," *Arch. Immunol. Ther. Exp.*, 49(6): 431-8, 2001.

Zhang et al., "Neutralization of endotoxin in vitro and in vivo by a human lactoferrin-derived peptide," *Infect. Immun.*, 67(3): 1353-8, 1999.

Ziere et al., "Removal of 14 N-terminal amino acids of lactoferrin enhances its affinity for parenchymal liver cells and potentiates the inhibition of beta- very low density lipoprotein binding," *J. Biol. Chem.*, 268: 27069-27075, 1993.

\* cited by examiner

| Sample | 0.2 mg/ml | | 2.0 mg/ml | |
|---|---|---|---|---|
| | 2 hours | 4 hours | 2 hours | 4 hours |
| Medium | 0.1556 | 0.7686 | - | - |
| LPF-21 | 4.53 | 3.08 | 5.92 | 4.73 |
| LPF-22 | 4.47 | 9.2 | 3.95 | 8.39 |
| LPF-23 | 6.48 | 5.42 | 4.54 | - |
| LPF-24 | 5.01 | 8.71 | 3.6 | 7.63 |
| LPF-25 | 4.22 | 7.13 | 4.25 | - |
| LPF-32 | 5.5 | 8.22 | 5.57 | 7.71 |
| LPF-33 | 4.11 | 8.33 | 0.82 | 7.47 |
| LPF-34 | 0.02 | - | 3.94 | - |
| LPF-35 | 7.95 | 9.57 | 1.86 | 2.17 |
| LPF-36 | 5 | 9.79 | 4.1 | 9.03 |

FIG. 9

COMPOSITION OF LACTOFERRIN RELATED PEPTIDES AND USES THEREOF

RELATED APPLICATIONS

This application claims priority to U.S. Provisional Application No: 60/622,176 filed Oct. 26, 2004, which is incorporated herein by reference in its entirety.

TECHNICAL FIELD

The present invention is directed to a composition consisting of a series of novel biologically active 33-mer peptides.

BACKGROUND OF THE INVENTION

Lactoferrin is a single chain metal binding glycoprotein. Many cell types, such as monocytes, macrophages, lymphocytes, and brush-border cells in the intestine, are known to have lactoferrin receptors. Lactoferrin is found mainly in external secretions of mucosal epithelia such as breast milk, saliva, tears, bile, and pancreatic fluid and has a wide array of functions related to host primary defense mechanisms. For example, lactoferrin has been reported to activate natural killer (NK) cells, induce colony stimulating activity, activate polymorphonuclear neutrophils (PMN), regulate granulopoeisis, enhance antibody-dependent cell cytotoxicity, stimulate lymphokine-activated killer (LAK) cell activity, and potentiate macrophage toxicity. Lactoferrins have been reported to have a number of beneficial effects including anti-infective, anti-inflammatory, immunomodulatory and anti-cancer activities.

Recombinant human lactoferrin has previously been described as being purified after expression in a variety of prokaryotic and eukaryotic organisms including *aspergillus* (U.S. Pat. No. 6,080,559), cattle (U.S. Pat. No. 5,919,913), rice, corn, *Sacharomcyes* (U.S. Pat. No. 6,228,614) and *Pichia pastoris* (U.S. Pat. Nos. 6,455,687, 6,277,817, 6,066,469). Also described are expression systems for the expression of full-length human lactoferrins (e.g. U.S. Pat. No. 6,100,054). In all cases, part of the teaching is expression of the full length cDNA and purification of the intact protein whose N-terminal, after processing of the leader peptide, is the amino acid glycine. Nuijens, et al. (U.S. Pat. No. 6,333,311) separately describe variants of human lactoferrin but their focus is limited to deletion or substitution of arginine residues found in the N-terminal domain of lactoferrin.

LF contains a strongly basic region close to its N-terminus and binds to a variety of anionic biological molecules including lipid A (Appelmelk et al., Infect. Immun. 62:2628-2632 (1994)) and glycosaminoglycans which occur on the surface of most cells and in most extracellular matrices (Mann et al., J. Biol. Chem. 269: 23661-7 (1994)). Lactoferricin H (residues 1-47) and lactoferricin B (residue 17-41) are released by pepsinolysis of human or bovine LF, respectively, and may have more potent antibacterial activity than the native proteins (Bellamy et al., Biochim. Biophys. Acta. 1121: 130-136 (1992)). A region composed of residues 28-34 is reported to contribute to the high affinity binding of human LF and lactoferricin H to endotoxin (Elass-Rochard et al., Biochem. J. 312: 839-845 (1995)). LF and lactoferricin B have been shown to inhibit the endotoxin-induced interleukin-6 response in human monocytic cells (Mattsby-Baltzer et al., Pediatr. Res. 40: 257-262 (1996)). Previously identified fragments of LF which exhibit antimicrobial activity were isolated from pepsin hydrolysates of LF (Tomita et al., (1993) U.S. Pat. No. 5,214,028; Tomita et al., (1994) U.S. Pat. No. 5,304,633; Tomita et al., (1994) U.S. Pat. No. 5,317,084; Tomita et al., (1997) U.S. Pat. No. 5,656,591).

Previous studies have established that the N-terminal 33 residues of human LF represent the minimal sequence that mediates binding of the protein to anionic polysaccharides such as glycosaminoglycans (Mann et al., J. Biol. Chem. 269: 23661-7 (1994)). This sequence contains a cationic head (residues 1-6) and tail (residues 28-33) which combine to form the glycosaminoglycan-binding site. In further studies described by Mann in U.S. Pat. No. 6,399,570, lactoferrin peptide fragments having up to the first 51 amino acids encompassed endotoxin neutralizing ability and antimicrobial activity. Mann further showed that up to 17 amino acids could be deleted from the C-terminus and up to 3 amino acids could be deleted N-terminus of the 51 amino acid long peptide while retaining the endotoxin neutralizing ability and antimicrobial activity.

The present invention is the first to describe a peptide composition that consists of lactoferrin related peptides which are at least 33 amino acids in length in which at least four amino acids at the C and/or N terminus are substituted for positive amino acids resulting in an enhancement of its biological activity.

BRIEF SUMMARY OF THE INVENTION

The present invention is directed to a composition consisting of a series of biologically active peptides. The peptides of the present invention comprise at least 33 amino acids in which at least four amino acids at the C and/or N terminus are substituted for positive amino acids. These biologically active peptides can be used to treat a variety of pathological conditions, for example, but not limited to hyperproliferative disease, respiratory disorder, cardiovascular disease, neurological condition, autoimmune disorder, infectious disease, gastrointestinal disorder, endocrine and/or metabolism disorder, hematological disorder, ocular disorder, integument disorder, pain and a wound.

One embodiment of the present invention comprises a pharmaceutical composition that induces modulation of the immune system whereby the composition stimulates production of MIP-3alpha from hepatocytes. The composition can also inhibit bacterial growth as measured by minimum inhibitory concentration (MIC). More specifically, the composition comprises an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11.

In certain embodiments, the pharmaceutical composition comprises at least four consecutive positively charged residues at the N-terminus or at least four positively charged residues at the C-terminus or at least four positively charged residues at each of the N- and C-termini. Thus, the pharmaceutical composition may comprise at least 25% positively charged residues or at least 33% positively charged residues. The positively charged residues are arginine, lysine or derivates thereof.

In further embodiments, the pharmaceutical composition can further comprise a metal chelator. The metal chelator is selected from the group consisting of ethylenediaminetetraacetic acid (EDTA), [ethylenebis(oxyethylenenitrilo)]tetraacetic acid (EGTA), 1,2-bis(2-aminophenoxy)ethane-N,N,N',N'-tetraacetic acid (BAPTA), and hydroxyethlene triamine diacetic acid, (HEDTA).

Another embodiment of the present invention comprises an isolated polypeptide having an amino acid sequence as defined in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or SEQ ID NO: 11. The polypeptide is admixed with a pharmaceutically acceptable carrier.

Yet further, another embodiment comprises an expression vector comprising a nucleic acid sequence encoding an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11. The expression vector is further defined as a viral or plasmid vector. The viral vector is an adenoviral vector, an adeno-associated viral vector, a retroviral vector, a lentiviral vector, a herpes viral vector, polyoma viral vector, pox vector, or hepatitis B viral vector.

In certain embodiments, the present invention comprises a method of treating a pathological condition comprising the step of administering the pharmaceutical composition, or the polypeptide or the expression vector. It is understood that the pharmaceutical composition or the polypeptide or the expression vector can be combined with a standard therapy to treat the pathological condition.

The pathological condition is selected from the group consisting of hyperproliferative disease, respiratory disorder, cardiovascular disease, neurological condition, autoimmune disorder, infectious disease, gastrointestinal disorder, endocrine and/or metabolism disorder, hematological disorder, ocular disorder, integument disorder, pain and a wound.

More specifically, the hyperproliferative disease is further defined as cancer. Exemplary cancers include, but are not limited to melanoma, non-small cell lung cancer, small-cell lung cancer, lung cancer, leukemia, hepatocarcinoma, retinoblastoma, astrocytoma, glioblastoma, gum cancer, tongue cancer, neuroblastoma, head cancer, neck cancer, breast cancer, pancreatic cancer, prostate cancer, renal cancer, bone cancer, testicular cancer, ovarian cancer, mesothelioma, cervical cancer, gastrointestinal cancer, lymphoma, myeloma, brain cancer, colon cancer, sarcoma or bladder cancer.

In certain embodiments the pharmaceutical composition or the polypeptide or the expression vector can be combined with a standard anti-cancer therapy to treat the cancer. The anti-cancer agent selected from the group consisting of chemotherapy, surgery, radiotherapy, an immunostimulant, anti-cancer biologic agent or a cancer vaccine Yet further, hyperproliferative disease can also encompass rheumatoid arthritis, infectious arthritis, inflammatory bowel disease, osteoarthritis, leiomyomas, adenomas, lipomas, hemangiomas, fibromas, vascular occlusion, restenosis, atherosclerosis, pre-neoplastic lesions, carcinoma in situ, oral hairy leukoplakia, or psoriasis.

Exemplary neurological conditions that may be treated using the pharmaceutical composition or the polypeptide or the expression vector of the present invention can include, but are not limited to multiple sclerosis, Alzheimer's disease, Parkinson's disease, muscular dystrophy, sleep or depression.

Gastrointestinal disorders that can be treated using the pharmaceutical composition or the polypeptide or the expression vector of the present invention can include, but are not limited to Crohn's disease, colitis, necrotizing enterocolitis, endometriosis, irritable bowel syndrome, pancreatitis, periodontal disease, and ulcerative colitis.

Exemplary autoimmune disorders that can be treated using the pharmaceutical composition or the polypeptide or the expression vector of the present invention can include, but are not limited to graft versus host disease (GVHD), organ transplant rejection, autoimmune hepatitis, primary biliary cirrhosis, autoimmune cholangitis, primary sclerosing cholangitis, irritable bowel syndrome (IBS), multiple sclerosis (MS), chronic granulomatous disease, ankylosing spondylitis, scleroderma, polymyositis, (dermato)myositis, systemic vasculitis, systemic lupus erythematosus (SLE), Chrohn's disease, insulin-dependent diabetes (type 1) or ulcerative colitis.

Endocrine and/or metabolism disorder that can be treated using the pharmaceutical composition or the polypeptide or the expression vector of the present invention can include, but are not limited to diabetes mellitus, thyroid disorder, or osteoporosis.

Hematological disorders that can be treated using the pharmaceutical composition or the polypeptide or the expression vector of the present invention can include, but are not limited to anemia, sickle cell anemia or cachexia.

Infectious diseases that can be treated using the pharmaceutical composition or the polypeptide or the expression vector of the present invention can include, but are not limited to a disease that result from infection of either a virus, a bacterium or a fungus or a combination thereof. Exemplary viruses include, but are not limited to herpes simplex, labilis zoster, HIV, hepatitis A, hepatitis, B, or hepatitis C. Infectious disease can include HIV, hepatitis, West Nile Virus bacterial meningitis, paramenigeal infections, septic thrombophlebitis, candidiasis, myocarditis, bacteremia, sepsis, or septic shock.

Ocular disorder that can be treated using the pharmaceutical composition or the polypeptide or the expression vector of the present invention can include, but are not limited to conjunctivitis, dry eye disease, glaucoma, allergic eye disease, uveitis or ocular infection.

Cardiovascular disease that can be treated using the pharmaceutical composition or the polypeptide or the expression vector of the present invention can include, but are not limited to congestive heart failure, hypertension, cardiomyopathy, myocarditis, atherosclerosis, chronic venous disease, or heart arrhythmia.

In further embodiments, the pathological condition is elevated cholesterol or dyslipidemia.

The wound that can be treated using the pharmaceutical composition or the polypeptide or the expression vector of the present invention can include, but are not limited to skin wound, internal wound, gastrointestinal wound, oral wound, ophthalmic wound, surgical wound and fractures.

The respiratory disorder that can be treated using the pharmaceutical composition or the polypeptide or the expression vector of the present invention can include, but are not limited to atopic asthma, non-atopic asthma, emphysema, bronchitis, chronic obstructive pulmonary disease (COPD), sinusitis, allergic rhinitis, fibrotic lung disease, ARDS, pulmonary vascular disease/pulmonary hypertension, Cor Pulmonale, or cystic fibrosis.

In further embodiments, the composition stimulates the production of IL-18. Yet further, the composition stimulates the production of IL-12, GM-CSF, or IFN-γ. Still further, composition stimulates or supplements immune cells, exemplary immune cells are T lymphocytes, B-lymphocytes, dendritic cells (DCs), other antigen presenting cells (APCs), natural killer (NK) cells, macrophages or monocytes. The T lymphocytes are selected from the group consisting of CD4+, CD8+, CD3+ and CD40+ cells and the B-lymphocytes are CD40+ cells.

In certain embodiments, the composition is administered orally, inhalation, nasally, topically or parenterally. Parenterally can include subcutaneously, intramuscularly, intraperitoneally, intravenously, intraarterially, intramyocardially, transendocardially, transepicardially, intrathecally or intratumorally.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 7A shows the effects on acceleration of wound closure. FIG. 7B shows the increase in incidence of wound healing.

FIG. 9 shows the effect of peptide LPF-35, at different doses and time points, on the expression of MIP-3-alpha in hepatocytes.

DETAILED DESCRIPTION OF THE INVENTION

I. Definitions

Figure 1:
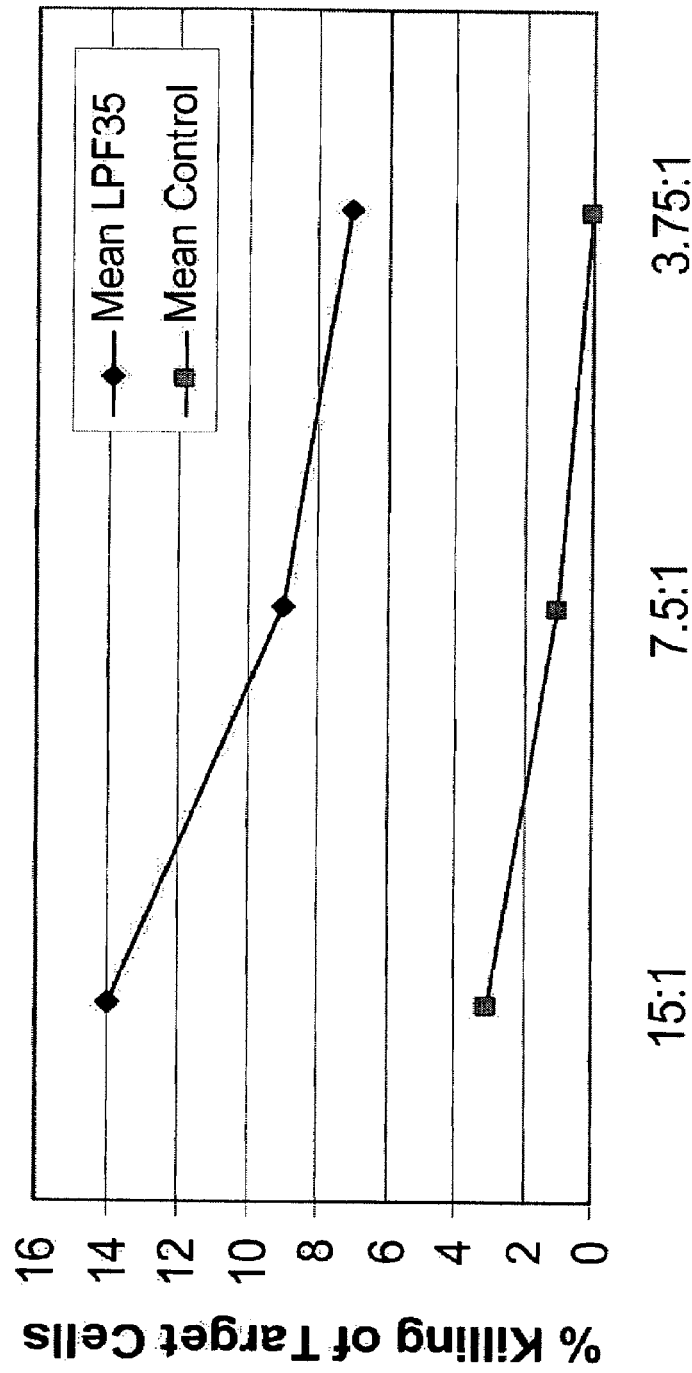
FIG. 1 shows in vitro NK cell activation, as measured by the percent killing of target cells, by peptide LPF-35.

Unless defined otherwise, technical and scientific terms used herein have the same meaning as commonly understood by one of ordinary skill in the art to which this invention belongs. For purposes of the present invention, the following terms are defined below.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "containing", "including" and "comprising" are interchangeable and one of skill in the art is cognizant that these terms are open ended terms.

The term "acute pain" as used herein includes tissue injury or pathology. For example, acute pain includes, but is not limited to pain following surgery (e.g., surgery), pain following trauma (e.g., blunt or sharp injury, bullet wounds), pain associated with athletic injury, and the occasional headache. Medically, acute pain can have a diagnostic value; that is, it leads to the discovery of a pathological condition. Yet further, acute pain lasts or is anticipated to last for a short period of time, typically less than one to two months. Acute pain is associated with hyperactivity of the sympathetic nervous system, for example, tachycardia, increased respiratory rate, increased blood pressure, increased cortisol release, diaphoresis and dilated pupils.

The term "antibiotic" as used herein is defined as a substance that inhibits the growth of microorganisms without damage to the host. For example, the antibiotic may inhibit cell wall synthesis, protein synthesis, nucleic acid synthesis, or alter cell membrane function. Classes of antibiotics that can possibly be used include, but are not limited to, macrolides (e.g., erythromycin), penicillins (e.g., nafcillin), cephalosporins (e.g., cefazolin), carbepenems (e.g., imipenem, aztreonam), other beta-lactam antibiotics, beta-lactam inhibitors (e.g., sulbactam), oxalines (i.e. linezolid), aminoglycosides (e.g., gentamicin), chloramphenicol, sulfonamides (e.g., sulfamethoxazole), glycopeptides (e.g., vancomycin), quinolones (e.g., ciprofloxacin), tetracyclines (e.g., minocycline), fusidic acid, trimethoprim, metronidazole, clindamycin, mupirocin, rifamycins (e.g., rifampin), streptogramins (e.g., quinupristin and dalfopristin) lipoprotein (e.g., daptomycin), polyenes (e.g., amphotericin B), azoles (e.g., fluconazole), and echinocandins (e.g., caspofungin acetate). The term "morbidity" as used herein is the state or condition of being diseased. Yet further, morbidity can also refer to the ratio of incidence, for example the number of sick subjects or cases of diseases in relationship to a specific population.

The term "anti-depressant drug" as used herein includes compounds that provide pain relief by reducing side-effects including anxiety. Anti-depressant drugs include, for example, but are not limited to tricyclin antidepressants, sedatives, tranquilizers, hypnotics, anti-histamines, and amphetamines.

The term "antimicrobial" as used herein is defined as a substance that inhibits the growth of microorganisms without damage to the host, for example antibiotics, anti-fungal and antiseptics.

The term "atherosclerosis" as used herein includes a form of arteriosclerosis characterized by a combination of changes in the intima of arteries, such changes include, but are not limited to accumulation of lipids, complex carbohydrates, blood and blood products, fibrous tissue and calcium deposits. Yet further, atherosclerotic plaques can be characterized into at least two areas. One type is characterized by prominent proliferation of cells with small accumulations of lipids. The second type consists mostly of intracellular and extracellular lipid accumulation and a small amount of cellular proliferation.

The term "bacteremia" as used herein is defined as having a focus of bacterial infection or bacteria in the blood of the subject.

The term "cancer" as used herein is defined as a hyperproliferation of cells whose unique trait—loss of normal control—results in unregulated growth, lack of differentiation, local tissue invasion, and metastasis. Examples include but are not limited to, melanoma, non-small cell lung, small-cell lung, lung, hepatocarcinoma, leukemia, retinoblastoma, astrocytoma, glioblastoma, gum, tongue, neuroblastoma, head, neck, breast, pancreatic, prostate, renal, bone, testicular, ovarian, mesothelioma, cervical, gastrointestinal, lymphoma, brain, colon, sarcoma or bladder cancer.

The term "cardiovascular disease or disorder" as used herein refers to disease and disorders related to the cardiovascular or circulatory system. Cardiovascular disease and/or disorders include, but are not limited to, diseases and/or disorders of the pericardium, heart valves (e.g., incompetent valves, stenosed valves, rheumatic heart disease, mitral valve prolapse, aortic regurgitation), myocardium (e.g., coronary artery disease, myocardial infarction, heart failure, ischemic heart disease, angina), blood vessels (e.g., hypertension, arteriosclerosis, aneurysm) or veins (e.g., varicose veins, hemorrhoids). Yet further, one skilled in the art recognizes that cardiovascular diseases and/or disorders can result from congenital defects, genetic defects, environmental influences (e.g., dietary influences, lifestyle, stress, etc.), and other defects or influences.

The term "cell," "cell line," and "cell culture" as used herein may be used interchangeably. All of these terms also include their progeny, which are any and all subsequent generations. It is understood that all progeny may not be identical due to deliberate or inadvertent mutations.

The term "chemokine" as used herein refers to small cytokines that are involved in the migration and activation of cells, for example phagocytic cells and lymphocytes. One of skill in the art realizes that chemokines play a central role in inflammatory and immune response processes.

The term "cholesterol" as used herein refers to the monohydric alcohol form, which is a white, powdery substance that is found in all animal cells and in animal-based foods (not in plants). Cholesterol is an essential nutrient necessary for many functions, including the following: repairing cell membranes, manufacturing vitamin D on the skin's surface, production of hormones, such as estrogen and testosterone, and possibly helping cell connections in the brain that are important for learning and memory.

The term "chronic pain" as used herein refers to pain that lasts longer than 1 month or beyond the resolution of an acute tissue injury or is recurring or is associated with tissue injury and/or chronic diseases that are expected to continue or progress, for example, cancer, arthritis, inflammatory disease, chronic wounds, cardiovascular accidents, spinal cord disorders, central nervous system disorder or recovery from surgery. Chronic pain can be associated with several factors that include, but are not limited to lassitude, sleep disturbance, decreased appetite, loss of taste for food, weight loss, diminished libido, constipation, or depression.

The term "chylomicron" as used herein refers to the largest in size and lowest in density of the triglyceride carrying lipoproteins.

The term "cytokine" as used herein refers to proteins that are made by cells that affect the behavior of other cells, for example stimulate or inhibit cell proliferation. For example, cytokines that are made by lymphocytes are often called lymphokines or interleukins. One of skill in the art realizes that the term cytokine is a generic term used in the literature to refer to proteins that are made by cells that can affect the behavior of other cells.

The term "diabetes mellitus" as used herein refers to a disorder of carbohydrate metabolism that is typically characterized by hyperglycemia and glycosuria, which results from inadequate production or utilization of insulin. Diabetes mellitus includes several syndromes or disorders, for example, but not limited to, primary diabetes mellitus (e.g., insulin-dependent (Type I) and non-insulin-dependent (Type II)); secondary diabetes [for example: pancreatic diabetes (e.g., destruction of the pancreas, removal of the pancreas, etc.); extrapancreatic/endocrine diabetes (e.g., hypersomatotropism, hyperadrenalism, hyperthyroidism, glucagonama, etc.); drug-induced diabetes (e.g., steroid diabetes, thiazides, etc.)] and rare/exceptional forms of diabetes (e.g., lipoatrophic diabetes, myatonic diabetes, disturbance of insulin receptors, genetic syndromes, etc). Long-term complications of diabetes include neuropathy, retinopathy, nephropathy, generalized degenerative changes in the blood vessels and increased susceptibility to infection.

The term "effective amount" or "therapeutically effective amount" as used herein refers to an amount that results in an improvement or remediation of the symptoms of the disease or condition.

The term "expression construct" or "transgene" is defined as any type of genetic construct containing a nucleic acid coding for gene products in which part or all of the nucleic acid encoding sequence is capable of being transcribed can be inserted into the vector. The transcript is translated into a protein, but it need not be. In certain embodiments, expression includes both transcription of a gene and translation of mRNA into a gene product. In other embodiments, expression only includes transcription of the nucleic acid encoding genes of interest. In the present invention, the term "therapeutic construct" may also be used to refer to the expression construct or transgene.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well and are described infra. In the present invention, the term "therapeutic vector" may also be used to refer to the expression vector.

The term "fragile bone condition" or "fragile bone disease" as used herein refers to a condition or disease characterized by low bone mass or structural deterioration of bone tissue, leading to bone fragility and increased susceptibility to fractures.

The term "gastrointestinal disorder or conditions" as used herein includes gastrointestinal disorders in which one or more of the symptoms and conditions affect the gastrointestinal tract from the mouth to the anus, as well as any organ that may play a role in digestion, for example, but not limited to the pancreas, or the gall bladder. Gastrointestinal disorders include, but are not limited to, heartburn, bloating, postoperative ileus, abdominal pain and discomfort, early satiety, epigastric pain, nausea, vomiting, burbulence, regurgitation, intestinal pseudoobstruction, anal incontinence, gastroesophageal reflux disease, irritable bowel syndrome, ulcerative colitis, Crohn's disease, renal disorders, menstrual cramps, pancreatitis, spastic and interstitial cystitis and ulcers and the visceral pain associated therewith.

The term "Grade 3 neutropenia" refers to the reduction of the absolute neutrophil cell count (ANC) to less than about 1000 cells/µL. The term "neutropenia" generally refers to a condition in which the ANC is reduced to 1000 cells//µL or less. Such a condition may be caused by depressed production, increased peripheral destruction of neutrophils. The most common neutropenias are iatrogenic, resulting from the widespread use of cytotoxic or immunosuppressive therapies for cancer treatment or control of autoimmune disorders. Other causes of neutropenia include induction by drugs, hematological diseases including idiopathic, cyclic neutropenia, Chediak-Higashi syndrome, aplastic anemia, infantile genetic disorders, tumor invasion such as myelofibrosis, nutritional deficiency; infections such as tuberculosis, typhoid fever, brucelloisis, tularemia, measles, infectious mononucleosis, malaria, viral hepatitis, leishmaniasis, AIDS, antineutrophil antibodies and/or splenetic or lung trapping, autoimmune disorders, wegner's granulomatosis, acute endotoxemia, hemodialysis, and cardiopulmonary bypass. The present invention applies to any acquired and inherited neutropenic conditions.

The term "graft-versus-host-disease" or "GVHD" as used herein is the pathological reaction that occurs between the host and grafted tissue. The grafted or donor tissue dominates the pathological reaction. Graft-versus-host-disease (GVHD) can be seen following stem cell and/or solid organ transplantation. GVHD occurs in immunocompromised subjects, who when transplanted, receive "passenger" lymphocytes in the transplanted stem cells or solid organ. These lymphocytes recognize the recipient's tissue as foreign. Thus, they attack and mount an inflammatory and destructive response in the recipient. GVHD has a predilection for epithelial tissues, especially skin, liver, and mucosa of the gastrointestinal tract. GVHD subjects are immunocompromised due to the fact that prior to transplant of the graft, the subject receives immunosuppressive therapy.

The term "gram-negative bacteria" or "gram-negative bacterium" as used herein is defined as bacteria which have been classified by the Gram stain as having a red stain. Gram-negative bacteria have thin walled cell membranes consisting of a single layer of peptidoglycan and an outer layer of lipopolysaccharide, lipoprotein, and phospholipID Exemplary organisms include, but are not limited to, Enterobacteriacea consisting of *Escherichia, Shigella, Edwardsiella, Salmonella, Citrobacter, Klebsiella, Enterobacter, Hafnia, Serratia, Proteus, Morganella, Providencia, Yersinia, Erwinia, Buttlauxella, Cedecea, Ewingella, Kluyvera, Tatumella* and *Rahnella*. Other exemplary gram-negative organisms not in the family Enterobacteriacea include, but are not limited to, *Pseudomonas aeruginosa, Stenotrophomonas maltophilia, Burkholderia, Cepacia, Gardenerella, Vaginalis*, and *Acinetobacter* species.

The term "gram-positive bacteria" or "gram-positive bacterium" as used herein refers to bacteria, which have been classified using the Gram stain as having a blue stain. Gram-positive bacteria have a thick cell membrane consisting of multiple layers of peptidoglycan and an outside layer of teichoic acid. Exemplary organisms include, but are not limited to, *Staphylococcus aureus*, coagulase-negative staphylococci, streptococci, enterococci, *corynebacteria*, and *Bacillus* species.

The term "high-density lipoprotein" or "HDL" as used herein is the smallest and most dense type of cholesterol-carrying lipoprotein and is often referred to as the "good" cholesterol.

The term "hyperproliferative disease" is defined as a disease that results from a hyperproliferation of cells. Exemplary hyperproliferative diseases include, but are not limited to cancer or autoimmune diseases. Other hyperproliferative diseases may include vascular occlusion, restenosis, atherosclerosis, or inflammatory bowel disease.

The term "immunocompromised" as used herein is defined as a subject who is, at the time of pathogen exposure, has a pre-existing condition that reduces one or more mechanisms for normal defense against infection. The immunocompromised condition may be due to a defect or dysfunction of the immune system or to other factors that heighten susceptibility to infection, for example immunosuppressive agents. Although such a categorization allows a conceptual basis for evaluation, immunocompromised individuals with infection often do not fit completely into one group or the other. More than one defect in the body's defense mechanisms may be affected. For example, an immunocompromised state can result from indwelling central lines or other types of impairment due to intravenous drug abuse; or be caused by secondary malignancy, malnutrition, or having been infected with other infectious agents such as tuberculosis, influenza, *Staphylococcus aureus* or sexually transmitted diseases, e.g., syphilis or hepatitis.

The term "insulin-dependent diabetes mellitus"; "IDDM" or "Type I" refer to diabetes that is characterized by a hyperglycemia, glycosuria, and low blood insulin levels. Type I diabetes can develop at any age. It typically has an abrupt onset during the first two decades of life. Insulin therapy is usually required.

The term "intermediate density lipoprotein" or "IDL" as used herein refers to a triglyceride-carrying lipoprotein.

The term "lactoferrin composition" as used herein refers to a composition having a lactoferrin related peptide.

The term "lactoferrin" or "LF" as used herein refers to native or recombinant lactoferrin. Native lactoferrin can be obtained by purification from mammalian milk or colostrum or from other natural sources. Recombinant lactoferrin (rLF) can be made by recombinant expression or direct production in genetically altered animals, plants, fungi, bacteria, or other prokaryotic or eukaryotic species, or through chemical synthesis.

The term "lipid" as used herein refers to the building blocks of any of the fats or fatty substances found in animals and plants, which are characterized by their insolubility in water and solubility in fat solvents such as alcohol, ether and chloroform. Lipids include fats (e.g., esters of fatty acids and glycerol); lipoids (e.g., phospholipids, cerebrosides, waxes) and sterols (e.g., cholesterol).

The term "lipoproteins" as used herein are protein spheres that transport cholesterol, triglyceride, or other lipid molecules through the bloodstream. Lipoproteins are categorized into five types according to size and density. They can be further defined by whether they carry cholesterol [the two smaller lipoproteins (HDL and LDL)] or triglycerides [the three largest lipoproteins (IDL, VLDL, and chylomicrons)].

The term "low density lipoprotein" or "LDL" as used herein is a type of cholesterol-carrying lipoprotein which is often called the "bad" cholesterol.

The term "metal chelator" as used herein refers to a compound which binds metal. Metal chelators that can be used in the present invention include the divalent metal chelators, for example, ethylenediaminetetraacetic acid (EDTA), [ethylenebis(oxyethylenenitrilo)]tetraacetic acid (EGTA), 1,2-bis(2-aminophenoxy)ethane-N,N,N',N'-tetraacetic acid (BAPTA), hydroxyethlene triamine diacetic acid (HEDTA), or salts thereof.

The term "morbidity" as used herein is the state of being diseased. Yet further, morbidity can also refer to the disease rate or the ratio of sick subjects or cases of disease in to a given population.

The term "mortality" as used herein is the state of being mortal or causing death. Yet further, mortality can also refer to the death rate or the ratio of number of deaths to a given population.

The term "neurology" or "neurological" refers to conditions, disorders, and/or diseases that are associated with the nervous system. Thus, any condition, disorder and/or disease that effects any component or aspect of the nervous system (either central or peripheral) is referred to as a neurological condition, disorder and/or disease. As used herein, the term "neurological" or "neurology" encompasses the terms "neuropsychiatric" or "neuropsychiatry" and "neuropsychological" or "neuropsychological". Thus, a neurological disease, condition, or disorder includes, but is not limited to cognitive disorders, affective disorders (e.g., depression disorders and/or anxiety disorders), movement disorders, mental disorders, pain disorders, sleep disorders, etc.

The term "neutropenia" as used herein refers to an a decrease or small number of neutrophils in the blood compared to normal. For example, the World Health Organization defines neutropenia as a subject having an absolute neutrophil cell count (ANC) of about 2000 cells/μL or less. Thus, as used herein a subject suffering from neutropenia is one having an ANC of about 2000 cells/μL or less, for example 1000 cells/μL or even less than 500 cells/μL.

The term "non-insulin-dependent diabetes mellitus"; "NIDDM" or Type II" refer to diabetes that is characterized by hyperglycemia and insulin levels being normal to high. Typically, Type II diabetes is a form of diabetes mellitus that has gradual onset in obese individuals over the age of 35. Insulin therapy is usually not required; however, Type II diabetics can be destined or prone to become fully insulin-dependent.

The term "oral administration" as used herein includes oral, buccal, enteral or intragastric administration.

The term "organ or tissue transplant rejection" as used herein refers to a consequence of organ or tissue transplantation caused by the recipient's or host's immune system in response to the transplanted organ/tissue, which can damage or destroy it. Thus, one of skill in the art realizes that "organ or tissue transplant rejection" is controlled by the host subject.

The term "osteoporosis" as used herein is defined as a general term for describing any disease process that results in reduction in the mass of bone.

The term "pain" as used herein refers to an unpleasant sensation. For example, the subject experiences discomfort, distress or suffering. Pain of a moderate or high intensity is typically accompanied by anxiety. Thus, one of skill in the art is cognizant that pain may have dual properties, for example sensation and emotion.

The term "parenteral administration" as used herein includes any form of administration in which the compound is absorbed into the subject without involving absorption via the intestines. Exemplary parenteral administrations that are used in the present invention include, but are not limited to intramuscular, intravenous, intraperitoneal, intraocular, subcutaneous, or intraarticular or intratumoral administration. Yet further, parenteral administration also includes administration into a surgical field.

The term "peptide composition" as used herein refers to a composition comprising at least one of the lactoferrin related peptides of the present invention. Such peptides include, but are not limited to SEQ ID NO: 1 (LFP-21), SEQ ID NO: 2 (LFP-22), SEQ ID NO: 3 (LFP-23), SEQ ID NO: 4 (LFP-24), SEQ ID NO: 5(LFP-25), SEQ ID NO: 6 (LFP-31), SEQ ID NO: 7 (LFP-32), SEQ ID NO: 8 (LFP-33), SEQ ID NO: 9 (LFP-34), SEQ ID NO: 10 (LFP-35), and SEQ ID NO: 11 (LFP-36).

The term "pharmaceutically acceptable carrier" as used herein includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The term "polynucleotide" is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means. Furthermore, one skilled in the art is cognizant that polynucleotides include mutations of the polynucleotides, include but are not limited to, mutation of the nucleotides, or nucleosides by methods well known in the art.

The term "polypeptide" is defined as a chain of amino acid residues, usually having a defined sequence. As used herein the term polypeptide is interchangeable with the terms "peptides" and "proteins".

The term "preventing" as used herein refers to minimizing, reducing or suppressing the risk of developing a disease state or parameters relating to the disease state or progression or other abnormal or deleterious conditions.

The term "respiratory disorder" refers to any condition and/or disorder relating to respiration and/or the respiratory system. The respiratory disorder can be an allergic or non-allergic respiratory disorder. More specifically, the respiratory disorder includes, but is not limited to atopic asthma, non-atopic asthma, emphysema, bronchitis, chronic obstructive pulmonary disease, sinusitis and allergic rhinitis.

The term "sepsis" as used herein is defined as a Systemic Inflammatory Response Syndrome to an infective process in which severe derangement of the host immune system fails to prevent extensive 'spill over' of inflammatory mediators from a local infection focus into the systemic circulation.

The term "septic shock" as used herein is a consequence of sepsis in which the systemic inflammatory response leads to the failure of vital organs' function (for example of the lungs as in ARDS).

The term "subject" as used herein, is taken to mean any mammalian subject to which a lactoferrin composition is administered according to the methods described herein. Thus, a skilled artisan realizes that a mammalian subject, includes, but is not limited to humans, monkeys, horses, pigs, cows, dogs, cats, rats and mice. In a specific embodiment, the methods of the present invention are employed to treat a human subject.

The term "Th$_2$ cells" as used herein is defined as a subset of CD4 T-cells that are characterized by the cytokines they produce. These cells are mainly involved in stimulating B cells to produce antibody and are often called helper T-cells. It is also known that extracellular antigens tend to stimulate the production of Th$_2$ cells. Thus, as used herein, "Th$_2$ cells" is interchangeable with "helper T-cells".

The term "topical administration" as used herein includes, but is not limited to topical, dermal, or epidermal.

The term "total cholesterol" as used herein refers to the sum of three kinds of lipids: high-density lipoprotein (HDL), low-density lipoprotein (LDL), and triglycerides. Levels of serum total cholesterol of >200 mg/dl are levels that are an indicating risk factor for atherosclerosis and cardiovascular disease.

The term "treating" and "treatment" as used herein refers to administering to a subject a therapeutically effective amount of a recombinant human lactoferrin composition so that the subject has an improvement in the said disease condition. The improvement is any observable or measurable improvement. Thus, one of skill in the art realizes that a treatment may improve the patient condition, but may not be a complete cure of the disease.

The term "triglycerides" as used herein are composed of fatty acid molecules and are the basic chemicals contained in fats in both animals and plants.

The term "type I osteoporosis" or "postmenopausal osteoporosis" as used herein is usually found in women after the beginning of menopause. The incidence in women is six to eight times higher than that in men. It has been postulated that the cause of this osteoporosis is accelerated bone resorption. The increased bone turnover results in a secondary decrease in parathyroid hormone (PTH) secretion as well as a secondary reduction in the renal production of calcitriol. Patients present with trabecular bone loss with vertebral fractures or distal forearm fractures.

The term "type II osteoporosis" or "age-associated osteoporosis" or "senile osteoporosis" occurs in men or women over the age of 70. The mechanisms of this bone mass loss are thought to be increased PTH secretion resulting from decreased gastrointestinal calcium absorption and decreased osteoblast function. Patients usually present with fractures of the hip or vertebrae, sites that contain cortical and trabecular bone, although fractures of the pelvis, ribs, and tibia can also occur.

The term "very low density lipoprotein" or "VLDL" as used herein refers to a triglyceride carrying lipoprotein.

The term "wound" as used herein refers to any injury, such as an ulcer, as a result of disease or disorder, or as a result of an accident, incident, or surgical procedure. Wound can be further defined as acute and/or chronic.

II. Lactoferrin

The lactoferrin can be obtained through isolation and purification from natural sources, for example, but not limited to mammalian milk. The lactoferrin is preferably mammalian lactoferrin, such as bovine or human lactoferrin. In preferred embodiments, the lactoferrin is produced recombinantly using genetic engineering techniques well known and used in the art, such as recombinant expression or direct production in genetically altered animals, plants or eukaryotes, or chemical synthesis. See, e.g., U.S. Pat. Nos. 5,571,896; 5,571,697 and 5,571,691, which are herein incorporated by reference.

In certain aspects, the present invention provides lactoferrin variants having enhanced biological activities over natural LF and or rLF, e.g., the ability to stimulate and/or inhibit cytokines or chemokines. In particular, the invention provides peptides related to lactoferrin, including deletional, substitutional or replacement variants.

A. Lactoferrin Related Peptides

In certain embodiments, the present invention concerns novel peptide compositions. As used herein, a "peptide," "amino acid molecule," "polypeptide", "peptide composition" generally refers, but is not limited to, a peptide of about 33 amino acids. As used herein, all the terms related to "peptide" are interchangeable.

More particularly, the peptides of the present invention are derived from lactoferrin. Thus, a lactoferrin related peptide includes related-compounds of the respective molecules that exhibit at least some biological activity in common with their native counterparts, for example lactoferrin. Such related-compounds include, but are not limited to, truncated polypeptides and polypeptides having fewer amino acids than the native polypeptide. The full length lactoferrin protein, which includes polypeptide sequences, for example, but are not limited to SEQ ID NO: 12 (GenBank accession AAA36159.1), SEQ ID NO: 13 (GenBank accession CAA38572.1); SEQ ID NO: 14 (GenBank accession NP_032548.2); SEQ ID NO: 15 (GenBank accession NP_002334.1); SEQ ID NO: 16 (GenBank accession NP_851341.1); SEQ ID NO: 17 (GenBank accession AAN11304.1); SEQ ID NO: 18 (GenBank accession AAN75578.2); SEQ ID NO: 19 (GenBank accession CAA06441.1); SEQ ID NO: 20 (GenBank accession BAA13633.1); SEQ ID NO: 21 (GenBank accession-AAG48753.1); SEQ ID NO: 22 (GenBank accession BAB03470. 1); SEQ ID NO: 23 (GenBank accession AAF82241.1); SEQ ID NO: 24 (GenBank accession CAB53387.1); SEQ ID NO: 25 (GenBank accession BAA07458.1); SEQ ID NO: 26 (GenBank accession CAA09407. 1); SEQ ID NO: 27 (GenBank accession AAB60324.1); SEQ ID NO: 28 (GenBank accession CAA555 17.1); SEQ ID NO: 29 (GenBank accession CAA40366.1); SEQ ID NO: 30 (GenBank accession CAA37914.1); SEQ ID NO: 31 (GenBank accession CAA37116.1); SEQ ID NO: 32 (GenBank accession AAA97958.1); SEQ ID NO: 33 (GenBank accession AAA59479.1); SEQ ID NO: 34 (GenBank accession AAA595 11.1); SEQ ID NO: 35 (GenBank accession AAA30610.1); SEQ ID NO: 36 (GenBank accession AAA31102.1); SEQ ID NO: 37 (GenBank accession AAA31059.1); SEQ ID NO: 38 (GenBank accession AAA30617.1); and SEQ ID NO: 39 (GenBank accession AAA30609.1), more fully described in US. Pat. Nos. 6,399, 570; 5,304,633; 5,317,084; 5,656,591; 5,849,885; 5,849,881; 5,766,939 which are incorporated herein by reference in its entirety. More specifically, the lactoferrin related peptides may include the following sequences, but are not limited to these sequences, SEQ ID NO: 1 (LFP-21), SEQ ID NO: 2 (LFP-22), SEQ ID NO: 3 (LFP-23), SEQ ID NO: 4 (LFP-24), SEQ ID NO: 5 (LFP-25), SEQ ID NO: 6 (LFP-31), SEQ ID NO: 7 (LFP-32), SEQ ID NO: 8 (LFP-33), SEQ ID NO: 9 (LFP-34), SEQ ID NO: 10 (LFP-35), and SEQ ID NO: 11 (LFP-36).

In certain embodiments the size of the peptide composition or amino acid molecule may comprise, but is not limited to, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 60 or greater amino molecule residues, and any range derivable therein.

As used herein, an "amino molecule" refers to any amino acid, amino acid derivative or amino acid mimic as would be known to one of ordinary skill in the art. In certain embodiments, the residues of the peptide are sequential or contiguous, without any non-amino molecule interrupting the sequence of amino molecule residues. In other embodiments, the sequence may comprise one or more non-amino molecule moieties. In particular embodiments, the sequence of residues of the peptide may be interrupted by one or more non-amino molecule moieties.

Accordingly, the term "peptide" encompasses amino molecule sequences comprising at least one of the 20 common amino acids in naturally synthesized proteins, or at least one modified or unusual amino acid, including but not limited to those shown on Table 1 below.

TABLE 1

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | AIle | allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

Peptide compositions may be made by any technique known to those of skill in the art, including the expression of proteins, polypeptides or peptides through standard molecular biological techniques, the isolation of peptide compounds from natural sources, or the chemical synthesis of peptides. The nucleotide and protein, polypeptide and peptide sequences for various genes have been previously disclosed, and may be found at computerized databases known to those of ordinary skill in the art. One such database is the National Center for Biotechnology Information's Genbank and GenPept databases. The coding regions for these known genes may be amplified and/or expressed using the techniques disclosed herein or as would be know to those of ordinary skill in the art. Alternatively, various commercial preparations of polypeptides and peptides are known to those of skill in the art.

In certain embodiments a peptide composition may be purified. Generally, "purified" will refer to a specific polypeptide, or peptide composition that has been subjected to fractionation to remove various other proteins, polypeptides, or peptides, and which composition substantially retains its activity, as may be assessed, for example, by the protein assays, as would be known to one of ordinary skill in the art for the specific or desired polypeptide or peptide.

B. Peptide Variants

Deletional variants can be produced by proteolysis of lactoferrin and/or expression of a polynucleotide encoding a truncated lactoferrin as described in U.S. Pat. No. 6,333,311, which is incorporated herein by reference.

Substitutional variants or replacement variants typically contain the exchange of one amino acid for another at one or more sites within the protein. Substitutions can be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, e.g., still obtain a biological functionally equivalent protein. In making such changes, the substitution of amino acids whose hydropathic indices are within ±2 is preferred, those that are within ±1 are particularly preferred, and those within ±0.5 are even more particularly preferred.

It is also understood in the art that the substitution of like amino acids can be made effectively on the basis of hydrophilicity. U.S. Pat. NO: 4,554,101, incorporated herein by reference, states that the greatest local average hydrophilicity of a protein, as governed by the hydrophilicity of its adjacent amino acids, correlates with a biological property of the protein. As detailed in U.S. Pat. NO: 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Still further, it is understood that an amino acid can be substituted for another having a similar hydrophilicity value and still obtains a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

Thus, in the present invention, substitutional variants or replacement can be produced using standard mutagenesis techniques, for example, site-directed mutagenesis as disclosed in U.S. Pat. Nos. 5,220,007; 5,284,760; 5,354,670; 5,366,878; 5,389,514; 5,635,377; 5,789,166, and 6,333,311, which are incorporated herein by reference. It is envisioned that at least the N-terminal glycine amino acid residue can be replaced or substituted with any of the twenty natural occurring amino acids, for example a positively charged amino acid (arginine, lysine, or histidine), a neutral amino acid (alanine, asparagine, cysteine, glutamine, glycine, isoleucine, leucine, methionine, phenylaline, proline, serine, threonine, tryptophan, tyrosine, valine) and/or a negatively charged amino acid (aspartic acid or glutamic acid).

In terms of functional equivalents, it is well understood by the skilled artisan that, inherent in the definition of a "biologically functional equivalent" protein is the concept that there is a limit to the number of changes that may be made within a defined portion of the molecule while retaining a molecule with an acceptable level of equivalent biological activity and/or enhancing the biological activity of the lactoferrin molecule. Biologically functional equivalents are thus defined herein as those proteins in which selected amino acids (or codons) may be substituted. Functional activity is defined as the ability of the lactoferrin related peptide to stimulate or inhibit various cytokines or chemokines. In particular, a biological functional equivalent will be able to stimulate production of macrophage inflammatory protein 3 alpha (MIP-3alpa).

Yet further, the lactoferrin peptides of this invention can be in glycosylated or unglycosylated form, can be modified post-translationally (e.g., acetylation, and phosphorylation) or can be modified synthetically (e.g., the attachment of a labeling group). Fragments of lactoferrin molecules that retain the prophylactic efficacy can also be used (see, e.g. PCT/IB00/00271, which is incorporated herein in reference in its entirety).

C. Production of Lactoferrin Related Peptides

1. Synthetic Variants

The present invention also describes lactoferrin related peptides for use in various embodiments of the present invention. Because of their relatively small size, the peptides of the invention can also be synthesized in solution or on a solid support in accordance with conventional techniques. Various automatic synthesizers are commercially available and can be used in accordance with known protocols. See, for example, Stewart and Young (1984); Tam et al. (1983); Merrifield (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

2. Recombinant Synthesis a) Nucleic Acid Compositions

Certain embodiments of the present invention concern a nucleic acid composition having a nucleic acid sequence of lactoferrin. In certain aspects, a lactoferrin nucleic acid comprises a wild-type or a mutant lactoferrin nucleic acid. In particular aspects, a lactoferrin nucleic acid sequence encodes for or comprises a transcribed nucleic acid. In other aspects, a lactoferrin nucleic acid sequence comprises a nucleic acid segment of SEQ ID NO: 40 (GenBank accession M93150); SEQ ID NO: 41 (GenBank accession X54801); SEQ ID NO: 42 (GenBank accession NM_008522); SEQ ID NO: 43 (GenBank accession NM_002343); SEQ ID NO: 44 (GenBank accession NM_180998); SEQ ID NO: 45 (GenBank accession AY137470); SEQ ID NO: 46 (GenBank accession AY178998); SEQ ID NO: 47 (GenBank accession AJ005203); SEQ ID NO: 48 (GenBank accession D885 10); SEQ ID NO: 49 (GenBank accession AF332 168); SEQ ID NO: 50 (GenBank accession AB046664); SEQ ID NO: 51 (GenBank accession AAF82241.1); 4SEQ ID NO: 52 (GenBank accession AJ131674); SEQ ID NO: 53 (GenBank accession D38380); SEQ ID NO: 54 (GenBank accession AJ010930); SEQ ID NO: 55 (GenBank accession U07643); SEQ ID NO: 56 (GenBank accession X78902); SEQ ID NO: 57 (GenBank accession X57084); SEQ ID NO: 58 (GenBank accession X53961); SEQ ID NO: 59 (GenBank accession X5294 1); SEQ ID NO: 60 (GenBank accession U53857); SEQ ID NO: 61 (GenBank accession M73700); SEQ ID NO: 62 (GenBank accession M83202); SEQ ID NO: 63 (GenBank accession L19981); SEQ ID NO: 64 (GenBank accession M92089); SEQ ID NO: 65 (GenBank accession M81327); SEQ ID NO: 66 (GenBank accession M63502); and SEQ ID NO: 67 (GenBank accession L08604) or a biologically functional equivalent thereof. In particular aspects, the nucleic acid sequence of the present invention encodes a polypeptide, peptide, for example, but not limited to SEQ ID NO: 1 (LFP-21), SEQ ID NO: 2 (LFP-22), SEQ ID NO: 3 (LFP-23), SEQ ID NO: 4 (LFP-24), SEQ ID NO: 5 (LFP-25), SEQ ID NO: 6 (LFP-31), SEQ ID NO: 7 (LFP-32), SEQ ID NO: 8 (LFP-33), SEQ ID NO: 9 (LFP-34), SEQ ID NO: 10 (LFP-35), and SEQ ID NO: 11 (LFP-36). Thus, nucleic acid compositions encoding lactoferrin and/or lactoferrin related peptides are herein provided and are also available to a skilled artisan at accessible databases, including the National Center for Biotechnology Information's GenBank database and/or commercially available databases, such as from Celera Genomics, Inc. (Rockville, Md.).

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acID" The term "oligonucleotide" refers to a molecule of between about 3 and about 100 nucleobases in length. The term "polynucleotide" refers to at least one molecule of greater than about 100 nucleobases in length.

These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or "complement(s)" of a particular sequence comprising a molecule. As used herein, a single stranded nucleic acid may be denoted by the prefix "ss," a double stranded nucleic acid by the prefix "ds," and a triple stranded nucleic acid by the prefix "ts."

The nucleic acids of the present invention encompass biologically functional equivalent lactoferrin proteins, polypeptides, or lactoferrin related peptides. Examples of such peptides include, but are not limited to SEQ ID NO: 1 (LFP-21), SEQ ID NO: 2 (LFP-22), SEQ ID NO: 3 (LFP-23), SEQ ID NO: 4 (LFP-24), SEQ ID NO: 5 (LFP-25), SEQ ID NO: 6 (LFP-31), SEQ ID NO: 7 (LFP-32), SEQ ID NO: 8 (LFP-33), SEQ ID NO: 9 (LFP-34), SEQ ID NO: 10 (LFP-35), and SEQ ID NO: 11 (LFP-36). Such sequences may arise as a consequence of codon redundancy or functional equivalency that is known to occur naturally within nucleic acid sequences or the proteins, polypeptides or peptides thus encoded. Alternatively, functionally equivalent proteins, polypeptides or peptides may be created via the application of recombinant DNA technology, in which changes in the protein, polypeptide or peptide structure may be engineered, based on considerations of the properties of the amino acids being exchanged. Changes designed by man may be introduced, for example, through the application of site-directed mutagenesis techniques as discussed herein below, e.g., to introduce improvements or alterations to the antigenicity of the protein, polypeptide or peptide.

Encompassed by the invention are nucleic acid sequences encoding relatively small peptides, such as, for example, peptides of from about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 35, about 36, about 37, about 38, about 39, about 40, about 41, about 42, about 43, about 44, about 45, about 46, about 47, about 48, about 49, to about 50 amino acids in length, or more preferably, of from about 1 to about 33 amino acids in length; as set forth in SEQ ID NO: 1, SEQ ID NO: 2, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11 and also larger peptides up to and from about 1 to about 34 amino acids in length; as set forth in SEQ ID NO: 3.

3. Expression Vectors

The present invention may involve using expression constructs as the pharmaceutical composition. In certain embodiments, it is contemplated that the expression construct comprises polynucleotide sequences encoding polypeptides which can enhance the immune system, for example the expression construct may comprise a nucleic acid sequence encoding the amino acid sequence of SEQ ID NO: 1 (LFP-21), SEQ ID NO: 2 (LFP-22), SEQ ID NO: 3 (LFP-23), SEQ ID NO: 4 (LFP-24), SEQ ID NO: 5 (LFP-25), SEQ ID NO: 6 (LFP-31), SEQ ID NO: 7 (LFP-32), SEQ ID NO: 8 (LFP-33), SEQ ID NO: 9 (LFP-34), SEQ ID NO: 10 (LFP-35), SEQ ID NO: 11 (LFP-36), SEQ ID NO: 12.

In certain embodiments, the present invention involves the manipulation of genetic material to produce expression constructs that encode the peptides of the present invention. Thus, the peptides are contained in an expression vector. Such methods involve the generation of expression constructs containing, for example, a heterologous nucleic acid sequence encoding the peptide of interest and a means for its expression, replicating the vector in an appropriate cell, obtaining viral particles produced therefrom, and infecting cells with the recombinant virus particles.

As used in the present invention, the term "expression vector" refers to any type of genetic construct comprising a nucleic acid coding for a lactoferrin related peptide, for example, but not limited to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11. In some cases, DNA molecules are then translated into a protein, polypeptide, or peptide. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra. It is contemplated in the present invention, that virtually any type of vector may be employed in any known or later discovered method to deliver nucleic acids encoding a lactoferrin related peptide. An expression vector comprising a nucleic acid encoding a lactoferrin related peptide may comprise a virus or engineered construct derived from a viral genome.

In particular embodiments of the invention, a plasmid vector is contemplated for use to transform a host cell. In general, plasmid vectors containing replicon and control sequences that are derived from species compatible with the host cell are used in connection with these hosts. The vector ordinarily carries a replication site, as well as marking sequences that are capable of providing phenotypic selection in transformed cells. Plasmid vectors are well known and are commercially available. Such vectors include, but are not limited to, the commercially available pSupervector (OligoEngine, Seattle, Wash.), and pSuppressor Neo vector (IMGENEX Corporation). Other vectors that may be employed in the present invention include, but are not limited to, the following eukaryotic vectors: pWLNEO, pSV2CAT, pOG44, PXT1, pSG (Stratagene) pSVK3, pBSK, pBR322, pUC vectors, vectors that contain markers that can be selected in mammalian cells, such as pcDNA3.1, episomally replicating vectors, such as the pREP series of vectors, pBPV, pMSG, pSVL (Pharmacia), adenovirus vector (AAV; pCWRSV, Chatterjee et al. (1992)); retroviral vectors, such as the pBABE vector series, a retroviral vector derived from MoMuLV (pGlNa, Zhou et al., (1994)); and pTZ18U (BioRad, Hercules, Calif.).

In one embodiment, a gene encoding a lactoferrin related peptide is introduced in vivo in a viral vector. The ability of certain viruses to enter cells via receptor-mediated endocytosis and to integrate into the host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). Such vectors include an attenuated or defective DNA virus, such as but not limited to herpes simplex virus (HSV), papilloma virus, Epstein Barr virus (EBV), adenovirus, adeno-associated virus (AAV), lentivirus and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, any tissue can be specifically targeted. Examples of particular vectors include, but are not limited to, a defective herpes virus 1 (HSV1) vector (Kaplitt et al., 1991) an attenuated adenovirus vector, (Stratford-Perricaudet et al., 1992), a defective adeno-associated virus vector (Samulski et al., 1987 and Samulski et al., 1989) or pox-vector. Such vectors may be used to (i) transform cell lines in vitro for the purpose of expressing the a lactoferrin related peptide or (ii) to transform cells in vitro or in vivo to provide therapeutic molecules for gene therapy. Thus, the present invention contemplates viral vectors such as, but not limited to, an adenoviral vector, an adeno-associated viral vector, a retroviral vector, a lentiviral vector, a herpes viral vector, polyoma viral vector, pox-vector or hepatitis B viral vector.

Preferably, for in vivo administration, an appropriate immunosuppressive treatment is employed in conjunction with the viral vector, e.g., adenovirus vector, to avoid immunodeactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors (Wilson, Nature Medicine (1995). In addition, it is advantageous to employ a viral vector that is engineered to express a minimal number of antigens.

In another embodiment the gene can be introduced in a retroviral vector, e.g., as described in U.S. Pat. No. 5,399,346; Mann et al., 1983; U.S. Pat. NO: 4,650,764; U.S. Pat. NO: 4,980,289; Markowitz et al., 1988; U.S. Pat. NO: 5,124,263; International Patent Publication NO: WO 95/07358; and Kuo et al., 1993, each of which is incorporated herein by reference in its entirety. Targeted gene delivery is described in International Patent Publication WO 95/28494.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker. The use of cationic lipids may promote encapsulation of negatively charged nucleic acids, and also promote fusion with negatively charged cell membranes. The use of lipofection to introduce exogenous genes into the specific organs in vivo has certain practical advantages. Molecular targeting of liposomes to specific cells represents one area of benefit. Lipids may be chemically coupled to other molecules for the purpose of targeting. Targeted peptides, e.g., hormones or neurotransmitters, and proteins such as antibodies, or non-peptide molecules could be coupled to liposomes chemically.

It is also possible to introduce the vector in vivo as a naked DNA plasmid Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (Wu and Wu, 1988).

As used herein, the terms "cell," "cell line," and "cell culture" may be used interchangeably. All of these terms also include their progeny, which is any and all subsequent generation formed by cell division. It is understood that all progeny may not be identical due to deliberate or inadvertent mutations. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a lactoferrin related peptide. Therefore, recombinant cells are distinguishable from naturally occurring cells that do not contain a recombinantly introduced nucleic acid Host cells may be derived from prokaryotes or eukaryotes, depending upon whether the desired result is replication of the vector or expression of part or all of the vector encoded nucleic acid sequences. Numerous cell lines and cultures are available for use as a host cell, and they can be obtained through the American Type Culture Collection (ATCC), which is an organization that serves as an archive for living cultures and genetic materials. In certain embodiments, a cell may comprise, but is not limited to, at least one skin, bone, neuron, axon, cartilage, blood vessel, cornea, muscle, facia, brain, prostate, breast, endometrium, lung, pancreas, small intestine, blood, liver, testes, ovaries, cervix, colon, skin, stomach, esophagus, spleen, lymph node, bone marrow, kidney, peripheral blood, embryonic or ascite cell, and all cancers thereof. An appropriate host can be determined by one of skill in the art based on the vector backbone and the desired result. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla).

Examples of eukaryotic host cells for replication and/or expression of a vector include HeLa, NIH3T3, Jurkat, 293, Cos, CHO, Saos, and PC12. Other eukaryotic cells include yeast cells, such as *Aspergillus* species and *Saccharomyces* species. Many host cells from various cell types and organisms are available and would be known to one of skill in the art. In addition, a host cell strain may be chosen that modulates the expression of the inserted sequences, and/or modifies and/or processes the gene product in the specific fashion desired. Such modifications (e.g., glycosylation) and/or processing (e.g., cleavage) of protein products may be important for the function of the protein.

III. Pharmaceutical Compositions

The present invention is drawn to a composition comprising a lactoferrin that is dispersed in a pharmaceutical carrier. The lactoferrin that is contained in the composition of the present invention comprises lactoferrin related peptides, for example, SEQ ID NO: 1, SEQ ID NO: 2, SEQ ID NO: 3, SEQ ID NO: 4, SEQ ID NO: 5, SEQ ID NO: 6, SEQ ID NO: 7, SE,SEQ ID NO: 8, SEQ ID NO: 9, SEQ ID NO: 10, and SEQ ID NO: 11 and/or expression vectors encoding a lactoferrin related peptide.

Yet further, the composition comprises lactoferrin related peptides in combination with a metal chelator dispersed in a pharmaceutical carrier. Thus, the present invention is drawn to a composition with or without a metal chelator that is dispersed in a pharmaceutical carrier. One of skill in the art understands that both compositions (e.g., lactoferrin related peptides alone or in combination with a metal chelator) are within the scope of the present invention and can be used interchangeably depending upon the type of response that is desired. It is envisioned that the addition of a metal chelator to the composition enhances the sequestering of metal ions and thus strengthens the immune system or enhances the effect of the lactoferrin related peptides.

Metal chelators that can be used in combination with lactoferrin, include the divalent metal chelators, for example, ethylenediaminetetraacetic acid (EDTA), [ethylenebis(oxyethylenenitrilo)]tetraacetic acid (EGTA), 1,2-bis(2-aminophenoxy)ethane-N,N,N',N'-tetraacetic acid (BAPTA), hydroxyethlene triamine diacetic acid, (HEDTA) or any salts thereof. The amount of the metal chelator in the composition may vary from about 0.01 μg to about 20 g. More preferably, EDTA is used in combination with lactoferrin.

The lactoferrin composition of the present invention may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The composition of the present invention suitable for administration is provided in a pharmaceutically acceptable carrier with or without an inert diluent. The carrier should be assimilable and includes liquid, semi-solid, e.g., pastes, or solid carriers. Except insofar as any conventional media, agent, diluent or carrier is detrimental to the recipient or to the therapeutic effectiveness of the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof.

Sterile injectable solutions are prepared by incorporating the lactoferrin in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach or in the open wound environment. Examples of stabilizers for use in an the composition include buffers, amino acids such as glycine and lysine, carbohydrates such as dextrose, mannose, galactose, fructose, lactose, sucrose, maltose, sorbitol, mannitol, etc., proteolytic enzyme inhibitors, and the like. Yet further, it is envisioned that divalent metal chelators, for example EDTA, can also be used to stabilize the composition of the present invention. More preferably, for an orally administered composition, the stabilizer can also include antagonists to the secretion of stomach acids. Yet further, for a topically administered composition, the stabilizer can also include antagonists to skin acids.

In further embodiments, the present invention may concern the use of a pharmaceutical lipid vehicle compositions that include lactoferrin or lactoferrin related peptides, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the lactoferrin or lactoferrin related peptides may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The composition for oral administration which is combined with a semi-solid or solid carrier can be further formulated into hard or soft shell gelatin capsules, tablets, or pills. More preferably, gelatin capsules, tablets, or pills are enterically coated. Enteric coatings prevent denaturation of the composition in the stomach or upper bowel where the pH is acidic. See, e.g., U.S. Pat. NO: 5,629,001. Upon reaching the small intestines, the basic pH therein dissolves the coating and permits the lactoferrin composition to be released and absorbed by specialized cells, e.g., epithelial enterocytes and Peyer's patch M cells.

Oral administration of the composition includes oral, buccal, enteral or intragastric administration. It is also envisioned that the composition may be used as a food additive. For example, the composition is sprinkled on food or added to a liquid prior to ingestion. In further embodiments, the oral composition is administered in conjunction with an antacid. Thus, an antacid is administered prior or substantially simultaneously with or after oral administration of the composition. The administration of an antacid just prior or immediately following the administration of the composition may help to reduce the degree of inactivation of the lactoferrin in the digestive tract. Examples of appropriate antacids include, but are not limited to, sodium bicarbonate, magnesium oxide, magnesium hydroxide, calcium carbonate, magnesium trisilicate, magnesium carbonate and alumin hydroxide gel.

In another embodiment, a powdered composition is combined with a liquid carrier such as, i.e., water or a saline solution, with or without a stabilizing agent.

In other preferred embodiments of the invention, lactoferrin or lactoferrin related peptides may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and laurocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays have been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. NO: 5,725,871, specifically incorporated herein by reference in its entirety) are also well-known in the pharmaceutical arts. Likewise, transmucosal drug delivery in the form of a polytetrafluoroethylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

In further embodiments, the compositions of this invention, can be incorporated into various types of ophthalmic formulations for delivery to the eye (e.g., topically, intracamerally, or via an implant). The compositions are preferably incorporated into topical ophthalmic formulations for delivery to the eye. The compositions may be combined with ophthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving a compositions in a physiologically acceptable isotonic aqueous buffer. Further, the ophthalmic solution may include an ophthalmologically acceptable surfactant to assist in dissolving the compositions. Furthermore, the ophthalmic solution may contain an agent to increase viscosity, such as, hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the compositions in a hydrophilic base prepared from the combination of, for example, carbopol-974, or the like, according to the published formulations for analogous ophthalmic preparations; preservatives and tonicity agents can be incorporated.

Further, the composition for topical administration which is combined with a semi-solid carrier can be further formulated into a gel ointment. A preferred carrier for the formation of a gel ointment is a gel polymer. Gel polymers prevent denaturation of the composition in the open skin by serum proteases. The gel formulation of the present invention also provides a controlled delivery system for lactoferrin or its activity on a wound site. Controlled delivery refers to drug release or activity release sufficient to maintain a therapeutic level over an extended period of time, such as up to 24 hours or more, preferably in the range of 1 to 12 hours. The present gel formulation increases the contact time of the lactoferrin at the wound site and provides a sustained release dosage form necessary to achieve a significant increase in the rate of wound healing. This is an important advantage because it permits less frequent application of the formulation to the wound and thereby permits fewer disturbances to the wound and its cellular components.

The gel formulation of the present invention has the advantage of adhering to a wound and conforming to irregular body or wound contours. The gels may be applied directly to a wound site or in conjunction with a compliant porous or microporous substrate, for example in the form of a coating, to be applied to the wound site. Gels have the further advantages of having a high water content (which keeps the wound moist), the ability to absorb wound exudate, easy application to a wound and easy removal by washing. Gels have a cool feeling when applied to a wound and thus can increase patient comfort and acceptance of the formulation, especially on sensitive wounds.

The aqueous gels of the present invention have different viscosities depending on the intended application of the gel. Viscosity is a measure of the resistance of a liquid to flow. It is defined as the ratio of the shearing stress to the rate of shearing. The shear stress is the resistance of the liquid to flow under the influence of an applied force, i.e., the molecular resistance within a body opposing an external force. The shear stress is defined as the ratio of the force to the area sheared. When a liquid is sheared, assuming laminar flow, the layers of the liquid move at different rates. The relative rate of motion of the layers is only one factor in the rate of shear. The other is the distance, or clearance between the shearing planes. Thus, shear rate is defined as the ratio of the velocity of the gel to the clearance. Viscosity has the dimensions of dynes/sec/cm$^2$. These dimensions are referred to as poise. The dimensions of viscosity referred to herein, unless otherwise indicated, are in centipoise (cP) as measured using a Brookfield viscometer. All viscosity values are at room temperature, e.g., 22° C.-25° C., unless otherwise indicated.

The gel forming materials of the present invention may be water-soluble polymers capable of forming a viscous aqueous solution or non-water soluble, water swellable polymers (e.g., collagen), which can also form a viscous solution. Swellable polymers are those that absorb water rather than dissolve in water. Cross-linked forms of the polymer described herein may not be water soluble but may be water-swellable. Therefore, cross-linked forms of the polymer are within the scope of the present invention. Cross-linking refers to covalently bonding polymer chains together with a bifunctional reagent such as glutaraldehyde. Also, it is understood by those skilled in the art that certain polymers may have to be used in the salt form or partially neutralized in order to be made water soluble. For example, it is preferable to use hyaluronic acid as sodium hyaluronate to provide suitable water solubility.

In the aqueous gel formulations for topical or incisional wound healing, the polymer may be selected from the group consisting of vinyl polymers, polyoxyethylene-polyoxypropylene copolymers, polysaccharides, proteins, poly(ethylene oxide), acrylamide polymers and derivatives or salts thereof. It is understood that poly(ethyleneoxide) includes polyethylene glycol. In the gel formulations for use in healing wounds in the anterior chamber of the eye, the polymers may be the same except that it is not preferred to use the polyoxyethylene-polyoxypropylene copolymers or poly(ethylene oxide). Also, for anterior chamber use, it is preferred that the polymer is biodegradable, i.e., it will break down into harmless constituents that can be drained from or metabolized in the anterior chamber. In the low viscosity, aqueous formulations for use in ophthalmic wound healing, the gel forming polymers may be the same as for topical or incisional wound healing, except that poly(ethylene oxide) is not preferred to be used.

The vinyl polymers useful in the present invention may be selected from the group consisting of polyacrylic acid, polymethacrylic acid, polyvinyl pyrrolidone and polyvinyl alcohol. The polysaccharides useful in the present invention are selected from the group consisting of cellulose or cellulose derivatives, glycosaminoglycans, agar, pectin, alginic acid, dextran, starch, and chitosan. Starch occurs in two forms, α-amylose and amylopectin. The more water-soluble α-amylose is preferred. The glycosaminoglycans are selected from the group consisting of hyaluronic acid, chondroitin, chondroitin-4-sulfate, chondroitin-6-sulfate, dermatan sulfate, keratan sulfate, heparin sulfate and heparin. The glycosaminoglycans are used to enhance wound healing in combination with any other gel-forming polymer. The proteins useful in the present invention are selected from the group consisting of collagen, gelatin and fibronectin. The acrylamide polymers are polyacrylamide or polymethacrylamide polymers. Biocompatible polyacrylamide polymers are preferred. In further embodiments, carbomers are the preferred polyacrylamide polymer. Carbomers are synthetic high molecular weight polymers of acrylic acid cross linked with either alkyl esters of sucrose or pentaerythritol. Suitable commercially available grades of carbomer include Carbopol 910, Carbopol 934P, Carbopol 940, Carbopol 941, Carbopol 971P, Carbopol 974P, Carbopol 980, Carbopol 981, Carbopol 1342, Rheogic 252L, Rheogic 250H, and Hostacerin PN73.

In the gel formulation for topical or incisional wound healing, the viscosity may be within the range 1,000-12,000,000 cps at room temperature. It is preferred that the viscosity range be 50,000-2,000,000. In one embodiment of the present invention, the topical gel formulation may comprise 0.01-5% by weight polyacrylic acid having an average molecular weight of about 450,000-4,000,000. In a preferred embodiment, the polyacrylic acid is present at 0.5-1.5% by weight and has an average molecular weight of 2,000,000-4,000,000. The pH of the polyacrylic acid gel should be within the range 4.5-8 and more preferably in the range 6.5-7.5.

In another embodiment, the topical and incisional gel of the present invention may comprise 15-60% by weight of a polyoxyethylene-polyoxypropylene block copolymer having an average molecular weight of about 500-50,000. In a preferred embodiment, the block copolymer is present at 15-40% by weight and has an average molecular weight in the range 1,000-15,000. The block copolymers used in the present invention are commonly known as Pluronics. Preferred Pluronics are Pluronic F88 and F127.

In a further embodiment, the topical or incisional gel may comprise 1 to 20% by weight of a cellulose polymer having a molecular weight of about 50,000 to 700,000. In a preferred embodiment, the cellulose polymer is present at 2-8% by weight and has an average molecular weight in the range 80,000-240,000. Preferred cellulose polymers are hydroxypropylmethyl cellulose (HPMC), carboxymethyl cellulose (CMC) and methyl cellulose (MC).

In a further embodiment, the topical and incisional gel may comprise 0.5-10% by weight of hyaluronic acid having an average molecular weight in the range 500,000 to 8,000,000. In a preferred embodiment, the hyaluronic acid is present at 1.5-6.0% by weight and the average molecular weight is greater than 1,000,000.

Acrylamide polymers may be useful for all types of wound healing, particularly in the anterior chamber of the eye. An absorbable acrylamide polymer, such as polyacrylamide, may be a good substitute for present carrier systems used in ophthalmic applications, such as hyaluronic acid. The acrylamide polymers may have an average molecular weight in the range 1-13 million, preferably about 4-6 million. The weight percent of the acrylamide polymer in the gel may be 2-5%, preferably 3.5-4.5%. Substituted acrylamide polymers, such as methyl and alkyl substituted polymers are also within the scope of the present invention.

For use in the anterior chamber of the eye, an acrylamide gel delivery system has the following characteristics: any products of the dissolution or degradation of the delivery matrix are nontoxic and do not clog the trabecular mesh work; the gel is optically transparent; and the gel can be left in the anterior chamber without causing adverse clinical effects such as an unacceptable increase in ocular pressure.

It will be readily apparent to one skilled in the art that the desired viscosity range may be achieved by varying the molecular weight and percent concentration of the polymer in the formulation. For example, a gel having a low viscosity may be achieved by using a low molecular weight polymer or a lower percent concentration or a combination of the two. A high viscosity gel may be achieved by using a higher molecular weight polymer and a higher percent concentration. Intermediate viscosities may be achieved by varying the molecular weight and percent concentration accordingly.

The low viscosity solution may comprise 0.01-2.0% by weight polyacrylic acid having an molecular weight of about 100,000-4,000,000. In a preferred embodiment, the polymer is present at 0.05-0.5%. In another embodiment, this dilute viscous solution may comprise 2-40% by weight of a polyoxyethylene-polyoxypropylene copolymer having an average molecular weight of 500-500,000. Preferably, the concentration is 2-20% and the molecular weight is 1,000-15,000. Alternatively, the dilute viscous solution may comprise a cellulose polymer at 1-20% and having a molecular weight of about 80,000-240,000. It is preferred that the concentration be in the range of 1-10%. In a further embodiment, the dilute viscous solution may comprise 0.5-5.0% by weight hyaluronic acid having an average molecular weight of about 500,000-8,000,000. Preferably, the concentration is 0.5-2.0% and the average molecular weight is 1,000,000-6,000,000. If the dilute viscous solution is to be used as eye drops, it is preferred that the viscosity be in the range 1-100 cps. If it is used for other applications, such as soaking a bandage, then any viscosity in the range 1.0-5,000 will be suitable.

Upon formulation, solutions are administered in a manner compatible with the dosage formulation and in such amount as is therapeutically effective to result in an improvement or remediation of the symptoms. The formulations are easily administered in a variety of dosage forms such as ingestible solutions, drug release capsules, gel ointments and the like. Some variation in dosage can occur depending on the condition of the subject being treated. The person responsible for administration can, in any event, determine the appropriate dose for the individual subject. Moreover, for human administration, preparations meet sterility, general safety and purity standards as required by FDA Office of Biologics standards.

IV. Methods of Treatment Using the Lactoferrin Related Peptides

In certain aspects of the present invention, a peptide composition comprising lactoferrin related peptides or related-compounds thereof is administered to treat a pathological condition, for example such conditions, include, but are not limited to hyperproliferative disease, respiratory disease, cardiovascular disease, neurological condition, autoimmune disorder, infectious disease, gastrointestinal disorder, endocrine and/or metabolism disorder, hematological disorder, ocular disorder, integument disorder, pain and a wound.

It is envisioned that the immune system, whether local, systemic or mucosal, is enhanced by lactoferrin related peptides stimulating cytokines and/or chemokines. Exemplary cytokines include interleukin-18 and GM-CSF in the gastrointestinal tract, which are known to enhance immune cells or stimulate production of immune cells. For example, interleukin-18 enhances natural killer cells or T lymphocytes, which can kill bacteria infecting a wound. In specific embodiments, interleukin-18 (IL-18) enhances CD4+, CD8+ and CD3+ cells. It is known by those of skill in the art that IL-18 is a Th1 cytokine that acts in synergy with interleukin-12 and interleukin-2 in the stimulation of lymphocyte IFN-gamma production. Other cytokines or chemokines may also be enhanced for example, but not limited to IL-12, IL-1b, MIP-3α, MIP-1α or IFN-gamma. Other cytokines or enzymes may be inhibited for example, but not limited to IL-2, IL-4, IL-5, IL-10, TNF-α, or matrix metalloproteinases.

In further embodiments, cytokines, for example, interleukin-18 or granulocyte/macrophage colony-stimulating factor, can stimulate the production or activity of immune cells. The immune cells include, but are not limited to T lymphocytes, natural killer cells, macrophages, dendritic cells, and polymorphonuclear cells. More specifically, the polymorphonuclear cells are neutrophils and the T lymphocytes are selected from the group consisting of CD4+, CD8+ and CD3+ T cells.

Still further, it is envisioned that lactoferrin related peptides stimulate production of MIP-3alpha from hepatocytes. Lactoferrin is known to contribute to the defense systems of the body through its anti-microbial properties. In addition, evidence suggests that recombinant human lactoferrin (rhLF) elicits a more general innate-like immune response when administered orally. The innate immune system is the 'first line of defense' of the body against hostile environments and comprise of a variety of effector and cellular mechanisms. This innate immune response is initially likely mediated by the 'detection system' of receptors known to be present on the surface of the gut epithelial cells, such as pattern recognition receptors, IL-1 receptor and general 'scavenger' receptors. These receptors recognize and respond to specific structural features of the presented molecules. As a result, various intracellular signaling pathways may be initiated (e.g., NFκB, Wnt, etc.) that result in the overall orchestration of the cellular response of the body to the prevailing biological situation (e.g., infection). RhLF and peptides derived from rhLF elicit a similar response of human hepatocytes in vitro in terms of producing an important chemokine—namely MIP-3-alpha. It is surmised that some general structural features that are responsible for the biological response to rhLF are retained in peptides that are structurally related to the parent molecule (rhLF).

The route of administration will vary, naturally, with the location and nature of the lesion, and include, for example parentally, orally or topically. Parenteral administrations include, but are not limited to intradermal, transdermal, intravenous, intramuscular, intranasal, subcutaneous, percutaneous, intratracheal, intraocular, intraperitoneal, intratumoral, perfusion, lavage, direct injection U.S. Pat. Nos. 6,613,308, 5,466,468, 5,543,158; 5,641,515; and 5,399,363 (each specifically incorporated herein by reference in its entirety). Alimentary administrations include, but are not limited to orally, buccally, rectally, or sublingually.

Treatment methods will involve treating an individual with an effective amount of a peptide composition as defined in the present invention. An effective amount is described, generally, as that amount sufficient to detectably and repeatedly ameliorate, reduce, minimize or limit the extent of a disease or its symptoms.

The effective amount or "therapeutically effective amounts" of the peptide composition to be used are those amounts effective to produce beneficial results, particularly with respect to cancer treatment, in the recipient animal or patient. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value.

As is well known in the art, a specific dose level of active compounds such as the peptide composition for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, and general safety and purity standards as required by FDA Office of Biologics standards.

A therapeutically effective amount of a peptide composition as a treatment vanes depending upon the host treated and the particular mode of administration. In one embodiment of the invention the dose range of a peptide composition will be about 0.5 mg/kg body weight to about 500 mg/kg body weight. The term "body weight" is applicable when an animal is being treated. When isolated cells are being treated, "body weight" as used herein should read to mean "total cell body weight". The term "total body weight" may be used to apply to both isolated cell and animal treatment. All concentrations and treatment levels are expressed as "body weight" or simply "kg" in this application are also considered to cover the analogous "total cell body weight "and" total body weight" concentrations. However, those of skill will recognize the utility of a variety of dosage range, for example, 0.1 µg/kg body weight to 1 µg/kg body weight, 1 µg/kg to 1 mg/kg body weight, 1 mg/kg body weight to 450 mg/kg body weight, 2 mg/kg body weight to 400 mg/kg body weight, 3 mg/kg body weight to 350 mg/kg body weight, 4 mg/kg body weight to 300 mg/kg body weight, 5 mg/kg body weight to 250 mg/kg body weight, 6 mg/kg body weight to 200 mg/kg body weight, 7 mg/kg body weight to 150 mg/kg body weight, 8 mg/kg body weight to 100 mg/kg body weight, or 9 mg/kg body weight to 50 mg/kg body weight. Further, those of skill will recognize that a variety of different dosage levels will be of use, for example, 0.1 µg/kg, 1 µg/kg, 10 µg/kg, 100 µg/kg, 200 µg/kg; 300 µg/kg; 400 µg/kg, 500 µg/kg, 600 µg/kg, 700 µg/kg, 800 µg/kg, 900 µg/kg, 1 mg/kg, 2 mg/kg, 3 mg/kg, 4 mg/kg, 5 mg/kg, 7.5 mg/kg, 10 mg/kg, 12.5 mg/kg, 15 mg/kg, 17.5 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 120 mg/kg, 140 mg/kg, 150 mg/kg, 160 mg/kg, 180 mg/kg, 200 mg/kg, 225 mg/kg, 250 mg/kg, 275 mg/kg, 300 mg/kg, 325 mg/kg, 350 mg/kg, 375 mg/kg, 400 mg/kg, 450 mg/kg, 500 mg/kg, 550 mg/kg, 600 mg/kg, 700 mg/kg, 750 mg/kg, 800 mg/kg, 900 mg/kg, 1000 mg/kg, 1250 mg/kg, 1500 mg/kg, 1750 mg/kg, 2000 mg/kg, 2500 mg/kg, and/or 3000 mg/kg. Of course, all of these dosages are exemplary, and any dosage in-between these points is also expected to be of use in the invention. Any of the above dosage ranges or dosage levels may be employed for the peptide composition of the present invention.

The treatments may include various "unit doses." Unit dose is defined as containing a predetermined quantity of the therapeutic composition (lactoferrin related peptides or its related-compounds thereof) calculated to produce the desired responses in association with its administration, i.e., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time.

In certain embodiments, the composition is given in a single dose or multiple doses. The single dose may be administered daily, or multiple times a day, or multiple times a week, or monthly or multiple times a month. In a further embodiment, the composition is given in a series of doses. The series of doses may be administered daily, or multiple times a day, weekly, or multiple times a week, or monthly, or multiple times a month.

A. Hyperproliferative Disease

The hyperproliferative disease, includes but is not limited to neoplasms. A neoplasm is an abnormal tissue growth, generally forming a distinct mass that grows by cellular proliferation more rapidly than normal tissue growth. Neoplasms show partial or total lack of structural organization and functional coordination with normal tissue. These can be broadly classified into three major types. Malignant neoplasms arising from epithelial structures are called carcinomas, malignant neoplasms that originate from connective tissues such as muscle, cartilage, fat or bone are called sarcomas and malignant tumors affecting hematopoietic structures (structures pertaining to the formation of blood cells) including components of the immune system, are called leukemias, lymphomas and myelomas. A tumor is the neoplastic growth of the disease cancer. As used herein, a "neoplasm", also referred to as a "tumor", is intended to encompass hematopoietic neoplasms as well as solid neoplasms. Examples of neoplasms include, but are not limited to melanoma, non-small cell lung, small-cell lung, lung, hepatocarcinoma, retinoblastoma, astrocytoma, glioblastoma, gum, tongue, leukemia, neuroblastoma, head, neck, breast, pancreatic, prostate, renal, bone, testicular, ovarian, mesothelioma, sarcoma, cervical, gastrointestinal, lymphoma, brain, colon, bladder, myeloma, or other malignant or benign neoplasms.

Other hyperproliferative diseases include, but are not limited to neurofibromatosis, rheumatoid arthritis, Waginer's granulomatosis, Kawasaki's disease, lupus erythematosis, midline granuloma, inflammatory bowel disease, osteoarthritis, leiomyomas, adenomas, lipomas, hemangiomas, fibromas, vascular occlusion, restenosis, atherosclerosis, pre-neoplastic lesions, carcinoma in situ, oral hairy leukoplakia, or psoriasis, and pre-leukemias, anemia with excess blasts, and myelodysplastic syndrome.

Particular neoplasms of interest in the present invention include, but are not limited to hematopoietic neoplasms. For example, a hematopoietic neoplasm may include acute myelogenous leukemia, acute lymphoblastic leukemia, myelodysplastic syndrome, chronic myelomonocytic leukemia, juvenile myelomonocyte leukemia, multiple myeloma, chronic lymphocytic leukemia or other malignancy of hematologic origin.

In a preferred embodiment of the present invention, the peptide compositions are administered in an effective amount to decrease, reduce, inhibit or abrogate the growth of a tumor. The amount may vary from about 0.1 µg to about 100 g of the lactoferrin composition. Preferably, the lactoferrin composition is orally administered in the range of 1 mg to 100 g per day, more preferably about 20 mg to about 10 g per day with the most preferred dose being 4.5 g per day. Intravenously administered lactoferrin can be in the range of 0.1 µg to about to 10 g per day, more preferably about 0.1 g to about 1 mg with the most preferred dose being 250 mg per day. Preferably, a peptide composition is intratumorally administered in the range of 0.1 µg to 10 g per day with the most preferred dose being 100 µg per day. Topically, the amount of lactoferrin related peptides may vary from about 1 µg to about 100 g. Preferably, the topical gel, solution, capsule or tablet comprises a concentration of about 0.01% to about 20% of lactoferrin related peptides. More preferably, the topical gel, solution, capsule or tablet may comprise a concentration of about 1% to about 8.5% lactoferrin related peptides.

In certain embodiments intratumoral administration of the composition includes intratumoral injection, electroporation, or surgical or endoscopic implantation. Intratumoral injection, or injection into the tumor vasculature is specifically contemplated for discrete, solid, accessible tumors. Local, regional or systemic administration also may be appropriate.

The tumor being treated may not, at least initially, be resectable. Treatments with the lactoferrin composition may increase the resectability of the tumor due to shrinkage at the margins or by elimination of certain particularly invasive portions. Following treatments, resection may be possible. Additional treatments subsequent to resection will serve to eliminate microscopic residual disease at the tumor site.

Alternatively, the present invention may be used at the time of surgery, and/or thereafter, to treat residual or metastatic disease. For example, a resected tumor bed may be injected or perfused with a formulation comprising the lactoferrin composition. The perfusion may be continued post-resection, for example, by leaving a catheter implanted at the site of the surgery. Periodic post-surgical treatment is also envisioned.

Continuous administration also may be applied where appropriate, for example, where a tumor is excised and the tumor bed is treated to eliminate residual, microscopic disease. Delivery via syringe or catherization is preferred. Such continuous perfusion may take place for a period from about 1-2 hours, to about 6-12 hours, to about 12-24 hours, to about 1-2 days, to about 1-2 weeks or longer following the initiation of treatment. Generally, the dose of the therapeutic composition via continuous perfusion will be equivalent to that given by a single or multiple injections, adjusted over a period of time during which the perfusion occurs. It was further contemplated that limb perfusion may be used to administer therapeutic compositions of the present invention, particularly in the treatment of melanomas and sarcomas.

Still yet, a further embodiment is a method of enhancing a mucosal immune response in the gastrointestinal tract in a subject comprising the step of administering orally to said subject a peptide composition. It is also envisioned that the lactoferrin related peptide stimulates interleukin-18 following oral administration, which inhibits angiogenesis and thereby has activity against tumor cells which are dependent on neovascularization.

A further embodiment of the present invention is a method of treating a hyperproliferative disease comprising the step of supplementing the systemic immune system by increasing the amount of lactoferrin related peptides in the systemic circulation. Preferably, the composition is administered intravenously. It is envisioned that the lactoferrin related peptides stimulate interleukin-18 following intravenous administration, which inhibits angiogenesis and thereby has activity against tumor cells which are dependent on neovascularization.

A further embodiment of the present invention is a method of treating a hyperproliferative disease comprising the step of supplementing a local or systemic immune system by increasing the amount of lactoferrin in the vicinity of the tumor. Vicinity of the tumor refers to the general area of the tumor, for example the lactoferrin can be administered directly into or on the tumor, or in the general area of the tumor, but not directly into the tumor. The general area may include the margin area or near or adjacent the margin area of the tumor. Preferably, the lactoferrin composition is administered intratumorally. It is envisioned that the lactoferrin related peptides stimulate interleukin-18 following intratumoral administration, which inhibits angiogenesis and thereby has activity against tumor cells which are dependent on neovascularization.

A further embodiment of the present invention is a method of treating a hyperproliferative disease comprising the step of supplementing a local or systemic immune system by increasing the amount of a lactoferrin related peptide in the skin in the vicinity of the tumor. Preferably, the composition is administered topically. As above, administration in the vicinity of the tumor includes administration near or adjacent to the margins of the tumor or directly in the margin area of the tumor. It is envisioned that the lactoferrin related peptides stimulate interleukin-18 and GM-CSF in the local tissue (e.g., keratinocytes), which enhances immune cells. It is envisioned that the lactoferrin related peptides stimulate interleukin-18 following intratumoral administration, which inhibits angiogenesis and thereby has activity against tumor cells which are dependent on neovascularization.

In certain embodiments, it may be desirable to combine the peptide composition of the present invention with other agents effective in the treatment of hyperproliferative disease, such as anti-cancer agents, or with surgery. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to tumor or cancer cells, promoting an immune response against cancer cells or a tumor, preventing or inhibiting the progression of cancer, or increasing the lifespan of a subject with cancer. Anti-cancer agents include biological agents (biotherapy), chemotherapy agents, and radiotherapy agents. More generally, these other compositions would be provided in a combined amount effective to kill or inhibit proliferation of the cell. This process may involve administering the peptide composition of the present invention and the agent(s) or multiple factor(s) at the same time. This may be achieved by administering a single composition or pharmacological formulation that includes both agents, or by administering two distinct compositions or formulations, at the same time, or at times close enough so as to result in an overlap of this effect, wherein one composition includes the peptide composition and the other includes the second agent(s).

Alternatively, the peptide composition of the present invention may precede or follow the other anti-cancer agent treatment by intervals ranging from minutes to weeks. In embodiments where the other anti-cancer agent and peptide composition are administered or applied separately to the cell, one would generally ensure that a significant period of time did not expire between the time of each delivery, such that the agent and peptide composition would still be able to exert an advantageously combined effect on the cell. In such instances, it is contemplated that one may contact the cell with/administer both modalities within about 1-14 days of each other and, more preferably, within about 12-24 hours of each other. In some situations, it may be desirable to extend the time period for treatment significantly, however, where several days (2, 3, 4, 5, 6 or 7) to several weeks (2, 3, 4, 5, 6, 7 or 8) lapse between the respective administrations.

a) Chemotherapy

Cancer therapies also include a variety of chemical based treatments. Some examples of chemotherapeutic agents include without limitation antibiotic chemotherapeutics such as Doxorubicin, Daunorubicin, Adriamycin, Mitomycin (also known as mutamycin and/or mitomycin-C), Actinomycin D (Dactinomycin), Bleomycin, Plicomycin, plant alkaloids such as Taxol, Vincristine, Vinblastine, miscellaneous agents such as platinum based agents (e.g., Cisplatin (CDDP)), etoposide (VP16), Tumor Necrosis Factor, and alkylating agents such as, Carmustine, Melphalan (also known as alkeran, L-phenylalanine mustard, phenylalanine mustard, L-PAM, or L-sarcolysin, (a phenylalanine derivative of nitrogen mustard), Cyclophosphamide, Chlorambucil, Busulfan (also known as myleran), taxane based agents (e.g., docetaxel) and Lomustine.

Some examples of other agents include, but are not limited to, Carboplatin, Procarbazine, Mechlorethamine, Irinotecan, Topotecan, Ifosfamide, Nitrosurea, Etoposide (VP16), Tamoxifen, Raloxifene, Toremifene, Idoxifene, Droloxifene, TAT-59, Zindoxifene, Trioxifene, ICI 182,780, EM-800, Estrogen Receptor Binding Agents, Gemcitabinen, Navelbine, Farnesyl-protein transferase inhibitors, Transplatinum, 5-Fluorouracil, hydrogen peroxide, and Methotrexate, Temazolomide (an aqueous form of DTIC), Mylotarg, Dolastatin-10, Bryostatin, or any analog or derivative variant of the foregoing.

b) Radiotherapeutic Agents

Radiotherapeutic agents and factors include radiation and waves that induce DNA damage for example, γ-irradiation, X-rays, UV-irradiation, microwaves, electronic emissions, radioisotopes, and the like. Therapy may be achieved by irradiating the localized tumor site with the above described forms of radiations. It is most likely that all of these factors effect a broad range of damage to DNA, the precursors of DNA, the replication and repair of DNA, and the assembly and maintenance of chromosomes.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

c) Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

d) Other Biotherapy Agents

It is contemplated that other biological agents may be used in combination with the present invention to improve the therapeutic efficacy of treatment. These additional agents include, without limitation, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents, as well as biotherapy such as for example, hyperthermia.

Hyperthermia is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

Hormonal therapy may also be used in conjunction with the present invention. The use of hormones may be employed in the treatment of certain cancers such as breast, prostate, ovarian, or cervical cancer to lower the level or block the effects of certain hormones such as testosterone or estrogen and this often reduces the risk of metastases.

Adjuvant therapy may also be used in conjunction with the present invention. The use of adjuvants or immunomodulatory agents include, but are not limited to tumor necrosis factor; interferon alpha, beta, and gamma; IL-2 and other cytokines; F42K and other cytokine analogs; or MIP-1, MIP-1 beta, MCP-1, RANTES, and other chemokines.

e) Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

It is contemplated that vaccines that are used to treat cancer may be used in combination with the present invention to improve the therapeutic efficacy of the treatment. Such vaccines include peptide vaccines or dendritic cell vaccines. Peptide vaccines may include any tumor-specific antigen that is recognized by cytolytic T lymphocytes. Yet further, one skilled in the art realizes that dendritic cell vaccination comprises dendritic cells that are pulsed with a peptide or antigen and the pulsed dendritic cells are administered to the patient.

Examples of tumor-specific antigens that are being used as vaccines in melanoma include, but are not limited to gp 100 or MAGE-3. These antigens are being administered as peptide vaccines and/or as dendritic cell vaccines.

B. Wounds and Other Integument Disorders

1. Wounds

In accordance with the present invention, a peptide composition provided in any of the above-described pharmaceutical carriers is orally, topically, or parenterally administered to a subject suspected of or having a wound.

The present invention is designed for the treatment of any type of wound, which includes, but is not limited to skin wound, internal wound, gastrointestinal wound, oral wound, bone wounds, ophthalmic wound, surgical wound, or any combination thereof. Wounds can be found on but not limited to skin, internal organs, stomach and intestines (gastrointestinal), oral mucosa, and eye (ophthalmic wounds, e.g., corneal ulcers, radiokeratotomy, corneal transplants, epikeratophakia and other surgically induced wounds in the eye). Depending on the process that causes the wounds, wounds can also be classified as but are not limited to incisional wounds, excisional wounds, diabetic ulcers, venous stasis ulcers, decubitus or pressure ulcers, chemical wounds, and burn wounds.

A further embodiment of the present invention is administering the inventive composition to treat skin wounds. Skin wounds further comprise but are not limited to full-thickness wounds and partial-thickness wounds. Full-thickness wounds involve the complete removal of epidermis and dermis to the depth of fascial planes or subcutaneous fat. In the loose-skinned species, the thin musculature of the panniculus carnosus, which firmly adheres to the base of the dermis, is usually removed as well. In partial-thickness wounds a substantial amount of dermis, mostly reticular, is left behind, and, more importantly, the bases of most epidermal appendages (sebaceous and sweat glands, hair follicles) remain intact.

Yet further, a wound can be further defined as an acute wound. Acute wounds have a relatively rapid rate of healing, especially in healthy subjects. However, in the elderly or immunocompromised healing can be prolonged. Healing is also prolonged if the wound becomes infected. Preferred acute wounds that are to be treated with the present composition include, but are not limited to partial-thickness burns, lacerations, bullet wounds or infected wounds.

A wound is also further defined as a chronic wound. Examples of chronic wounds or chronic ulcers include, but are not limited to diabetic ulcers, venous stasis ulcers, decubitus or pressure ulcers. Yet further, chronic wounds can also include infected wounds. Chronic wounds are wounds that do not repair or do so extremely slowly, and show partial or total lack of structural organization and functional coordination with normal tissue. Chronic wounds or chronic ulcers can be broadly classified into three major types: diabetic ulcers, venous stasis ulcers, decubitus or pressure ulcers. Diabetic ulcers often occur on a foot. Chronic diabetic state and poor glucose control results in poor peripheral circulation and microcirculation due to progressive arteriosclerosis; neuropathic changes that result in an insensate extremity prone to trauma; and intrinsic defects in the wound healing process that may include reduced abundance and response to cellular growth factors. In the case of venous ulcers, venous hypertension causes disturbed microcirculation and pathological changes of the capillaries, elevated persistent levels of proinflammatory cytokines and proteases. Fibroblast senesce and respond less to growth factors, which distribute unfavorably. Proteolytic enzymes and their inhibitors are imbalanced. Pressure ulcers occur when skin is under pressure without movement to allow blood flow for 8-12 hours.

In a preferred embodiment of the present invention, the inventive composition is administered in an effective amount to seal, to close, to improve or to repair the wound. Also, it is envisioned that the composition of the present invention can also decrease, reduce, or inhibit, bacterial infections of the wound, which aid in the healing process of a wound. Thus, one of skill in the art realizes that depending upon the wound type, location, health of the subject, etc., the peptide composition of the present invention may be administered for any given period of time until the wound is healed at least by 5%, 10%, 20%, 30%, 40%, 50%, 55%, 60%, 65%, 70%, 75%, 80%, 85%, 90%, 95% or 100% or any range in between.

For topical administration, the gel formulation of the present invention may be used to coat fibers of an absorbent gauze dressing to form a wound healing bandage which may then be placed on a wound. The low viscosity formulation is preferred for this use. The wound healing bandage may be prepared by soaking a gauze dressing with an aqueous gel solution containing lactoferrin having wound healing activity. The bandage can then be applied to the wound so that the coated fibers of the gauze contacts the wound and stimulate the rate of wound healing.

In those applications where the present invention is a gel that is applied to an internal or incisional wound, it is preferred that the gel forming polymer be biodegradable. The naturally occurring polymers are generally biodegradable. Examples of these are collagen, the glycosaminoglycans, gelatin and starch. The cellulosics are not biodegradable. The synthetic polymers such as the vinyl polymers are not degradable. The biodegradability of the polymers described herein is well known to those skilled in the art.

A further embodiment of the present invention is a method of treating a wound comprising the step of supplementing the local immune system by increasing the amount of a lactoferrin related peptide in the vicinity of the wound. Preferably, the peptide is administered topically to the wound.

Yet further, the present invention also provides a method of treating a wound comprising the step of supplementing the systemic immune system by increasing the amount of a lactoferrin related peptide in the systemic circulation. Preferably, the lactoferrin is administered via a parenteral route, which includes, but is not limited to intramuscular, intravenous, intraperitoneal, intraocular, intraarticular or into a surgical field.

In further embodiments, the present invention provides a method of enhancing the immune system of a subject suffering from a wound by administering to the subject a peptide composition. Depending upon the mode of administration, different arms of the immune system are enhanced. For example, topical administration of the composition results in enhancement of the local immune system, i.e., in the vicinity of the wound. Parenteral administration of the composition results in enhancement of the systemic immune system. Yet further, oral administration of the composition results in enhancement of the mucosal immune system, which can also result in systemic effects as well. It is further contemplated that IL-18 or GM-CSF stimulate the production or activity of cells involved in wound repair, for example, but not limited to keratinocytes, endothelial cells, dendritic cells, fibroblasts, and myofibroblasts. Yet further, it is envisioned that lactoferrin related peptides inhibit the production of TNF-alpha, which may lead to excess inflammation and tissue destruction for example by stimulating the production of metalloproteinases.

It is further envisioned that supplementing the local immune system in a subject by administering topically a therapeutically effective amount of the inventive composition in the vicinity of the wound can result in the killing of bacteria infecting the wound. Still further, topical administration of a composition comprising a lactoferrin peptide related compound may stimulate the production of a cytokine or a chemokine. Cytokines, for example, interleukin-18 or granulocyte/macrophage colony-stimulating factor, can also stimulate the production or activity of cells involved in wound repair. The cells involved in wound repair include, but are not limited to keratinocytes, endothelial cells, fibroblasts, dendritic cells, and myofibroblasts. The inhibition of TNF-alpha further inhibits the migration and maturation of dendritic cells and the production of metalloproteinases. The dendritic cells can be Langerhans cells.

In order to increase the effectiveness of the composition of the present invention, it may be desirable to combine the composition of the present invention with other agents effective in the treatment of wounds, such as growth factors, skin replacement therapy, enzymatic and surgical debridement, moist wound dressings, cleansers, antibiotics. Such wound healing agents are capable of negatively affecting a wound in a subject, for example, by enhancing the growth rate of skin cells, augmenting the blood supply to skin cells, promoting an immune response against bacteria infecting the wound, killing bacteria, cleaning ischemic tissue, promoting the closure of the wound. More generally, these other wound healing agents are provided in a combined amount effective to promote the healing of a wound. This process may involve administering the composition of the present invention and the agent(s) or multiple factor(s) at the same time. This may be achieved by administering a single composition or pharmacological formulation that includes both agents, or by administering two distinct compositions or formulations, at the same time, or at times close enough so as to result in an overlap of this effect, wherein one composition includes the lactoferrin composition and the other includes the second agent(s).

Alternatively, the composition of the present invention may precede or follow the other wound healing agent treatment by intervals ranging from minutes to weeks. In embodiments where the other wound healing agent and inventive composition are administered or applied separately to the wound, one would generally ensure that a significant period of time did not expire between the time of each delivery, such that the agent and human lactoferrin composition would still be able to exert an advantageously combined effect on the wound. In such instances, it is contemplated that one may contact the wound with/administer both modalities within about 1-14 days of each other and, more preferably, within about 12-24 hours of each other. In some situations, it may be desirable to extend the time period for treatment significantly, however, where several days (2, 3, 4, 5, 6 or 7) to several weeks (2, 3, 4, 5, 6, 7 or 8) lapse between the respective administrations.

a) Growth Factors

Wound healing therapies include growth factor based treatments. Examples include, but are not limited to Regranex™ (Becaplermin-BB gel), AuTolo-Gel (autologous activated platelet releasate), Procuren (autologous thrombin-induced platelet releasate). Growth factors act without limitation by promoting granulation or the formation of new highly vascularized connective tissue; stimulating proliferation, differentiation and migration of epithelial cells, vascular endothelial cells and other skin cells; enhancing the production of collagen, collagenase, and extracellular matrix.

b) Skin Replacement Therapy

Examples include but are not limited to Apligraf (bilayered living skin), Trancyte (Human fibroblast-derived temporary skin substitute), Dermagraft (permanent, one-layer skin substitute), Epicel (living one-layer artificial skin), Integra (collagen-based skin regeneration template), AlloDerm (single-layer artificial skin made from human cadavers), CCS (living, cultured, artificial skin).

c) Enzymatic and Surgical Debridement

Debridement is a process or procedure to clean ischemic or dead tissue. Enzymatic debriders include Accuzyme papain-urea debriding ointment and Collagenase Santyl. Surgical debridement refers to physical removal of at least part of the ischemic or dead tissue in a wound. Debridement may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. Enzymatic debridement treatments may be of varying dosages as well. It is further contemplated that the present invention may be used in conjunction with enzymatic or surgical debridement.

d) Dressings

Wound healing therapies include a variety of treatments based on dressings. Dressing categories include but are not limited to amorphous hydrogels, hydrogel sheets, absorptives, alginates, biological and synthetic dressings, collagens, composites, contact layers, elastic gauzes, foams, gauzes and non-woven dressings, hydrocolloids, impregnated dressings, silicone gel sheets, silver dressings, transparent films, wound fillers e) Cleansers Examples include but are not limited to Biolex, Lamin, Wound Wash Saline, Techni-Care, CarraKlenz, DiaB Klenz, MicroKlenz, RadiaCare Klenz, UltraKlenz, Comfee Sea-Clens, Optipore Sponge, Saf-Clens, Shur-Clens, Dermagran, DermaKlenz, Dumex, Gene Klenz, GRX, Allclenz, Restore, Hyperion, Medi Tech, Skintegrity, MPM Antimicrobial, ClinsWound, Septicare, Lobana Saline.

f) Antimicrobials

Examples of include but are not limited to Sulfamylon Cream, Thermazene Cream (1% silver sulfadiazine), cadexomer-iodine pads or gel. Examples of intravenous antimicrobials include but are not limited to imipenem/cilastatin, β-lactam/β-lactamase inhibitors (ampicillin/sulbactam, piperacillin/tazobactam), and broad-spectrum cephalosporins (cefoxitin, ceftizoxime, ceftazidime). Other examples include, but are not limited to Bensal HP, Barri-Care, Care-Creme, Formula Magic, Baza, Micro-Guard, Ca-Rezz, Diabet-X products, Mitrazol Powder, PiercingCare, Triple Care products, and various antifungal creams and powders.

g) Compression

Dynamic compression examples, include pumps and sleeves such as but not limited to ArtAssist, ArterialFlow, EdemaFlow, PulStar, Circulator Boot, Flowplus, Flowpress, Flowtron. Static compression include but are not limited to leg wrappings, gloves, socks, leg wears, leg supports, arm sleeves, stasis pads, compression hosieries, non-elastic bands, high compression bandages, zinc impregnated bandages, elastic bandages.

h) Oxygen Therapy

Examples of systemic hyperbaric oxygen therapy include but are not limited to compartments for one patient to lay down, for one patient to sit up to 25 degree angle, for one patient to sit up to 90 degree angle, for more than one patient to be treated simultaneously. Examples of topical hyperbaric oxygen therapy include but are not limited to disposable topical hyperbaric oxygen systems for extremity ulcers, disposable topical hyperbaric oxygen systems for decubitis, post-op and trauma wounds.

i) Hydrotherapy, Electric Therapy

Examples include but are not limited to dry hydrotherapy machines; non-contact thermal wound care systems for use on partial- and full-thickness wounds that maintain warmth and humidity in the wound area; systems that provide non-thermal, pulsed high frequency, high peak power, electromagnetic energy to treat edema and pain in acute and chronic wounds; systems that use controlled, localized negative pressure and support for moist wound healing; pulsatile irrigators with controllable pressures below 15 psi for site-specific treatment of various wounds with variety of tips; various wound irrigation and whirlpool systems.

j) Nutritional Therapy Products

Examples include but are not limited to isotonic, high-protein, fiber-containing tube feedings to support wound healing; high-protein, cholesterol-free nutritional supplements.

k) Cohesives, Glues, Sealants, Patches

Examples include but are not limited to Dermabond, CoStasis, CoSeal, BioGlue, FibRx, FocalSeal, FloSeal, AutoSeal, Indermil, Syvek, LiquiSheild, LiquiBand, Quixil, CryoSeal, VIGuard Fibrin Sealant, and various tapes, closures, and securement products.

l) Topical Wound Healing Promoters

Examples include but are not limited to topical aerosols which stimulate the capillary bed of chronic wounds; skin protectants with zinc-nutrient formulations; topical gels to help scars feel softer and smoother; hydrophilic ointments that cleanse degraded proteins, promote healthy granulation, control local inflammation and reduce wound odors; oil-and-water wound dressing emulsions that selectively recruit macrophages.

m) Other Biotherapy Agents

Adjuvant therapy may also be used in conjunction with the present invention. The use of adjuvants or immunomodulatory agents include, but are not limited to tumor necrosis factor; interferon alpha, beta, and gamma; IL-2 and other cytokines; F42K and other cytokine analogs; or MIP-1, MIP-1beta, MCP-1, RANTES, and other chemokines.

2. Psoriasis

In accordance with the present invention, a peptide composition provided in any of the above-described pharmaceutical carriers is orally, topically, or parenterally administered to a subject suspected of or having psoriasis.

Psoriasis is a chronic inflammatory skin disorder that undergoes repeated relapse and remission and affects one to three percent of the world's population. The disease can begin at any age and has its peak appearance in the third decade. Its severity, course, and remissions are unpredictable. (See, T. P. Habif, in: Clinical Dermatology, Mosby, Mo. (1996) and The Textbook of Medicine edts: J. B. Wyngaarden and L. H. Smith, W., W. B. Saundres Company, Philadelphia (1985)).

Patients with psoriasis can be divided into two groups, those with a genetic predisposition and those that respond to epigenetic, i.e. environmental factors. The most common form is chronic plaque psoriasis and is characterized by hyperplasia of the epidermis and inflammation of the dermis and epidermis. These changes arise due to activation of a T-lymphocyte cell mediated dermal immune reaction in regional lymph nodes in response to unidentified antigenic stimuli. The activated T-cells cause keratinocyte cells to proliferate and assume a psoriasis phenotype. The inflammatory reaction is caused by proinflammatory cytokine proteins that are induced in response to the environmental stimulus and results in infiltration of the dermis and epidermis by inflammatory white blood cells.

The present invention provides a method of enhancing the immune system of a subject suffering from psoriasis by administering to the subject a peptide composition. Depending upon the mode of administration, different arms of the immune system are enhanced. For example, topical administration of the composition results in enhancement of the local immune system, i.e., in the vicinity of the wound. Parenteral administration of the composition results in enhancement of the systemic immune system. Yet further, oral administration of the composition results in enhancement of the mucosal immune system, which can also result in systemic effects as well.

Psoriasis has been shown to be caused by inappropriate local immune responses which involve the de novo production of TNF-α by keratinocytes (Gilhar et al., 1996, Clin. Exp. Immunol. 106: 134-142). Accordingly, in one embodiment, the present invention provides compositions that directly interfere with the production of TNF-α by keratinocytes, thus preventing the inappropriate local immune response causing psoriasis. More specifically, the present invention provides novel pharmaceutical compositions comprising a lactoferrin related peptide product for the treatment of psoriasis. In a preferred embodiment, the compositions are formulated for topical application in about 0.5% to about 5% carrier. In alternative embodiments, the compositions are formulated for intradermal injections.

In order to increase the effectiveness of the composition of the present invention, it may be desirable to combine the composition of the present invention with other agents effective in the treatment of psoriasis, such as anti-inflammatory agents. This process may involve administering the composition of the present invention and the agent(s) or multiple factor(s) at the same time. This may be achieved by administering a single composition or pharmacological formulation that includes both agents, or by administering two distinct compositions or formulations, at the same time, or at times close enough so as to result in an overlap of this effect, wherein one composition includes the lactoferrin composition and the other includes the second agent(s).

Alternatively, the composition of the present invention may precede or follow the other anti-inflammatory agent treatment by intervals ranging from minutes to weeks. In embodiments where the other anti-inflammatory agent and inventive composition are administered or applied separately to the anti-inflammatory, one would generally ensure that a significant period of time did not expire between the time of each delivery, such that the agent and the inventive composition would still be able to exert an advantageously combined effect on the psoriasis.

Typical anti-inflammatory agents are topical agents, for example, but not limited to are corticosteroids (hydrocortisone and analogs). Systemic corticosteroids, for example, can induce prompt resolution of psoriatic lesions, but suppression requires ever-increasing doses.

C. Respiratory Disorders

In accordance with the present invention, the composition provided in any of the above-described pharmaceutical carriers is orally administered to a subject suspected of or having a respiratory disorder. The respiratory disorder can be an allergic or non-allergic respiratory disorder.

According to the invention, an allergic or non-allergic respiratory disorder includes asthma, emphysema, bronchitis, chronic obstructive pulmonary disease, sinusitis and allergic rhinitis. In specific embodiments, the respiratory disorder is characterized by increased responsiveness of the trachea and bronchi to various stimuli, i.e., allergens, resulting in widespread narrowing of the airways.

The composition is administered in an effective amount to decrease, reduce, inhibit or abrogate the obstruction of the airway or the hyperresponsiveness of the respiratory system to the allergen or other stimuli. The amount of lactoferrin related peptide in the composition may vary from about 1 mg to about 100 g. Preferably, the composition that is orally administered contains the range of 1 mg to 10 g of peptide per day, more preferably, 10 mg to about 1 g. More preferably, the composition of the present invention also contains metal chelators. A preferred metal chelator is EDTA. More preferably, the composition that is orally administered contains the ratio of 1:10,000 to about 2:1 EDTA to lactoferrin related peptide.

A further embodiment is a method of enhancing a mucosal immune response in the gastrointestinal tract in a subject comprising the step of administering orally to said subject the composition of the present invention. It is envisioned that oral administration of lactoferrin related peptides stimulate IL-18 in the lungs, sinuses or systemically. Yet further, it is contemplated that an enhancement of lactoferrin related peptides can reduce the infiltration of inflammatory cells into the lung.

In order to increase the effectiveness of administration of the composition of the present invention, it is desirable to combine these compositions with an additional agent. For example, known asthma agents are used in combination with the composition of the present invention. Exemplary agents known to treat asthma include mast cell degranulation agents (i.e., Cromylyn sodium or Nedocromil sodium), leukotriene inhibitors (i.e., Monteleukast sodium, Zafirlukast, or Pranlukast hydrate), corticosteroids (i.e., Beclomethasone, Budesonide, Ciclesonide, Hydrolysable glucocorticoid, Triamcinolone acetonide, Flunisolide, Mometasone furoate, or Fluticasone propionate), β-Antagonists (i.e., Albuterol, Bambuterol, Formoterol, Salbutamol, Terbutaline sulfate, or Salmeterol), IgE binding inhibitors (i.e., Omalizumab), Adenosine A2 agonists, Anti-CD23 antibody, E-Selectin antagonists, P-Selectin antagonists, L-Selectin antagonists, interleukin inhibitors/monoclonal antibodies, pulmonary surfactants, neurokinin antagonists, NF-Kappa-B inhibitors, PDE-4 inhibitors (i.e., Cilomilast, or Roflumilast), Thromboxan A2 inhibitors (i.e., Ramatroban, or Seratrodast), tryptase inhibitors, VIP agonists or antisense agents.

Yet further, the agent is a known agent used to treat allergic rhinitis. Exemplary agents include, but are not limited to H1 antihistamines i.e., terfendine or astemizole; alpha-adrenergic agents; and glucocorticoids, i.e., beclomethasone or flunisolide.

In addition, the agent is a known agent to treat sinusitis, more specifically, chronic sinusitis. Exemplary agents/therapies include, but are not limited to surgery (e.g., enlarging a sinus passage, remove obstructing bone or nasal polyps, mucosal stripping, removal of sinuses); corticosteroids (e.g., oral, intranasal, nebulized, or inhaled); antibiotics (e.g., oral, intranasal, nebulized, inhaled or intravenous); anti-fungal agents; salt-water nasal washes and mist sprays; anti-inflammatory agents; decongestants (oral or nasal); guaifenesin; potassium iodide; leukotriene inhibitors (e.g., monteleukast); mast cell degranulating agents; topical moisturizing applications (e.g., nasal sprays or gels which may contain moisturizing agents such as propylene glycol or glycerin); hot air inhalation; mechanical devices to aid in breathing; enzymatic cleansers (e.g., papaya enzymes); and antihistamine sprays.

Still further, the agent is a known agent to treat COPD or chronic bronchitis or emphysema. Exemplary agents/interventions include, but are not limited to oxygen; bronchodilator drugs [e.g., short and long acting beta-2 stimulants, anticholinergics (e.g., ipratoprium bromide, theophylline compounds or a combination), steroids (topical or oral), or mucolytic agents (e.g., ambroxol, ergosterin, carbocysteine, iodinated glycerol)]; antibiotics; anti-fungals; moisterization by nebulization; anti-tussives; respiratory stimulants (e.g., doxapram, almitrine bismesylate); surgery (e.g., bullectomy, lung volume reduction surgery, lung transplantation); and alpha 1 antitrypsin administration.

The composition of the present invention may precede, be co-current with and/or follow the other agent(s) by intervals ranging from minutes to weeks. In embodiments where the composition of the present invention, and other agent(s) are applied separately to a cell, tissue or organism, one would generally ensure that a significant period of time did not expire between the time of each delivery, such that the composition and agent(s) would still be able to exert an advantageously combined effect on the cell, tissue or organism.

Various combination regimens of the composition and one or more agents are employed. One of skill in the art is aware that the composition of the present invention and agents can be administered in any order or combination.

D. Infectious Diseases

In certain embodiment of the invention, the present invention is useful for the treatment and/or prevention of infectious disease. Infectious diseases include infections of viral etiology such as HIV, West Nile Virus, influenza, Herpes, viral hepatitis, Epstein Bar, polio, viral encephalitis, measles, chicken pox, Papilloma virus etc.; or infections of bacterial etiology such as bacterial meningitis, paramenigeal infections, septic thrombophlebitis, pneumonia, tuberculosis, myocarditis, bacteremia, syphilis, etc.; or infections of parasitic etiology such as malaria, trypanosomiasis, leishmaniasis, candidiasis, trichomoniasis, amoebiasis, etc.

1. Viral

The present invention can have applications therefore in the prevention and treatment of viral diseases. The following pathogenic viruses which are mentioned by way of example, influenza A, B and C, parainfluenza, paramyxoviruses, Newcastle disease virus, respiratory syncytial virus, measles, mumps, adenoviruses, adenoassociated viruses, parvoviruses, Epstein-Barr virus (EBV), rhinoviruses, coxsackieviruses, echoviruses, reoviruses, rhabdoviruses, lymphocytic choriomeningitis, coronavirus, polioviruses, herpes simplex (HSV), human immunodeficiency viruses (HIV), cytomegaloviruses, papillomaviruses, human papillomavirus (HPV), hepatitis B virus (HBV), hepatitis C virus (HCV), varicella-zoster, poxviruses, rubella, rabies, picornaviruses, rotavirus and Kaposi associated herpes virus.

2. Bacterial

In addition to the viral diseases mentioned above, the present invention is also useful in the prevention, inhibition, or treatment of bacterial infections. The following bacteria are mention by way of example, including, but not limited to, serotypes of pneumococci, streptococci such as *S. pyogenes, S. agalactiae, S. equi, S. canis, S. bovis, S. equinus, S. anginosus, S. sanguis, S. salivarius, S. mitis, S. mutans*, other viridans streptococci, peptostreptococci, other related species of streptococci, enterococci such as *Enterococcus faecalis, Enterococcus faecium*, Staphylococci, such as *Staphylococcus epidermidis, Staphylococcus aureus*, particularly in the nasopharynx, *Hemophilus influenzae*, pseudomonas species such as *Pseudomonas aeruginosa, Pseudomonas pseudomallei, Pseudomonas mallei*, brucellas such as *Brucella melitensis, Brucella suis, Brucella abortus, Bordetella pertussis, Neisseria meningitidis, Neisseria gonorrhoeae, Moraxella catarrhalis, Corynebacterium diphtheriae, Corynebacterium ulcerans, Corynebacterium pseudotuberculosis, Corynebacterium pseudodiphtheriticum, Corynebacterium urealyticum, Corynebacterium hemolyticum, Corynebacterium equi*, etc. *Listeria monocytogenes, Nocordia asteroides, Bacteroides* species, *Actinomycetes* species, *Treponema pallidum, Leptospirosa* species and related organisms. The invention may also be useful against gram negative bacteria such as *Klebsiella pneumoniae, Escherichia coli, Proteus, Serratia* species, *Acinetobacter, Yersinia pestis, Francisella tularensis, Enterobacter* species, *Bacteriodes* and *Legionella* species and the like.

3. Fungal Infections

Yet further, either fungal and other mycotic pathogens or cells infected with fungal or other mycotic pathogens may be used in the present invention to prevent and/or treat diseases, ranging from mycoses involving skin, hair, or mucous membranes, such as, but not limited to, Aspergillosis, Black piedra, Candidiasis, Chromomycosis, Cryptococcosis, Onychomycosis, or Otitis externa (otomycosis), Phaeohyphomycosis, Phycomycosis, Pityriasis versicolor, ringworm, *Tinea barbae, Tinea capitis, Tinea corporis, Tinea cruris, Tinea favosa, Tinea imbricata, Tinea manuum, Tinea nigra* (palmaris), *Tinea pedis, Tinea unguium*, Torulopsosis, Trichomycosis axillaris, White piedra. Fungal and mycotic pathogens that can be used in the present invention include, but are not limited to, *Absidia* spp., *Actinomadura madurae, Actinomyces* spp., *Allescheria boydii, Alternaria* spp., *Anthopsis deltoidea, Apophysomyces elegans, Arnium leoporinum, Aspergillus* spp., *Aureobasidium pullulans, Basidiobolus ranarum, Bipolaris* spp., *Blastomyces dermatitidis, Candida* spp., *Cephalosporium* spp., *Chaetoconidium* spp., *Chaetomium* spp., *Cladosporium* spp., *Coccidioides immitis, Conidiobolus* spp., *Corynebacterium tenuis, Cryptococcus* spp., *Cunninghamella bertholletiae, Curvularia* spp., *Dactylaria* spp., *Epidermophyton* spp., *Epidermophyton floccosum, Exserophilum* spp., *Exophiala* spp., *Fonsecaea* spp., *Fusarium* spp., *Geotrichum* spp., *Helminthosporium* spp., *Histoplasma* spp., *Lecythophora* spp., *Madurella* spp., *Malassezia furfur, Microsporum* spp., *Mucor* spp., *Mycocentrospora acerina, Nocardia* spp., *Paracoccidioides brasiliensis, Penicillium* spp., *Phaeosclera dematioides, Phaeoannellomyces* spp., *Phialemonium obovatum, Phialophora* spp., *Phoma* spp., *Piedraia hortai, Pneumocystis carinii, Pythium insidiosum, Rhinocladiella aquaspersa, Rhizomucor pusillus, Rhizopus* spp., *Saksenaea vasiformis, Sarcinomyces phaeomuriformis, Sporothrix schenckii, Syncephalastrum racemosum, Taeniolella boppii, Torulopsosis* spp., *Trichophyton* spp., *Trichosporon* spp., *Ulocladium chartarum, Wangiella dermatitidis, Xylohypha* spp., and *Zygomyetes* spp.

In addition, the invention may prove useful in controlling protozoan or macroscopic infections by organisms such as *Cryptosporidium, Isospora belli, Toxoplasma gondii, Trichomonas vaginalis, Cyclospora* species, for example, and for *Chlamydia trachomatis* and other *Chlamydia* infections such as *Chlamydia psittaci*, or *Chlamydia pneumoniae*, for example.

4. Bacteremia and Septic Shock

In accordance with the present invention, the composition provided in any of the above-described pharmaceutical carriers is administered to a subject suspected of or having bacteremia, sepsis, septic shock or sequelae. These conditions could be caused by gram-negative, gram-positive bacteria or other infectious agents such as *Candida* in any foci of the body and are at a risk of developing into or have developed into a systemic inflammatory response syndrome.

Yet further, bacteremia may be caused by surgical manipulation of infected oral tissues or routine dental manipulations; catheterization of an infected lower urinary tract; incision and drainage of an abscess; and colonization of indwelling devices, especially IV and intracardiac catheters, urethral catheters, and ostomy devices and tubes. The primary site of infection is usually in the lungs, in the GU or GI tract, or in soft tissues including the skin in patients with decubitus ulcer. In chronically ill and immunocompromised subjects, gram-negative bacteremia occurs more commonly, than in a healthy subject. Additionally, these immunocompromised subjects may develop bloodstream infections caused by aerobic bacilli, anaerobes, and fungi.

Predisposing factors for septic shock include diabetes mellitus; cirrhosis; leukopenic states, especially those associated with underlying neoplasms or treatment with cytotoxic agents; antecedent infection in the urinary, biliary, or GI tracts; invasive devices, including catheters, drainage tubes, and other foreign materials; and prior treatment with antibiotics, corticosteroids, or ventilatory devices. Septic shock occurs more often in newborns, subjects >35 yr, pregnant women, and those seriously immunocompromised by underlying diseases or iatrogenic complications of treatment.

According to the invention, the above-described method is used for the prophylaxis of bacteremia, sepsis, septic shock, related conditions or their consequences. In specific embodiments, the disorder is characterized by a risk of endotoxemia resulting from the use of antibiotic and the subsequent release of endotoxin, as well as positively identified bacteremia.

A person at risk for developing bacteremia, sepsis, septic shock and/or related conditions is a person that is considered to be immunocompromised and/or chronically ill. The immunocompromised subject, who is, at the time of bacterial exposure, has a pre-existing condition that reduces one or more mechanisms for normal defense against infection. The immunocompromised condition may be due to a defect or dysfunction of the immune system or to other factors that heighten susceptibility to infection, for example immunosuppressive agents. Thus, prophylatically, it is envisioned that the lactoferrin composition can reduce any of the following: the levels of circulating bacteria, the risk of the subject developing sepsis, septic shock, organ failure, and decrease the morbidity and mortality associated with bacteremia.

In a preferred embodiment of the present invention, the composition is administered in an effective amount to decrease, reduce, inhibit or abrogate the risk of developing bacteremia and minimizing the effects of already existing bacteremia, sepsis, septic shock or related conditions. The amount of lactoferrin related peptides in the composition may vary from about 1 mg to about 100 g.

The guiding principle in the use of lactoferrin related peptides is to administer the treatment at the earliest signs of bacteremia, sepsis or septic shock being developed to attenuate the development of bacteremia and to reduce the extent of organ damage that results from sepsis and septic shock. The improvement is any observable or measurable improvement. Thus, one of skill in the art realizes that a treatment may improve the patient or subject's condition, but may not be a complete cure of the disease. In certain aspects, the composition is administered in an effective amount to decrease, reduce, inhibit or abrogate levels of bacteria in circulation. In further aspects, an improvement can consist of any of the following, for example, decrease in the levels of circulating bacteria, attenuating the development of sepsis, attenuating the development of septic shock, attenuating the development of organ failure, decreasing morbidity associated with bacteremia and decreasing mortality (death) associated with bacteremia. Thus, after administration of lactoferrin related peptides, if any of the above conditions improve, then the amount of lactoferrin related peptides are considered to be an effective amount. Yet further, administration of lactoferrin related peptides will also attenuate the development of sepsis, septic shock and other conditions related thereto.

In certain aspects, the composition is administered in an effective amount to decrease, reduce, inhibit or abrogate the severity of sepsis or septic shock. In further aspects, an improvement can consist of any of the following, for example, decreasing mortality, decreasing morbidity, attenuating the development organ failure, decreasing days of hospitalization, decreasing or eliminating days of intensive care such as in an intensive care unit, decreasing or eliminating the use of supportive care such as a mechanical ventilator or decreasing the incidence of sequelae such as ARDS. Survival in patients with organ failure at baseline and prevention and reversal of organ failure are also evaluated. Thus, after administration of lactoferrin related peptides, if any of the above conditions improve, then the amount of lactoferrin related peptides are considered to be an effective amount.

In certain aspects, the composition is administered in an effective amount to decrease, reduce, inhibit or abrogate the severity of ALI or ARDS. In further aspects, an improvement can consist of any of the following, for example, decrease in mortality, attenuating the development organ failure, decreasing days of hospitalization, decreasing or eliminating days of intensive care such as in an intensive care unit, or decreasing or eliminating the use of supportive care such as a mechanical ventilator or $PaO_2/FiO_2$ ratios. Thus, after administration of lactoferrin related peptides, if any of the above conditions improve, then the amount of are considered to be an effective amount.

In order to increase the effectiveness of the composition, it may be desirable to combine these compositions and methods of the invention with a known agent effective in the treatment or prevention of bacteremia, sepsis, septic shock and related conditions, for example known agents to treat bacterial infections, e.g., antibiotics, known agents for the treatment of sepsis, e.g., Drotrecogin alfa (activated) and agents to treat inflammation. In some embodiments, it is contemplated that a conventional therapy or agent, including but not limited to, a pharmacological therapeutic agent may be combined with the composition of the present invention.

The composition of the present invention may precede, be co-current with and/or follow the other agent(s) by intervals ranging from minutes to weeks. In embodiments where the composition of the present invention, and other agent(s) are applied separately to a cell, tissue or organism, one would generally ensure that a significant period of time did not expire between the time of each delivery, such that the composition and agent(s) would still be able to exert an advantageously combined effect on the cell, tissue or organism.

Various combination regimens of the composition and one or more agents are employed. One of skill in the art is aware that the composition of the present invention and agents can be administered in any order or combination. In other aspects, one or more agents may be administered substantially simultaneously, or within about minutes to hours to days to weeks and any range derivable therein, prior to and/or after administering the composition.

Administration of the composition to a cell, tissue or organism may follow general protocols for the administration of cardiovascular therapeutics, taking into account the toxicity, if any. It is expected that the treatment cycles would be repeated as necessary. In particular embodiments, it is contemplated that various additional agents may be applied in any combination with the present invention.

Pharmacological therapeutic agents and methods of administration, dosages, etc. are well known to those of skill in the art (see for example, the "Physicians Desk Reference", Goodman & Gilman's "The Pharmacological Basis of Therapeutics", "Remington's Pharmaceutical Sciences", and "The Merck Index, Eleventh Edition", incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

Non-limiting examples of a pharmacological therapeutic agent that may be used in the present invention include an antimicrobial agent, an anti-sepsis agent, an anti-inflammatory agent, an antithrombotic/fibrinolytic agent, a blood coagulant, an antiarrhythmic agent, an antihypertensive agent, a vasopressor, or agents to treat metabolic acidosis. In certain aspects of the present invention, antimicrobial agents, e.g., antibiotics are used in combination with the composition of the present invention.

a) Anti-microbial Agents

In certain embodiments, an "antimicrobial agent" can be used in combination with the lactoferrin composition. An antimicrobial agent may comprise an antibiotic, anti-fungal, and anti-viral agent.

Antibiotics inhibits the growth of microorganisms without damage to the host. For example, the antibiotic may inhibit cell wall synthesis, protein synthesis, nucleic acid synthesis, or alter cell membrane function. Classes of antibiotics that can possibly be used in conjunction with the peptide include, but are not limited to, macrolides (i.e., erythromycin), penicillins (i.e., nafcillin), cephalosporins (i.e., cefazolin), carbepenems (i.e., imipenem, aztreonam), other beta-lactam antibiotics, beta-lactam inhibitors (i.e., sulbactam), oxalines (i.e. linezolid), aminoglycosides (i.e., gentamicin), chloramphenicol, sulfonamides (i.e., sulfamethoxazole), glycopeptides (i.e., vancomycin), quinolones (i.e., ciprofloxacin), tetracyclines (i.e., minocycline), fusidic acid, trimethoprim, metronidazole, clindamycin, mupirocin, rifamycins (i.e., rifampin), streptogramins (i.e., quinupristin and dalfopristin) lipoprotein (i.e., daptomycin), polyenes (i.e., amphotericin B), azoles (i.e., fluconazole), and echinocandins (i.e., caspofungin acetate). Examples of specific antibiotics that can be used include, but are not limited to, erythromycin, nafcillin, cefazolin, imipenem, aztreonam, gentamicin, sulfamethoxazole, vancomycin, ciprofloxacin, trimethoprim, rifampin, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, gatifloxacin, moxifloxacin, gemifloxacin, enoxacin, fleroxacin, minocycline, linezolid, temafloxacin, tosufloxacin, clinafloxacin, sulbactam, clavulanic acid, amphotericin B, fluconazole, itraconazole, ketoconazole, and nystatin. Other examples of antibiotics, such as those listed in Sakamoto et al, U.S. Pat. NO: 4,642,104 herein incorporated by reference will readily suggest themselves to those of ordinary skill in the art.

Anti-viral agents can also be used in combination the peptide composition to treat and/or prevent a viral infection or disease. Such anti-viral agents include, but are not limited to protease inhibitors (e.g., saquinavir, ritonavir, amprenavir), reverse transcriptase inhibitors (e.g., azidothymidine (AZT), lamioridine (3TC), dideoxyinosine (ddI)), dideoxycytidine (ddC), zidovudine), nucleoside analogs (e.g., acyclovir, penciclovir).

In certain embodiments, anti-fungal agents can be used in combination with the peptide composition to treat and/or prevent a fungal infection. Such anti-fungal agents include, amphotericin B (Amphocin®, Fungizone®), butoconazole (Femstat®), clotrimazole (Mycelex®, Gyne-Lotrimin®, Lotrimin®, Lotrisone®), fluconazole (Diflucan®), flucytosine (Ancobon®), griseofulvin (Fulvicin P/G®, Grifulvin V®, Gris-PEG®), itraconazole (Sporanox®), ketoconazole (Nizoral®), miconazole (Femizol-M®, Monistat®), nystatin (Mycostatin®), terbinafine (Lamisil®), terconazole (Terazol®), or tioconazole (Vagistat®).

b) Other Agents

Anti-sepsis agents include, but are not limited to Drotrecogin alfa (activated). Agents used for the treatment of ALI and ARDS include but are not limited to intra-pulmonary instillation of surfactants, and leukotriene modifiers. Anti-inflammatory agents include, but are not limited to non-steroidal anti-inflammatory agents (e.g., naproxen, ibuprofen, celeoxib) and steroidal anti-inflammatory agents (e.g., glucocorticoids).

Non-limiting examples of non-pharmacologic interventions that may be used in the present invention include supportive care such as organ support in sepsis and septic shock and low tidal volume ventilation protocols in ALI and ARDS.

E. Pain

In accordance with the present invention, the composition provided in any of the above-described pharmaceutical carriers is administered to a subject who has experienced pain which may be acute or chronic in nature.

Causes of acute pain include, but are not limited to pain following trauma such as a blunt or sharp injury, bullet wounds, or surgery.

Causes of chronic pain include, but are not limited to pain associated with chronic diseases such as cancer, arthritis, inflammatory disease, chronic wounds, cardiovascular accidents, disorders of the spinal chord or central nervous system, and recovery from surgery.

In a preferred embodiment of the present invention, the composition is administered in an effective amount to decrease, reduce, inhibit or abrogate pain. Thus, a subject is administered a therapeutically effective amount of a lactoferrin composition so that the subject has an improvement in the parameters relating to pain including subjective measures such as pain scores and grading and objective measures including use of additional pain medications. The improvement is any observable or measurable improvement. Thus, one of skill in the art realizes that a treatment may improve the patient condition, but may not be a complete cure of the disease. The amount of lactoferrin in the composition may vary from about 1 ng to about 100 g each day.

In certain embodiments, the lactoferrin related peptide composition is administered to a subject to modulate chronic or acute pain in the subject. Modulation of pain is achieved by administering an effective amount of the composition to decrease, reduce, inhibit or abrogate pain. Specifically, it is contemplated that lactoferrin stimulates or enhances cytokine production or activity. For example, lactoferrin can enhance the production or activity of TNF-α resulting in modulation of pain, acute or chronic, in the subject.

In order to increase the effectiveness of the composition, it may be desirable to combine these compositions and methods of the invention with a known agent effective in the treatment of pain both directly and indirectly. In some embodiments, it is contemplated that a conventional therapy or agent, including but not limited to, a pharmacological therapeutic agent, a non-pharmacological pain management techniques or a combination thereof, may be combined with the composition of the present invention.

The composition of the present invention may precede, be co-current with and/or follow the other agent(s) by intervals ranging from minutes to weeks. In embodiments where the composition of the present invention, and other agent(s) are applied separately to a cell, tissue or organism, one would generally ensure that a significant period of time did not expire between the time of each delivery, such that the composition and agent(s) would still be able to exert an advantageously combined effect on the cell, tissue or organism.

Various combination regimens of the composition and one or more agents are employed. One of skill in the art is aware that the composition of the present invention and agents can be administered in any order or combination. In other aspects, one or more agents may be administered within of from substantially simultaneously, about minutes to hours to days to weeks and any range derivable therein, prior to and/or after administering the composition.

Administration of the composition to a cell, tissue or organism may follow general protocols for the administration of pain therapeutics, taking into account the toxicity, if any. It is expected that the treatment cycles would be repeated as necessary. In particular embodiments, it is contemplated that various additional agents may be applied in any combination with the present invention.

a) Pharmacological Therapeutic Agents

Pharmacological therapeutic agents and methods of administration, dosages, etc. are well known to those of skill in the art (see for example, the "Physicians Desk Reference", Goodman & Gilman's "The Pharmacological Basis of Therapeutics", "Remington's Pharmaceutical Sciences", and "The Merck Index, Eleventh Edition", incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

Non-limiting examples of a pharmacological therapeutic agent that may be used in the present invention include non-steroidal anti-inflammatory drugs (NSAIDS) (e.g., aspirin, indomethacin, ibuprofen, naproxen, acetaminophen, and ketoprofen); opioid analgesics (e.g., codeine, morphine, methadone, demerol, fentanyl, oxymorphone, and levorphanol), second generation NSAIDs (e.g., COX-2 inhibitors); and anti-depressant drugs (e.g., tricyclin antidepressants, sedatives, tranquilizers, hypnotics, anti-histamines, and amphetamines).

b) Non-Pharmacological Pain Techniques

In certain aspects, a therapeutic agent may comprise a non-pharmacological pain management techniques Non-pharmacological pain management techniques are well known to those of skill in the art, and may comprise, but are not limited to acupuncture or acupressure, local anesthesia/analgesia, regional anesthesia/analgesia (e.g., epidural or spinal analgesia/anesthesia), general anesthesia/analgesia (e.g., intravenous anesthetics or opioid pump) and chiropractic. Non-pharmacological pain-reduction agents include, but are not limited to devil's, capsaicin, menthold or L-phenylalanine.

F. Cardiovascular Diseases

In accordance with the present invention, the composition provided in any of the above-described pharmaceutical carriers is administered to a subject who has experienced or is at risk of developing cardiovascular disease. Risk factors include, but are not limited to elevated levels of cholesterol or CRP. One of skill in the art can determine the patients who would potentially benefit from a therapeutic agent that would reduce circulating levels of total cholesterol or triglycerides or cardiovascular inflammation.

Cardiovascular diseases and/or disorders include, but are not limited to, diseases and/or disorders of the pericardium, heart valves (e.g., incompetent valves, stenosed valves, Rheumatic heart disease, mitral valve prolapse, aortic regurgitation), myocardium (e.g., coronary artery disease, myocardial infarction, heart failure, ischemic heart disease, angina) blood vessels (e.g., hypertension, arteriosclerosis, aneurysm) or veins (e.g., varicose veins, hemorrhoids). In specific embodiments, the cardiovascular disease is atherosclerosis.

In specific embodiments of the present invention, the peptide composition is administered to a subject suffering from or at risk for developing atherosclerosis. Thus, it is envisioned that the peptide composition modulates or reduces the severity and/or incidence of atherosclerosis.

Prophylactic treatment can be administered to those subjects at risk for developing atherosclerosis. One risk factor is an atherogenic lipoprotein profile. For example, a ratio of serum cholesterol to high density lipoproteins of above 5:1 indicates a higher than average risk of developing atherosclerosis. Other factors indicating increased risk for atherosclerosis include a serum cholesterol level of above 240 mg/dl; a high density lipoprotein level below about 35 mg/dl; and a low density lipoprotein level above about 160 mg/dl.

Another embodiment includes treating a human subject with an elevated level of circulating total cholesterol or CRP according to the then medically established guidelines. It is contemplated that the composition of the present invention reduces or attenuates the levels of circulating total cholesterol, low density lipoproteins or very low density lipoproteins. It is contemplated that the composition of the present invention can interfere with how cholesterol enters the circulation either via absorption from food (exogenous pathway) or synthesis by the liver (endogenous pathway).

Another embodiment includes treating a human subject having dyslipidemia. Dyslipidemias are disorders of lipoprotein metabolism, including lipoprotein overproduction or deficiency. These disorders may be manifested by elevation of the serum total cholesterol, low-density lipoprotein (LDL) cholesterol and triglyceride concentrations, and a decrease in the high-density lipoprotein (HDL) cholesterol concentration. Thus, it is envisioned that the composition of the present invention can reduce or abborage the effects of lipoprotein metabolism, such as dyslipidemia.

In a preferred embodiment of the present invention, the composition is administered in an effective amount to decrease, reduce, inhibit or abrogate cardiovascular disease. Thus, a subject is administered a therapeutically effective amount of a lactoferrin composition so that the subject has an improvement in the parameters relating to cardiovascular disease including circulating levels of total cholesterol, HDL, LDL, VLDL, triglycerides and C-reactive protein (CRP). The amount of lactoferrin in the composition may vary from about 1 ng to about 20 g. Preferably, the composition that is orally administered contains the range of 0.5 g to 5 g of lactoferrin per day.

The improvement is any observable or measurable improvement. Thus, one of skill in the art realizes that a treatment may improve the patient condition, but may not be a complete cure of the disease. In certain aspects, the composition is administered in an effective amount to decrease, reduce, inhibit or abrogate excess amounts of cholesterol levels in circulation. A subject requires treatment for cholesterol levels based upon any of the following situations: LDL of 160 mg/ml or greater; LDL of 130-159 mg/ml and also have two or more cardiovascular risk factors; LDL of 100 mg/ml or greater in subjects with coronary heart disease (CHD); triglycerides of 200 mg/dl or higher; total cholesterol of 240 mg/dl or higher or HDL of less than 40 mg/dl. Thus, after administration of lactoferrin related compounds, if any of the above conditions improve, then the amount is considered an effective amount to decrease, reduce, inhibit or abrogate cholesterol levels in the circulation.

Another embodiment is a method of reducing vascular inflammation by administering the composition of the present invention. Vascular inflammation can be tied to a number of the underlying processes contributing to atherosclerosis which include endothelial dysfunction, vascular proliferation and matrix alteration. Recent studies have emphasized the involvement of inflammation in mediating all stages of atherosclerosis. Vascular inflammation is thought to be a consequence of damage to the vascular endothelium and may also involve the proliferation of vascular smooth muscle cells (vsmcs). One precursor of lesion development in humans may be focal accumulation of vsmcs within the intima. In early atherosclerosis, vsmcs may contribute to the development of the atheroma through the production of pro-inflammatory mediators such as monocyte chemoattractant protein 1 and vascular cell adhesion molecule, and through the synthesis of matrix molecules required for the retention of lipoproteins. Inflammation of the vascular endothelium and proliferation of vsmcs may also impact the stability of the plaque through the formation of a firm fibrous cap. Indeed, in lipid-laden lesions in which the fibrous cap is thin and weak, there is evidence of vsmc apoptosis, especially at the "shoulder" region, associated with inflammation. In addition, the local inflammatory milieu can induce expression of collagenase and inhibit expression of proteolytic inhibitors, thus rendering the fibrous cap weak and susceptible to rupture. Lactoferrin, having known anti-inflammatory properties, may thus serve to inhibit the underlying processes associated with the development of atherosclerosis.

In further embodiments, the composition may also reduce vascular spasms or vascular hyper-reactivity. Vascular spasms are a sudden, brief tightening of a blood vessel, which can temporarily reduce blood flow to tissues supplied by that vessel.

Still further, the composition may also promote endothelial integrity or healing. Endothelia are the layer of cells lining the blood vessels. Endothelial dysfunction most commonly refers to impairment of endothelium-dependent vasodilation and widespread abnormalities in endothelial integrity and homeostasis. It is believed that HDLs help maintain endothelial integrity, facilitate vascular relaxation, inhibit blood cell adhesion to vascular endothelium, reduce platelet aggregability and coagulation, and may favor fibrinolysis. The integrity or completeness of the endothelia lining of the vessels is important to preventing/treating the development of plaques and atherosclerosis. Thus, it is envisioned that the composition of the present invention will promote or modulate endothelial integrity or healing.

Yet further, another embodiment is a method of preventing a cardiovascular disease in a subject at risk for developing a cardiovascular disease comprising the step of administering to the subject a peptide composition in an amount sufficient to result in prophylaxis of the cardiovascular disease in the subject. In preferred embodiments, the cardiovascular disease is atherosclerosis. It is envisioned that the composition not only possess therapeutic benefits for those subjects suffering from cardiovascular diseases, but also possess prophylactic properties for those subjects at risk for developing cardiovascular disease. A subject at risk may or may not be cognizant of their disease state or potential disease state and may or may not be aware that they are need of treatment. Thus, prophylatically, it is envisioned that the composition can reduce any of the following: the levels of circulating total cholesterol, low density lipoproteins (LDL), very low density lipoproteins (VLDL), levels of vascular inflammation, circulating C-reactive protein (CRP), triglycerides, and the proliferation of vascular smooth muscle cells in the subject. Yet further, the composition may also increase the levels of circulating high density lipoproteins (HDL).

In order to increase the effectiveness of the composition, it may be desirable to combine these compositions and methods of the invention with a known agent effective in the treatment or prevention of cardiovascular disease or disorder, for example known agents to treat or prevent atherosclerosis. In some embodiments, it is contemplated that a conventional therapy or agent, including but not limited to, a pharmacological therapeutic agent, a surgical therapeutic agent (e.g., a surgical procedure) or a combination thereof, may be combined with the composition of the present invention.

The composition of the present invention may precede, be co-current with and/or follow the other agent(s) by intervals ranging from minutes to weeks. In embodiments where the composition of the present invention, and other agent(s) are applied separately to a cell, tissue or organism, one would generally ensure that a significant period of time did not expire between the time of each delivery, such that the composition and agent(s) would still be able to exert an advantageously combined effect on the cell, tissue or organism.

Various combination regimens of the composition and one or more agents are employed. One of skill in the art is aware that the composition of the present invention and agents can be administered in any order or combination. In other aspects, one or more agents may be administered substantially simultaneously, or within about minutes to hours to days to weeks and any range derivable therein, prior to and/or after administering the composition.

Administration of the composition to a cell, tissue or organism may follow general protocols for the administration of cardiovascular therapeutics, taking into account the toxicity, if any. It is expected that the treatment cycles would be repeated as necessary. In particular embodiments, it is contemplated that various additional agents may be applied in any combination with the present invention.

a) Pharmacological Therapeutic Agents

Pharmacological therapeutic agents and methods of administration, dosages, etc. are well known to those of skill in the art (see for example, the "Physicians Desk Reference", Goodman & Gilman's "The Pharmacological Basis of Therapeutics", "Remington's Pharmaceutical Sciences", and "The Merck Index, Eleventh Edition", incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

Non-limiting examples of a pharmacological therapeutic agent that may be used in the present invention include an antihyperlipoproteinemic agent, an antiarteriosclerotic agent, an anti-cholesterol agent, an anti-inflammatory agent, an anti-thrombotic/fibrinolytic agent, a blood coagulant, an antiarrhythmic agent, an antihypertensive agent, or a vasopressor. In certain aspects of the present invention, anti-cholesterolemic agents are used in combination with the composition of the present invention. Anti-cholesterol agents include but are not limited to HMG-CoA Reductase inhibitors, cholesterol absorption inhibitors, bile acid sequestrants, nicotinic acid and derivatives thereof, fibric acid and derivatives thereof. HMG-CoA Reductase inhibitors include statins, for example, but not limited to atorvastatin calcium (Lipitor®), cerivastatin sodium (Baycol®), fluvastatin sodium (Lescol®), lovastatin (Advicor®), pravastatin sodium (Pravachol®), and simvastatin (Zocor®). Agents known to reduce the absorption of ingested cholesterol include, for example, Zetia®. Bile acid sequestrants include, but are not limited to cholestyramine, cholestipol and colesevalam. Other anti-cholesterol agents include fibric acids and derivatives thereof (e.g., gemfibrozil, fenofibrate and clofibrate); nicotinic acids and derivatives thereof (e.g., nician, lovastatin) and agents that extend the release of nicotinic acid, for example niaspan. Anti-inflammatory agents include, but are not limited to non-steroidal anti-inflammatory agents (e.g., naproxen, ibuprofen, celeoxib) and steroidal anti-inflammatory agents (e.g., glucocorticoids).

b) Surgical Therapeutic Agents

In certain aspects, a therapeutic agent may comprise a surgery of some type, which includes, for example, preventative, diagnostic or staging, curative and palliative surgery. Surgery, and in particular a curative surgery, may be used in conjunction with other therapies, such as the present invention and one or more other agents.

Such surgical therapeutic agents for cardiovascular diseases and disorders are well known to those of skill in the art, and may comprise, but are not limited to, performing surgery on an organism, providing a cardiovascular mechanical prostheses, angioplasty, coronary artery reperfusion, catheter ablation, providing an implantable cardioverter defibrillator to the subject, mechanical circulatory support or a combination thereof. Non-limiting examples of a mechanical circulatory support that may be used in the present invention comprise an intra-aortic balloon counterpulsation, left ventricular assist device or combination thereof.

G. Autoimmune Disorders

According to the present invention, a subject that is suspected of an autoimmune disease or a subject suffering from an autoimmune disease is treated with the peptide composition of the present invention.

The pathogenesis of autoimmune disorders is mediated by the aberrant activation, differentiation and trafficking of leukocytes in response to tissue self-antigens. Autoimmune reactions can often have fatal consequences. They can cause the destruction of vital tissue which manifests in the development of chronic autoimmune diseases. The driving forces in the progression of these diseases are autoreactive immune cells. In most cases, these autoreactive cells are CD4+ T-cells which somehow escaped the self-tolerance control mechanisms of the immune system. In non-pathogenic situations, CD4+ T-cells act as T helper cells, which control or mediate the activation and differentiation of other immune cells such as cytotoxic CD8+ T-cells, NK cells, granulocytes, macrophages and B-cells. However, in the situation of chronic autoimmune diseases, CD4+ T-cells are no longer just mediators, but are rather key players of the autoimmune response. In particular, they are either directly or indirectly responsible for the characteristic tissue destruction that occurs in autoimmune diseases, which is triggered by the recognition of autoantigens. These autoantigens are derived from self-proteins of the attacked tissue and are presented to the autoreactive CD4+ T-cells by antigen-presenting cells (APCs), such as macrophages, dendritic cells or B-cells. In addition, aberrant T cell-dependent or T cell-independent antibody production by activated B cells plays a critical role in initiating and amplifying tissue damage in autoimmune disorders.

Such autoimmune disorders that can be treated using the composition of the present invention include, but are not limited to, the following: Alopecia Areata, Ankylosing Spondylitis, Antiphospholipid Syndrome, aplastic anemia, myelodysplastic syndromes, paroxysmal nocturnal hemoglobulinemia, pure red cell aplasia, chronic neutropenias, amegakaryocytic thrombocytopenia, antiphospholipid syndromes, autoimmune thrombocytopenia, autoimmune hemolytic syndromes, antiphospholipid syndromes, autoimmune gastritis, achlorhydria, Autoimmune Addison's Disease, Autoimmune Diabetes, Autoimmune Hemolytic Anemia, Autoimmune Hepatitis, Autoimmune hypophysitis, Autoimmune orchiditis, autoimmune ovarian failure, Behcet's Disease, Bullous Pemphigoid, Cardiomyopathy, Celiac Sprue-Dermatitis, Cicatrical pemphigoid, Chronic Fatigue Immune Dysfunction Syndrome (CFIDS), Chronic Inflammatory Demyelinating Polyneuropathy, Interstitial cystitis, Churg-Strauss Syndrome, Cicatricial Pemphigoid, CREST Syndrome, Cold Agglutinin Disease, Crohn's Disease, Dermatitis herpetiformis, Discoid Lupus, Drug-induced autoimmune disorders, Endometriosis, Epidermolysis bullosa acquisita, Essential Mixed Cryoglobulinemia, Fibromyalgia-Fibromyositis, Glomerulonephritis, Good Pasture Syndrome, Graft Versus Host Disease, Graves' Disease, Guillain-Barré, Hashimoto's Thyroiditis, Idiopathic Inflammatory Myopathies, Idiopathic Pulmonary Fibrosis, Idiopathic Thrombocytopenia Purpura (ITP), IgA Nephropathy, Insulin Dependent Diabetes, Juvenile Arthritis, Lichen Planus, Systemic Lupus Erythmatosis, Ménière's Disease, Metal-induced autoimmunity disorders, Mixed Connective Tissue Disease, Multiple Sclerosis, Myasthenia Gravis, Myocarditis, Myositis, Optic neuritis, Painless/postpartum thyroiditis, Peripheral nerve vasculitis, Pemphigus Foliaceus, Pemphigus Vulgaris, Pernicious Anemia, Polyarteritis Nodosa, Polychondritis, Polyglandular Syndromes, Polymyalgia Rheumatica, Polymyositis and Dermatomyositis, Postinfectious autoimmune disorders, Primary Agammaglobulinemia, Primary Biliary Cirrhosis, Psoriasis, Psoriatic Arthritis, Reactive Arthritis, Raynaud's Phenomenon, Reiter's Syndrome, Rheumatic Fever, Rheumatoid Arthritis, Sarcoidosis, Scleritis, Scleroderma, Sjögren's Syndrome, Stiff-Man Syndrome, Takayasu Arteritis, Temporal Arteritis/Giant-cell Arteritis, Ulcerative Colitis, Uveitis, Vasculitis, Vitiligo, and Wegener's Granulomatosis.

In certain embodiments, the composition of the present invention is administered to a subject suffering from graft versus host disease (GVHD), organ transplant rejection, autoimmune hepatitis, primary biliary cirrhosis, autoimmune cholangitis, primary sclerosing cholangitis, irritable bowel syndrome (IBS), multiple sclerosis (MS), chronic granulomatous disease, ankylosing spondylitis, scleroderma, polymyositis, (dermato)myositis, systemic vasculitis, systemic lupus erythematosus (SLE), Chrohn's disease, insulin-dependent diabetes (type 1) or ulcerative colitis.

1. Organ Transplant Rejection and GVHD

In accordance with the present invention, the composition provided in any of the above-described pharmaceutical carriers is administered as a therapeutic drug to a subject who has undergone organ transplant (kidney, heart, lung, liver, pancreas, bone marrow, peripheral stem cells) and/or as a prophylactic drug to organ and/or tissue transplant, for example bone marrow (BM) or peripheral stem cell donor cells, to prevent the development of GVHD in recipients and/or to prevent or attenuate transplant rejection in the recipients. One of skill in the art can determine the patients who would potentially benefit from a therapeutic agent that would reduce chronic allograft rejection and toxicity associated with standard therapy, or the development of GVHD.

A further embodiment is treating, preventing or reducing the risk of developing graft-versus-host-disease by administering a lactoferrin composition to the donor organ or donor tissue prior to transplantation into the recipient. It is envisioned that administering the composition to the donor tissue/organ will attenuate the immune cells in the donor/organ and prevent the development of the immune response that is mounted against the recipient's tissue, thus preventing or attenuating GVHD. In further embodiments, the recipient and the donor organ/tissue can be treated with the composition of the present invention.

Additional embodiments of the present invention include a method of treating, preventing or attenuating the severity of tissue or organ transplant rejection in a recipient comprising the step of administering to the donor a lactoferrin composition in an amount sufficient to attenuate the tissue or organ transplant rejection in the recipient. It is envisioned that the composition reduces allogeneic immune responses in the recipient. The composition can also be administered to both the recipient and the donor.

Another embodiment is a method of treating, preventing or attenuating the severity of xenograft tissue or xenograft organ transplant rejection in a recipient comprising the step of administering to the xenograft donor a composition in an amount sufficient to attenuate the tissue or organ transplant rejection in the recipient. The composition can also be administered to both the recipient and the xenograft donor.

In particular embodiments, progenitor cells or stem cells may be isolated from at least one organ, cell, tissue or organism. Stem cells can be isolated from embryonic or nonembryonic donors. The tissues from which the stem cells can be isolated include, for example, but are not limited to the bone marrow, the spleen, the liver, peripheral blood, umbilical cord tissue, umbilical cord blood, adipose tissue or skin. Yet further, tissue grafts may be used in the present invention. The tissue may be part or separated from an organism. In certain embodiments, a tissue may comprise, but is not limited to, adipocytes, alveolar, ameloblasts, axon, basal cells, blood (e.g., lymphocytes), blood vessel, bone, bone marrow, peripheral stem cells, brain, breast, cartilage, cervix, colon, cornea, embryonic, endometrium, endothelial, epithelial, esophagus, facia, fibroblast, follicular, ganglion cells, glial cells, goblet cells, kidney, liver, lung, lymph node, muscle, neuron, ovaries, pancreas, peripheral blood, prostate, skin, skin, small intestine, spleen, stem cells, stomach, testes, or ascite tissue.

In specific embodiments, an organ is the graft. Organs are comprised of tissues having a special function. Exemplary organs that are used in grafts in the present invention include, but are not limited to heart, kidney, pancreas, lung, or liver.

In a preferred embodiment of the present invention, the composition is administered in an effective amount to decrease, reduce, inhibit or abrogate chronic allograft rejection and toxicity related to standard therapy. The amount of lactoferrin in the composition may vary from about 1 ng to about 100 g, more preferably, 1 mg to about 20 g. Preferably, the composition that is orally administered contains the range of 0.1 g to 5 g of lactoferrin per day.

The improvement is any observable or measurable improvement. Thus, one of skill in the art realizes that a treatment may improve the patient or subject's condition, but may not be a complete cure of the disease. In certain aspects, the composition is administered in an effective amount to decrease, reduce, inhibit or abrogate levels of an immune response against a graft in the recipient. In further aspects, an improvement can consist of any of the following, for example, increased function of the graft, for example, increased urine output for kidney grafts or decreased jaundice for liver grafts; reduction in inflammation; reduction in general discomfort of the recipient; an overall increased tolerance for the graft. Thus, after administration of lactoferrin related peptides, if any of the above conditions improve, then the amount is considered to be an effective amount.

An improvement in GHVD is also any observable or measurable improvement. Thus, one of skill in the art realizes that a treatment may improve the patient or subject's condition, but may not be a complete cure of the disease. In certain aspects, the composition is administered in an effective amount to decrease, reduce, inhibit or abrogate levels of immune response from the donor's cells, tissue and/or organ against the host's tissues. GVHD can be acute or chronic or mild or severe. Improvements in acute symptoms include any of the following, for example, decrease skin rash, decrease diarrhea, increase in liver function, a decrease in susceptibility to infection. Improvements in chronic symptoms include, but are not limited to decrease skin rash, decrease dermatitis, decrease hair loss, a decrease liver damage, decrease dry eyes and mouth, a decrease susceptibility to infections and decrease lung and/or gastrointestinal disorders. Thus, after administration of lactoferrin related peptides, if any of the above conditions improve, then the amount is considered to be an effective amount.

Still yet, a further embodiment is a method of regulating a mucosal immune response in the gastrointestinal tract or a systemic immune response in a subject comprising the step of administering a lactoferrin related peptide composition to said subject the composition of the present invention. It is envisioned that composition stimulates MIP-3α and interleukin-18 in the gastrointestinal tract, which regulates immune responses. For example, interleukin-18 modulates both Th1/Th2 responses. It is known by those of skill in the art that IL-18 plays an important role in allogeneic stem cell transplantation. Pre-treatment of allogeneic donors with IL-18 significantly improves survival and reduces clinical and pathological indices of acute GVHD in BMT recipients. Other cytokines may also be enhanced or repressed for example, but not limited to IL-1, IL-2, IL-6, IL10, IL-12 and GM-CSF. It is also envisioned that lactoferrin stimulates Th1/Th2 type-responses through the induction and/or repression of Th1 and Th2 cytokines.

In order to increase the effectiveness of administration of the composition of the present invention, it is desirable to combine these compositions with standard therapy. For example, known immunosuppressant agents are used in combination with the composition of the present invention. Exemplary agents known to prevent organ rejection are T cell modifiers such as cyclosporine (Neoral®, Sandimmune®), prednisone (Novo Prednisone®, Apo Prednisone®), azathioprine (Imuran®), tacrolimus or FK506 (Prograf®), mycophenolate mofetil (CellCept®), OKT3 (Muromorab CO3®, Orthoclone®), ATGAM® & Thymoglobulin® or serine-threonine phosphatase calcineurin (CN) inhibitors. In specific embodiments, the standard or approved treatment of GVHD, which is high doses corticosteroids, primarily high-dose methylprednisolone, is used in combination with the lactoferrin composition of the present invention.

In addition to immunosuppressant other anti-rejection and/or anti-GVHD therapies can be used in combination with the lactoferrin composition of the present invention. For example, therapies for preconditioning and prophylaxis of GVHD include, but are not limited to total body irradiation, cytosine arabinoside, L-phenylalanine mustard, cyclophosphamide, etoposide, triethylene thiophosphoramide, antithymocyte globulin, bisulfan, tacrolimus, methylprednisolone, cyclosporin, or methotrexate. Experimental therapies for treatment of GVHD include, but are not limited to cytokine inhibitors/antagonists (e.g., anti-TNFα antibody); IL-1 receptor antagonist; recombinant IL-1 receptor; inhibitors of T-cell activation (e.g., tacrolimus); antimetabolites (e.g., mycophenolate mofetil); anti-CD3 antibody (muromonab, OKT3); anti-CD25 antibody; anti-IL2 receptor monoclonal antibody daclizumab; extracorporeal photopheresis using ex vivo 8-methoxypsoralen; anti-thymocyte globulins (Thymoglobulin® or ATGAM®); ABX-CBL or CBL-1; or Visilizumab (Nuvion®).

The composition of the present invention may precede, be co-current with and/or follow the other agent(s) by intervals ranging from minutes to weeks. In embodiments where the composition of the present invention, and other agent(s) are applied separately to a cell, tissue or organism, one would generally ensure that a significant period of time did not expire between the time of each delivery, such that the composition and agent(s) would still be able to exert an advantageously combined effect on the cell, tissue or organism.

Various combination regimens of the composition and one or more agents are employed. One of skill in the art is aware that the composition of the present invention and agents can be administered in any order or combination.

H. Endocrine/Metabolism Disorders

1. Diabetes Mellitus

In accordance with the present invention, the composition provided in any of the above-described pharmaceutical carriers is administered to a subject who has experienced or is at high risk of having diabetes mellitus. Thus, it is envisioned that the composition of the present invention may be administered to a subject to regulate diabetes mellitus. The composition modulates at least one symptom of diabetes mellitus, for example, decrease blood glucose or modulate blood insulin levels.

Risk factors for type I diabetes include islet-cell antibodies and those of type 2 or gestational diabetes include inactivity, obesity, siblings with diabetes, and history of diabetes during pregnancy. One of skill in the art can determine the patients who would potentially benefit from a therapeutic agent that would reduce circulating levels of glucose.

In a preferred embodiment of the present invention, the composition is administered in an effective amount to decrease, reduce, inhibit or abrogate high glucose, or to reduce total body weight, glycosylated hemoglobin (HbA1c), or blood pressure or to modulate blood insulin levels. In the case of a diabetic condition, successful reduction of hyperglycemia by the lactoferrin composition may be manifested by the fasting plasma glucose level falling below 126 mg/dL, the 2-hour plasma glucose level during an oral glucose tolerance test (OGTT) falling below 200 mg/dL, or if a random plasma glucose determination reading below 200 mg/dL in a symptomatic individual. In the case of a pre-diabetic condition, a successful reduction of hyperglycemia by the lactoferrin composition may be manifested by the fasting plasma glucose falling below 110 mg/dL and/or the 2-hour plasma glucose on the OGTT falling below between 140 mg/dL. The amount of lactoferrin related peptides in the composition may vary from about 0.1 µg to about 100 g, more preferably, from about 1 µg to about 20 g, or any range therebetween. In specific embodiments, the composition that is administered contains the range of 0.1 g to 5 g of lactoferrin per day.

Glycohemoglobin (or glycosylated hemoglobin) is measured to monitor or accurately record blood glucose levels, and it is not influenced by acute changes in blood glucose or by the interval since the last meal. Glycohemoglobin is formed when glucose reacts non-enzymatically with the hemoglobin A molecule and is composed of several fractions, the major one being HbA1c. Total glycohemoglobin (HbA1) and HbA1c (expressed as the percentage of total hemoglobin) vary in proportion to the average level of glucose over the lifespan of the red blood cell (RBC), thereby providing an index of glycemic control.

Further aspects of the invention include reducing blood glucose in a patient suffering from diabetes mellitus by administering to a subject an effective amount of the composition such that the amount of the lactoferrin related peptides modulates blood glucose. The blood glucose is monitored by the level of glycosylated hemoglobin (HbA1c).

Another aspect is a method of modulating blood insulin in a patient suffering from diabetes mellitus by administering to a subject an effective amount of the composition such that the amount modulates blood insulin. Modulating blood insulin includes reducing or maintaining blood insulin levels or increasing blood insulin levels. Modulating blood insulin levels in the present invention includes increasing blood insulin levels in insulin-dependent diabetes (Type I) or decreasing or maintaining insulin levels in non-insulin-dependent diabetes (Type II).

In order to increase the effectiveness of administration of the composition of the present invention, it is desirable to combine the compositions with an additional agent. For example, known diabetes agents are used in combination with the composition of the present invention. Exemplary agents known to treat high glucose or insulin sulfonylureas, biguanides, alpha-glucosidase, thiazolidinedione, meglitinide, and amino acid D-phenylalanine derivative. Other antidiabetic agents may also include, a weight loss regimen and/or a diet alteration.

The composition of the present invention may precede, be co-current with and/or follow the other agent(s) by intervals ranging from minutes to weeks. In embodiments where the composition of the present invention, and other agent(s) are applied separately to a cell, tissue or organism, one would generally ensure that a significant period of time did not expire between the time of each delivery, such that the composition and agent(s) would still be able to exert an advantageously combined effect on the cell, tissue or organism.

Various combination regimens of the composition and one or more agents are employed. One of skill in the art is aware that the composition of the present invention and agents can be administered in any order or combination.

2. Treatment of Fragile Bone Diseases

In accordance with the present invention, the peptide composition provided in any of the above-described pharmaceutical carriers is administered to a subject suspected of or having a fragile bone condition.

The present invention is designed for the treatment of any type of fragile bone condition or any disorder relating to bone loss including but not limited to osteoporosis, age-associated osteoporosis, postmenopausal osteoporosis, osteitis deformans (Paget's disease), osteogenesis imperfecta (brittle bones), and osteopetrosis.

Bone loss disorders arise from an imbalance in the formation of new healthy bone and the resorption of old bone, skewed toward a net loss of bone tissue. This bone loss includes a decrease in both mineral content and protein matrix components of the bone, and leads to an increased fracture rate of, predominantly, femoral bones and bones in the forearm and vertebrae. These fractures, in turn, lead to an increase in general morbidity, a marked loss of stature and mobility, and, in many cases, an increase in mortality resulting from complications.

Bone loss occurs in a wide range of subjects, including postmenopausal women, patients who have undergone hysterectomy, patients who are undergoing or have undergone long-term administration of corticosteroids, patients suffering from Cushing's syndrome, and patients having gonadal dysgensis.

Unchecked, bone loss can lead to osteoporosis, a major debilitating disease whose prominent feature is the loss of bone mass (decreased density and enlargement of bone spaces) without a reduction in bone volume, producing porosity and fragility.

Osteoporosis is common in the elderly of both sexes but is more pronounced in postmenopausal women. Osteoporosis may occur as a primary disorder or as a secondary complication of several diseases. It is proposed that genetic factors determine the size of the bone mass achieved in young adulthood. With aging, the increased osteoclastic function and the slowing of osteoblastic activity induced by endocrine influences, particularly decreased estrogen levels, result in a net negative balance in the continued turnover of bone. Osteoporosis causes bone pain owing to microfractures; results in loss in height and stability of the vertebral column; and predisposes to fractures of femoral necks, wrists, and vertebrae. The condition remains asymptomatic until skeletal fragility is well advanced.

Paget's disease is currently considered to be a slow paramyxoviral infection of osteoblasts and then osteoclasts. The condition is divided into an initial osteolytic stage, followed by a mixed osteolytic-osteoblastic stage, evolving ultimately into burn-out quiescent osteosclerotic stage. Because new bone formation in active disease is disordered and poorly mineralized, it is soft and porous, lacks structural stability, and is vulnerable to fracture or deformation under stress. Patients may demonstrate fractures, nerve compression, osteoarthritis, and skeletal deformities.

Osteogenesis imperfecta or brittle bones refers to a group of closely related genetic disorders caused by qualitative or quantitative abnormal synthesis of type I collagen, constituting about 90% of the matrix of bone. Syndromes range from one variant (type II) that is uniformly fatal in the perinatal period (from multiple bone fractures) to other variants marked by increased predisposition to fracture but compatible with survival. Morphologically the basic change in all is osteopenia or too little bone, with marked thinning of the cortices and rarefication of the trabeculae.

Osteopetrosis refers to a group of rare hereditary diseases characterized by overgrowth and sclerosis of bone, with marked thickening of the cortex and narrowing or filling of the medullary cavity impairing hematopoiesis. Despite too much bone, it is brittle and fractures easily. The autosomal recessive form is evident from birth, with anemia, neutropenia, infections and eventual death. The autosomal dominant form is benign but predisposes to fractures. Common to all forms is a hereditary defect in osteoclast function resulting in reduced bone resorption and enhanced net bone overgrowth.

In a preferred embodiment of the present invention, lactoferrin related peptides are administered in an effective amount to stabilize or reduce bone fragility, to strengthen the bone, inducing the growth of healthy bone, modulate calcium levels, and modulate mineral accumulation in the skeleton. The amount may vary from about 1 µg to about 100 g of lactoferrin related peptides. Preferably, the amount that is administered is in the range of 10 mg to 25 g. Most preferably, the amount that is administered is in the range of 10 µg to 5 g.

It is often desirable to deliver the composition of the present invention to the subject over prolonged periods of time, for example, for periods of one week to one year from a single administration. Various slow release, depot or implant dosage forms may be utilized. For example, a dosage form a may contain a pharmaceutically acceptable non-toxic salt of the compounds which has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b) e.g. a zinc tannate salt. Additionally, the compounds of the present invention or, preferably, a relatively insoluble salt such as those just described, may be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed for encapsulation in a slow degrading, non-toxic, non-antigenic polymer such as a polylactic acid/polyglycolic acid polymer for example as described in U.S. Pat. No. 3,773,919. The compounds or, preferably, relatively insoluble salts such as those described above may also be formulated in cholesterol matrix silastic pellets, particularly for use in animals. Additional slow release, depot or implant formulations, e.g. liposomes, are well known in the literature. See, for example, "Sustained and Controlled Release Drug Delivery Systems", J. R. Robinson ed., Marcel Dekker, Inc., N.Y., 1978.

Still yet, a further embodiment is a method of promoting the stimulation or inhibition of cytokines, growth factors or mediators of bone growth or resorption. Such growth factors include, but not limited to insulin-like growth factor-1 (IGF-1), transforming growth factor-beta (TGF-b), and growth hormone releasing factor (GRF). Mediators of bone growth or resorption include, but are not limited to parathyroid hormone (PTH), calcitonin or 1,25-dihydroxycholecalciferol (1,25 (OH)2D3).

Still yet, a further embodiment is a method of activating or inhibiting cells involved in bone remodeling including but not limited to osteoblasts, osteoclasts, chondrocytes, endothelial cells, and fibroblasts.

In order to increase the effectiveness of the composition of the present invention, it may be desirable to combine the composition of the present invention with other agents effective in the treatment of fragile bone diseases including but not limited to calcium and cholecalciferol (vitamin D) supplements, estrogen replacement therapy (ERT), raloxifene, calcitonin, bisphosphonates such as alendronate and cyclical etidronate, statins, recombinant human parathyroid hormone (rhPTH), insulin-like growth factor-1 (IGF-1), and transforming growth factor-beta (TGF-1). This process may involve administering the lactoferrin composition of the present invention and the agent(s) or multiple factor(s) at the same time. This may be achieved by administering a single composition or pharmacological formulation that includes both agents, or by administering two distinct compositions or formulations, at the same time, or at times close enough so as to result in an overlap of this effect, wherein one composition includes the human lactoferrin composition and the other includes the second agent(s).

Alternatively, the composition of the present invention may precede or follow the other bone healing agent treatment by intervals ranging from minutes to weeks. In embodiments where the other bone healing agent and the inventive composition are administered or applied separately, one would generally ensure that a significant period of time did not expire between the time of each delivery, such that the agent and the composition would still be able to exert an advantageously combined effect on the condition.

I. Immunosuppressed Subjects

In order to carry out methods of the present invention, the composition of the present invention is administered to an immunosuppressed individual or an individual whose immune system is expected to be suppressed.

As noted above, the subject method is suited for preventing infection and/or inflammation in immunosuppressed individuals or individuals whose immune systems are expected to be repressed. In one aspect, the immunosuppressed subject exhibits neutropenia, or suffers from AIDS or any form of cancer including lymphoma and myeloma. In yet another aspect, the subject undergoes or is expected to undergo a therapy selected from the group consisting of chemotherapy, radiotherapy, and autologous peripheral stem cell transplant.

An effective amount of the lactoferrin composition depends on the severity and/or course of immunosuppression, the patient's clinical history and response, and the discretion of the attending physician. The composition is suitably administered to the patient at one time or over a series of treatments. The initial candidate dosage may be administered to a patient. The proper dosage and treatment regimen can be established by monitoring the progress of therapy using conventional techniques known to the people skilled of the art.

The amount of active ingredients that may be combined with the carrier materials to produce a single dosage form will vary depending upon the subject treated and the particular mode of administration. It will be understood, however, that the specific dose level for any particular patient will depend upon a variety of factors, including the activity of the specific composition employed, the age, body weight, general health, sex, diet, time of administration, route of administration, and rate of excretion, drug combination and the severity of the particular disease undergoing therapy, and can be determined by those skilled in the art.

In order to achieve effective prophylaxis, preferably, the lactoferrin composition is administered prior to the inception neutropenia, more specifically Grade 3 or higher neutropenia and continued on the same schedule daily for the entire period during which the patient is at a high risk of neutropenic fever, infection or mucositis.

It is envisioned that the immune response is enhanced by lactoferrin stimulating cytokines and/or chemokines. Exemplary cytokines include interleukin-18 and GM-CSF in the gastrointestinal tract, which are known to enhance immune cells or stimulate production of immune cells.

Certain treatment regimens include administering the composition in which the concentration of lactoferrin related peptides that is provided is in the range of 1 g to about 100 g/ml and the composition is a solution that is swished in the mouths of the subjects for a few minutes (e.g., about 4 minutes) and then swallowed. This process can be repeated multiple times a day, for example twice or more each day, for a total of three doses per 24 hour period. The doses are taken immediately after meals (one each after breakfast, lunch and dinner), or at similarly spaced intervals throughout the day. Subjects are asked not to eat or drink anything for a least one hour after swallowing the dose. The treatment may be terminated in the event of significant drug related adverse effects observed during one of the interim safety analyses.

The multiple administration of lactoferrin related peptides each day can maximize the exposure of the oral cavity and gut to the drug. Preferably, patients an effective amount of the composition prophylactically for 21-28 days starting from the commencement of chemotherapy. Daily dosing continues through the neutropenic phase until the earliest of the following: a) Absolute Neutrophil Count (ANC) is $\geq 600$ cells/$\mu$L for three consecutive days, and mucositis (if present) has improved to Grade 2 or better for three consecutive days; or b) patient is discharged from the hospital or outpatient transplant setting. A last-day-of-therapy evaluation is performed within 24 hours after the last dose. The patients are also required to return for an end-of-treatment evaluation, to be performed 3-7 days after the last dose.

The treatment regimen in the present invention can prevent or attenuate infections in immunosuppressed patients, for example, patients undergoing aggressive chemotherapy or radiotherapy. The treatment reduces incidence, duration, and severity, and prolongs the infection-free interval of neutropenic infection (neutropenic fever). For the purpose of this invention, fever is considered as an oral temperature of at least 38.0° C. on at least two occasions within 24 hours, or a single oral temperature of at least 38.3° C. Neutropenic fever is defined as fever that begins when the patient is neutropenic (ANC<500). The end of neutropenic fever is defined as the point at which the patient begins a period of 48 hours without fever (as defined above), whether or not the patient is still neutropenic. Incidence of neutropenic fever is calculated as the number of patients experiencing one or more episodes of neutropenic fever. Onset of neutropenic fever is determined in two ways: (1) days between the transfusion and the first episode of neutropenic fever and (2) days between a neutrophil count <1000/$\mu$L and the first episode of neutropenic fever. Duration of neutropenic fever is defined as the number of days between the onset and the end of neutropenic fever. Severity of neutropenic fever is determined by the average temperature of the patient during the period of neutropenic fever. Infection-free interval is the period between the end of an infective fever and the onset of the next infective fever.

The present treatment also reduces the incidence, severity, and duration of oral and GI mucositis by improving all clinical criteria used for mucositis evaluation (pain, salivation, appetite, and oral inflammation). The incidence, duration, and severity of oral mucositis are assessed for each patient. Oral mucositis is graded using the Oral Mucositis Assessment Scale (OMAS).

Prophylactic and concomitant use of antibiotics may be used during the treatment according to patient's conditions and usual standard of care in the medical profession. Use of hematopoietic growth factors is not recommended routinely, but G-CSF may be used as part of the standard of clinical carte at the discretion of the doctors. All medications necessary for the patient's well being may also be administered.

The responses of the patients in the course of treatment are closely monitored by evaluating various response parameters. The treatment protocol may be adjusted accordingly depending on the improvement of the patient's physical conditions.

J. Gastrointestinal Disorders

In accordance with the present invention, the peptide composition provided in any of the above-described pharmaceutical carriers is administered to a subject suspected of or having a gastrointestinal disorder.

Gastrointestinal disorders include, but are not limited to, heartburn, bloating, postoperative ileus, abdominal pain and discomfort, early satiety, epigastric pain, nausea, vomiting, burbulence, regurgitation, intestinal pseudoobstruction, anal incontinence, gastroesophageal reflux disease, irritable bowel syndrome, ulcerative colitis, Crohn's disease, menstrual cramps, pancreatitis, spastic and interstitial cystitis and ulcers and the visceral pain associated therewith.

In certain embodiments, the peptide composition is administered to a subject suffering from Crohn's disease, colitis, necrotizing enterocolitis, endometriosis, irritable bowel syndrome, pancreatitis, periodontal disease, and ulcerative colitis.

K. Neurological Conditions

In accordance with the present invention, the peptide composition provided in any of the above-described pharmaceutical carriers is administered to a subject suspected of or having a neurological disorder.

It is envisioned that the composition of the present invention when administered to a subject suffering from a neurological disorder, stimulates the immune system thereby alleviating the neurological conditions. Thus, the composition of the present invention can be useful with regard to the prevention, treatment, or amelioration of neurological, psychiatric, psychological, conscious state, behavioral, mood, and thought activity (unless otherwise indicated these will be collectively referred to herein as "neurological activity" which includes "psychological activity" or "psychiatric activity"). When referring to a pathological or undesirable condition associated with the activity, reference may be made to a neurological disorder which includes "psychiatric disorder" or "psychological disorder" instead of neurological activity or psychiatric or psychological activity. Although the activity to be modulated usually manifests itself in the form of a disorder such as a attention or cognitive disorders (e.g., Autistic Spectrum Disorders); mood disorder (e.g., major depressive disorder, bipolar disorder, and dysthymic disorder) or an anxiety disorder (e.g., panic disorder, posttraumatic stress disorder, obsessive-compulsive disorder and phobic disorder); neurodegenerative diseases (e.g., multiple sclerosis, Alzheimer's disease, amyotrophic lateral sclerosis (ALS), Parkinson's disease, Huntington's Disease, Guillain-Barre syndrome, myasthenia gravis, sleep disorders, and chronic idiopathic demyelinating disease (CID)), one skilled in the art appreciates that the invention may also find application in conjunction with enhancing or diminishing any neurological or psychiatric function, not just an abnormality or disorder.

In certain embodiments, the lactoferrin related peptide composition is administered to a subject suffering from multiple sclerosis, Alzheimer's disease, Parkinson's disease, muscular dystrophy, sleep or depression.

Neurological are diagnosed based upon the accumulation of physical, chemical, and historical behavioral data on each patient. One of skill in the art is able to perform the appropriate examinations to accumulate such data. One type of examination can include neurological examinations, which can include mental status evaluations, which can further include a psychiatric assessment. Other types of examinations can include, but are not limited to, motor examination, cranial nerve examination, and neuropsychological tests (e.g., Minnesota Multiphasic Personality Inventory, Beck Depression Inventory, or Hamilton Rating Scale for Depression). Thus, any improvement is based upon an improvement in any of the examinations that are used to diagnose a neurological disorder.

In addition to the above examinations, imaging techniques can be used to determine normal and abnormal brain function that can result in disorders. Functional brain imaging allows for localization of specific normal and abnormal functioning of the nervous system. This includes electrical methods such as electroencephalography (EEG), magnetoencephalography (MEG), single photon emission computed tomography (SPECT), (SPECT), as well as metabolic and blood flow studies such as functional magnetic resonance imaging (fMRI), and positron emission tomography (PET) which can be utilized to localize brain function and dysfunction.

In order to increase the effectiveness of administration of the composition of the present invention, it is desirable to combine the compositions with an additional agent. For example, known agents that are known to be stimulatory or inhibitory are used in combination with the composition of the present invention to treat a variety of neurological conditions.

Herein, stimulating drugs comprise medications, anesthetic agents, synthetic or natural peptides or hormones, neurotransmitters, cytokines and other intracellular and intercellular chemical signals and messengers, and the like. In addition, certain neurotransmitters, hormones, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug.

Similarly, excitatory neurotransmitter agonists (e.g., norepinephrine, epinephrine, glutamate, acetylcholine, serotonin, dopamine), agonists thereof, and agents that act to increase levels of an excitatory neurotransmitter(s) (e.g., edrophonium; Mestinon; trazodone; SSRIs (e.g., flouxetine, paroxetine, sertraline, citalopram and fluvoxamine); tricyclic antidepressants (e.g., imipramine, amitriptyline, doxepin, desipramine, trimipramine and nortriptyline), monoamine oxidase inhibitors (e.g., phenelzine, tranylcypromine, isocarboxasid)), generally have an excitatory effect on neural tissue, while inhibitory neurotransmitters (e.g., dopamine, glycine, and gamma-aminobutyric acid (GABA)), agonists thereof, and agents that act to increase levels of an inhibitory neurotransmitter(s) generally have an inhibitory effect. (Dopamine acts as an excitatory neurotransmitter in some locations and circumstances, and as an inhibitory neurotransmitter in other locations and circumstances.) However, antagonists of inhibitory neurotransmitters (e.g., bicuculline) and agents that act to decrease levels of an inhibitory neurotransmitter(s) have been demonstrated to excite neural tissue, leading to increased neural activity. Similarly, excitatory neurotransmitter antagonists (e.g., prazosin, and metoprolol) and agents that decrease levels of excitatory neurotransmitters may inhibit neural activity. Yet further, lithium salts and anesthetics (e.g., lidocane) may also be used in combination with the present invention.

In specific embodiments, antidepressants are administered in combination with the present invention to treat an affective disorder, such as depression. Such antidepressants include, but are not limited to monoamine oxidase inhibitors, 5-HT1A agonists, selective 5-HT uptake inhibitors, imipramine or clomipramine.

The composition of the present invention may precede, be co-current with and/or follow the other agent(s) by intervals ranging from minutes to weeks. In embodiments where the composition of the present invention, and other agent(s) are applied separately to a cell, tissue or organism, one would generally ensure that a significant period of time did not expire between the time of each delivery, such that the composition and agent(s) would still be able to exert an advantageously combined effect on the cell, tissue or organism.

Various combination regimens of the composition and one or more agents are employed. One of skill in the art is aware that the composition of the present invention and agents can be administered in any order or combination.

L. Hematological Disorders

In accordance with the present invention, the peptide composition provided in any of the above-described pharmaceutical carriers is administered to a subject suspected of or having a hematological disorder. Such disorders can include, but are not limited to anemia, sickle cell anemia or cachexia.

M. Ocular Disorders

In accordance with the present invention, the peptide composition provided in any of the above-described pharmaceutical carriers is administered to a subject suspected of or having an ocular disorder. Such disorders include, but are not limited to conjunctivitis, dry eye disease, glaucoma, allergic eye disease, uveitis or ocular infection.

Dry eye disease or keratoconjunctivitis sicca affects about 4 million people in the U.S. of which about 1.5 million have moderate to severe disease. Globally, 60 million people use artificial tears (Damato et al. 1984, Hikichi et al. 1995, Bjerrum et al. 1997, Schein et al. 1997). Despite the high levels of incidence, there is currently no highly effective treatment. Development of therapeutic treatments has been hampered by the lack of knowledge regarding the etiology of the condition to its complexity. However, it has now been suggested that inflammation affecting the lacrimal gland and ocular surface underlies the pathophysiological process (Pflugfelder et al. 1986, Raphael et al. 1988, Pepose et al. 1990, Kroemer et al. 1991, Jones et al. 1994, Pflugfelder et al. 1999, Turner et al. 2000). Thus, it is contemplated that the peptide composition of the present invention can be used to decrease the inflammatory response thereby treating the ocular disease or disorder.

In certain embodiments, the lactoferrin compositions are preferably formulated as topical ophthalmic suspensions or solutions, with a pH of about 4 to 8. The establishment of a specific dosage regimen for each individual is left to the discretion of the clinicians. The amount of lactoferrin will normally be contained in these formulations in an amount 0.01% to 5% by weight, but preferably in an amount of 0.05% to 2% and most preferably in an amount 0.1 to 1.0% by weight. The dosage form may be a solution, suspension microemulsion. Thus, for topical presentation 1 to 2 drops of these formulations would be delivered to the surface of the eye 1 to 4 times per day according to the discretion of a skilled clinician.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Anti-Microbial Effects of said Peptides

The novel peptides described in this application have shown substantial anti-microbial activity. Peptide MICs were determined by the broth microdilution method recommended by the NCCLS (M7-A5). In each medium, the concentrations of peptide were serial two-fold dilutions ranging from 8192 to 8 μg/mL. Mueller-Hinton broth and Peptone broth were used throughout, using the following media: 1) 5rCAMHB, 2) CAMHB supplemented with 3% lysed horse blood, 3) Haemophilus test medium, 4) peptone broth at pH 7, 5) peptone broth at pH 7.5, 6) peptone broth supplemented with 25 μg/mL calcium and 12.5 μg/mL magnesium, 7) peptone broth supplemented with 1.5 g/L soluble starch. On each day of testing, colony counts were performed on the broth from the growth control well immediately after inoculation from two randomly selected isolates to assure appropriate inoculum density. A total of 742 clinical bacterial isolates representing 35 species were tested.

TABLE 2

MIC Geomeans for Said Novel Peptides

| Peptide | Sequence Position | | | | | | | | | | | | | | | | | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| LPF-21 | R | R | R | R | R | R | S | V | Q | W | C | A | V | S | Q | P | E | A | T | K |
| LPF-22 | R | R | R | R | R | R | V | Q | W | C | A | V | S | Q | P | E | A | T | K | C |
| LPF-23 | R | R | R | R | R | R | S | V | Q | W | C | A | V | S | Q | P | E | A | T | K |
| LPF-24 | R | R | R | R | R | R | S | V | Q | W | Q | A | V | S | Q | P | I | A | T | E |
| LPF-25 | R | R | R | R | R | R | S | V | Q | W | A | A | V | S | Q | P | I | A | T | E |
| LPF-31 | R | R | R | R | R | R | S | V | Q | W | Q | A | V | S | Q | P | E | A | T | K |
| LPF-32 | R | R | R | R | R | R | S | V | Q | W | Q | A | V | S | Q | P | G | A | T | K |
| LPF-33 | R | R | R | R | R | R | S | V | Q | W | Q | A | V | S | Q | P | I | A | T | K |
| LPF-34 | R | R | R | R | R | R | S | V | Q | W | Q | A | V | S | Q | P | Q | A | T | G |
| LPF-35 | R | R | R | R | R | R | S | V | Q | W | Q | A | V | S | Q | P | I | A | T | I |

TABLE 2-continued

MIC Geomeans for Said Novel Peptides

| LPF-36 | R | R | R | R | R | R | S | V | Q | W | A | A | V | S | Q | P | I | A | T | K |
|---|---|---|---|---|---|---|---|---|---|---|---|---|---|---|---|---|---|---|---|---|

Sequence Position

| Peptide | 21 | 22 | 23 | 24 | 25 | 26 | 27 | 28 | 29 | 30 | 31 | 32 | 33 | 34 | MIC GeoMean |
|---|---|---|---|---|---|---|---|---|---|---|---|---|---|---|---|
| LPF-21 | C | F | Q | W | Q | R | N | M | R | K | R | R | R |   | 84 |
| LPF-22 | F | Q | W | Q | R | N | M | R | K | R | R | R |   |   | 91 |
| LPF-23 | C | F | Q | W | Q | R | N | M | R | K | R | R | R | R | 84 |
| LPF-24 | Q | F | Q | W | Q | R | N | M | R | K | R | R | R |   | 43/51 |
| LPF-25 | A | F | Q | W | Q | R | N | M | R | K | R | R | R |   | 66 |
| LPF-31 | Q | F | Q | W | Q | R | N | M | R | K | R | R |   |   | 41 |
| LPF-32 | Q | F | Q | W | Q | R | N | M | R | K | R | R |   |   | 25 |
| LPF-33 | Q | F | Q | W | Q | R | N | M | R | K | R | R |   |   | 28 |
| LPF-34 | Q | F | Q | W | Q | R | N | M | R | K | R | R |   |   | 32 |
| LPF-35 | Q | F | Q | W | Q | R | N | M | R | K | R | R |   |   | 15 |
| LPF-36 | A | F | Q | W | Q | R | N | M | R | K | R | R |   |   | 24 |

Example 2

Stimulation of Immune Response by LPF-35

Figure 2:
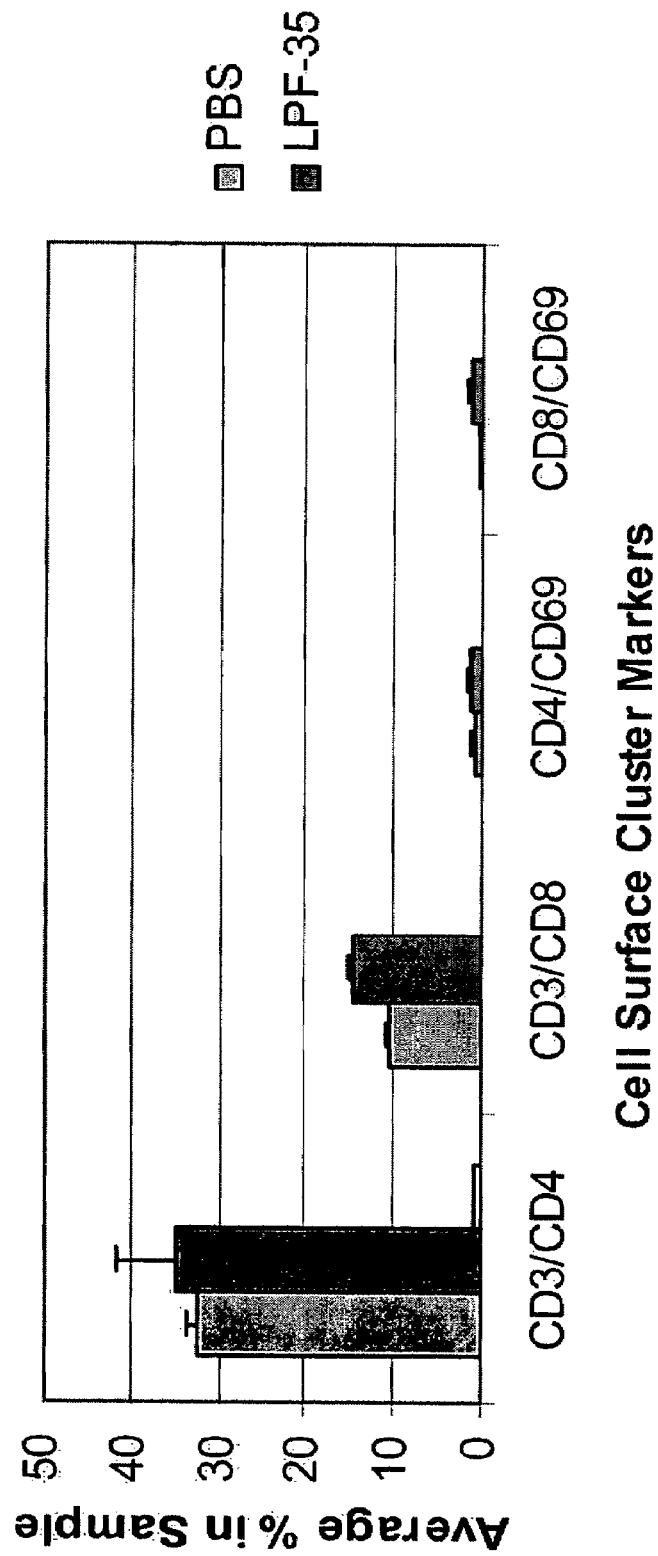
FIG. 2 shows T cell stimulation by peptide LPF-35 for various cell surface cluster markers including CD3/CD4, CD3/CD8, CD4/CD69 and CD8/CD69.

Balb/c naïve mice were treated orally with LPF-35 (5 mg/kg) or placebo once a day for 3 days. One day later (day 4), mice were sacrificed and spleens & whole blood (PBMC) were collected. Spleen: NK cells were separated and counted. Cells were tested in vitro for NK-activity (FIG. 1) against YAC targets using an LDH-releasing test. PBMC: cells were analyzed by FACS for the expression of the following T-cell markers: CD3/CD4, CD3/CD8, CD4/CD69 and CD8/CD69. T-cell activity is shown in FIG. 2.

Example 3

LPF-35 in a Mouse Paw Edema Model of Inflammation

Using the following experimental arrangement it was determined that LPF-35 acts as a systemic anti-inflammatory agent after oral administration. Test substance LPF-35 at 5 mg/kg and reference agent Aspirin at 100 mg/kg were administered orally once daily for 5 consecutive days to groups of 8 ICR (4 male and 4 female) derived mice weighing 22±2 gms. One hour after 5th dose, right hind paw was injected with carrageenan (0.05 ml of 1% suspension intraplantar). The hind paw edema was measured 4 hours later. Convention: reduction of hind paw edema by 30 percent or more indicates significant acute anti-inflammatory activity. Each animal was fasted overnight before Carrageenan challenge.

The Table 3 below shows the average (n=8) paw swelling volume (mL/100).

TABLE 3

| | | | Paw Volume (×0.01 ml) | | | |
|---|---|---|---|---|---|---|
| Treatment | Route | Dose | RP | LP | Diff. | % Inhibition. |
| Vehicle (PBS Buffer) | PO | 5 ml/kg × 5 | 19.63 | 12.25 | 7.38 | — |
| LPF-35 | PO | 5 mg/kg × 5 | 18.75 | 12.63 | 6.13 | 17 |
| Aspirin | PO | 100 mg/kg × 5 | 17.38 | 12.38 | 5.00 | 32 |

LPF35 vs vehicle, unpaired t test, one-tailed p = 0.0101
LPF35 vs. Aspirin, unpaired t test, one-tailed p = 0.0233

Example 4

Effect of LPF-35 in Lipopolysaccharide-induced Septic Shock in Mice

An LPS-induced model of endotoxemia was used to demonstrate that LPF-35 is effective in reducing mortality in a mouse model of sepsis. Groups of 8-10 C57BL/6J mice 18±1 g were used. Animals received 20 ng/mouse doses of $E.$ $coli$ Lipopolysaccharide (LPS) (IV) immediately after pre-treatment with D(+)-Galactosamine (20 mg/mouse IV). Animals were treated by an oral administration of LPF-35 at 1, 6 and 12 hours after challenge with LPS. Mortality was recorded every 12 hours over a 3-day period. In this model, reduction of mortality by 50% or more relative to the vehicle-treated group indicates significant protection. In this experiment doses of LPF-35 ranging between 5-100 µg were tested.

TABLE 4

| Treatment | Route & dose | N of animals used | % Survival |
|---|---|---|---|
| LPF-35 | 5 µg × 3, p.o. | 8 | 25 |
| LPF-35 | 25 µg × 3, p.o. | 8 | 25 |
| LPF-35 | 100 µg × 3, p.o. | 8 | 50 |
| vehicle | 0 µg × 3, p.o. | 8 | 0 |

Example 5

Effect of LPF-35 in a Mouse Model of Septic Shock

Figure 3:
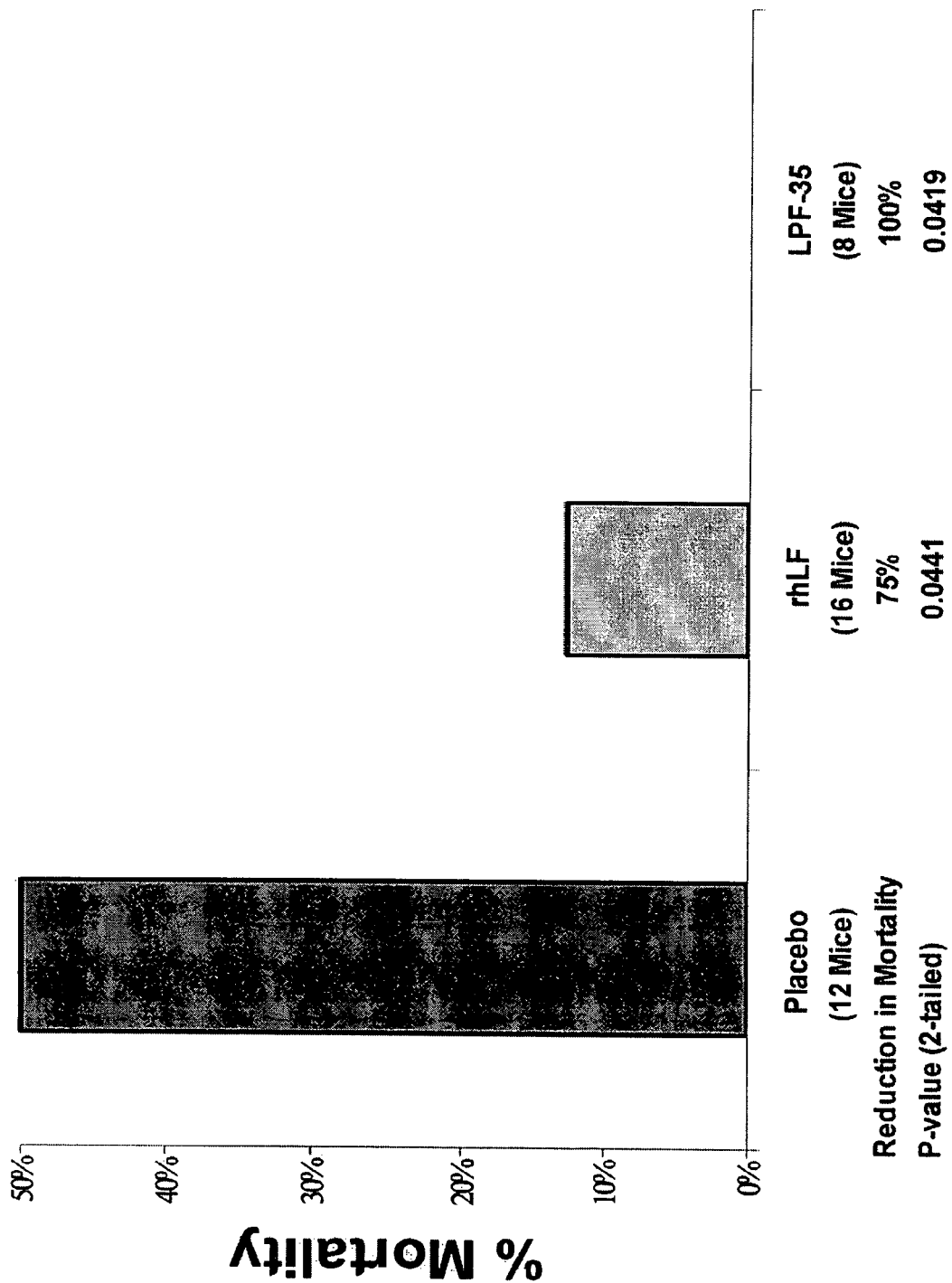
FIG. 3 shows the reduction in mortality achieved with peptide LPF-35 in a mouse model of sepsis versus placebo and a positive control using recombinant human lactoferrin.

In a second experiment with LPF-35 in a mouse model of sepsis the highest effective dose of LPF-35 was shown to be more effective than a positive control, recombinant human lactoferrin (rhLF). Groups of 8-16 C57BL/6J mice 18±1 g were used. Animals received 20 ng/mouse doses of $E.$ $coli$ Lipopolysaccharide (LPS) (IV) immediately after pre-treatment with D(+)-Galactosamine (20 mg/mouse IV). Animals were treated by an oral administration of LPF-35, rhLF or vehicle control at 1, 6 and 12 hours after challenge with LPS. Mortality was recorded every 12 hours over a 3-day period. Results of Experiments with LPF-35 and rhLF in a Model of Sepsis are shown in FIG. 3.

Example 6

LPF-35 in a Rabbit Model of Dry Eye Disease

Figure 4:
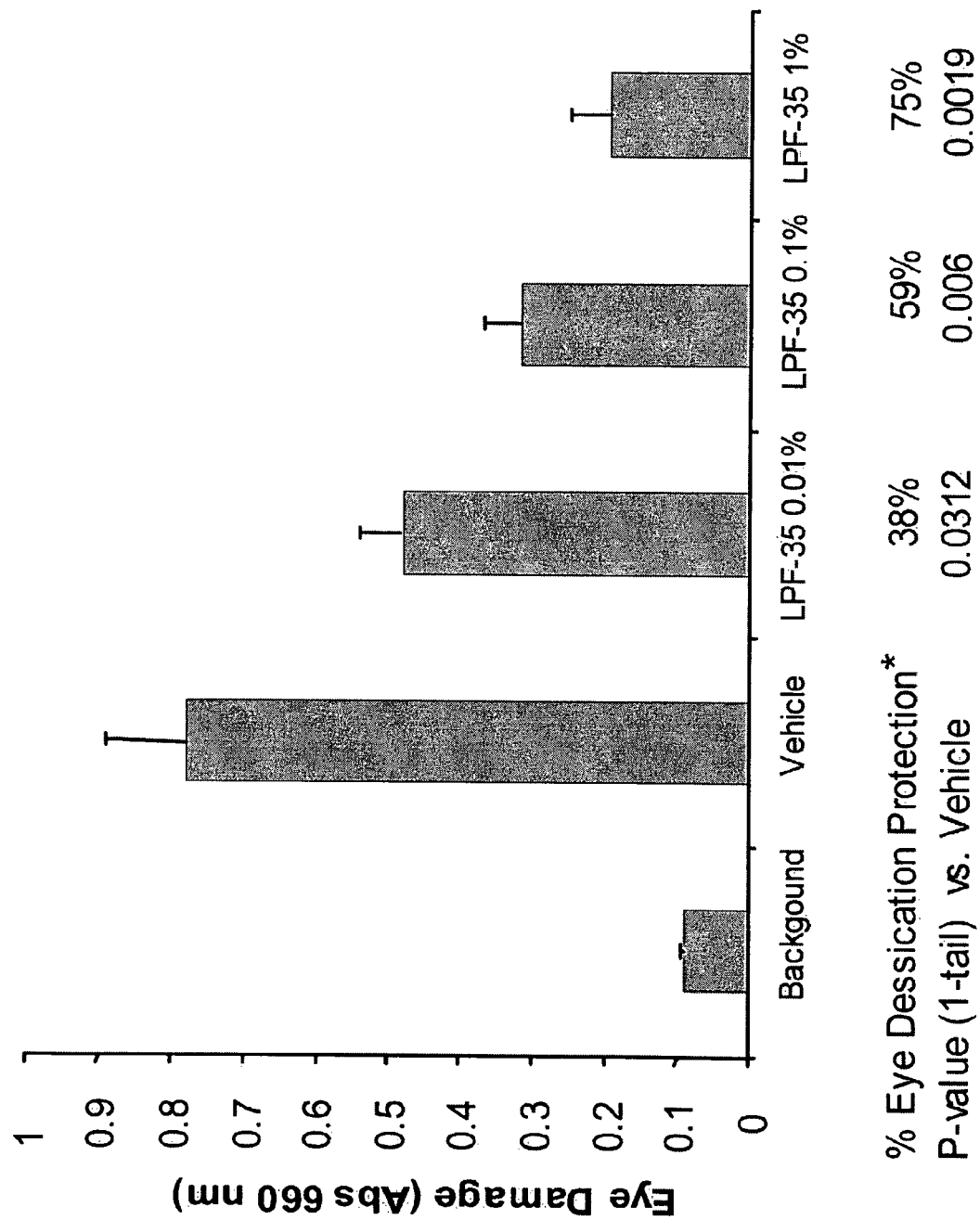
FIG. 4 shows the reduction in eye damage achieved using various concentrations of peptide LPF-35 versus saline control in a rabbit model of dry eye disease.

Experimental evidence suggests that peptide LPF-35 is effective in an animal model of dry eye disease. Rabbits were dosed in the eyes with 50 uL of isotonic saline (Vehicle n=6) or LPF-35 peptide (n=3) and the eyes were held open for 2 hr except for the Background (untreated) group (n=3). After sacrifice, the corneas were stained with methylene blue, the stain extracted with acetone and sodium sulfate and analyzed with a spectrophotometer at absorbance 660 nm (Abs 660 nm) as a measure of eye damage. Results of experiments with LPF-35 in a Model of Dry Eye Disease are shown in FIG. 4.

Example 7

LPF-32 and LPF-35 in a Sheep Model of Allergic Asthma

Peptides LPF-32 and LPF-35 were both tested in an established sheep model of allergic asthma. In both cases these peptides demonstrated the ability to substantially inhibit late phase inflammation and airway hyperresponsiveness. Allergic sheep previously characterized as dual responders (displaying early and late phases of bronchoconstriction), were administered peptide followed by inhalation challenge with *Ascaris suum* antigen.

Baseline dose response curves to aerosolized carbachol were obtained in all sheep 1-3 days before the start of dosing. Sheep were dosed with peptide or placebo by nebulization or oral gavage in the inhaled and oral experiments respectively. The sensitized sheep were then challenged with *Ascaris suum* antigen to produce early and late airway responses, as measured by mean lung resistance (pulmonary flow resistance, RL). Mean lung resistance was measured using tracheal and pleural pressure catheters connected to a differential pressure transducer. On the challenge day measurements of RL were obtained before the antigen challenge and then repeated 30 min after rhLF treatment, after which the sheep were challenged with *Ascaris suum* antigen. Measurements of RL were obtained immediately after challenge, and hourly from 1-6 h after challenge and on the half-hour from 6½-8 h after challenge. Measurements of RL were obtained 24 h after challenge followed by the 24 h post challenge dose response curve.

Figure 5:
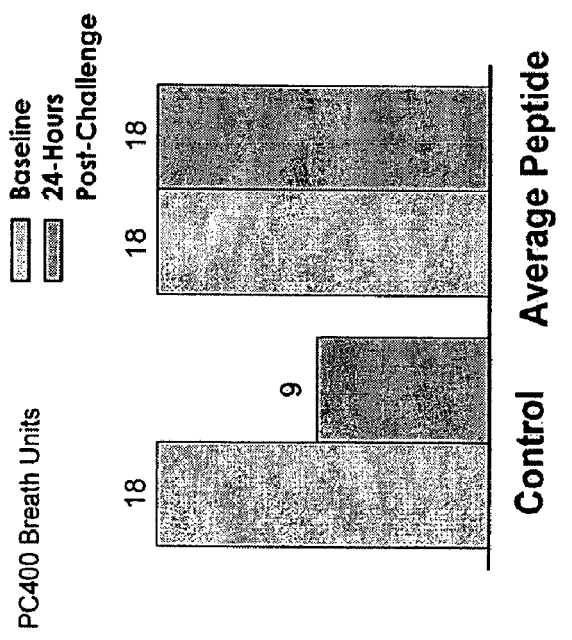
FIGS. 5A and 5B show the effects of a single oral dose of either peptide LPF-32 or peptide LPF-35 on lung resistance (FIG. 5A) and airway hyperresponsiveness (FIG. 5B) to carbachol in a sheep model of asthma.
Figure 5:
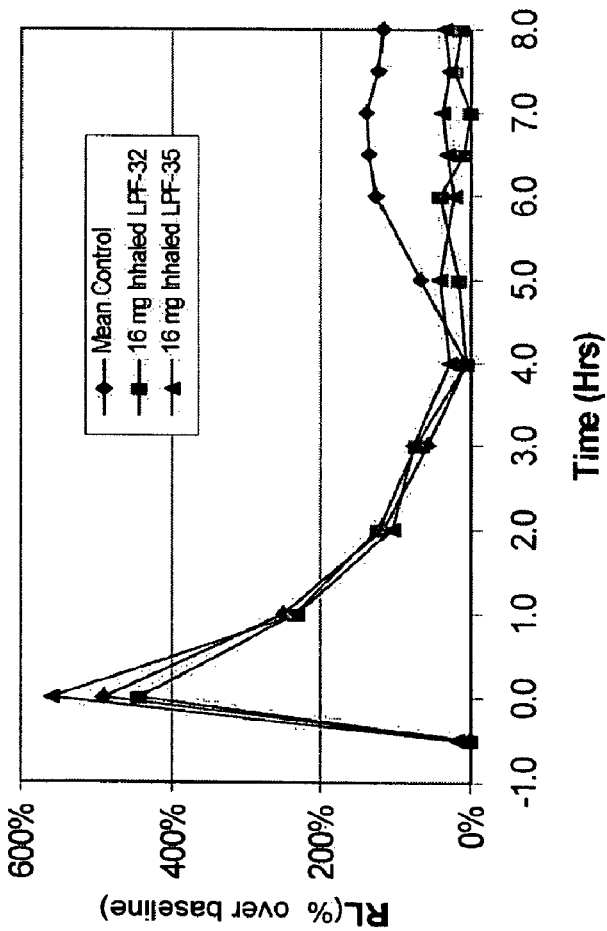
Figure 6:
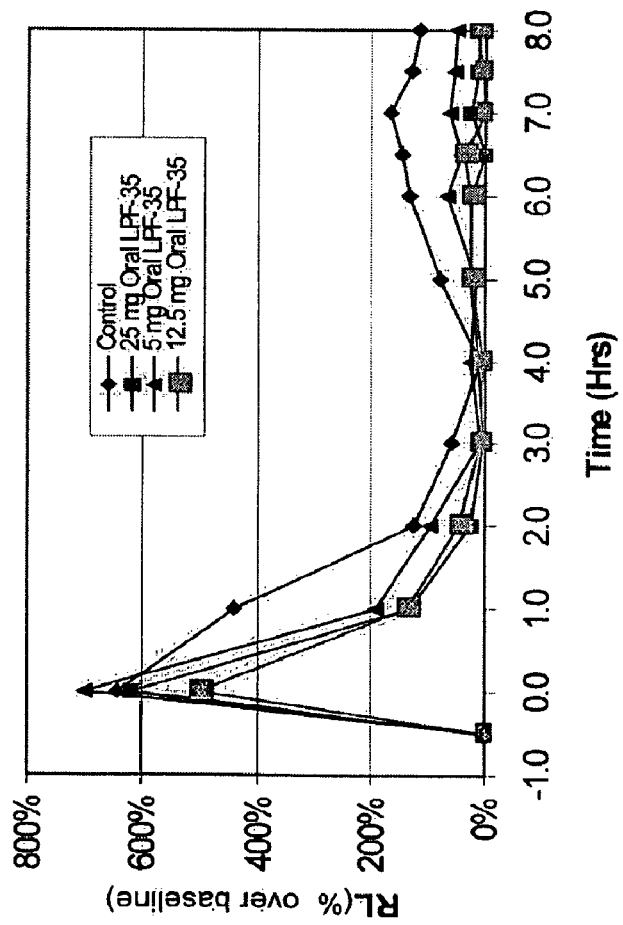
FIGS. 6A and 6B show the effects of peptide LPF-35, at various doses after 3 days of oral administration, on lung resistance (FIG. 6A) and airway hyperresponsiveness (FIG. 6B) to carbachol in a sheep model of asthma.

To assess airway responsiveness, cumulative dose response curves to carbachol were obtained, as measured by specific lung resistance, or SRL (SRL=RL * thoracic gas volume). The sheep inhaled a saline solution, then 10 consecutive breaths of increasing carbachol concentrations up to 4% wt/vol. The provocation test was discontinued when SRL increased 400% from the post saline value, or after the highest carbachol concentration had been administered. Airway hypersensitivity (AH) was determined by calculating the cumulative carbachol dose that increased SRL by 400% over the post-saline value by interpolation from the dose response curve. Actively dosed animals were compared to placebo treated animals or their own historical controls. Results of Experiments with Inhaled LPF-32/35 in a Sheep Model of Asthma are shown in FIG. 5. Results of Experiments with Oral LPF-35 in a Sheep Model of Asthma are shown in FIG. 6.

Example 8

LPF-35 in Wound Healing

Figure 7:
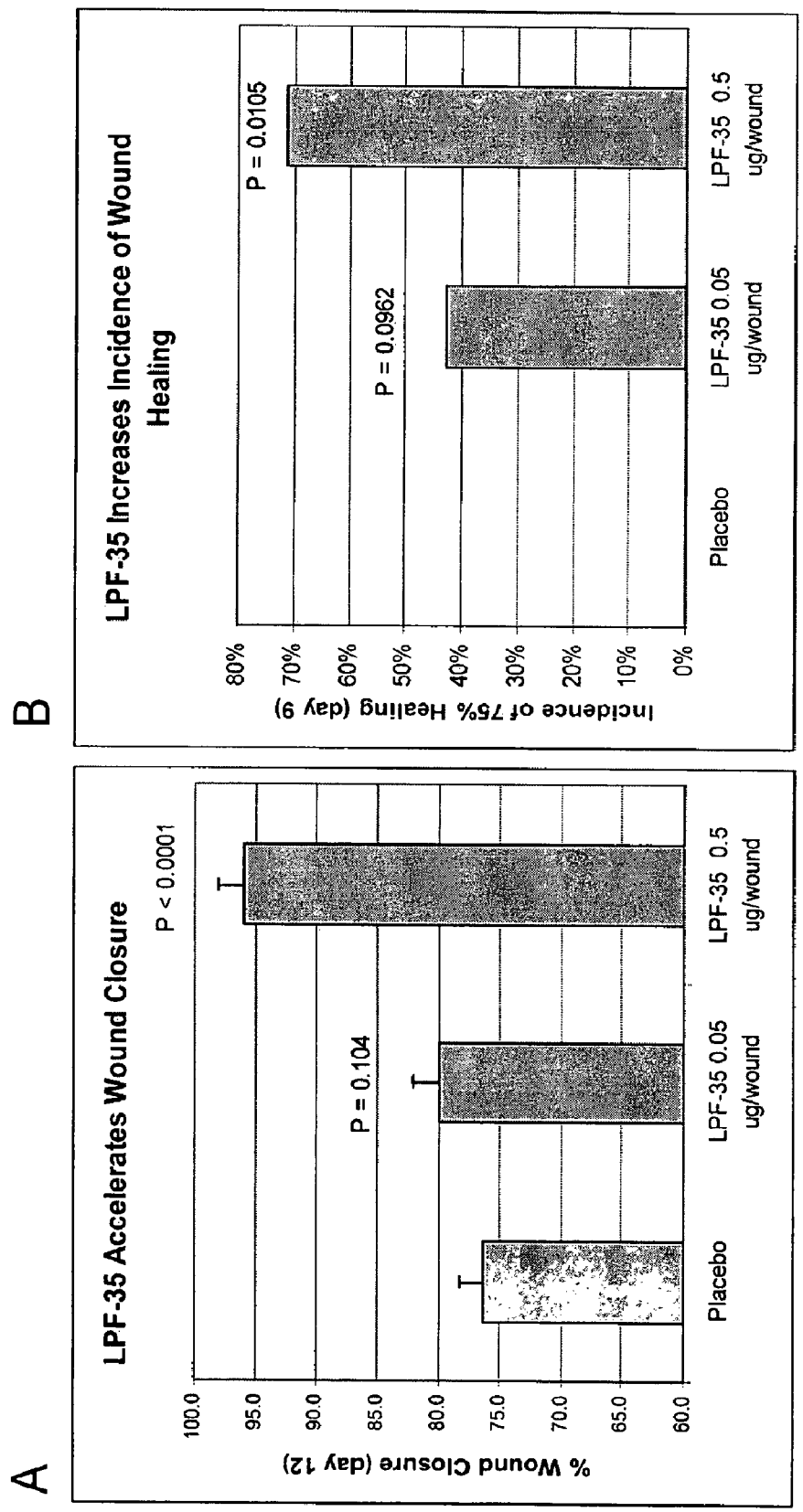
FIGS. 7A and 7B show that the rate and incidence of wound healing are increased following topical treatment with different concentrations of peptide LPF-35 in a mouse model of chronic wounds.

Experiments have shown that LPF-35 is effective in accelerating the rate and incidence of wound healing. Groups of 7 ICR male mice were anesthetized, the shoulder and back region of each animal was shaved, and a sharp punch (ID 12 mm) was used to remove the skin including panniculus carnosus and adherent tissues. The wound area, traced onto clear plastic sheets on days 3, 5, 7, 9 and 11 or 12, was quantitated with an Image Analyzer. An LPF-35 solution and placebo (PBS) were applied topically at 0.02 ml per wound immediately following injury and once daily thereafter for a total of 11 consecutive days. The unpaired Student's t test was applied for comparison between treated and vehicle group. Differences were considered statistical significant at $P<0.05$. In addition, the incidence of animals reaching 75% wound closure was assessed and differences compared using Fisher's exact test. Differences were considered of statistical significance at $p<0.05$ levels. Results of experiments with Oral LPF-35 in a Mouse Model of Wound Healing are shown in FIG. 7.

Example 9

LPF-35 in a Mouse Model of Diabetes

Figure 8:
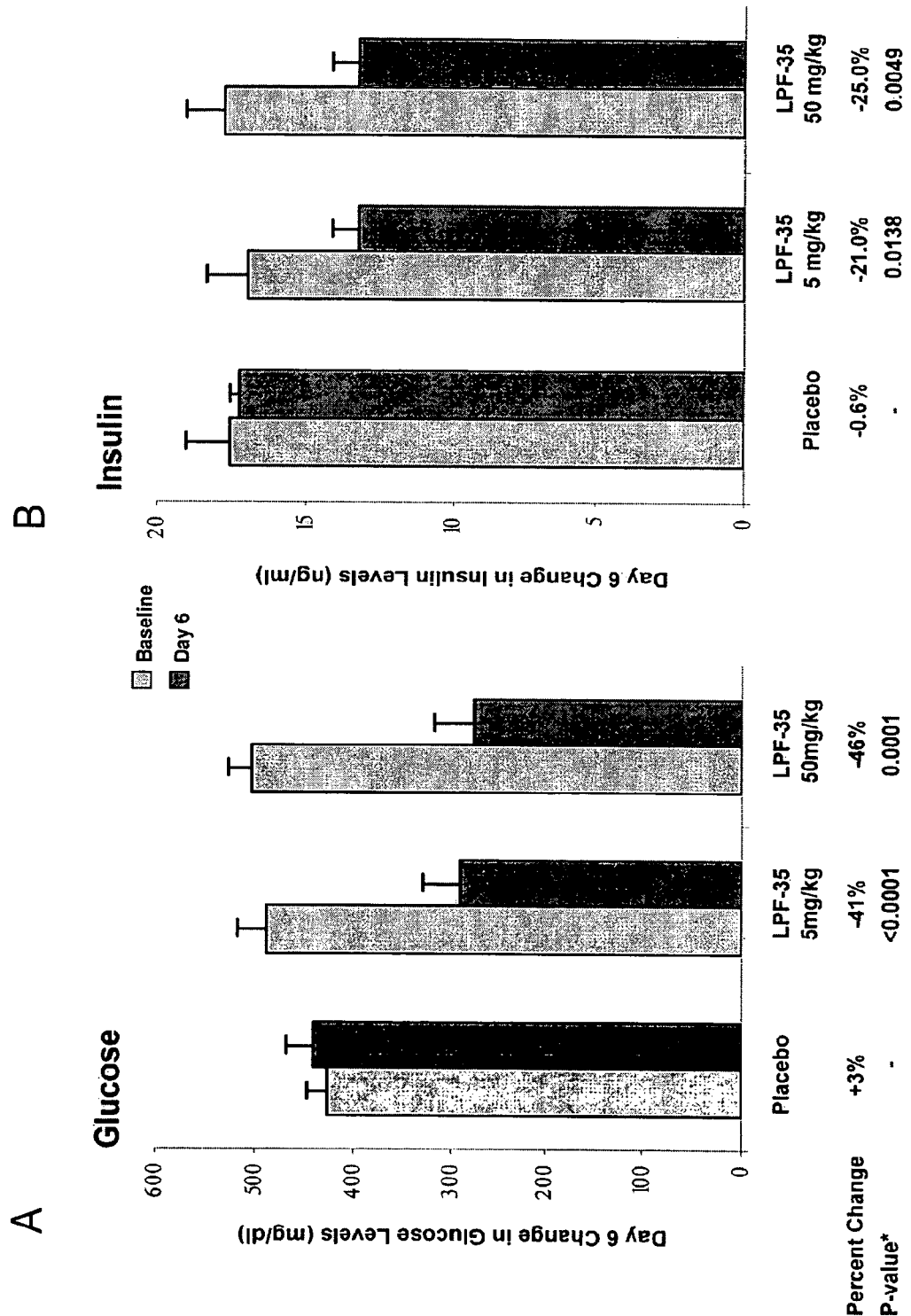
FIGS. 8A and 8B show the effect of oral administration of peptide LPF-35, at different doses, on decreasing the blood levels of glucose (FIG. 8A) and insulin (FIG. 8B) in a mouse model of diabetes.

In this experiment LPF-35 was tested in a mouse model of diabetes. C57BL mice (n=4) were used to test serum glucose and insulin levels in treated mice versus controls. Mice were administered oral LPF-3 once daily for 3 days. Baseline glucose and insulin levels were determined and compared to levels 90 minutes after the last dose. The percentage change was recorded. LPF-35 produced significant declines in both serum glucose and insulin relative to placebo. Results of Experiments with Oral LPF-35 in a Mouse Model of Diabetes are shown in FIG. 8.

Example 10

LPF-35 Stimulates MIP3-α In Vitro

In this experiment it was demonstrated, in vitro, that LPF-35 stimulates the expression of MIP3-α in Hepatocytes. MIP3-α has been associated with the stimulation of innate immune responses. Using a 96-well format, we exposed tissue samples to various concentrations of placebo or test compound (LPF-35 at 0.04 and 0.2 mg/mL). Supernatant was collected (in 75 microL aliquots) from cells at 2 h and 4 h after the administration of test compounds and was tested for concentration of MIP3-α by ELISA. LPF-35 Stimulates MIP3-a In vitro as shown in FIG. 9.

Example 11

LPF-35 in a Phenylquinone (PQ) Writhing Model of Pain in Mice

In this experiment, vehicle (LPF-35 diluent buffer, pH 7.0, 10 mL/kg) and LPF-35 (1000 mg/kg) are administered orally to 2 groups of 3 ICR mice weighing 22+/−2 g one hour before PQ is injected intraperitoneally at 2 mg/kg. The number of writhings observed over the subsequent 5-10 minute period is recorded. Similarly, mice are pre-treated with vehicle or LPF-35 at the same doses as above twice daily for 3 days. Two groups of 3 ICR mice weighing 22+/−2 g are used. Sixty minutes following the last dose, PQ is injected intraperitoneally at 2 mg/kg. The number of writhings is recorded over the following 5-10 minutes. Reduction in the number of writhing indicates analgesic activity. Morphine is used as a positive control.

Example 12

LPF-35 in a Paw Flinch Model of Pain in Rats

In this experiment the formalin paw flinch rat model is used to test the potential analgesic effect and dose response of oral LPF-35. The formalin test is widely used as a peripheral inflammatory nociceptive test. Briefly, rats are given a subplantar injection of 2% formalin into the right hind paw in a volume of 50 microliters. The animals are then transferred to a Persplex observation chamber where pain behavior is quantified by counting the incidents of spontaneous flinching of the injected paw during two distinct periods of flinching activity; (0-10 min after injection) and (10-30 min after injection). Reduction in the number of paw flinches indicates analgesic activity. To define the best experimental conditions for LPF-35, several doses are tested. In addition, LPF-35 is administered orally at several time points before the nociceptive test. Morphine is used as a positive control.

Example 13

LPF-35 in a Tail Flick Model of Pain in Rats

In this model the tail-flick test was used to assess the analgesic properties of LPF-35. Rats were restrained with a cloth restrainer. The middle dorsal surface of tail was heated with a focused beam of radiant heat. To measure analgesic effect, the time required to elicit a flick of the tail was recorded. An increase in the time required to elicit a tail flick indicates analgesic activity. Various doses of LPF-35 were administered at different time points prior to the test. Morphine was used as a positive control. A single oral dose of LPF-35 increased the tail-flick response time to heat by 16% compared to control.

Example 14

LPF-35 in an Acetic Acid Writhing Model of Pain in Rats

Another model that was used to test the analgesic efficacy of LPF-35 was the acetic acid writhing test in rats. Rats were administered an i.p. injection of acetic acid (0.5%, 20 mL/kg). The number of writhes exhibited for each animal during the 10 minutes following administration of acetic acid was recorded. Reduction in the number of writhing indicates analgesic activity. Various doses of LPF-35 were administered at different time points prior to the test. Morphine was used as a positive control. Immediately after the test, the rats were sacrificed and ascites were collected for measurement of PGE2 contents. PGE2 is believed to be an important mediator of inflammatory nociception. A single oral dose of LPF-35 administered 60 minutes prior to the test reduced the number of writhings by 18% compared to control.

Example 15

Tolerance Development with LPF-35 Versus Morphine

Chronic administration of morphine is known to result in the development of tolerance and a loss of analgesic effect in the rat. To test whether rats can become tolerant to LPF-35, use the tail-flick model of pain in rats. This test is the most widely used nociceptive assay to measure the development of opioid tolerance in the rat spinal cord. Intrathecal catheters are implanted under anesthesia. Rats are shaved and sterilized. The posterior superficial neck muscles are separated and a catheter inserted through the occipital membrane, gently advancing it caudally to the subarachnoid space. The external end of the catheter is capped until the day of the experiment. Animals showing normal motor function 5 days after surgery are used. Under light anesthesia, the test compound is injected at a volume of 5 microliters and flushed with 10 microliters saline 15 minutes before the test. Osmotic minipumps, implanted subcutaneously on the back under anesthesia, are used to continuously infuse the test compound. Various doses of LPF-35 are administered over a period of days to assess the development of tolerance. Morphine is used as a positive control.

Example 16

Enhancement of Morphine Analgesia with LPF-35

Co-administration of LPF-35 may result in a synergistic response that could allow the reduction in the dose of morphine used. To examine whether morphine and LPF-35 act synergistically, the rat tail flick model is used to test various doses of morphine with and without LPF-35 co-administration. Briefly, rats are restrained with a cloth restrainer. The middle dorsal surface of tail is heated with a focused beam of radiant heat. To measure analgesic effect, the time required to elicit a flick of the tail is recorded. Various doses of LPF-35, with and without co-administration of a sub-effective dose of morphine, are used to test whether LPF-35 can potentiate the effects of Morphine.

Example 17

LPF-35 Effects on the 1-Opioid Receptor

This experiment examines whether LPF-35's analgesic effect is mediated via the µ-opioid receptor. In this experiment the paw flinch model in rats is used to determine whether co-administration of naloxone (NLX) and D-Phe-Cys-Tyr-D-Trp-Om-Thr-Nh2 (CTOP), 2 specific µ-opioid receptor antagonists, abrogate the analgesic effect of LPF-35.

Example 18

LPF-35 Effects on West Nile Virus in Hamsters

In this experiment one group of hamsters receives oral placebo (rhLF vehicle: PBS solution) and 4 additional groups receive 4 doses of oral LPF-35 (10, 50, 200 or 500 mg/kg) once per day via oral gavage. Three different regimens are tested: 3 days before virus inoculation, the same day of infection (day 0), and 3 days after infection for a total of 3 experiments. 14 days after injection of the virus, the two groups of hamsters are inoculated intraperitoneally with 104 TCID50 of WNV strain NY385-99. After virus inoculation (day 0), the animals are bled daily for 6-7 days to measure their level of viremia and immune response. The hamsters are observed for 20 additional days for signs of illness or death.

Example 19

LPF-35 Effects in a Mouse Model of Squamous Cell Cancer

The effect of orally administered LPF-35 on the development of 012 subcutaneous tumors are examined and compared to the effect of LPF-35 administered by an intravenous (i.v.) route. Human squamous cell carcinoma (012) is used, employing 5×106 cell in 200 mL injected to the right flank of athymic nude mice. Eleven days post tumor injection, when tumor volumes measure ~20 mm3, mice are divided in three groups (1 placebo control and two LPF-35-treated) at 8 animals per group. One group is treated with 5 mg/kg LPF-35 i.v. (50 mL injections) once a day for five days; a second group is treated with 25 mg/kg LPF-35 orally by gavage (0.2 mL per dose) twice a day for eight days; the placebo group is treated following the oral schedule. Tumors are measured twice a week for the duration of the experiment and the body weights are determined at the time of tumor measurements.

Example 20

LPF-35 Effects in an Animal Model of Obesity

LPF-35 is tested in a mouse model of obesity. Four-week-old-male mice are fed D12492i 60% kcal fat diet from Research Diets Inc. until they reach 8 weeks of age (total time on diet is 4 weeks). Control mice are fed D12450Bi 10% kcal diet from Research Diets, Inc. Mice are individually ear-notched and housed 4 per cage. All 24 mice are weighed at the start of the protocol and weekly thereafter. Serum is collected and stored at −80° C. from all 24 mice at the start and the end of the feeding protocol. Diet is weighed twice daily to determine food intake. The 16 DIO mice are divided into groups of eight. Group 1 receives a placebo by oral gavage daily starting on day 15 for 15 days. Group 2 receives LPF-35 by oral gavage daily starting on day 15 for 15 days. Following the 4 week feeding protocol for each group, mice are weighed and serum is analyzed for changes relative to control.

Example 21

LPF-35 Effects in an Animal Model of Hypercholesterolemia

The effects of LPF-35 on cholesterol are tested in a mouse model of diet-induced hypercholesterolemia. Mice (n=5) are fed a high cholesterol diet until serum lipid levels stabilize. Oral LPF-35 or placebo is then administered daily for 5 consecutive days. At the end of that period serum lipids are again measured and changes from baseline recorded.

Example 22

LPF-35 Effects in an In Vitro Model of Osteoporosis

The effect of LPF-35 in osteoporosis is determined by testing osteoclast motility in vitro. Osteoclasts are taken from new-born rats (n=3-6). The osteoclast suspension is then applied to culture dish (20 min). Unattached cells are washed away and incubated for 2 hours. At time 0, cells are viewed by inverted phase-contrast microscope. LPF-35 is administered to incubation medium at time 30 min. Every 5 min cell images are taken using time-lapse video (90 min). Change in position and spread area of osteoclasts is measured to calculate an index of osteoclast motility.

Example 23

LPF-35 Effects in Organ Transplant and Graft-Versus-Host Disease

FK506 and cyclosporine are principal treatments for organ transplant and have also been shown to inhibit GVHD. The activity of LPF-35 in combination with FK506 was compared with FK506 alone in a heart allograft survival model in rats. Wistar Furh (WF; RT1) recipients of heart allograft from Baffalo donors (BUF; RT1b) were administered oral LPF-35 (5 mg/kg) plus FK506 (0.8 mg/kg), FK506 alone or placebo. The results are presented as a mean±standard deviation (MST±SD). Significance between groups was calculated using Student T-test with $p<0.05$ considered as significant. In group # 1 control WF recipients of BUF heart allografts (n=5) were untreated and heart allografts were rejected in an acute fashion within 6.4±0.5 days. In group # 2 WF recipients of BUF heart allografts (n=10) were treated daily once (days 0 to +14) with 0.8 mg/kg FK506 delivered by oral gavage. This protocol was effective in prolonging the survival of heart allografts to a MST of 22.3±6.7 days (p=0.0002). These results suggest that FK506 alone in this therapeutic protocol is very effective in protecting allografts from rejection. In group # 3 WF recipients of BUF heart allografts (n=6) were treated daily once (days 0 to +14) with 0.8 mg/kg FK506 delivered by oral gavage in combination with LPF-35 daily for 14 days. This protocol was effective in prolonging the survival of heart allografts to a MST of 49.5±28 days (p=0.0077). The results showed that LPF-35 was effective in improving the results produced by FK506 alone. An effect of reducing organ transplant rejection is indicative of beneficial effects in GVHD.

Example 24

LPF-35 Effects in an Rat Model of Alzheimer's

The effects of LPF-35 in Alzheimer's is tested using the Fimbria Fornix Lesion Model in rats. Axotomy of the fimbria formix, a cholinergic pathway that goes from the septum to the hippocampus, leads to a decrease in hippocampal ChAT content, memory impairment and hippocampal reorganization (sprouting). This procedure induces a degenerative process both at the hippocampal terminals and at the septal cellular bodies. This model mimics some of the changes observed in Alzheimer's patients and thus has been proposed to be a useful test in search of a therapy that could prevent or slow down the cholinergic neuron degeneration occurring in Alzheimer's disease.

Male Sprague-Dawley rats are anesthetized with pentobarbital. Electrolytic lesion (1 mA, 40 sec) of the fimbria-formix is then done unilaterally. Animals are left to recover for 10 days. Oral LPF-35 is administered for 10 days, first administration starting 1 hour before lesion. ChAT activity is then measured in the hippocampus. Additionally, the number of ChAT immunoreactive positive neurons is counted in the septum.

Example 25

LPF-35 Effects in a Mouse Model of Multiple Sclerosis

To test whether LPF-35 is potentially effective in Multiple Sclerosis, the experimental autoimmune encephalomyelitis model in mice is used. In this experiment it will also be investigated whether anterior uveitis (AU), which often accompanies central nervous system (CNS) and systemic inflammatory diseases including multiple sclerosis (MS), also develops in this murine relapsing model of MS.

Experimental autoimmune encephalomyelitis (EAE) closely resembling relapsing-remitting MS, is induced in the mice by immunization with myelin basic protein (MBP). F1 female mice are immunized with MBP in Complete Freund's Adjuvant (CFA) using Pertussis toxin as co-adjuvant. LPF-35 or placebo is then administered orally for five days. Following the treatment period, EAE is scored clinically on a scale of 0-5 based on the degree of paralysis observed in the mice. Uveitis is assessed by slit-lamp biomicroscopy. Histological analysis of the CNS and eye is also performed.

Example 26

LPF-35 Effects in a Rat Model of Irritable Bowel Syndrome

The effects of LPF-35 on symptoms of Irritable Bowel Syndrome are tested using a rat model of post-inflammatory visceral hyperalgesia. Administering an inflammatory compound to the gastro-intestinal tract is known to produce symptoms similar to IBS including reduced G.I. motility and colonic compliance. After stimulating G.I inflammation, Oral LPF-35 or placebo is administered once a day for 5 days. G.I. motility and compliance is measured and compared to baseline. Afterwards, animals are sacrificed and histopathology of the gut performed.

Example 27

LPF-35 Effects in an Animal Model of Crohn's Disease

This experiment the effects of LPF-35 are tested in an immunologic mouse model of Crohn's Disease. Immunologically mediated models are defined as models of adoptively transferred T cells or bone marrow precursors, which are introduced into immunodeficient mice. TH1 polarization may play a key role in the pathogenesis of Crohn's. This model is used to induce a TH1 immune response in mice that is then assessed with and without treatment with orally administered LPF-35. T cell response are measured along with serum cytokines to determine whether LPF-35 can alter the immunologic pathogenesis associated with Crohn's disease.

Example 28

LPF-35 Effects in a Rat Model of Endometriosis

This experiment LPF-35 is tested in a rat model of endometriosis. The primary method used for induction of endometriosis in rats has been autotransplantation of uterine squares (implants) into the peritoneal cavity. Beyond mere growth of endometrium in ectopic locations, rats with endometriosis display similar symptoms, including a reduction in fertility and fecundity, and the endometriotic implants react similarly to therapeutics as those of humans with the disease. Using this technique it is determined whether the administration of oral LPF-35 has an effect on the development of lesions in the endometrium and reduces the other symptoms of endometriosis.

Example 29

LPF-35 Effects in a Mouse Model of Parkinson's Disease

LPF-35 is tested in a mouse model of Parkinson's Disease by using MPTP to test for changes in Parkinson's associated neurochemicals. MPTP is known to cause an irreversible destruction of the dopaminergic nigrostriatal pathway and symptoms of parkinsonism in humans and in monkeys. When MPTP is administered to mice, a decrease in concentrations of striatal dopamine (DA) and its metabolites DOPAC and HVA and a disappearance of nerve cells in the zona compacta of the substantia nigra are observed. Thus, MPTP administration causes biochemical and histological changes in mice similar to those seen in Parkinson's disease. This model allows the determination of the potential neuroprotective properties of a test compound on dopaminergic neurons after MPTP damage.

On day 1 MPTP (15 mg/kg, s.c.) is injected into male C57/BL6 mice once daily for 7 days. Oral LPF-35 is then administered daily for 14 days. On day 28 striata are removed, homogenized in perchloric acid, and centrifuged. The supernatant is removed and stored at −80° C. Dopamine, DOPAC, HVA, NA, 5-HT, 5-HIAA are determined by reverse-phase HPLC and electrochemical detection.

Example 30

LPF-35 Effects in an Animal Model of Periodontal Disease

To test the effects of LPF-35 in periodontal disease, P/E-selectin adhesion molecule deficient mice that mimic the human syndrome leukocyte adhesion deficiency ere used. In comparison to wild type animals, P/E-/- mice exhibit a 10-fold elevation in bacterial colonization of their oral cavities and elevated gingival tissue levels of the bone resorptive cytokine IL-1alpha. Mice are administered oral LPF-35 or placebo for 14 days. Subsequently, bacterial colonization of the oral cavities and extent of gingival tissue are measured and compared to control groups.

Example 31

LPF-35 Effects in a Mouse Model of Depression

This test creates a condition in which exposure to inescapable foot shocks, an uncontrolled aversive stimulus, leads to a decreased ability to escape future aversive situations. Antidepressants such as monoamine oxidase inhibitors, 5-HT1A agonists, selective 5-HT uptake inhibitors, imipramine or clomipramine have been shown to restore, at least partially, the ability of animals to escape these aversive situations.

Male Wistar rats are used in the following paradigm. For Phase 1: Helplessness induction: Inescapable electric foot shocks (0.8 mA, 10 sec duration every 20 sec for 60 min) are administered. For Phase 2. Conditioned avoidance training: Avoidance training is performed in a 2-way shuttle box on days 3, 4 and 5; 5 min habituation followed by 30 avoidance trials; At 3 seconds light signal, animal can escape to safe side of box; 0.55 mA shock is delivered if animals fail to escape; Failure—animal fails to escape during second shock. Oral LPF-35 is administered for 5 days followed by the helplessness induction test.

Example 32

LPF-35 Effects in an Animal Model of Sleep Disorder

Hexobarbital potentiation in mice (n=3) is used to determine the effects of LPF-35 on sleep time in mice. Oral LPF-35 is administered once per day for five days prior to the test. On the test day hexobarbital sodium (90 mg/kg i.p.) is administered to induce sleep. Sleep time is then recorded. Sleep time is measured in each animal as time (maximum 180 min) from loss to recovery of righting reflex.

Example 33

LPF-35 Effects in a Rat Model of Conjunctivitis

The aim of this study is to determine whether the presence of lymphocytic infiltrates observed in the histology of ocular allergic conditions in humans or in the late phase of ocular anaphylactic reactions in experimental animals is a non-specific event dependent only on the degranulation of mast cells, or is conditioned by a specific response to antigen. With this in mind, responses to antigen and to LPF-35 are compared in an experimental model of allergic conjunctivitis. Rats are sensitised to ovalbumin and challenged topically in the left conjunctival sac either with ovalbumin or LPF-35. The presence of T cells and activated T cells in the infiltrate is studied by immunohistochemical staining on conjunctival tissue obtained at 4, 24, and 48 hours after challenge. Numbers of T cells in the conjunctival infiltrate are compared with LPF-35 challenged rats at 48 hours and with controls at 4, 24, and 48 hours.

Example 34

LPF-35 Effects in a Mouse Model of *Candida Albicans*

Specific-pathogen-free inbred CBA/N female mice 8 weeks old are intraperitoneally challenged with $5 \times 10^8$ or $1 \times 10^9$ blastoconidia. From the day of the challenge, LPF-35 or saline is injected intravenously for 5 days. Survival at day ten is measured as the primary endpoint. Five mice are used in each treatment.

Example 35

LPF-35 Effects in an Animal Model of Lupus

An active chromatin-induced systemic lupus erythematosus (SLE)-like mouse model shown to be similar to idiopathic SLE in humans, is used.

Female BALB/c mice 6-week-old are immunized with 100 μg active or resting chromatin, isolated from ConA-actived syngeneic spleno-lymphocytes, in 200 μL Freund's complete adjuvant (containing BCG 10 g/L) on d 0 and then boosted in Freund's incomplete adjuvant on d 14 and chromatin suspension on d 28. Mice are treated with LPF-35 peptide by oral gavage, once-a-day at a dose range from 5 to 20 mg/kg, from day 30 until the end of experiment. Mice are sacrificed on d 45 or d 60.

Plasma samples of mice are tested by enzyme-linked immunosorbent assays (ELISA) for the presence of IgG anti-dsDNA, -ssDNA, and anti-histone antibodies. Sera are tested by ELISA for tumor necrosis factor-a (TNF-a). Spleno-lymphocyte proliferation assays is carried out and the levels of interferon-g (IFN-g) in supernatants are measured. Proteinuria is measured. Kidneys are examined by direct immunohistochemical method and light microscopy.

It is shown that the peptide attenuates the indicators of active chromatin-induced SLE-like disease in this mouse model of idiopathic human SLE.

Example 36

LPF-35 Effects in an Animal Model of Rheumatoid Arthritis

A rat model of arthritis is used in which paw swelling is induced by injecting Complete Freund's Adjuvant (CFA) (0.3 mg of killed *M. tuberculosis* in 0.1 mL of light mineral oil). The paw swelling is measured on days 1 and 5 (acute phase) and also on days 14 and 18 (delayed phase). Additionally, changes in animal weight are also recorded over the 18 days of the experiment.

Typically, groups of 5 rats are used per each dosing condition. LPF-35 peptide is administered orally once-a-day for 5 consecutive days beginning 1 h before CFA administration.

Administration of the peptide is expected to reduce the hind paw swelling compared to a vehicle-treated control animals.

Example 37

LPF-35 Effects in an Animal Model of Osteo Arthritis

The effects of peptides are examined using articular cartilage slices treated with hyaluronan hexasaccharides (HA6). Full-thickness slices of the human articular cartilage (~10× 10×1 mm) are cultured directly in 1.0 mL of medium containing 10% FBS. Following 2 days of culture for recovery, the tissue slices are treated in the presence of HA6 (250 μg/mL) with or without the peptide (LPF-35) in the presence of 5% of fetal bovine serum (FBS). The concentration of LPF-35 peptide is in the range from 0.1 mg/mL to 1.0 mg/mL. The culture medium containing HA6 with or without LPF-35 is changed every 4 days. Following 14 days of incubation the slices are removed and embedded in O.C.T. embedding compound (Tissue-TekR, Electron Microscopy Sciences, Washington, Pa.). Cryostat sections (8.0 μm) are prepared and stained for Safranin-O and HA. Cartilage proteoglycan biosynthesis is examined by a (35)S-sulfate incorporation assay. Cartilage slices are also examined for accumulation of proteoglycan by Safranin-O, and hyaluronan by a specific biotinylated probe.

It is shown that treatment with the peptide results in an increased synthesis of cartilage proteoglycan especially retained in the cell-associated matrix. Co-treatment with the peptide inhibits the HA6-induced depletion of cell-associated matrices as well as HA6-induced depletion of hyaluronan and proteoglycan within cartilage tissue slices.

These results demonstrate that treatment with the peptide can abrogate the catabolic events associated with a HA6-induced matrix depletion model of osteoarthritis.

Example 38

Protective Role of Lactoferrin Derived Peptides in a Mouse Model of Colitis

A WT strain of *C. rodentium* is used. Before infection, *C. rodentium* are grown in Luria broth overnight, washed, and re-suspended in PBS. Bacteria concentration is determined by OD and confirmed by serial dilution and culture. WT and iNOS-/- C57BL/6 eight-week-old mice are gavaged with *C. rodentium* in 100 μl of PBS or PBS vehicle alone, at the inoculum concentration of 5×108 bacteria/mouse to produce consistent induction of colitis. Mice are treated with peptides starting day 1 postinfection, at pH 7 in the drinking water. Daily weights are obtained for each mouse. Water consumption is measured to determine the peptide intake for individual animals. Mice are sacrificed after 14 days or when moribund. Blood samples are obtained by intracardiac puncture, and colons are collected, weighed, and divided. Tissues fixed in 10% buffered formalin are used for histology.

Sections (6 μm) are cut from paraffin sections and stained with H&E. Tissues are examined in a blinded manner by a pathologist (C.B.D.). Acute (neutrophilic) and chronic (lymphocytic) inflammation, and epithelial regenerative changes are each scored on a 0-4 scale, and the sum is used as an index of histologic injury.

Serum is deproteinized with an equal volume of 6% 5-sulfosalicylic acid. Concentrations of total reactive nitrogen metabolites are determined in the serum, by HPLC analysis and chemiluminescence with an NO analyzer.

Histology and serum analysis suggest a protective effect of peptides in this model of colitis.

REFERENCES CITED

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

U.S. Pat. No. 5,571,691
U.S. Pat. No. 5,571,697
U.S. Pat. No. 5,571,896
U.S. Pat. No. 5,629,001
U.S. Pat. No. 6,080,559
U.S. Pat. No. 5,919,913
U.S. Pat. No. 6,228,614
U.S. Pat. No. 6,455,687
U.S. Pat. No. 6,277,817
U.S. Pat. No. 6,066,469
U.S. Pat. No. 6,100,054
U.S. Pat. No. 6,333,311

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A pharmaceutical composition comprising a lactoferrin related peptide that is capable of stimulating production of macrophage inflammatory protein-3alpha from hepatocytes, and wherein said composition comprises the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 11.

2. The pharmaceutical composition of claim 1, wherein said composition inhibits bacterial growth as measured by minimum inhibitory concentration (MIC).

3. The pharmaceutical composition of claim 1, further comprising a metal chelator.

4. The pharmecutical composition of claim 3, wherein the metal chelator is selected from the group consisting of ethylenediaminetetraacetic acid, [ethylenebis (oxyethylenenitrilo)] tetraacetic acid, 1,2-bis(2-aminophenoxy)ethane-N,N,N',N'-tetraacetic acid, and hydroxyethlene triamine diacetic acid.

5. An isolated polypeptide having the amino acid sequence as defined in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 11.

6. The isolated polypeptide of claim 5, wherein said polypeptide is admixed with a pharmaceutically acceptable carrier.

* * * * *

SEQUENCE LISTING

```
<160> NUMBER OF SEQ ID NOS: 67

<210> SEQ ID NO 1
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 1

Arg Arg Arg Arg Arg Arg Ser Val Gln Trp Cys Ala Val Ser Gln Pro
1               5                   10                  15

Glu Ala Thr Lys Cys Phe Gln Trp Gln Arg Asn Met Arg Lys Arg Arg
            20                  25                  30

Arg

<210> SEQ ID NO 2
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 2
```

-continued

```
Arg Arg Arg Arg Arg Ser Val Gln Trp Cys Ala Val Ser Gln Pro Glu
1               5                   10                  15

Ala Thr Lys Cys Phe Gln Trp Gln Arg Asn Met Arg Lys Arg Arg
            20                  25                  30

Arg

<210> SEQ ID NO 3
<211> LENGTH: 34
<212> TYPE: PRT
<213> ORGANISM: Artificial Sequence
<220> FEATURE:
<223> OTHER INFORMATION: Synthetic Peptide

<400> SEQUENCE: 3

Arg Arg Arg Arg Arg Arg Ser Val Gln Trp Cys Ala Val Ser Gln Pro
1               5                   10                  15

Glu Ala Thr Lys Cys Phe Gln Trp Gln Arg Asn Met Arg Lys Arg Arg
            20                  25                  30

Arg Arg

<210> SEQ ID NO 4
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 4

Arg Arg Arg Arg Arg Arg Ser Val Gln Trp Gln Ala Val Ser Gln Pro
1               5                   10                  15

Ile Ala Thr Glu Gln Phe Gln Trp Gln Arg Asn Met Arg Lys Arg Arg
            20                  25                  30

Arg

<210> SEQ ID NO 5
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 5

Arg Arg Arg Arg Arg Arg Ser Val Gln Trp Ala Ala Val Ser Gln Pro
1               5                   10                  15

Ile Ala Thr Glu Ala Phe Gln Trp Gln Arg Asn Met Arg Lys Arg Arg
            20                  25                  30

Arg

<210> SEQ ID NO 6
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 6

Arg Arg Arg Arg Arg Arg Ser Val Gln Trp Gln Ala Val Ser Gln Pro
1               5                   10                  15

Glu Ala Thr Lys Gln Phe Gln Trp Gln Arg Asn Met Arg Lys Arg Arg
            20                  25                  30

Arg
```

<210> SEQ ID NO 7
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 7

Arg Arg Arg Arg Arg Arg Ser Val Gln Trp Gln Ala Val Ser Gln Pro
1               5                   10                  15

Gly Ala Thr Lys Gln Phe Gln Trp Gln Arg Asn Met Arg Lys Arg Arg
            20                  25                  30

Arg

<210> SEQ ID NO 8
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 8

Arg Arg Arg Arg Arg Arg Ser Val Gln Trp Gln Ala Val Ser Gln Pro
1               5                   10                  15

Ile Ala Thr Lys Gln Phe Gln Trp Gln Arg Asn Met Arg Lys Arg Arg
            20                  25                  30

Arg

<210> SEQ ID NO 9
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 9

Arg Arg Arg Arg Arg Arg Ser Val Gln Trp Gln Ala Val Ser Gln Pro
1               5                   10                  15

Gln Ala Thr Gly Gln Phe Gln Trp Gln Arg Asn Met Arg Lys Arg Arg
            20                  25                  30

Arg

<210> SEQ ID NO 10
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 10

Arg Arg Arg Arg Arg Arg Ser Val Gln Trp Gln Ala Val Ser Gln Pro
1               5                   10                  15

Ile Ala Thr Ile Gln Phe Gln Trp Gln Arg Asn Met Arg Lys Arg Arg
            20                  25                  30

Arg

<210> SEQ ID NO 11
<211> LENGTH: 33
<212> TYPE: PRT
<213> ORGANISM: Artificial Sequence
<220> FEATURE:

<223> OTHER INFORMATION: Synthetic Peptide

<400> SEQUENCE: 11

Arg Arg Arg Arg Arg Arg Ser Val Gln Trp Ala Ala Val Ser Gln Pro
1               5                   10                  15

Ile Ala Thr Lys Ala Phe Gln Trp Gln Arg Asn Met Arg Lys Arg Arg
                20                  25                  30

Arg

<210> SEQ ID NO 12
<211> LENGTH: 711
<212> TYPE: PRT
<213> ORGANISM: HUMAN

<400> SEQUENCE: 12

Met Lys Leu Val Phe Leu Val Leu Leu Phe Leu Gly Ala Leu Gly Leu
1               5                   10                  15

Cys Leu Ala Gly Arg Arg Arg Ser Val Gln Trp Cys Thr Val Ser
                20                  25                  30

Gln Pro Glu Ala Thr Lys Cys Phe Gln Trp Gln Arg Asn Met Arg Arg
                35                  40                  45

Val Arg Gly Pro Pro Val Ser Cys Ile Lys Arg Asp Ser Pro Ile Gln
        50                  55                  60

Cys Ile Gln Ala Ile Ala Glu Asn Arg Ala Asp Ala Val Thr Leu Asp
65                  70                  75                  80

Gly Gly Phe Ile Tyr Glu Ala Gly Leu Ala Pro Tyr Lys Leu Arg Pro
                85                  90                  95

Val Ala Ala Glu Val Tyr Gly Thr Glu Arg Gln Pro Arg Thr His Tyr
                100                 105                 110

Tyr Ala Val Ala Val Val Lys Lys Gly Gly Ser Phe Gln Leu Asn Glu
            115                 120                 125

Leu Gln Gly Leu Lys Ser Cys His Thr Gly Leu Arg Arg Thr Ala Gly
        130                 135                 140

Trp Asn Val Pro Ile Gly Thr Leu Arg Pro Phe Leu Asn Trp Thr Gly
145                 150                 155                 160

Pro Pro Glu Pro Ile Glu Ala Ala Val Ala Arg Phe Phe Ser Ala Ser
                165                 170                 175

Cys Val Pro Gly Ala Asp Lys Gly Gln Phe Pro Asn Leu Cys Arg Leu
                180                 185                 190

Cys Ala Gly Thr Gly Glu Asn Lys Cys Ala Phe Ser Ser Gln Glu Pro
            195                 200                 205

Tyr Phe Ser Tyr Ser Gly Ala Phe Lys Cys Leu Arg Asp Gly Ala Gly
        210                 215                 220

Asp Val Ala Phe Ile Arg Glu Ser Thr Val Phe Glu Asp Leu Ser Asp
225                 230                 235                 240

Glu Ala Glu Arg Asp Glu Tyr Glu Leu Leu Cys Pro Asp Asn Thr Arg
                245                 250                 255

Lys Pro Val Asp Lys Phe Lys Asp Cys His Leu Ala Arg Val Pro Ser
                260                 265                 270

His Ala Val Val Ala Arg Ser Val Asn Gly Lys Glu Asp Ala Ile Trp
            275                 280                 285

Asn Leu Leu Arg Gln Ala Gln Glu Lys Phe Gly Lys Asp Lys Ser Pro
        290                 295                 300

Lys Phe Gln Leu Phe Gly Ser Pro Ser Gly Gln Lys Asp Leu Leu Phe
305                 310                 315                 320

-continued

```
Lys Asp Ser Ala Ile Gly Phe Ser Arg Val Pro Arg Ile Asp Ser
            325                 330                 335
Gly Leu Tyr Leu Gly Ser Gly Tyr Phe Thr Ala Ile Gln Asn Leu Arg
            340                 345                 350
Lys Ser Glu Glu Val Ala Ala Arg Arg Ala Arg Val Val Trp Cys
        355                 360                 365
Ala Val Gly Glu Gln Leu Arg Lys Cys Asn Gln Trp Ser Gly Leu
    370                 375                 380
Ser Glu Gly Ser Val Thr Cys Ser Ser Ala Ser Thr Thr Glu Asp Cys
385                 390                 395                 400
Ile Ala Leu Val Leu Lys Gly Glu Ala Asp Ala Met Ser Leu Asp Gly
                405                 410                 415
Gly Tyr Val Tyr Thr Ala Gly Lys Cys Gly Leu Val Pro Val Leu Ala
            420                 425                 430
Glu Asn Tyr Lys Ser Gln Gln Ser Ser Asp Pro Asp Pro Asn Cys Val
            435                 440                 445
Asp Arg Pro Val Glu Gly Tyr Leu Ala Val Ala Val Val Arg Arg Ser
        450                 455                 460
Asp Thr Ser Leu Thr Trp Asn Ser Val Lys Gly Lys Lys Ser Cys His
465                 470                 475                 480
Thr Ala Val Asp Arg Thr Ala Gly Trp Asn Ile Pro Met Gly Leu Leu
                485                 490                 495
Phe Asn Gln Thr Gly Ser Cys Lys Phe Asp Glu Tyr Phe Ser Gln Ser
            500                 505                 510
Cys Ala Pro Gly Ser Asp Pro Arg Ser Asn Leu Cys Ala Leu Cys Ile
        515                 520                 525
Gly Asp Glu Gln Gly Glu Asn Lys Cys Val Pro Asn Ser Asn Glu Arg
    530                 535                 540
Tyr Tyr Gly Tyr Thr Gly Ala Phe Arg Cys Leu Ala Glu Asn Ala Gly
545                 550                 555                 560
Asp Val Ala Phe Val Lys Asp Val Thr Val Leu Gln Asn Thr Asp Gly
                565                 570                 575
Asn Asn Asn Glu Ala Trp Ala Lys Asp Leu Lys Leu Ala Asp Phe Ala
            580                 585                 590
Leu Leu Cys Leu Asp Gly Lys Arg Lys Pro Val Thr Glu Ala Arg Ser
            595                 600                 605
Cys His Leu Ala Met Ala Pro Asn His Ala Val Val Ser Arg Met Asp
        610                 615                 620
Lys Val Glu Arg Leu Lys Gln Val Leu Leu His Gln Gln Ala Lys Phe
625                 630                 635                 640
Gly Arg Asn Gly Ser Asp Cys Pro Asp Lys Phe Cys Leu Phe Gln Ser
                645                 650                 655
Glu Thr Lys Asn Leu Leu Phe Asn Asp Asn Thr Glu Cys Leu Ala Arg
            660                 665                 670
Leu His Gly Lys Thr Thr Tyr Glu Lys Tyr Leu Gly Pro Gln Tyr Val
        675                 680                 685
Ala Gly Ile Thr Asn Leu Lys Lys Cys Ser Thr Ser Pro Leu Leu Glu
    690                 695                 700
Ala Cys Glu Phe Leu Arg Lys
705                 710

<210> SEQ ID NO 13
<211> LENGTH: 681
```

```
<212> TYPE: PRT
<213> ORGANISM: COW

<400> SEQUENCE: 13

Cys Thr Ile Ser Gln Pro Glu Trp Phe Lys Cys Arg Arg Trp Gln Trp
1               5                   10                  15

Arg Met Lys Lys Leu Gly Ala Pro Ser Ile Thr Cys Val Arg Arg Ala
            20                  25                  30

Phe Ala Leu Glu Cys Ile Arg Ala Ile Ala Glu Lys Lys Ala Asp Ala
        35                  40                  45

Val Thr Leu Asp Gly Gly Met Val Phe Glu Ala Cys Arg Asp Pro Tyr
50                  55                  60

Lys Leu Arg Pro Val Ala Ala Glu Ile Tyr Gly Thr Lys Glu Ser Pro
65                  70                  75                  80

Gln Thr His Tyr Tyr Ala Val Ala Val Val Lys Lys Gly Ser Asn Phe
                85                  90                  95

Gln Leu Asp Gln Leu Gln Gly Arg Lys Ser Cys His Thr Gly Leu Gly
            100                 105                 110

Arg Ser Ala Gly Trp Ile Ile Pro Met Gly Ile Leu Arg Pro Tyr Leu
        115                 120                 125

Ser Trp Thr Glu Ser Leu Glu Pro Leu Gln Gly Ala Val Ala Lys Phe
130                 135                 140

Phe Ser Ala Ser Cys Val Pro Cys Ile Asp Arg Gln Ala Tyr Pro Asn
145                 150                 155                 160

Leu Cys Gln Leu Cys Lys Gly Glu Gly Glu Asn Gln Cys Ala Cys Ser
                165                 170                 175

Ser Arg Glu Pro Tyr Phe Gly Tyr Ser Gly Ala Phe Lys Cys Leu Gln
            180                 185                 190

Asp Gly Ala Gly Asp Val Ala Phe Val Lys Glu Thr Thr Val Phe Glu
        195                 200                 205

Asn Leu Pro Glu Lys Ala Asp Arg Asp Gln Tyr Glu Leu Leu Cys Leu
210                 215                 220

Asn Asn Ser Arg Ala Pro Val Asp Ala Phe Lys Glu Cys His Leu Ala
225                 230                 235                 240

Gln Val Pro Ser His Ala Val Val Ala Arg Ser Val Asp Gly Lys Glu
                245                 250                 255

Asp Leu Ile Trp Lys Leu Leu Ser Lys Ala Gln Glu Lys Phe Gly Lys
            260                 265                 270

Asn Lys Ser Arg Ser Phe Gln Leu Phe Gly Ser Pro Pro Gly Gln Arg
        275                 280                 285

Asp Leu Leu Phe Lys Asp Ser Ala Leu Gly Phe Leu Arg Ile Pro Ser
        290                 295                 300

Lys Val Asp Ser Ala Leu Tyr Leu Gly Ser Arg Tyr Leu Thr Thr Leu
305                 310                 315                 320

Lys Asn Leu Arg Glu Thr Ala Glu Glu Val Lys Ala Arg Tyr Thr Arg
                325                 330                 335

Val Val Trp Cys Ala Val Gly Pro Glu Glu Lys Lys Cys Gln Gln
            340                 345                 350

Trp Ser Gln Gln Ser Gly Gln Asn Val Thr Cys Ala Thr Ala Ser Thr
        355                 360                 365

Thr Asp Asp Cys Ile Val Leu Val Leu Lys Gly Glu Ala Asp Ala Leu
    370                 375                 380

Asn Leu Asp Gly Gly Tyr Ile Tyr Thr Ala Gly Lys Cys Gly Leu Val
385                 390                 395                 400
```

```
Pro Val Leu Ala Glu Asn Arg Lys Ser Ser Lys His Ser Ser Leu Asp
                405                 410                 415
Cys Val Leu Arg Pro Thr Glu Gly Tyr Leu Ala Val Ala Val Val Lys
            420                 425                 430
Lys Ala Asn Glu Gly Leu Thr Trp Asn Ser Leu Lys Asp Lys Lys Ser
        435                 440                 445
Cys His Thr Ala Val Asp Arg Thr Ala Gly Trp Asn Ile Pro Met Gly
    450                 455                 460
Leu Ile Val Asn Gln Thr Gly Ser Cys Ala Phe Asp Glu Phe Phe Ser
465                 470                 475                 480
Gln Ser Cys Ala Pro Gly Ala Asp Pro Lys Ser Arg Leu Cys Ala Leu
                485                 490                 495
Cys Ala Gly Asp Asp Gln Gly Leu Asp Lys Cys Val Pro Asn Ser Lys
            500                 505                 510
Glu Lys Tyr Tyr Gly Tyr Thr Gly Ala Phe Arg Cys Leu Ala Glu Asp
        515                 520                 525
Val Gly Asp Val Ala Phe Val Lys Asn Asp Thr Val Trp Glu Asn Thr
    530                 535                 540
Asn Gly Glu Ser Thr Ala Asp Trp Ala Lys Asn Leu Asn Arg Glu Asp
545                 550                 555                 560
Phe Arg Leu Leu Cys Leu Asp Gly Thr Arg Lys Pro Val Thr Glu Ala
                565                 570                 575
Gln Ser Cys His Leu Ala Val Ala Pro Asn His Ala Val Val Ser Arg
            580                 585                 590
Ser Asp Arg Ala Ala His Val Lys Gln Val Leu Leu His Gln Gln Ala
        595                 600                 605
Leu Phe Gly Lys Asn Gly Lys Asn Cys Pro Asp Lys Phe Cys Leu Phe
    610                 615                 620
Lys Ser Glu Thr Lys Asn Leu Leu Phe Asn Asp Asn Thr Glu Cys Leu
625                 630                 635                 640
Ala Lys Leu Gly Gly Arg Pro Thr Tyr Glu Glu Tyr Leu Gly Thr Glu
                645                 650                 655
Tyr Val Thr Ala Ile Ala Asn Leu Lys Lys Cys Ser Thr Ser Pro Leu
            660                 665                 670
Leu Glu Ala Cys Ala Phe Leu Thr Arg
    675                 680

<210> SEQ ID NO 14
<211> LENGTH: 707
<212> TYPE: PRT
<213> ORGANISM: MOUSE

<400> SEQUENCE: 14

Met Arg Leu Leu Ile Pro Ser Leu Ile Phe Leu Glu Ala Leu Gly Leu
1               5                   10                  15
Cys Leu Ala Lys Ala Thr Thr Val Gln Trp Cys Ala Val Ser Asn Ser
            20                  25                  30
Glu Glu Glu Lys Cys Leu Arg Trp Gln Asn Glu Met Arg Lys Val Gly
        35                  40                  45
Gly Pro Pro Leu Ser Cys Val Lys Lys Ser Ser Thr Arg Gln Cys Ile
    50                  55                  60
Gln Ala Ile Val Thr Asn Arg Ala Asp Ala Met Thr Leu Asp Gly Gly
65                  70                  75                  80
Thr Met Phe Asp Ala Gly Lys Pro Pro Tyr Lys Leu Arg Pro Val Ala
```

-continued

```
                85                  90                  95
Ala Glu Val Tyr Gly Thr Lys Glu Gln Pro Arg Thr His Tyr Tyr Ala
            100                 105                 110
Val Ala Val Val Lys Asn Ser Ser Asn Phe His Leu Asn Gln Leu Gln
            115                 120                 125
Gly Leu Arg Ser Cys His Thr Gly Ile Gly Arg Ser Ala Gly Trp Lys
            130                 135                 140
Ile Pro Ile Gly Thr Leu Arg Pro Tyr Leu Asn Trp Asn Gly Pro Pro
145                 150                 155                 160
Ala Ser Leu Glu Glu Ala Val Ser Lys Phe Phe Ser Lys Ser Cys Val
            165                 170                 175
Pro Gly Ala Gln Lys Asp Arg Phe Pro Asn Leu Cys Ser Ser Cys Ala
            180                 185                 190
Gly Thr Gly Ala Asn Lys Cys Ala Ser Ser Pro Glu Glu Pro Tyr Ser
            195                 200                 205
Gly Tyr Ala Gly Ala Leu Arg Cys Leu Arg Asp Asn Ala Gly Asp Val
            210                 215                 220
Ala Phe Thr Arg Gly Ser Thr Val Phe Glu Glu Leu Pro Asn Lys Ala
225                 230                 235                 240
Glu Arg Asp Gln Tyr Lys Leu Leu Cys Pro Asp Asn Thr Trp Lys Pro
            245                 250                 255
Val Thr Glu Tyr Lys Glu Cys His Leu Ala Gln Val Pro Ser His Ala
            260                 265                 270
Val Val Ser Arg Ser Thr Asn Asp Lys Glu Glu Ala Ile Trp Glu Leu
            275                 280                 285
Leu Arg Gln Ser Gln Glu Lys Phe Gly Lys Lys Gln Ala Ser Gly Phe
            290                 295                 300
Gln Leu Phe Ala Ser Pro Ser Gly Gln Lys Asp Leu Leu Phe Lys Glu
305                 310                 315                 320
Ser Ala Ile Gly Phe Val Arg Val Pro Gln Lys Val Asp Val Gly Leu
            325                 330                 335
Tyr Leu Thr Phe Ser Tyr Thr Thr Ser Ile Gln Asn Leu Asn Lys Lys
            340                 345                 350
Gln Gln Asp Val Ile Ala Ser Lys Ala Arg Val Thr Trp Cys Ala Val
            355                 360                 365
Gly Ser Glu Glu Lys Arg Lys Cys Asp Gln Trp Asn Arg Ala Ser Arg
            370                 375                 380
Gly Arg Val Thr Cys Ile Ser Phe Pro Thr Thr Glu Asp Cys Ile Val
385                 390                 395                 400
Ala Ile Met Lys Gly Asp Ala Asp Ala Met Ser Leu Asp Gly Gly Tyr
            405                 410                 415
Ile Tyr Thr Ala Gly Lys Cys Gly Leu Val Pro Val Leu Ala Glu Asn
            420                 425                 430
Gln Lys Ser Ser Lys Ser Asn Gly Leu Asp Cys Val Asn Arg Pro Val
            435                 440                 445
Glu Gly Tyr Leu Ala Val Ala Val Arg Arg Glu Asp Ala Gly Phe
            450                 455                 460
Thr Trp Ser Ser Leu Arg Gly Lys Lys Ser Cys His Thr Ala Val Asp
465                 470                 475                 480
Arg Thr Ala Gly Trp Asn Ile Pro Met Gly Leu Leu Ala Asn Gln Thr
            485                 490                 495
Arg Ser Cys Lys Phe Asn Glu Phe Phe Ser Gln Ser Cys Ala Pro Gly
            500                 505                 510
```

```
Ala Asp Pro Lys Ser Asn Leu Cys Ala Leu Cys Ile Gly Asp Glu Lys
            515                 520                 525

Gly Glu Asn Lys Cys Ala Pro Asn Ser Lys Glu Arg Tyr Gln Gly Tyr
        530                 535                 540

Thr Gly Ala Leu Arg Cys Leu Ala Glu Lys Ala Gly Asn Val Ala Phe
545                 550                 555                 560

Leu Lys Asp Ser Thr Val Leu Gln Asn Thr Asp Gly Lys Asn Thr Glu
            565                 570                 575

Glu Trp Ala Arg Asn Leu Lys Leu Lys Asp Phe Glu Leu Leu Cys Leu
        580                 585                 590

Asp Asp Thr Arg Lys Pro Val Thr Glu Ala Lys Asn Cys His Leu Ala
595                 600                 605

Ile Ala Pro Asn His Ala Val Val Ser Arg Thr Asp Lys Val Glu Val
            610                 615                 620

Leu Gln Gln Val Leu Leu Asp Gln Gln Val Gln Phe Gly Arg Asn Gly
625                 630                 635                 640

Gln Arg Cys Pro Gly Glu Phe Cys Leu Phe Gln Ser Lys Thr Lys Asn
            645                 650                 655

Leu Leu Phe Asn Asp Asn Thr Glu Cys Leu Ala Lys Ile Pro Gly Lys
        660                 665                 670

Thr Thr Ser Glu Lys Tyr Leu Gly Lys Glu Tyr Val Ile Ala Thr Glu
        675                 680                 685

Arg Leu Lys Gln Cys Ser Ser Ser Pro Leu Leu Glu Ala Cys Ala Phe
        690                 695                 700

Leu Thr Gln
705

<210> SEQ ID NO 15
<211> LENGTH: 711
<212> TYPE: PRT
<213> ORGANISM: HUMAN

<400> SEQUENCE: 15

Met Lys Leu Val Phe Leu Val Leu Leu Phe Leu Gly Ala Leu Gly Leu
1               5                   10                  15

Cys Leu Ala Gly Arg Arg Arg Ser Val Gln Trp Cys Ala Val Ser
            20                  25                  30

Gln Pro Glu Ala Thr Lys Cys Phe Gln Trp Gln Arg Asn Met Arg Lys
            35                  40                  45

Val Arg Gly Pro Pro Val Ser Cys Ile Lys Arg Asp Ser Pro Ile Gln
    50                  55                  60

Cys Ile Gln Ala Ile Ala Glu Asn Arg Ala Asp Ala Val Thr Leu Asp
65                  70                  75                  80

Gly Gly Phe Ile Tyr Glu Ala Gly Leu Ala Pro Tyr Lys Leu Arg Pro
                85                  90                  95

Val Ala Ala Glu Val Tyr Gly Thr Glu Arg Gln Pro Arg Thr His Tyr
            100                 105                 110

Tyr Ala Val Ala Val Val Lys Lys Gly Gly Ser Phe Gln Leu Asn Glu
            115                 120                 125

Leu Gln Gly Leu Lys Ser Cys His Thr Gly Leu Arg Arg Thr Ala Gly
        130                 135                 140

Trp Asn Val Pro Thr Gly Thr Leu Arg Pro Phe Leu Asn Trp Thr Gly
145                 150                 155                 160

Pro Pro Glu Pro Ile Glu Ala Ala Val Ala Arg Phe Phe Ser Ala Ser
```

-continued

```
                165                 170                 175
Cys Val Pro Gly Ala Asp Lys Gly Gln Phe Pro Asn Leu Cys Arg Leu
            180                 185                 190
Cys Ala Gly Thr Gly Glu Asn Lys Cys Ala Phe Ser Ser Gln Glu Pro
            195                 200                 205
Tyr Phe Ser Tyr Ser Gly Ala Phe Lys Cys Leu Arg Asp Gly Ala Gly
            210                 215                 220
Asp Val Ala Phe Ile Arg Glu Ser Thr Val Phe Glu Asp Leu Ser Asp
225                 230                 235                 240
Glu Ala Glu Arg Asp Glu Tyr Glu Leu Leu Cys Pro Asp Asn Thr Arg
                245                 250                 255
Lys Pro Val Asp Lys Phe Lys Asp Cys His Leu Ala Arg Val Pro Ser
            260                 265                 270
His Ala Val Val Ala Arg Ser Val Asn Gly Lys Glu Asp Ala Ile Trp
            275                 280                 285
Asn Leu Leu Arg Gln Ala Gln Glu Lys Phe Gly Lys Asp Lys Ser Pro
290                 295                 300
Lys Phe Gln Leu Phe Gly Ser Pro Ser Gly Gln Lys Asp Leu Leu Phe
305                 310                 315                 320
Lys Asp Ser Ala Ile Gly Phe Ser Arg Val Pro Pro Arg Ile Asp Ser
            325                 330                 335
Gly Leu Tyr Leu Gly Ser Gly Tyr Phe Thr Ala Ile Gln Asn Leu Arg
            340                 345                 350
Lys Ser Glu Glu Glu Val Ala Ala Arg Arg Ala Arg Val Val Trp Cys
            355                 360                 365
Ala Val Gly Glu Gln Glu Leu Arg Lys Cys Asn Gln Trp Ser Gly Leu
            370                 375                 380
Ser Glu Gly Ser Val Thr Cys Ser Ser Ala Ser Thr Thr Glu Asp Cys
385                 390                 395                 400
Ile Ala Leu Val Leu Lys Gly Glu Ala Asp Ala Met Ser Leu Asp Gly
                405                 410                 415
Gly Tyr Val Tyr Thr Ala Cys Lys Cys Gly Leu Val Pro Val Leu Ala
            420                 425                 430
Glu Asn Tyr Lys Ser Gln Gln Ser Ser Asp Pro Asp Pro Asn Cys Val
            435                 440                 445
Asp Arg Pro Val Glu Gly Tyr Leu Ala Val Ala Val Val Arg Arg Ser
            450                 455                 460
Asp Thr Ser Leu Thr Trp Asn Ser Val Lys Gly Lys Lys Ser Cys His
465                 470                 475                 480
Thr Ala Val Asp Arg Thr Ala Gly Trp Asn Ile Pro Met Gly Leu Leu
                485                 490                 495
Phe Asn Gln Thr Gly Ser Cys Lys Phe Asp Glu Tyr Phe Ser Gln Ser
            500                 505                 510
Cys Ala Pro Gly Ser Asp Pro Arg Ser Asn Leu Cys Ala Leu Cys Ile
            515                 520                 525
Gly Asp Glu Gln Gly Glu Asn Lys Cys Val Pro Asn Ser Asn Glu Arg
            530                 535                 540
Tyr Tyr Gly Tyr Thr Gly Ala Phe Arg Cys Leu Ala Glu Asn Ala Gly
545                 550                 555                 560
Asp Val Ala Phe Val Lys Asp Val Thr Val Leu Gln Asn Thr Asp Gly
                565                 570                 575
Asn Asn Asn Glu Ala Trp Ala Lys Asp Leu Lys Leu Ala Asp Phe Ala
            580                 585                 590
```

```
Leu Leu Cys Leu Asp Gly Lys Arg Lys Pro Val Thr Glu Ala Arg Ser
            595                 600                 605

Cys His Leu Ala Met Ala Pro Asn His Ala Val Val Ser Arg Met Asp
        610                 615                 620

Lys Val Glu Arg Leu Lys Gln Val Leu Leu His Gln Gln Ala Lys Phe
625                 630                 635                 640

Gly Arg Asn Gly Ser Asp Cys Pro Asp Lys Phe Cys Leu Phe Gln Ser
                645                 650                 655

Glu Thr Lys Asn Leu Leu Phe Asn Asp Asn Thr Glu Cys Leu Ala Arg
            660                 665                 670

Leu His Gly Lys Thr Thr Tyr Glu Lys Tyr Leu Gly Pro Gln Tyr Val
        675                 680                 685

Ala Gly Ile Thr Asn Leu Lys Lys Cys Ser Thr Ser Pro Leu Leu Glu
        690                 695                 700

Ala Cys Glu Phe Leu Arg Lys
705                 710

<210> SEQ ID NO 16
<211> LENGTH: 708
<212> TYPE: PRT
<213> ORGANISM: COW

<400> SEQUENCE: 16

Met Lys Leu Phe Val Pro Ala Leu Leu Ser Leu Gly Ala Leu Gly Leu
1               5                   10                  15

Cys Leu Ala Ala Pro Arg Lys Asn Val Arg Trp Cys Thr Ile Ser Gln
                20                  25                  30

Pro Glu Trp Phe Lys Cys Arg Arg Trp Gln Trp Arg Met Lys Lys Leu
            35                  40                  45

Gly Ala Pro Ser Ile Thr Cys Val Arg Arg Ala Phe Ala Leu Glu Cys
        50                  55                  60

Ile Arg Ala Ile Ala Glu Lys Lys Ala Asp Ala Val Thr Leu Asp Gly
65                  70                  75                  80

Gly Met Val Phe Glu Ala Gly Arg Asp Pro Tyr Lys Leu Arg Pro Val
                85                  90                  95

Ala Ala Glu Ile Tyr Gly Thr Lys Glu Ser Pro Gln Thr His Tyr Tyr
            100                 105                 110

Ala Val Ala Val Val Lys Lys Gly Ser Asn Phe Gln Leu Asp Gln Leu
        115                 120                 125

Gln Gly Arg Lys Ser Cys His Thr Gly Leu Gly Arg Ser Ala Gly Trp
130                 135                 140

Ile Ile Pro Met Gly Ile Leu Arg Pro Tyr Leu Ser Trp Thr Glu Ser
145                 150                 155                 160

Leu Glu Pro Leu Gln Gly Ala Val Ala Lys Phe Phe Ser Ala Ser Cys
                165                 170                 175

Val Pro Cys Ile Asp Arg Gln Ala Tyr Pro Asn Leu Cys Gln Leu Cys
            180                 185                 190

Lys Gly Glu Gly Glu Asn Gln Cys Ala Cys Ser Ser Arg Glu Pro Tyr
        195                 200                 205

Phe Gly Tyr Ser Gly Ala Phe Lys Cys Leu Gln Asp Gly Ala Gly Asp
        210                 215                 220

Val Ala Phe Val Lys Glu Thr Thr Val Phe Glu Asn Leu Pro Glu Lys
225                 230                 235                 240

Ala Asp Arg Asp Gln Tyr Glu Leu Leu Cys Leu Asn Asn Ser Arg Ala
```

-continued

```
                245                 250                 255
Pro Val Asp Ala Phe Lys Glu Cys His Leu Ala Gln Val Pro Ser His
                260                 265                 270
Ala Val Val Ala Arg Ser Val Asp Gly Lys Glu Asp Leu Ile Trp Lys
                275                 280                 285
Leu Leu Ser Lys Ala Gln Glu Lys Phe Gly Lys Asn Lys Ser Arg Ser
                290                 295                 300
Phe Gln Leu Phe Gly Ser Pro Pro Gly Gln Arg Asp Leu Leu Phe Lys
305                 310                 315                 320
Asp Ser Ala Leu Gly Phe Leu Arg Ile Pro Ser Lys Val Asp Ser Ala
                325                 330                 335
Leu Tyr Leu Gly Ser Arg Tyr Leu Thr Thr Leu Lys Asn Leu Arg Glu
                340                 345                 350
Thr Ala Glu Glu Val Lys Ala Arg Tyr Thr Arg Val Val Trp Cys Ala
                355                 360                 365
Val Gly Pro Glu Glu Gln Lys Lys Cys Gln Gln Trp Ser Gln Gln Ser
                370                 375                 380
Gly Gln Asn Val Thr Cys Ala Thr Ala Ser Thr Thr Asp Asp Cys Ile
385                 390                 395                 400
Val Leu Val Leu Lys Gly Glu Ala Asp Ala Leu Asn Leu Asp Gly Gly
                405                 410                 415
Tyr Ile Tyr Thr Ala Gly Lys Cys Gly Leu Val Pro Val Leu Ala Glu
                420                 425                 430
Asn Arg Lys Ser Ser Lys His Ser Ser Leu Asp Cys Val Leu Arg Pro
                435                 440                 445
Thr Glu Gly Tyr Leu Ala Val Ala Val Val Lys Lys Ala Asn Glu Gly
                450                 455                 460
Leu Thr Trp Asn Ser Leu Lys Asp Lys Lys Ser Cys His Thr Ala Val
465                 470                 475                 480
Asp Arg Thr Ala Gly Trp Asn Ile Pro Met Gly Leu Ile Val Asn Gln
                485                 490                 495
Thr Gly Ser Cys Ala Phe Asp Glu Phe Phe Ser Gln Ser Cys Ala Pro
                500                 505                 510
Gly Ala Asp Pro Lys Ser Arg Leu Cys Ala Leu Cys Ala Gly Asp Asp
                515                 520                 525
Gln Gly Leu Asp Lys Cys Val Pro Asn Ser Lys Glu Lys Tyr Tyr Gly
                530                 535                 540
Tyr Thr Gly Ala Phe Arg Cys Leu Ala Glu Asp Val Gly Asp Val Ala
545                 550                 555                 560
Phe Val Lys Asn Asp Thr Val Trp Glu Asn Thr Asn Gly Glu Ser Thr
                565                 570                 575
Ala Asp Trp Ala Lys Asn Leu Asn Arg Glu Asp Phe Arg Leu Leu Cys
                580                 585                 590
Leu Asp Gly Thr Arg Lys Pro Val Thr Glu Ala Gln Ser Cys His Leu
                595                 600                 605
Ala Val Ala Pro Asn His Ala Val Val Ser Arg Ser Asp Arg Ala Ala
                610                 615                 620
His Val Lys Gln Val Leu Leu His Gln Gln Ala Leu Phe Gly Lys Asn
625                 630                 635                 640
Gly Lys Asn Cys Pro Asp Lys Phe Cys Leu Phe Lys Ser Glu Thr Lys
                645                 650                 655
Asn Leu Leu Phe Asn Asp Asn Thr Glu Cys Leu Ala Lys Leu Gly Gly
                660                 665                 670
```

```
Arg Pro Thr Tyr Glu Glu Tyr Leu Gly Thr Glu Tyr Val Thr Ala Ile
        675                 680                 685

Ala Asn Leu Lys Lys Cys Ser Thr Ser Pro Leu Leu Glu Ala Cys Ala
        690                 695                 700

Phe Leu Thr Arg
705

<210> SEQ ID NO 17
<211> LENGTH: 711
<212> TYPE: PRT
<213> ORGANISM: HUMAN

<400> SEQUENCE: 17

Met Lys Leu Val Phe Leu Val Leu Leu Phe Leu Gly Ala Leu Gly Leu
1               5                   10                  15

Cys Leu Ala Gly Arg Arg Arg Ser Val Gln Trp Cys Thr Val Ser
            20                  25                  30

Gln Pro Glu Ala Thr Lys Cys Phe Gln Trp Gln Arg Asn Met Arg Arg
        35                  40                  45

Val Arg Gly Pro Pro Val Ser Cys Ile Lys Arg Asp Ser Pro Ile Gln
    50                  55                  60

Cys Ile Gln Ala Ile Ala Glu Asn Arg Ala Asp Ala Val Thr Leu Asp
65                  70                  75                  80

Gly Gly Phe Ile Tyr Glu Ala Gly Leu Ala Pro Tyr Lys Leu Arg Pro
                85                  90                  95

Val Ala Ala Glu Val Tyr Gly Thr Glu Arg Gln Pro Arg Thr His Tyr
            100                 105                 110

Tyr Ala Val Ala Val Val Lys Lys Gly Gly Ser Phe Gln Leu Asn Glu
        115                 120                 125

Leu Gln Gly Leu Lys Ser Cys His Thr Gly Leu Arg Arg Thr Ala Gly
    130                 135                 140

Trp Asn Val Pro Ile Gly Thr Leu Arg Pro Phe Leu Asn Trp Thr Gly
145                 150                 155                 160

Pro Pro Glu Pro Ile Glu Ala Ala Val Ala Arg Phe Phe Ser Ala Ser
                165                 170                 175

Cys Val Pro Gly Ala Asp Lys Gly Gln Phe Pro Asn Leu Cys Arg Leu
            180                 185                 190

Cys Ala Gly Thr Gly Glu Asn Lys Cys Ala Phe Ser Ser Gln Glu Pro
        195                 200                 205

Tyr Phe Ser Tyr Ser Gly Ala Phe Lys Cys Leu Arg Asp Gly Ala Gly
    210                 215                 220

Asp Val Ala Phe Ile Arg Glu Ser Thr Val Phe Glu Asp Leu Ser Asp
225                 230                 235                 240

Glu Ala Glu Arg Asp Glu Tyr Glu Leu Leu Cys Pro Asp Asn Thr Arg
                245                 250                 255

Lys Pro Val Asp Lys Phe Lys Asp Cys His Leu Ala Arg Val Pro Ser
            260                 265                 270

His Ala Val Val Ala Arg Ser Val Asn Gly Lys Glu Asp Ala Ile Trp
        275                 280                 285

Asn Leu Leu Arg Gln Ala Gln Glu Lys Phe Gly Lys Asp Lys Ser Pro
    290                 295                 300

Lys Phe Gln Leu Phe Gly Ser Pro Ser Gly Gln Lys Asp Leu Leu Phe
305                 310                 315                 320

Lys Asp Ser Ala Ile Gly Phe Ser Arg Val Pro Pro Arg Ile Asp Ser
```

```
                    325                 330                 335
Gly Leu Tyr Leu Gly Ser Gly Tyr Phe Thr Ala Ile Gln Asn Leu Arg
            340                 345                 350

Lys Ser Glu Glu Val Ala Ala Arg Arg Ala Arg Val Val Trp Cys
        355                 360                 365

Ala Val Gly Glu Gln Glu Leu Arg Lys Cys Asn Gln Trp Ser Gly Leu
    370                 375                 380

Ser Glu Gly Ser Val Thr Cys Ser Ser Ala Ser Thr Thr Glu Asp Cys
385                 390                 395                 400

Ile Ala Leu Val Leu Lys Gly Glu Ala Asp Ala Met Ser Leu Asp Gly
                405                 410                 415

Gly Tyr Val Tyr Thr Ala Gly Lys Cys Gly Leu Val Pro Val Leu Ala
            420                 425                 430

Glu Asn Tyr Lys Ser Gln Gln Ser Ser Asp Pro Asp Pro Asn Cys Val
        435                 440                 445

Asp Arg Pro Val Glu Gly Tyr Leu Ala Val Ala Val Val Arg Arg Ser
    450                 455                 460

Asp Thr Ser Leu Thr Trp Asn Ser Val Lys Gly Lys Lys Ser Cys His
465                 470                 475                 480

Thr Ala Val Asp Arg Thr Ala Gly Trp Asn Ile Pro Met Gly Leu Leu
                485                 490                 495

Phe Asn Gln Thr Gly Ser Cys Lys Phe Asp Glu Tyr Phe Ser Gln Ser
            500                 505                 510

Cys Ala Pro Gly Ser Asp Pro Arg Ser Asn Leu Cys Ala Leu Cys Ile
        515                 520                 525

Gly Asp Glu Gln Gly Glu Asn Lys Cys Val Pro Asn Ser Asn Glu Arg
    530                 535                 540

Tyr Tyr Gly Tyr Thr Gly Ala Phe Arg Cys Leu Ala Glu Asn Ala Gly
545                 550                 555                 560

Asp Val Ala Phe Val Lys Asp Val Thr Val Leu Gln Asn Thr Asp Gly
                565                 570                 575

Asn Asn Asn Glu Ala Trp Ala Lys Asp Leu Lys Leu Ala Asp Phe Ala
            580                 585                 590

Leu Leu Cys Leu Asp Gly Lys Arg Lys Pro Val Thr Glu Ala Arg Ser
        595                 600                 605

Cys His Leu Ala Met Ala Pro Asn His Ala Val Val Ser Arg Met Asp
    610                 615                 620

Lys Val Glu Arg Leu Lys Gln Val Leu Leu His Gln Gln Ala Lys Phe
625                 630                 635                 640

Gly Arg Asn Gly Ser Asp Cys Pro Asp Lys Phe Cys Leu Phe Gln Ser
                645                 650                 655

Glu Thr Lys Asn Leu Leu Phe Asn Asp Asn Thr Glu Cys Leu Ala Arg
            660                 665                 670

Leu His Gly Lys Thr Thr Tyr Glu Lys Tyr Leu Gly Pro Gln Tyr Val
        675                 680                 685

Ala Gly Ile Thr Asn Leu Lys Lys Cys Ser Thr Ser Pro Leu Leu Glu
    690                 695                 700

Ala Cys Glu Phe Leu Arg Lys
705                 710

<210> SEQ ID NO 18
<211> LENGTH: 711
<212> TYPE: PRT
<213> ORGANISM: HUMAN
```

<400> SEQUENCE: 18

```
Met Lys Leu Val Phe Leu Val Leu Leu Phe Leu Gly Ala Leu Gly Leu
1               5                   10                  15

Cys Leu Ala Gly Arg Arg Arg Ser Val Gln Trp Cys Thr Val Ser
            20                  25                  30

Gln Pro Glu Ala Thr Lys Cys Phe Gln Trp Gln Arg Asn Met Arg Arg
                35                  40                  45

Val Arg Gly Pro Pro Val Ser Cys Ile Lys Arg Asp Ser Pro Ile Gln
    50                  55                  60

Cys Ile Gln Ala Ile Ala Glu Asn Arg Ala Asp Ala Val Thr Leu Asp
65                  70                  75                  80

Gly Gly Phe Ile Tyr Glu Ala Gly Leu Ala Pro Tyr Lys Leu Arg Pro
                85                  90                  95

Val Ala Ala Glu Val Tyr Gly Thr Glu Arg Gln Pro Arg Thr His Tyr
            100                 105                 110

Tyr Ala Val Ala Val Val Lys Lys Gly Gly Ser Phe Gln Leu Asn Glu
            115                 120                 125

Leu Gln Gly Leu Lys Ser Cys His Thr Gly Leu Arg Arg Thr Ala Gly
    130                 135                 140

Trp Asn Val Pro Ile Gly Thr Leu Arg Pro Phe Leu Asn Trp Thr Gly
145                 150                 155                 160

Pro Pro Glu Pro Ile Glu Ala Ala Val Ala Arg Phe Phe Ser Ala Ser
                165                 170                 175

Cys Val Pro Gly Ala Asp Lys Gly Gln Phe Pro Asn Leu Cys Arg Leu
            180                 185                 190

Cys Ala Gly Thr Gly Glu Asn Lys Cys Ala Phe Ser Ser Gln Glu Pro
            195                 200                 205

Tyr Phe Ser Tyr Ser Gly Ala Phe Lys Cys Leu Arg Asp Gly Ala Gly
    210                 215                 220

Asp Val Ala Phe Ile Arg Glu Ser Thr Val Phe Glu Asp Leu Ser Asp
225                 230                 235                 240

Glu Ala Glu Arg Asp Glu Tyr Glu Leu Leu Cys Pro Asp Asn Thr Arg
                245                 250                 255

Lys Pro Val Asp Lys Phe Lys Asp Cys His Leu Ala Arg Val Pro Ser
            260                 265                 270

His Ala Val Val Ala Arg Ser Val Asn Gly Lys Glu Asp Ala Ile Trp
            275                 280                 285

Asn Leu Leu Arg Gln Ala Gln Glu Lys Phe Gly Lys Asp Lys Ser Pro
    290                 295                 300

Lys Phe Gln Leu Phe Gly Ser Pro Ser Gly Gln Lys Asp Leu Leu Phe
305                 310                 315                 320

Lys Asp Ser Ala Ile Gly Phe Ser Arg Val Pro Pro Arg Ile Asp Ser
                325                 330                 335

Gly Leu Tyr Leu Gly Ser Gly Tyr Phe Thr Ala Ile Gln Asn Leu Arg
            340                 345                 350

Lys Ser Glu Glu Glu Val Ala Ala Arg Arg Ala Arg Val Val Trp Cys
            355                 360                 365

Ala Val Gly Glu Gln Glu Leu Arg Lys Cys Asn Gln Trp Ser Gly Leu
    370                 375                 380

Ser Glu Gly Ser Val Thr Cys Ser Ser Ala Ser Thr Thr Glu Asp Cys
385                 390                 395                 400

Ile Ala Leu Val Leu Lys Gly Glu Ala Asp Ala Met Ser Leu Asp Gly
```

-continued

```
                405                 410                 415
Gly Tyr Val Tyr Thr Ala Gly Lys Cys Gly Leu Val Pro Val Leu Ala
            420                 425                 430

Glu Asn Tyr Lys Ser Gln Gln Ser Ser Asp Pro Asp Pro Asn Cys Val
            435                 440                 445

Asp Arg Pro Val Glu Gly Tyr Leu Ala Val Ala Val Val Arg Arg Ser
450                 455                 460

Asp Thr Ser Leu Thr Trp Asn Ser Val Lys Gly Lys Lys Ser Cys His
465                 470                 475                 480

Thr Ala Val Asp Arg Thr Ala Gly Trp Asn Ile Pro Met Gly Leu Leu
                485                 490                 495

Phe Asn Gln Thr Gly Ser Cys Lys Phe Asp Glu Tyr Phe Ser Gln Ser
            500                 505                 510

Cys Ala Pro Gly Ser Asp Pro Arg Ser Asn Leu Cys Ala Leu Cys Ile
            515                 520                 525

Gly Asp Glu Gln Gly Glu Asn Lys Cys Val Pro Asn Ser Asn Glu Arg
            530                 535                 540

Tyr Tyr Gly Tyr Thr Gly Ala Phe Arg Cys Leu Ala Glu Asn Ala Gly
545                 550                 555                 560

Asp Val Ala Phe Val Lys Asp Val Thr Val Leu Gln Asn Thr Asp Gly
                565                 570                 575

Asn Asn Asn Asp Ala Trp Ala Lys Asp Leu Lys Leu Ala Asp Phe Ala
            580                 585                 590

Leu Leu Cys Leu Asp Gly Lys Arg Lys Pro Val Thr Glu Ala Arg Ser
            595                 600                 605

Cys His Leu Ala Met Ala Pro Asn His Ala Val Ser Arg Met Asp
610                 615                 620

Lys Val Glu Arg Leu Lys Gln Val Leu Leu His Gln Gln Ala Lys Phe
625                 630                 635                 640

Gly Arg Asn Gly Ser Asp Cys Pro Asp Lys Phe Cys Leu Phe Gln Ser
                645                 650                 655

Glu Thr Lys Asn Leu Leu Phe Asn Asp Asn Thr Glu Cys Leu Ala Arg
            660                 665                 670

Leu His Gly Lys Thr Thr Tyr Glu Lys Tyr Leu Gly Pro Gln Tyr Val
            675                 680                 685

Ala Gly Ile Thr Asn Leu Lys Lys Cys Ser Thr Ser Pro Leu Leu Glu
            690                 695                 700

Ala Cys Glu Phe Leu Arg Lys
705                 710

<210> SEQ ID NO 19
<211> LENGTH: 708
<212> TYPE: PRT
<213> ORGANISM: WATER BUFFALO

<400> SEQUENCE: 19

Met Lys Leu Phe Val Pro Ala Leu Leu Ser Leu Gly Ala Leu Gly Leu
1               5                   10                  15

Cys Leu Ala Ala Pro Arg Lys Asn Val Arg Trp Cys Thr Ile Ser Gln
            20                  25                  30

Pro Glu Trp Leu Lys Cys His Arg Trp Gln Trp Arg Met Lys Lys Leu
            35                  40                  45

Gly Ala Pro Ser Ile Thr Cys Val Arg Arg Ala Phe Val Leu Glu Cys
            50                  55                  60
```

-continued

```
Ile Arg Ala Ile Thr Glu Lys Lys Ala Asp Ala Val Thr Leu Asp Gly
65                  70                  75                  80

Gly Met Val Phe Glu Ala Gly Leu Asp Pro Tyr Lys Leu Arg Pro Val
                85                  90                  95

Ala Ala Glu Ile Tyr Gly Thr Lys Glu Ser Pro Gln Thr His Tyr Tyr
            100                 105                 110

Ala Val Ala Val Val Lys Lys Gly Ser Asn Phe Gln Leu Asp Gln Leu
                115                 120                 125

Gln Gly Arg Asn Ser Cys His Thr Gly Leu Gly Arg Ser Ala Gly Trp
        130                 135                 140

Asn Ile Pro Met Gly Ile Leu Arg Pro Tyr Leu Ser Trp Thr Glu Ser
145                 150                 155                 160

Leu Glu Pro Phe Gln Gly Ala Val Ala Lys Phe Phe Ser Ala Ser Cys
                165                 170                 175

Val Pro Cys Val Asp Arg Gln Ala Tyr Pro Asn Leu Cys Gln Leu Cys
                180                 185                 190

Lys Gly Glu Gly Glu Asn Gln Cys Ala Cys Ser Pro Arg Glu Pro Tyr
            195                 200                 205

Phe Gly Tyr Ser Gly Ala Phe Lys Cys Leu Gln Asp Gly Ala Gly Asp
210                 215                 220

Val Ala Phe Val Lys Glu Thr Thr Val Phe Glu Asn Leu Pro Glu Lys
225                 230                 235                 240

Ala Asp Arg Asp Gln Tyr Glu Leu Leu Cys Leu Asn Asn Thr Arg Ala
            245                 250                 255

Pro Val Asp Ala Phe Lys Glu Cys His Leu Ala Gln Val Pro Ser His
                260                 265                 270

Ala Val Val Ala Arg Ser Val Asp Gly Lys Glu Asp Leu Ile Trp Lys
            275                 280                 285

Leu Leu Ser Lys Ala Gln Glu Lys Phe Gly Lys Asn Lys Ser Gly Ser
290                 295                 300

Phe Gln Leu Phe Gly Ser Pro Pro Gly Gln Arg Asp Leu Leu Phe Lys
305                 310                 315                 320

Asp Cys Ala Leu Gly Phe Leu Arg Ile Pro Ser Lys Val Asp Ser Ala
                325                 330                 335

Leu Tyr Leu Gly Ser Arg Tyr Leu Thr Ala Leu Lys Asn Leu Arg Glu
            340                 345                 350

Thr Ala Glu Glu Val Gln Ala Arg Arg Ala Arg Val Val Trp Cys Ala
        355                 360                 365

Val Gly Pro Glu Glu Gln Lys Lys Cys Gln Gln Trp Ser Gln Gln Ser
370                 375                 380

Gly Gln Ile Val Thr Cys Ala Thr Ala Ser Thr Thr Asp Asp Cys Ile
385                 390                 395                 400

Ala Leu Val Leu Lys Gly Glu Ala Asp Ala Leu Ser Leu Asp Gly Gly
                405                 410                 415

Tyr Ile Tyr Thr Ala Gly Lys Cys Gly Leu Val Pro Val Leu Ala Glu
            420                 425                 430

Asn Arg Lys Ser Ser Lys His Ser Ser Leu Asp Cys Val Leu Arg Pro
        435                 440                 445

Thr Glu Gly Tyr Leu Ala Val Ala Val Val Lys Lys Ala Asn Glu Gly
    450                 455                 460

Leu Thr Trp Asn Ser Leu Lys Gly Lys Lys Ser Cys His Thr Ala Val
465                 470                 475                 480

Asp Arg Thr Ala Gly Trp Asn Ile Pro Met Gly Leu Ile Ala Asn Gln
```

-continued

```
                485                 490                 495
Thr Gly Ser Cys Ala Phe Asp Glu Phe Phe Ser Gln Ser Cys Ala Pro
            500                 505                 510
Gly Ala Asp Pro Lys Ser Arg Leu Cys Ala Leu Cys Ala Gly Asp Asp
            515                 520                 525
Gln Gly Leu Asp Lys Cys Val Pro Asn Ser Lys Glu Lys Tyr Tyr Gly
        530                 535                 540
Tyr Thr Gly Ala Phe Arg Cys Leu Ala Glu Asp Val Gly Asp Val Ala
545                 550                 555                 560
Phe Val Lys Asn Asp Thr Val Trp Glu Asn Thr Asn Gly Glu Ser Thr
                565                 570                 575
Ala Asp Trp Ala Lys Asn Leu Asn Arg Glu Asp Phe Arg Leu Leu Cys
            580                 585                 590
Leu Asp Gly Thr Arg Lys Pro Val Thr Glu Ala Gln Ser Cys His Leu
            595                 600                 605
Ala Val Ala Pro Asn His Ala Val Val Ser Leu Ser Glu Arg Ala Ala
            610                 615                 620
His Val Glu Gln Val Leu Leu His Gln Gln Ala Leu Phe Gly Glu Asn
625                 630                 635                 640
Gly Lys Asn Cys Pro Asp Lys Phe Cys Leu Phe Lys Ser Glu Thr Lys
                645                 650                 655
Asn Leu Leu Phe Asn Asp Asn Thr Glu Cys Leu Ala Lys Leu Gly Gly
            660                 665                 670
Arg Pro Thr Tyr Glu Glu Tyr Leu Gly Thr Glu Tyr Val Thr Ala Ile
            675                 680                 685
Ala Asn Leu Lys Lys Cys Ser Thr Ser Pro Leu Leu Glu Ala Cys Ala
            690                 695                 700
Phe Leu Thr Arg
705

<210> SEQ ID NO 20
<211> LENGTH: 707
<212> TYPE: PRT
<213> ORGANISM: MOUSE

<400> SEQUENCE: 20

Met Arg Leu Leu Ile Pro Ser Leu Ile Phe Leu Glu Ala Leu Gly Leu
1               5                   10                  15
Cys Leu Ala Lys Ala Thr Thr Val Gln Trp Cys Ala Val Ser Asn Ser
            20                  25                  30
Glu Glu Glu Lys Cys Leu Arg Trp Gln Asn Glu Met Arg Lys Val Gly
            35                  40                  45
Gly Pro Pro Leu Ser Cys Val Lys Lys Ser Ser Thr Arg Gln Cys Ile
        50                  55                  60
Gln Ala Ile Val Thr Asn Arg Ala Asp Ala Met Thr Leu Asp Gly Gly
65                  70                  75                  80
Thr Leu Phe Asp Ala Gly Lys Pro Pro Tyr Lys Leu Arg Pro Val Ala
                85                  90                  95
Ala Glu Val Tyr Gly Thr Lys Glu Gln Pro Arg Thr His Tyr Tyr Ala
            100                 105                 110
Val Ala Val Val Lys Asn Ser Ser Asn Phe His Leu Asn Gln Leu Gln
            115                 120                 125
Gly Leu Arg Ser Cys His Thr Gly Ile Gly Arg Ser Ala Gly Trp Lys
        130                 135                 140
```

-continued

```
Ile Pro Ile Gly Thr Leu Arg Pro Tyr Leu Asn Trp Asn Gly Pro Pro
145                 150                 155                 160

Ala Ser Leu Glu Glu Ala Val Ser Lys Phe Ser Lys Ser Cys Val
                165                 170                 175

Pro Gly Ala Gln Lys Asp Arg Phe Pro Asn Leu Cys Ser Ser Cys Ala
                180                 185                 190

Gly Thr Gly Ala Asn Lys Cys Ala Ser Ser Pro Glu Glu Pro Tyr Ser
                195                 200                 205

Gly Tyr Ala Gly Ala Leu Arg Cys Leu Arg Asp Asn Ala Gly Asp Val
                210                 215                 220

Ala Phe Thr Arg Gly Ser Thr Val Phe Glu Glu Leu Pro Asn Lys Ala
225                 230                 235                 240

Glu Arg Asp Gln Tyr Lys Leu Leu Cys Pro Asp Asn Thr Trp Lys Pro
                245                 250                 255

Val Thr Glu Tyr Lys Glu Cys His Leu Ala Gln Val Pro Ser His Ala
                260                 265                 270

Val Val Ser Arg Ser Thr Asn Asp Lys Glu Glu Ala Ile Trp Glu Leu
                275                 280                 285

Leu Arg Gln Ser Gln Glu Lys Phe Gly Lys Lys Gln Ala Ser Gly Phe
                290                 295                 300

Gln Leu Phe Ala Ser Pro Ser Gly Gln Lys Asp Leu Leu Phe Lys Glu
305                 310                 315                 320

Ser Ala Ile Gly Phe Val Arg Val Pro Gln Lys Val Asp Val Gly Leu
                325                 330                 335

Tyr Leu Thr Phe Ser Tyr Thr Thr Ser Ile Gln Asn Leu Asn Lys Lys
                340                 345                 350

Gln Gln Asp Val Ile Ala Thr Lys Ala Arg Val Thr Trp Cys Ala Val
                355                 360                 365

Gly Ser Glu Glu Lys Arg Lys Cys Asp Gln Trp Asn Arg Ala Ser Arg
                370                 375                 380

Gly Arg Val Thr Cys Ile Ser Phe Pro Thr Thr Glu Asp Cys Ile Val
385                 390                 395                 400

Ala Ile Met Lys Gly Asp Ala Asp Ala Met Ser Leu Asp Gly Gly Tyr
                405                 410                 415

Ile Tyr Thr Ala Gly Lys Cys Gly Leu Val Pro Val Leu Ala Glu Asn
                420                 425                 430

Gln Lys Ser Ser Lys Ser Asn Gly Leu Asp Cys Val Asn Arg Pro Val
                435                 440                 445

Gly Gly Tyr Leu Ala Val Ala Val Arg Arg Glu Asp Ala Gly Phe
                450                 455                 460

Thr Trp Ser Ser Leu Arg Gly Lys Lys Ser Cys His Thr Ala Val Asp
465                 470                 475                 480

Arg Thr Ala Gly Trp Asn Ile Pro Met Gly Leu Leu Ala Asn Gln Thr
                485                 490                 495

Arg Ser Cys Lys Phe Asn Glu Phe Phe Ser Gln Ser Cys Ala Pro Gly
                500                 505                 510

Ala Asp Pro Lys Ser Asn Leu Cys Ala Leu Cys Ile Gly Asp Glu Lys
                515                 520                 525

Gly Glu Asn Lys Cys Ala Pro Asn Ser Lys Glu Arg Tyr Gln Gly Tyr
                530                 535                 540

Thr Gly Ala Leu Arg Cys Leu Ala Glu Lys Ala Gly Asn Val Ala Phe
545                 550                 555                 560

Leu Lys Asp Ser Thr Val Leu Gln Asn Thr Asp Gly Lys Asn Thr Glu
```

```
                        565                 570                 575
Glu Trp Ala Arg Asn Leu Lys Leu Lys Asp Phe Glu Leu Leu Cys Leu
            580                 585                 590

Asp Asp Thr Arg Lys Pro Val Thr Glu Ala Lys Asn Cys His Leu Ala
            595                 600                 605

Ile Ala Pro Asn His Ala Val Val Ser Arg Thr Asp Lys Val Glu Val
            610                 615                 620

Leu Gln Gln Val Leu Leu Asp Gln Gln Val Gln Phe Gly Arg Asn Gly
625                 630                 635                 640

Gln Arg Cys Pro Gly Glu Phe Cys Leu Phe Gln Ser Lys Thr Lys Asn
            645                 650                 655

Leu Leu Phe Asn Asp Asn Thr Glu Cys Leu Ala Lys Ile Pro Gly Lys
            660                 665                 670

Thr Thr Ser Glu Lys Tyr Leu Gly Lys Glu Tyr Val Ile Ala Thr Glu
            675                 680                 685

Arg Leu Lys Gln Cys Ser Ser Pro Leu Leu Glu Ala Cys Ala Phe
            690                 695                 700

Leu Thr Gln
705

<210> SEQ ID NO 21
<211> LENGTH: 711
<212> TYPE: PRT
<213> ORGANISM: HUMAN

<400> SEQUENCE: 21

Met Lys Leu Val Phe Leu Val Leu Leu Phe Leu Gly Ala Leu Gly Leu
1               5                   10                  15

Cys Leu Ala Gly Arg Arg Arg Ser Val Gln Trp Cys Thr Val Ser
            20                  25                  30

Gln Pro Glu Ala Thr Lys Cys Phe Gln Trp Gln Arg Asn Met Arg Arg
        35                  40                  45

Val Arg Gly Pro Pro Val Ser Cys Ile Lys Arg Asp Ser Pro Ile Gln
    50                  55                  60

Cys Ile Gln Ala Ile Ala Glu Asn Arg Ala Asp Ala Val Thr Leu Asp
65                  70                  75                  80

Gly Gly Phe Ile Tyr Glu Ala Gly Leu Ala Pro Tyr Lys Leu Arg Pro
                85                  90                  95

Val Ala Ala Glu Val Tyr Gly Thr Glu Arg Gln Pro Arg Thr His Tyr
            100                 105                 110

Tyr Ala Val Ala Val Val Lys Lys Gly Gly Ser Phe Gln Leu Asn Glu
        115                 120                 125

Leu Gln Gly Leu Lys Ser Cys His Thr Gly Leu Arg Arg Thr Ala Gly
130                 135                 140

Trp Asn Val Pro Ile Gly Thr Leu Arg Pro Phe Leu Asn Trp Thr Gly
145                 150                 155                 160

Pro Pro Glu Pro Ile Glu Ala Ala Val Ala Arg Phe Phe Ser Ala Ser
                165                 170                 175

Cys Val Pro Gly Ala Asp Lys Gly Gln Phe Pro Asn Leu Cys Arg Leu
            180                 185                 190

Cys Ala Gly Thr Gly Glu Asn Lys Cys Ala Phe Ser Ser Gln Glu Pro
        195                 200                 205

Tyr Phe Ser Tyr Ser Gly Ala Phe Lys Cys Leu Arg Asp Gly Ala Gly
    210                 215                 220
```

-continued

```
Asp Val Ala Phe Ile Arg Glu Ser Thr Val Phe Glu Asp Leu Ser Asp
225                 230                 235                 240

Glu Ala Glu Arg Asp Glu Tyr Glu Leu Leu Cys Pro Asp Asn Thr Arg
            245                 250                 255

Lys Pro Val Asp Lys Phe Lys Asp Cys His Leu Ala Arg Val Pro Ser
                260                 265                 270

His Ala Val Val Ala Arg Ser Val Asn Gly Lys Glu Asp Ala Ile Trp
        275                 280                 285

Asn Leu Leu Arg Gln Ala Gln Glu Lys Phe Gly Lys Asp Lys Ser Pro
290                 295                 300

Lys Phe Gln Leu Phe Gly Ser Pro Ser Gly Gln Lys Asp Leu Leu Phe
305                 310                 315                 320

Lys Asp Ser Ala Ile Gly Phe Ser Arg Val Pro Pro Arg Ile Asp Ser
                325                 330                 335

Gly Leu Tyr Leu Gly Ser Gly Tyr Phe Thr Ala Ile Gln Asn Leu Arg
                340                 345                 350

Lys Ser Glu Glu Glu Val Ala Ala Arg Arg Ala Arg Val Val Trp Cys
            355                 360                 365

Ala Val Gly Glu Gln Glu Leu Arg Lys Cys Asn Gln Trp Ser Gly Leu
        370                 375                 380

Ser Glu Gly Ser Val Thr Cys Ser Ser Ala Ser Thr Thr Glu Asp Cys
385                 390                 395                 400

Ile Ala Leu Val Leu Lys Gly Glu Ala Asp Ala Met Ser Leu Asp Gly
                405                 410                 415

Gly Tyr Val Tyr Thr Ala Gly Lys Cys Gly Leu Val Pro Val Leu Ala
            420                 425                 430

Glu Asn Tyr Lys Ser Gln Gln Ser Ser Asp Pro Asp Pro Asn Cys Val
        435                 440                 445

Asp Arg Pro Val Glu Gly Tyr Leu Ala Val Ala Val Val Arg Arg Ser
450                 455                 460

Asp Thr Ser Leu Thr Trp Asn Ser Val Lys Gly Lys Lys Ser Cys His
465                 470                 475                 480

Thr Ala Val Asp Arg Thr Ala Gly Trp Asn Ile Pro Met Gly Leu Leu
                485                 490                 495

Phe Asn Gln Thr Gly Ser Cys Lys Phe Asp Glu Tyr Phe Ser Gln Ser
            500                 505                 510

Cys Ala Pro Gly Ser Asp Pro Arg Ser Asn Leu Cys Ala Leu Cys Ile
        515                 520                 525

Gly Asp Glu Gln Gly Glu Asn Lys Cys Val Pro Asn Ser Asn Glu Arg
530                 535                 540

Tyr Tyr Gly Tyr Thr Gly Ala Phe Arg Cys Leu Ala Glu Asn Ala Gly
545                 550                 555                 560

Asp Val Ala Phe Val Lys Asp Val Thr Val Leu Gln Asn Thr Asp Gly
                565                 570                 575

Asn Asn Asn Asp Ala Trp Ala Lys Asp Leu Lys Leu Ala Asp Phe Ala
            580                 585                 590

Leu Leu Cys Leu Asp Gly Lys Arg Lys Pro Val Thr Glu Ala Arg Ser
        595                 600                 605

Cys His Leu Ala Met Ala Pro Asn His Ala Val Ser Arg Met Asp
610                 615                 620

Lys Val Glu Arg Leu Lys Gln Val Leu Leu His Gln Gln Ala Lys Phe
625                 630                 635                 640

Gly Arg Asn Gly Ser Asp Cys Pro Asp Lys Phe Cys Leu Phe Gln Ser
```

-continued

```
                     645                 650                 655
Glu Thr Lys Asn Leu Leu Phe Asn Asp Asn Thr Glu Cys Leu Ala Arg
            660                 665                 670

Leu His Gly Lys Thr Thr Tyr Glu Lys Tyr Leu Gly Pro Gln Tyr Val
        675                 680                 685

Ala Gly Ile Thr Asn Leu Lys Lys Cys Ser Thr Ser Pro Leu Leu Glu
    690                 695                 700

Ala Cys Glu Phe Leu Arg Lys
705                 710

<210> SEQ ID NO 22
<211> LENGTH: 708
<212> TYPE: PRT
<213> ORGANISM: COW

<400> SEQUENCE: 22

Met Lys Leu Phe Val Pro Ala Leu Leu Ser Leu Gly Ala Leu Gly Leu
1               5                   10                  15

Cys Leu Ala Ala Pro Arg Lys Asn Val Arg Trp Cys Thr Ile Ser Gln
            20                  25                  30

Pro Glu Trp Phe Lys Cys Arg Arg Trp Gln Trp Arg Met Lys Lys Leu
        35                  40                  45

Gly Ala Pro Ser Ile Thr Cys Val Arg Ala Phe Ala Leu Glu Cys
    50                  55                  60

Ile Arg Ala Ile Ala Glu Lys Lys Ala Asp Ala Val Thr Leu Asp Gly
65                  70                  75                  80

Gly Met Val Phe Glu Ala Gly Arg Asp Pro Tyr Lys Leu Arg Pro Val
                85                  90                  95

Ala Ala Glu Ile Tyr Gly Thr Lys Glu Ser Pro Gln Thr His Tyr Tyr
            100                 105                 110

Ala Val Ala Val Val Lys Lys Gly Ser Asn Phe Gln Leu Asp Gln Leu
        115                 120                 125

Gln Gly Arg Lys Ser Cys His Thr Gly Leu Gly Arg Ser Ala Gly Trp
    130                 135                 140

Ile Ile Pro Met Gly Ile Leu Arg Pro Tyr Leu Ser Trp Thr Glu Ser
145                 150                 155                 160

Leu Glu Pro Leu Gln Gly Ala Val Ala Lys Phe Phe Ser Ala Ser Cys
                165                 170                 175

Val Pro Cys Ile Asp Arg Gln Ala Tyr Pro Asn Leu Cys Gln Leu Cys
            180                 185                 190

Lys Gly Glu Gly Glu Asn Gln Cys Ala Cys Ser Ser Arg Glu Pro Tyr
        195                 200                 205

Phe Gly Tyr Ser Gly Ala Phe Lys Cys Leu Gln Asp Gly Ala Gly Asp
    210                 215                 220

Val Ala Phe Val Lys Glu Thr Thr Val Phe Glu Asn Leu Pro Glu Lys
225                 230                 235                 240

Ala Asp Arg Asp Gln Tyr Glu Leu Leu Cys Leu Asn Asn Ser Arg Ala
                245                 250                 255

Pro Val Asp Ala Phe Lys Glu Cys His Leu Ala Gln Val Pro Ser His
            260                 265                 270

Ala Val Val Ala Arg Ser Val Asp Gly Lys Glu Asp Leu Ile Trp Lys
        275                 280                 285

Leu Leu Ser Lys Ala Gln Glu Lys Phe Gly Lys Asn Lys Ser Arg Ser
    290                 295                 300
```

```
Phe Gln Leu Phe Gly Ser Pro Pro Gly Gln Arg Asp Leu Leu Phe Lys
305                 310                 315                 320

Asp Ser Ala Leu Gly Phe Leu Arg Ile Pro Ser Lys Val Asp Ser Ala
                325                 330                 335

Leu Tyr Leu Gly Ser Arg Tyr Leu Thr Thr Leu Lys Asn Leu Arg Glu
                340                 345                 350

Thr Ala Glu Glu Val Lys Ala Arg Tyr Thr Arg Val Val Trp Cys Ala
                355                 360                 365

Val Gly Pro Glu Glu Gln Lys Lys Cys Gln Gln Trp Ser Gln Gln Ser
            370                 375                 380

Gly Gln Asn Val Thr Cys Ala Thr Ala Ser Thr Thr Asp Asp Cys Ile
385                 390                 395                 400

Val Leu Val Leu Lys Gly Glu Ala Asp Ala Leu Asn Leu Asp Gly Gly
                405                 410                 415

Tyr Ile Tyr Thr Ala Gly Lys Cys Gly Leu Val Pro Val Leu Ala Glu
                420                 425                 430

Asn Arg Lys Ser Ser Lys His Ser Ser Leu Asp Cys Val Leu Arg Pro
            435                 440                 445

Thr Glu Gly Tyr Leu Ala Val Ala Val Val Lys Lys Ala Asn Glu Gly
            450                 455                 460

Leu Thr Trp Asn Ser Leu Lys Asp Lys Lys Ser Cys His Thr Ala Val
465                 470                 475                 480

Asp Arg Thr Ala Gly Trp Asn Ile Pro Met Gly Leu Ile Val Asn Gln
                485                 490                 495

Thr Gly Ser Cys Ala Phe Asp Glu Phe Phe Ser Gln Ser Cys Ala Pro
                500                 505                 510

Gly Ala Asp Pro Lys Ser Arg Leu Cys Ala Leu Cys Ala Gly Asp Asp
            515                 520                 525

Gln Gly Leu Asp Lys Cys Val Pro Asn Ser Lys Glu Lys Tyr Tyr Gly
            530                 535                 540

Tyr Thr Gly Ala Phe Arg Cys Leu Ala Glu Asp Val Gly Asp Val Ala
545                 550                 555                 560

Phe Val Lys Asn Asp Thr Val Trp Glu Asn Thr Asn Gly Glu Ser Thr
                565                 570                 575

Ala Asp Trp Ala Lys Asn Leu Asn Arg Glu Asp Phe Arg Leu Leu Cys
                580                 585                 590

Leu Asp Gly Thr Arg Lys Pro Val Thr Glu Ala Gln Ser Cys His Leu
            595                 600                 605

Ala Val Ala Pro Asn His Ala Val Val Ser Arg Ser Asp Arg Ala Ala
            610                 615                 620

His Val Lys Gln Val Leu Leu Arg Gln Gln Ala Leu Phe Gly Lys Asn
625                 630                 635                 640

Gly Lys Asn Cys Pro Asp Lys Phe Cys Leu Phe Lys Ser Glu Thr Lys
                645                 650                 655

Asn Leu Leu Phe Asn Asp Asn Thr Glu Cys Leu Ala Lys Leu Gly Gly
                660                 665                 670

Arg Pro Thr Tyr Glu Glu Tyr Leu Gly Thr Glu Tyr Val Thr Ala Ile
            675                 680                 685

Ala Asn Leu Lys Lys Cys Ser Thr Ser Pro Leu Leu Glu Ala Cys Ala
            690                 695                 700

Phe Leu Thr Arg
705
```

<210> SEQ ID NO 23
<211> LENGTH: 708
<212> TYPE: PRT
<213> ORGANISM: CAMEL

<400> SEQUENCE: 23

```
Met Lys Leu Phe Phe Pro Ala Leu Leu Ser Leu Gly Ala Leu Gly Leu
 1               5                  10                  15

Cys Leu Ala Ala Ser Lys Lys Ser Val Arg Trp Cys Thr Thr Ser Pro
            20                  25                  30

Ala Glu Ser Ser Lys Cys Ala Gln Trp Gln Arg Arg Met Lys Lys Val
        35                  40                  45

Arg Gly Pro Ser Val Thr Cys Val Lys Lys Thr Ser Arg Phe Glu Cys
    50                  55                  60

Ile Gln Ala Ile Ser Thr Glu Lys Ala Asp Ala Val Thr Leu Asp Gly
 65                  70                  75                  80

Gly Leu Val Tyr Asp Ala Gly Leu Asp Pro Tyr Lys Leu Arg Pro Ile
                85                  90                  95

Ala Ala Glu Val Tyr Gly Thr Glu Asn Asn Pro Gln Thr His Tyr Tyr
           100                 105                 110

Ala Val Ala Ile Ala Lys Lys Gly Thr Asn Phe Gln Leu Asn Gln Leu
       115                 120                 125

Gln Gly Leu Lys Ser Cys His Thr Gly Leu Gly Arg Ser Ala Gly Trp
   130                 135                 140

Asn Ile Pro Met Gly Leu Leu Arg Pro Phe Leu Asp Trp Thr Gly Pro
145                 150                 155                 160

Pro Glu Pro Leu Gln Lys Ala Val Ala Lys Phe Phe Ser Ala Ser Cys
                165                 170                 175

Val Pro Cys Val Asp Gly Lys Glu Tyr Pro Asn Leu Cys Gln Leu Cys
            180                 185                 190

Ala Gly Thr Gly Glu Asn Lys Cys Ala Cys Ser Ser Gln Glu Pro Tyr
        195                 200                 205

Phe Gly Tyr Ser Gly Ala Phe Lys Cys Leu Gln Asp Gly Ala Gly Asp
    210                 215                 220

Val Ala Phe Val Lys Asp Ser Thr Val Phe Glu Ser Leu Pro Ala Lys
225                 230                 235                 240

Ala Asp Arg Asp Gln Tyr Glu Leu Leu Cys Pro Asn Asn Thr Arg Lys
                245                 250                 255

Pro Val Asp Ala Ser Gln Glu Cys His Leu Ala Arg Val Pro Ser His
            260                 265                 270

Ala Val Val Ala Arg Ser Val Asn Gly Lys Glu Asp Leu Ile Trp Lys
        275                 280                 285

Leu Leu Val Lys Ala Gln Glu Lys Phe Gly Arg Gly Lys Pro Ser Ala
    290                 295                 300

Phe Gln Leu Phe Gly Ser Pro Ala Gly Gln Lys Asp Leu Leu Phe Lys
305                 310                 315                 320

Asp Ser Ala Leu Gly Leu Leu Arg Ile Pro Ser Lys Ile Asp Ser Gly
                325                 330                 335

Leu Tyr Leu Gly Ser Asn Tyr Ile Thr Ala Ile Arg Gly Leu Arg Glu
            340                 345                 350

Thr Ala Ala Glu Val Glu Leu Arg Arg Ala Gln Val Val Trp Cys Ala
        355                 360                 365

Val Gly Ser Asp Glu Gln Leu Lys Cys Gln Glu Trp Ser Arg Gln Ser
    370                 375                 380
```

```
Asn Gln Ser Val Val Cys Ala Thr Ala Ser Thr Glu Asp Cys Ile
385                 390                 395                 400

Ala Leu Val Leu Lys Gly Glu Ala Asp Ala Leu Ser Leu Asp Gly Gly
                405                 410                 415

Tyr Ile Tyr Ile Ala Gly Lys Cys Gly Leu Val Pro Val Leu Ala Glu
                420                 425                 430

Ser Gln Gln Ser Pro Glu Ser Ser Gly Leu Asp Cys Val His Arg Pro
                435                 440                 445

Val Lys Gly Tyr Leu Ala Val Ala Val Val Arg Lys Ala Asn Asp Lys
            450                 455                 460

Ile Thr Trp Asn Ser Leu Arg Gly Lys Lys Ser Cys His Thr Ala Val
465                 470                 475                 480

Asp Arg Thr Ala Gly Trp Asn Ile Pro Met Gly Pro Leu Phe Lys Asn
                485                 490                 495

Thr Asp Ser Cys Arg Phe Asp Glu Phe Phe Ser Gln Ser Cys Ala Pro
                500                 505                 510

Gly Ser Asp Pro Arg Ser Lys Leu Cys Ala Leu Cys Ala Gly Asn Glu
            515                 520                 525

Glu Gly Gln Asn Lys Cys Val Pro Asn Ser Ser Glu Arg Tyr Tyr Gly
            530                 535                 540

Tyr Thr Gly Ala Phe Arg Cys Leu Ala Glu Asn Val Gly Asp Val Ala
545                 550                 555                 560

Phe Val Lys Asp Val Thr Val Leu Asp Asn Thr Asp Gly Lys Asn Thr
                565                 570                 575

Glu Gln Trp Ala Lys Asp Leu Lys Leu Gly Asp Phe Glu Leu Leu Cys
                580                 585                 590

Leu Asn Gly Thr Arg Lys Pro Val Thr Glu Ala Glu Ser Cys His Leu
            595                 600                 605

Pro Val Ala Pro Asn His Ala Val Val Ser Arg Ile Asp Lys Val Ala
            610                 615                 620

His Leu Glu Gln Val Leu Leu Arg Gln Gln Ala His Phe Gly Arg Asn
625                 630                 635                 640

Gly Gln Asp Cys Pro Gly Lys Phe Cys Leu Phe Gln Ser Lys Thr Lys
                645                 650                 655

Asn Leu Leu Phe Asn Asp Asn Thr Glu Cys Leu Ala Lys Leu Gln Gly
                660                 665                 670

Lys Thr Thr Tyr Glu Glu Tyr Leu Gly Pro Gln Tyr Val Thr Ala Ile
            675                 680                 685

Ala Lys Leu Arg Arg Cys Ser Thr Ser Pro Leu Leu Glu Ala Cys Ala
            690                 695                 700

Phe Leu Met Arg
705

<210> SEQ ID NO 24
<211> LENGTH: 708
<212> TYPE: PRT
<213> ORGANISM: CAMEL

<400> SEQUENCE: 24

Met Lys Leu Phe Phe Pro Ala Leu Leu Ser Leu Gly Ala Leu Gly Leu
1               5                   10                  15

Cys Leu Ala Ala Ser Lys Lys Ser Val Arg Trp Cys Thr Thr Ser Pro
                20                  25                  30

Ala Glu Ser Ser Lys Cys Ala Gln Trp Gln Arg Arg Met Lys Lys Val
            35                  40                  45
```

```
Arg Gly Pro Ser Val Thr Cys Val Lys Lys Thr Ser Arg Phe Glu Cys
    50                  55                  60

Ile Gln Ala Ile Ser Thr Glu Lys Ala Asp Ala Val Thr Leu Asp Gly
65              70                  75                  80

Gly Leu Val Tyr Asp Ala Gly Leu Asp Pro Tyr Lys Leu Arg Pro Ile
                85                  90                  95

Ala Ala Glu Val Tyr Gly Thr Glu Asn Asn Pro Gln Thr His Tyr Tyr
            100                 105                 110

Ala Val Ala Ile Ala Lys Lys Gly Thr Asn Phe Gln Leu Asn Gln Leu
            115                 120                 125

Gln Gly Leu Lys Ser Cys His Thr Gly Leu Gly Arg Ser Ala Gly Trp
    130                 135                 140

Asn Ile Pro Met Gly Leu Leu Arg Pro Phe Leu Asp Trp Thr Gly Pro
145                 150                 155                 160

Pro Glu Pro Leu Gln Lys Ala Val Ala Lys Phe Phe Ser Ala Ser Cys
                165                 170                 175

Val Pro Cys Val Asp Gly Lys Glu Tyr Pro Asn Leu Cys Gln Leu Cys
            180                 185                 190

Ala Gly Thr Gly Glu Asn Lys Cys Ala Cys Ser Ser Gln Glu Pro Tyr
            195                 200                 205

Phe Gly Tyr Ser Gly Ala Phe Lys Cys Leu Gln Asp Gly Ala Gly Asp
    210                 215                 220

Val Ala Phe Val Lys Asp Ser Thr Val Phe Glu Ser Leu Pro Ala Lys
225                 230                 235                 240

Ala Asp Arg Asp Gln Tyr Glu Leu Leu Cys Pro Asn Asn Thr Arg Lys
                245                 250                 255

Pro Val Asp Ala Phe Gln Glu Cys His Leu Ala Arg Val Pro Ser His
            260                 265                 270

Ala Val Val Ala Arg Ser Val Asn Gly Lys Glu Asp Leu Ile Trp Lys
            275                 280                 285

Leu Leu Val Lys Ala Gln Glu Lys Phe Gly Arg Gly Lys Pro Ser Gly
    290                 295                 300

Phe Gln Leu Phe Gly Ser Pro Ala Gly Gln Lys Asp Leu Leu Phe Lys
305                 310                 315                 320

Asp Ser Ala Leu Gly Leu Leu Arg Ile Ser Ser Lys Ile Asp Ser Gly
                325                 330                 335

Leu Tyr Leu Gly Ser Asn Tyr Ile Thr Ala Ile Arg Gly Leu Arg Glu
            340                 345                 350

Thr Ala Ala Glu Val Glu Leu Arg Arg Ala Gln Val Val Trp Cys Ala
            355                 360                 365

Val Gly Ser Asp Glu Gln Leu Lys Cys Gln Glu Trp Ser Arg Gln Ser
    370                 375                 380

Asn Gln Ser Val Val Cys Ala Thr Ala Ser Thr Thr Glu Asp Cys Ile
385                 390                 395                 400

Ala Leu Val Leu Lys Gly Glu Ala Asp Ala Leu Ser Leu Asp Gly Gly
                405                 410                 415

Tyr Ile Tyr Ile Ala Gly Lys Cys Gly Leu Val Pro Val Leu Ala Glu
            420                 425                 430

Ser Gln Gln Ser Pro Glu Ser Ser Gly Leu Asp Cys Val His Arg Pro
            435                 440                 445

Val Lys Gly Tyr Leu Ala Val Ala Val Arg Lys Ala Asn Asp Lys
    450                 455                 460
```

```
Ile Thr Trp Asn Ser Leu Arg Gly Lys Lys Ser Cys His Thr Ala Val
465                 470                 475                 480

Asp Arg Thr Ala Gly Trp Asn Ile Pro Met Gly Leu Leu Ser Lys Asn
            485                 490                 495

Thr Asp Ser Cys Arg Phe Asp Glu Phe Leu Ser Gln Ser Cys Ala Pro
        500                 505                 510

Gly Ser Asp Pro Arg Ser Lys Leu Cys Ala Leu Cys Ala Gly Asn Glu
    515                 520                 525

Glu Gly Gln Asn Lys Cys Val Pro Asn Ser Ser Glu Arg Tyr Tyr Gly
530                 535                 540

Tyr Thr Gly Ala Phe Arg Cys Leu Ala Glu Asn Val Gly Asp Val Ala
545                 550                 555                 560

Phe Val Lys Asp Val Thr Val Leu Asp Asn Thr Asp Gly Lys Asn Thr
                565                 570                 575

Glu Gln Trp Ala Lys Asp Leu Lys Leu Gly Asp Phe Glu Leu Leu Cys
            580                 585                 590

Leu Asn Gly Thr Arg Lys Pro Val Thr Glu Ala Glu Ser Cys His Leu
        595                 600                 605

Ala Val Ala Pro Asn His Ala Val Val Ser Arg Ile Asp Lys Val Ala
    610                 615                 620

His Leu Glu Gln Val Leu Leu Arg Gln Gln Ala His Phe Gly Arg Asn
625                 630                 635                 640

Gly Arg Asp Cys Pro Gly Lys Phe Cys Leu Phe Gln Ser Lys Thr Lys
                645                 650                 655

Asn Leu Leu Phe Asn Asp Asn Thr Glu Cys Leu Ala Lys Leu Gln Gly
            660                 665                 670

Lys Thr Thr Tyr Glu Glu Tyr Leu Gly Pro Gln Tyr Val Thr Ala Ile
        675                 680                 685

Ala Lys Leu Arg Arg Cys Ser Thr Ser Pro Leu Leu Glu Ala Cys Ala
    690                 695                 700

Phe Leu Met Arg
705

<210> SEQ ID NO 25
<211> LENGTH: 698
<212> TYPE: PRT
<213> ORGANISM: RAT

<400> SEQUENCE: 25

Met Arg Phe Ala Val Gly Ala Leu Leu Ala Cys Ala Ala Leu Gly Leu
1               5                   10                  15

Cys Leu Ala Val Pro Asp Lys Thr Val Lys Trp Cys Ala Val Ser Glu
            20                  25                  30

His Glu Asn Thr Lys Cys Ile Ser Phe Arg Asp His Met Lys Thr Val
        35                  40                  45

Leu Pro Ala Asp Gly Pro Arg Leu Ala Cys Val Lys Lys Thr Ser Tyr
    50                  55                  60

Gln Asp Cys Ile Lys Ala Ile Ser Gly Gly Glu Ala Asp Ala Ile Thr
65                  70                  75                  80

Leu Asp Gly Gly Trp Val Tyr Asp Ala Gly Leu Thr Pro Asn Asn Leu
                85                  90                  95

Lys Pro Val Ala Ala Glu Phe Tyr Gly Ser Leu Glu His Pro Gln Thr
            100                 105                 110

His Tyr Leu Ala Val Ala Val Val Lys Lys Gly Thr Asp Phe Gln Leu
        115                 120                 125
```

-continued

```
Asn Gln Leu Gln Gly Lys Lys Ser Cys His Thr Gly Leu Gly Arg Ser
    130                 135                 140
Ala Gly Trp Ile Ile Pro Ile Gly Leu Leu Phe Cys Asn Leu Pro Glu
145                 150                 155                 160
Pro Arg Lys Pro Leu Glu Lys Ala Val Ala Ser Phe Phe Ser Gly Ser
                165                 170                 175
Cys Val Pro Cys Ala Asp Pro Val Ala Phe Pro Gln Leu Cys Gln Leu
            180                 185                 190
Cys Pro Gly Cys Gly Cys Ser Pro Thr Gln Pro Phe Phe Gly Tyr Val
        195                 200                 205
Gly Ala Phe Lys Cys Leu Arg Asp Gly Gly Asp Val Ala Phe Val
    210                 215                 220
Lys His Thr Thr Ile Phe Glu Val Leu Pro Gln Lys Ala Asp Arg Asp
225                 230                 235                 240
Gln Tyr Glu Leu Leu Cys Leu Asp Asn Thr Arg Lys Pro Val Asp Gln
                245                 250                 255
Tyr Glu Asp Cys Tyr Leu Ala Arg Ile Pro Ser His Ala Val Val Ala
            260                 265                 270
Arg Asn Gly Asp Gly Lys Glu Asp Leu Ile Trp Glu Ile Leu Lys Val
        275                 280                 285
Ala Gln Glu His Phe Gly Lys Gly Lys Ser Lys Asp Phe Gln Leu Phe
    290                 295                 300
Gly Ser Pro Leu Gly Lys Asp Leu Leu Phe Lys Asp Ser Ala Phe Gly
305                 310                 315                 320
Cys Tyr Gly Val Pro Pro Arg Met Asp Tyr Arg Leu Tyr Leu Gly His
                325                 330                 335
Ser Tyr Val Thr Ala Ile Arg Asn Gln Arg Glu Gly Val Cys Pro Glu
            340                 345                 350
Ala Ser Ile Asp Ser Ala Pro Val Lys Trp Cys Ala Leu Ser His Gln
        355                 360                 365
Glu Arg Ala Lys Cys Asp Glu Trp Ser Val Thr Ser Asn Gly Gln Ile
    370                 375                 380
Glu Cys Glu Ser Ala Glu Ser Thr Glu Asp Cys Ile Asp Lys Ile Val
385                 390                 395                 400
Asn Gly Glu Ala Asp Ala Met Ser Leu Asp Gly Gly His Ala Tyr Ile
                405                 410                 415
Ala Gly Gln Cys Gly Leu Val Pro Val Met Ala Glu Asn Tyr Asp Ile
            420                 425                 430
Ser Ser Cys Thr Asn Pro Gln Ser Asp Val Phe Pro Lys Gly Tyr Tyr
        435                 440                 445
Ala Val Ala Val Val Lys Ala Ser Asp Ser Ser Ile Asn Trp Asn Asn
    450                 455                 460
Leu Lys Gly Lys Lys Ser Cys His Thr Gly Val Asp Arg Thr Ala Gly
465                 470                 475                 480
Trp Asn Ile Pro Met Gly Leu Leu Phe Ser Arg Ile Asn His Cys Lys
                485                 490                 495
Phe Asp Glu Phe Phe Ser Gln Gly Cys Ala Pro Gly Tyr Lys Lys Asn
            500                 505                 510
Ser Thr Leu Cys Asp Leu Cys Ile Gly Pro Ala Lys Cys Ala Pro Asn
        515                 520                 525
Asn Arg Glu Gly Tyr Asn Gly Tyr Thr Gly Ala Phe Gln Cys Leu Val
    530                 535                 540
```

```
Glu Lys Gly Asp Val Ala Phe Val Lys His Gln Thr Val Leu Glu Asn
545                 550                 555                 560

Thr Asn Gly Lys Asn Thr Ala Ala Trp Ala Lys Asp Leu Lys Gln Glu
                565                 570                 575

Asp Phe Gln Leu Leu Cys Pro Asp Gly Thr Lys Lys Pro Val Thr Glu
            580                 585                 590

Phe Ala Thr Cys His Leu Ala Gln Ala Pro Asn His Val Val Val Ser
        595                 600                 605

Arg Lys Glu Lys Ala Ala Arg Val Ser Thr Val Leu Thr Ala Gln Lys
    610                 615                 620

Asp Leu Phe Trp Lys Gly Asp Lys Asp Cys Thr Gly Asn Phe Cys Leu
625                 630                 635                 640

Phe Arg Ser Ser Thr Lys Asp Leu Leu Phe Arg Asp Asp Thr Lys Cys
                645                 650                 655

Leu Thr Lys Leu Pro Glu Gly Thr Thr Tyr Glu Glu Tyr Leu Gly Ala
            660                 665                 670

Glu Tyr Leu Gln Ala Val Gly Asn Ile Arg Lys Cys Ser Thr Ser Arg
        675                 680                 685

Leu Leu Glu Ala Cys Thr Phe His Lys Ser
    690                 695

<210> SEQ ID NO 26
<211> LENGTH: 695
<212> TYPE: PRT
<213> ORGANISM: HORSE

<400> SEQUENCE: 26

Leu Gly Leu Cys Leu Ala Ala Pro Arg Lys Ser Val Arg Trp Cys Thr
1               5                   10                  15

Ile Ser Pro Ala Glu Ala Ala Lys Cys Ala Lys Phe Gln Arg Asn Met
                20                  25                  30

Lys Lys Val Arg Gly Pro Ser Val Ser Cys Ile Arg Lys Thr Ser Ser
            35                  40                  45

Phe Glu Cys Ile Gln Ala Ile Ala Ala Asn Lys Ala Asp Ala Val Thr
    50                  55                  60

Leu Asp Gly Gly Leu Val Tyr Glu Ala Gly Leu His Pro Tyr Lys Leu
65                  70                  75                  80

Arg Pro Val Ala Ala Glu Val Tyr Gln Thr Arg Gly Lys Pro Gln Thr
                85                  90                  95

Arg Tyr Tyr Ala Val Ala Val Val Lys Lys Gly Ser Gly Phe Gln Leu
            100                 105                 110

Asn Gln Leu Gln Gly Val Lys Ser Cys His Thr Gly Leu Gly Arg Ser
        115                 120                 125

Ala Gly Trp Asn Ile Pro Ile Gly Thr Leu Arg Pro Tyr Leu Asn Trp
130                 135                 140

Thr Gly Pro Pro Glu Pro Leu Gln Lys Ala Val Ala Asn Phe Phe Ser
145                 150                 155                 160

Ala Ser Cys Val Pro Cys Ala Asp Gly Lys Gln Tyr Pro Asn Leu Cys
                165                 170                 175

Arg Leu Cys Ala Gly Thr Glu Ala Asp Lys Cys Ala Cys Ser Ser Gln
            180                 185                 190

Glu Pro Tyr Phe Gly Tyr Ser Gly Ala Phe Lys Cys Leu Glu Asn Gly
        195                 200                 205

Ala Gly Asp Val Ala Phe Val Lys Asp Ser Thr Val Phe Glu Asn Leu
210                 215                 220
```

```
Pro Asp Glu Ala Asp Arg Asp Lys Tyr Glu Leu Leu Cys Pro Asp Asn
225                 230                 235                 240

Thr Arg Lys Pro Val Asp Ala Phe Lys Glu Cys His Leu Ala Arg Val
            245                 250                 255

Pro Ser His Ala Val Val Ala Arg Ser Val Asp Gly Arg Glu Asp Leu
                260                 265                 270

Ile Trp Arg Leu Leu His Arg Ala Gln Glu Glu Phe Gly Arg Asn Lys
        275                 280                 285

Ser Ser Ala Phe Gln Leu Phe Lys Ser Thr Pro Glu Asn Lys Asp Leu
    290                 295                 300

Leu Phe Lys Asp Ser Ala Leu Gly Phe Val Arg Ile Pro Ser Gln Ile
305                 310                 315                 320

Asp Ser Gly Leu Tyr Leu Gly Ala Asn Tyr Leu Thr Ala Thr Gln Asn
                325                 330                 335

Leu Arg Glu Thr Ala Ala Glu Val Ala Ala Arg Arg Glu Arg Val Val
            340                 345                 350

Trp Cys Ala Val Gly Pro Glu Glu Arg Lys Cys Lys Gln Trp Ser
        355                 360                 365

Asp Val Ser Asn Arg Lys Val Ala Cys Ala Ser Ala Ser Thr Thr Glu
370                 375                 380

Glu Cys Ile Ala Leu Val Leu Lys Gly Glu Ala Asp Ala Leu Asn Leu
385                 390                 395                 400

Asp Gly Gly Phe Ile Tyr Val Ala Gly Lys Cys Gly Leu Val Pro Val
                405                 410                 415

Leu Ala Glu Asn Gln Lys Ser Gln Asn Ser Asn Ala Pro Asp Cys Val
            420                 425                 430

His Arg Pro Pro Glu Gly Tyr Leu Ala Val Ala Val Val Arg Lys Ser
        435                 440                 445

Asp Ala Asp Leu Thr Trp Asn Ser Leu Ser Gly Lys Lys Ser Cys His
450                 455                 460

Thr Gly Val Gly Arg Thr Ala Ala Trp Asn Ile Pro Met Gly Leu Leu
465                 470                 475                 480

Phe Asn Gln Thr Gly Ser Cys Lys Phe Asp Lys Phe Phe Ser Gln Ser
                485                 490                 495

Cys Ala Pro Gly Ala Asp Pro Gln Ser Ser Leu Cys Ala Leu Cys Val
            500                 505                 510

Gly Asn Asn Glu Asn Glu Asn Lys Cys Met Pro Asn Ser Glu Glu Arg
        515                 520                 525

Tyr Tyr Gly Tyr Thr Gly Ala Phe Arg Cys Leu Ala Glu Lys Ala Gly
530                 535                 540

Asp Val Ala Phe Val Lys Asp Val Thr Val Leu Gln Asn Thr Asp Gly
545                 550                 555                 560

Lys Asn Ser Glu Pro Trp Ala Lys Asp Leu Lys Gln Glu Asp Phe Glu
                565                 570                 575

Leu Leu Cys Leu Asp Gly Thr Arg Lys Pro Val Ala Glu Ala Glu Ser
            580                 585                 590

Cys His Leu Ala Arg Ala Pro Asn His Ala Val Val Ser Gln Ser Asp
    595                 600                 605

Arg Ala Gln His Leu Lys Lys Val Leu Phe Leu Gln Gln Asp Gln Phe
610                 615                 620

Gly Gly Asn Gly Pro Asp Cys Pro Gly Lys Phe Cys Leu Phe Lys Ser
625                 630                 635                 640
```

```
Glu Thr Lys Asn Leu Leu Phe Asn Asp Asn Thr Glu Cys Leu Ala Glu
                645                 650                 655

Leu Gln Gly Lys Thr Thr Tyr Glu Gln Tyr Leu Gly Ser Glu Tyr Val
            660                 665                 670

Thr Ser Ile Thr Asn Leu Arg Arg Cys Ser Ser Pro Leu Leu Glu
        675                 680                 685

Ala Cys Ala Phe Leu Arg Ala
    690                 695

<210> SEQ ID NO 27
<211> LENGTH: 711
<212> TYPE: PRT
<213> ORGANISM: HUMAN

<400> SEQUENCE: 27

Met Lys Leu Val Phe Leu Val Leu Leu Phe Leu Gly Ala Leu Gly Leu
1               5                   10                  15

Cys Leu Ala Gly Arg Arg Arg Ser Val Gln Trp Cys Ala Val Ser
            20                  25                  30

Gln Pro Glu Ala Thr Lys Cys Phe Gln Trp Gln Arg Asn Met Arg Lys
            35                  40                  45

Val Arg Gly Pro Pro Val Ser Cys Ile Lys Arg Asp Ser Pro Ile Gln
        50                  55                  60

Cys Ile Gln Ala Ile Ala Glu Asn Arg Ala Asp Ala Val Thr Leu Asp
65                  70                  75                  80

Gly Gly Phe Ile Tyr Glu Ala Gly Leu Ala Pro Tyr Lys Leu Arg Pro
                85                  90                  95

Val Ala Ala Glu Val Tyr Gly Thr Glu Arg Gln Pro Arg Thr His Tyr
            100                 105                 110

Tyr Ala Val Ala Val Val Lys Lys Gly Gly Ser Phe Gln Leu Asn Glu
        115                 120                 125

Leu Gln Gly Leu Lys Ser Cys His Thr Gly Leu Arg Arg Thr Ala Gly
    130                 135                 140

Trp Asn Val Pro Ile Gly Thr Leu Arg Pro Phe Leu Asn Trp Thr Gly
145                 150                 155                 160

Pro Pro Glu Pro Ile Glu Ala Ala Val Ala Arg Phe Phe Ser Ala Ser
                165                 170                 175

Cys Val Pro Gly Ala Asp Lys Gly Gln Phe Pro Asn Leu Cys Arg Leu
            180                 185                 190

Cys Ala Gly Thr Gly Glu Asn Lys Cys Ala Phe Ser Ser Gln Glu Pro
        195                 200                 205

Tyr Phe Ser Tyr Ser Gly Ala Phe Lys Cys Leu Arg Asp Gly Ala Gly
    210                 215                 220

Asp Val Ala Phe Ile Arg Glu Ser Thr Val Phe Glu Asp Leu Ser Asp
225                 230                 235                 240

Glu Ala Glu Arg Asp Glu Tyr Glu Leu Leu Cys Pro Asp Asn Thr Arg
                245                 250                 255

Lys Pro Val Asp Lys Phe Lys Asp Cys His Leu Ala Arg Val Pro Ser
            260                 265                 270

His Ala Val Val Ala Arg Ser Val Asn Gly Lys Glu Asp Ala Ile Trp
        275                 280                 285

Asn Leu Leu Arg Gln Ala Gln Glu Lys Phe Gly Lys Asp Lys Ser Pro
    290                 295                 300

Lys Phe Gln Leu Phe Gly Ser Pro Ser Gly Gln Lys Asp Leu Leu Phe
305                 310                 315                 320
```

-continued

```
Lys Asp Ser Ala Ile Gly Phe Ser Arg Val Pro Arg Ile Asp Ser
                325                 330                 335
Gly Leu Tyr Leu Gly Ser Gly Tyr Phe Thr Ala Ile Gln Asn Leu Arg
            340                 345                 350
Lys Ser Glu Glu Val Ala Ala Arg Arg Ala Arg Val Val Trp Cys
        355                 360                 365
Ala Val Gly Glu Gln Leu Arg Lys Cys Asn Gln Trp Ser Gly Leu
    370                 375                 380
Ser Glu Gly Ser Val Thr Cys Ser Ser Ala Ser Thr Thr Glu Asp Cys
385                 390                 395                 400
Ile Ala Leu Val Leu Lys Gly Glu Ala Asp Ala Met Ser Leu Asp Gly
                405                 410                 415
Gly Tyr Val Tyr Thr Ala Gly Lys Cys Gly Leu Val Pro Val Leu Ala
            420                 425                 430
Glu Asn Tyr Lys Ser Gln Gln Ser Ser Asp Pro Asp Pro Asn Cys Val
        435                 440                 445
Asp Arg Pro Val Glu Gly Tyr Leu Ala Val Ala Val Val Arg Arg Ser
    450                 455                 460
Asp Thr Ser Leu Thr Trp Asn Ser Val Lys Gly Lys Lys Ser Cys His
465                 470                 475                 480
Thr Ala Val Asp Arg Thr Ala Gly Trp Asn Ile Pro Met Gly Leu Leu
                485                 490                 495
Phe Asn Gln Thr Gly Ser Cys Lys Phe Asp Glu Tyr Phe Ser Gln Ser
            500                 505                 510
Cys Ala Pro Gly Ser Asp Pro Arg Ser Asn Leu Cys Ala Leu Cys Ile
        515                 520                 525
Gly Asp Glu Gln Gly Glu Asn Lys Cys Val Pro Asn Ser Asn Glu Arg
    530                 535                 540
Tyr Tyr Gly Tyr Thr Gly Ala Phe Arg Cys Leu Ala Glu Asn Ala Gly
545                 550                 555                 560
Asp Val Ala Phe Val Lys Asp Val Thr Val Leu Gln Asn Thr Asp Gly
                565                 570                 575
Asn Asn Asn Glu Ala Trp Ala Lys Asp Leu Lys Leu Ala Asp Phe Ala
            580                 585                 590
Leu Leu Cys Leu Asp Gly Lys Arg Lys Pro Val Thr Glu Ala Arg Ser
        595                 600                 605
Cys His Leu Ala Met Ala Pro Asn His Ala Val Val Ser Arg Met Asp
    610                 615                 620
Lys Val Glu Arg Leu Lys Gln Val Leu Leu His Gln Gln Ala Lys Phe
625                 630                 635                 640
Gly Arg Asn Gly Ser Asp Cys Pro Asp Lys Phe Cys Leu Phe Gln Ser
                645                 650                 655
Glu Thr Lys Asn Leu Leu Phe Asn Asp Asn Thr Glu Cys Leu Ala Arg
            660                 665                 670
Leu His Gly Lys Thr Thr Tyr Glu Lys Tyr Leu Gly Pro Gln Tyr Val
        675                 680                 685
Ala Gly Ile Thr Asn Leu Lys Lys Cys Ser Thr Ser Pro Leu Leu Glu
    690                 695                 700
Ala Cys Glu Phe Leu Arg Lys
705                 710

<210> SEQ ID NO 28
<211> LENGTH: 708
```

```
<212> TYPE: PRT
<213> ORGANISM: GOAT

<400> SEQUENCE: 28

Met Lys Leu Phe Val Pro Ala Leu Leu Ser Leu Gly Ala Leu Gly Leu
1               5                   10                  15

Cys Leu Ala Ala Pro Arg Lys Asn Val Arg Trp Cys Ala Ile Ser Leu
            20                  25                  30

Pro Glu Trp Ser Lys Cys Tyr Gln Trp Gln Arg Arg Met Arg Lys Leu
        35                  40                  45

Gly Ala Pro Ser Ile Thr Cys Val Arg Thr Ser Ala Leu Glu Cys
    50                  55                  60

Ile Arg Ala Ile Ala Gly Lys Asn Ala Asp Ala Val Thr Leu Asp Ser
65                  70                  75                  80

Gly Met Val Phe Glu Ala Gly Arg Asp Pro Tyr Lys Leu Arg Pro Val
                85                  90                  95

Ala Ala Glu Ile Tyr Gly Thr Glu Lys Ser Pro Gln Thr His Tyr Tyr
            100                 105                 110

Ala Val Ala Val Val Lys Lys Gly Ser Asn Phe Lys Leu Asp Gln Leu
        115                 120                 125

Gln Gly Gln Lys Ser Cys His Met Gly Leu Gly Arg Ser Ala Gly Trp
130                 135                 140

Asn Ile Pro Val Gly Ile Leu Arg Pro Leu Ser Trp Thr Glu Ser
145                 150                 155                 160

Ala Glu Pro Leu Gln Gly Ala Val Ala Arg Phe Phe Ser Ala Ser Cys
            165                 170                 175

Val Pro Cys Val Asp Gly Lys Ala Tyr Pro Asn Leu Cys Gln Leu Cys
        180                 185                 190

Lys Gly Val Gly Glu Asn Lys Cys Ala Cys Ser Ser Gln Glu Pro Tyr
    195                 200                 205

Phe Gly Tyr Ser Gly Ala Phe Lys Cys Leu Gln Asp Gly Ala Gly Asp
210                 215                 220

Val Ala Phe Val Lys Glu Thr Thr Val Phe Glu Asn Leu Pro Glu Lys
225                 230                 235                 240

Ala Asp Arg Asp Gln Tyr Glu Leu Leu Cys Leu Asn Asn Thr Arg Ala
            245                 250                 255

Pro Val Asp Ala Phe Lys Glu Cys His Leu Ala Gln Val Pro Ser His
        260                 265                 270

Ala Val Val Ala Arg Ser Val Asp Gly Lys Glu Asn Leu Ile Trp Glu
    275                 280                 285

Leu Leu Arg Lys Ala Gln Glu Lys Phe Gly Lys Asn Lys Ser Gln Arg
290                 295                 300

Phe Gln Leu Phe Gly Ser Pro Glu Gly Arg Arg Asp Leu Leu Phe Lys
305                 310                 315                 320

Asp Ser Ala Leu Gly Phe Val Arg Ile Pro Ser Lys Val Asp Ser Ala
            325                 330                 335

Leu Tyr Leu Gly Ser Arg Tyr Leu Thr Ala Leu Lys Asn Leu Arg Glu
        340                 345                 350

Thr Ala Glu Glu Leu Lys Ala Arg Cys Thr Arg Val Val Trp Cys Ala
    355                 360                 365

Val Gly Pro Glu Glu Gln Ser Lys Cys Gln Gln Trp Ser Glu Gln Ser
370                 375                 380

Gly Gln Asn Val Thr Cys Ala Thr Ala Ser Thr Thr Asp Asp Cys Ile
385                 390                 395                 400
```

```
Ala Leu Val Leu Lys Gly Glu Ala Asp Ala Leu Ser Leu Gly Gly Gly
                405                 410                 415

Tyr Ile Tyr Thr Ala Gly Lys Cys Gly Leu Val Pro Val Met Ala Glu
            420                 425                 430

Asn Arg Lys Ser Ser Lys Tyr Ser Ser Leu Asp Cys Val Leu Arg Pro
        435                 440                 445

Thr Glu Gly Tyr Leu Ala Val Ala Val Val Lys Ala Asn Glu Gly
    450                 455                 460

Leu Thr Trp Asn Ser Leu Lys Gly Lys Lys Ser Cys His Thr Ala Val
465                 470                 475                 480

Asp Arg Thr Ala Gly Trp Asn Ile Pro Met Gly Leu Ile Ala Asn Gln
                485                 490                 495

Thr Gly Ser Cys Ala Phe Asp Glu Phe Phe Ser Gln Ser Cys Ala Pro
            500                 505                 510

Gly Ala Asp Pro Lys Ser Ser Leu Cys Ala Leu Cys Ala Gly Asp Asp
        515                 520                 525

Gln Gly Leu Asp Lys Cys Val Pro Asn Ser Lys Glu Lys Tyr Tyr Gly
    530                 535                 540

Tyr Thr Gly Ala Phe Arg Cys Leu Ala Glu Asp Val Gly Asp Val Ala
545                 550                 555                 560

Phe Val Lys Asn Asp Thr Val Trp Glu Asn Thr Asn Gly Glu Ser Ser
                565                 570                 575

Ala Asp Trp Ala Lys Asn Leu Asn Arg Glu Asp Phe Arg Leu Leu Cys
            580                 585                 590

Leu Asp Gly Thr Thr Lys Pro Val Thr Glu Ala Gln Ser Cys Tyr Leu
        595                 600                 605

Ala Val Ala Pro Asn His Ala Val Val Ser Arg Ser Asp Arg Ala Ala
    610                 615                 620

His Val Glu Gln Val Leu Leu His Gln Gln Ala Leu Phe Gly Lys Asn
625                 630                 635                 640

Gly Lys Asn Cys Pro Asp Gln Phe Cys Leu Phe Lys Ser Glu Thr Lys
                645                 650                 655

Asn Leu Leu Phe Asn Asp Asn Thr Glu Cys Leu Ala Lys Leu Gly Gly
            660                 665                 670

Arg Pro Thr Tyr Glu Lys Tyr Leu Gly Thr Glu Tyr Val Thr Ala Ile
        675                 680                 685

Ala Asn Leu Lys Lys Cys Ser Thr Ser Pro Leu Leu Glu Ala Cys Ala
    690                 695                 700

Phe Leu Thr Arg
705

<210> SEQ ID NO 29
<211> LENGTH: 708
<212> TYPE: PRT
<213> ORGANISM: COW

<400> SEQUENCE: 29

Met Lys Leu Phe Val Pro Ala Leu Leu Ser Leu Gly Ala Leu Gly Leu
1               5                   10                  15

Cys Leu Ala Ala Pro Arg Lys Asn Val Arg Trp Cys Thr Ile Ser Gln
            20                  25                  30

Pro Glu Trp Phe Lys Cys Arg Arg Trp Gln Trp Arg Met Lys Lys Leu
        35                  40                  45

Gly Ala Pro Ser Ile Thr Cys Val Arg Arg Ala Phe Ala Leu Glu Cys
```

```
                50                  55                  60
Ile Arg Ala Ile Ala Glu Lys Lys Ala Asp Ala Val Thr Leu Asp Gly
 65                  70                  75                  80

Gly Met Val Phe Glu Ala Gly Arg Asp Pro Tyr Lys Leu Arg Pro Val
                 85                  90                  95

Ala Ala Glu Ile Tyr Gly Thr Lys Glu Ser Pro Gln Thr His Tyr Tyr
                100                 105                 110

Ala Val Ala Val Val Lys Lys Gly Ser Asn Phe Gln Leu Asp Gln Leu
                115                 120                 125

Gln Gly Arg Lys Ser Cys His Thr Gly Leu Gly Arg Ser Ala Gly Trp
130                 135                 140

Val Ile Pro Met Gly Ile Leu Arg Pro Tyr Leu Ser Trp Thr Glu Ser
145                 150                 155                 160

Leu Glu Pro Pro Gly Ala Val Ala Lys Phe Phe Ser Ala Ser Cys
                165                 170                 175

Val Pro Cys Ile Asp Arg Gln Ala Tyr Pro Asn Leu Cys Gln Leu Cys
                180                 185                 190

Lys Gly Glu Gly Glu Asn Gln Cys Ala Cys Ser Ser Arg Glu Pro Tyr
                195                 200                 205

Phe Gly Tyr Ser Gly Ala Phe Lys Cys Leu Gln Asp Gly Ala Gly Asp
                210                 215                 220

Val Ala Phe Val Lys Glu Thr Thr Val Phe Glu Asn Leu Pro Glu Lys
225                 230                 235                 240

Ala Asp Arg Asp Gln Tyr Glu Leu Leu Cys Leu Asn Asn Ser Arg Ala
                245                 250                 255

Pro Val Asp Ala Phe Lys Glu Cys His Leu Ala Gln Val Pro Ser His
                260                 265                 270

Ala Val Val Ala Arg Ser Val Asp Gly Lys Glu Asp Leu Ile Trp Lys
                275                 280                 285

Leu Leu Ser Lys Ala Gln Glu Lys Phe Gly Lys Asn Lys Ser Arg Ser
                290                 295                 300

Phe Gln Leu Phe Gly Ser Pro Pro Gly Gln Arg Asp Leu Leu Phe Lys
305                 310                 315                 320

Asp Ser Ala Leu Gly Phe Leu Arg Ile Pro Ser Lys Val Asp Ser Ala
                325                 330                 335

Leu Tyr Leu Ala Ser Arg Tyr Leu Thr Thr Leu Lys Asn Leu Arg Glu
                340                 345                 350

Thr Ala Glu Glu Val Lys Ala Arg Tyr Thr Arg Val Val Trp Cys Ala
                355                 360                 365

Val Gly Pro Glu Glu Gln Lys Lys Cys Gln Gln Trp Ser Gln Gln Ser
                370                 375                 380

Gly Gln Asn Val Thr Cys Ala Thr Ala Ser Thr Thr Asp Asp Cys Ile
385                 390                 395                 400

Val Leu Val Leu Lys Gly Glu Ala Asp Ala Leu Asn Leu Asp Gly Gly
                405                 410                 415

Tyr Ile Tyr Thr Ala Gly Lys Cys Gly Leu Val Pro Val Leu Ala Glu
                420                 425                 430

Asn Arg Lys Ser Ser Lys Tyr Ser Ser Leu Asp Cys Val Leu Arg Pro
                435                 440                 445

Thr Glu Gly Tyr Leu Ala Val Ala Val Val Lys Lys Ala Asn Glu Gly
                450                 455                 460

Leu Thr Trp Asn Ser Leu Lys Asp Lys Lys Ser Cys His Thr Ala Val
465                 470                 475                 480
```

-continued

```
Asp Arg Thr Ala Gly Trp Asn Ile Pro Met Gly Leu Ile Val Asn Gln
            485                 490                 495

Thr Gly Ser Cys Ala Phe Asp Glu Phe Phe Ser Gln Ser Cys Ala Pro
        500                 505                 510

Gly Arg Asp Pro Lys Ser Arg Leu Cys Ala Leu Cys Ala Gly Asp Asp
    515                 520                 525

Gln Gly Leu Asp Lys Cys Val Pro Asn Ser Lys Glu Lys Tyr Tyr Gly
530                 535                 540

Tyr Thr Gly Ala Phe Arg Cys Leu Ala Glu Asp Val Gly Asp Val Ala
545                 550                 555                 560

Phe Val Lys Asn Asp Thr Val Trp Glu Asn Thr Asn Gly Glu Ser Thr
                565                 570                 575

Ala Asp Trp Ala Lys Asn Leu Asn Arg Glu Asp Phe Arg Leu Leu Cys
            580                 585                 590

Leu Asp Gly Thr Arg Lys Pro Val Thr Glu Ala Gln Ser Cys His Leu
        595                 600                 605

Ala Val Ala Pro Asn His Ala Val Val Ser Arg Ser Asp Arg Ala Ala
    610                 615                 620

His Val Lys Gln Val Leu Leu His Gln Gln Ala Leu Phe Gly Lys Asn
625                 630                 635                 640

Gly Lys Asn Cys Pro Asp Lys Phe Cys Leu Phe Lys Ser Glu Thr Lys
                645                 650                 655

Asn Leu Leu Phe Asn Asp Asn Thr Glu Cys Leu Ala Lys Leu Gly Gly
            660                 665                 670

Arg Pro Thr Tyr Glu Glu Tyr Leu Gly Thr Glu Tyr Val Thr Ala Ile
        675                 680                 685

Ala Asn Leu Lys Lys Cys Ser Thr Ser Pro Leu Leu Glu Ala Cys Ala
    690                 695                 700

Phe Leu Thr Arg
705

<210> SEQ ID NO 30
<211> LENGTH: 711
<212> TYPE: PRT
<213> ORGANISM: HUMAN

<400> SEQUENCE: 30

Met Lys Leu Val Phe Leu Val Leu Leu Phe Leu Gly Ala Leu Gly Leu
1               5                   10                  15

Cys Leu Ala Gly Arg Arg Arg Ser Val Gln Trp Cys Ala Val Ser
            20                  25                  30

Gln Pro Glu Ala Thr Lys Cys Phe Gln Trp Gln Arg Asn Met Arg Lys
        35                  40                  45

Val Arg Gly Pro Pro Val Ser Cys Ile Lys Arg Asp Ser Pro Ile Gln
    50                  55                  60

Cys Ile Gln Ala Ile Ala Glu Asn Arg Ala Asp Ala Val Thr Leu Asp
65                  70                  75                  80

Gly Gly Phe Ile Tyr Glu Ala Gly Leu Ala Pro Tyr Lys Leu Arg Pro
                85                  90                  95

Val Ala Ala Glu Val Tyr Gly Thr Glu Arg Gln Pro Arg Thr His Tyr
            100                 105                 110

Tyr Ala Val Ala Val Val Lys Lys Gly Gly Ser Phe Gln Leu Asn Glu
        115                 120                 125

Leu Gln Gly Leu Lys Ser Cys His Thr Gly Leu Arg Arg Thr Ala Gly
```

-continued

```
        130                 135                 140
Trp Asn Val Pro Thr Gly Thr Leu Arg Pro Phe Leu Asn Trp Thr Gly
145                 150                 155                 160

Pro Pro Glu Pro Ile Glu Ala Ala Val Ala Arg Phe Phe Ser Ala Ser
                165                 170                 175

Cys Val Pro Gly Ala Asp Lys Gly Gln Phe Pro Asn Leu Cys Arg Leu
                180                 185                 190

Cys Ala Gly Thr Gly Glu Asn Lys Cys Ala Phe Ser Ser Gln Glu Pro
                195                 200                 205

Tyr Phe Ser Tyr Ser Gly Ala Phe Lys Cys Leu Arg Asp Gly Ala Gly
210                 215                 220

Asp Val Ala Phe Ile Arg Glu Ser Thr Val Phe Glu Asp Leu Ser Asp
225                 230                 235                 240

Glu Ala Glu Arg Asp Glu Tyr Glu Leu Leu Cys Pro Asp Asn Thr Arg
                245                 250                 255

Lys Pro Val Asp Lys Phe Lys Asp Cys His Leu Ala Arg Val Pro Ser
                260                 265                 270

His Ala Val Val Ala Arg Ser Val Asn Gly Lys Glu Asp Ala Ile Trp
                275                 280                 285

Asn Leu Leu Arg Gln Ala Gln Glu Lys Phe Gly Lys Asp Lys Ser Pro
290                 295                 300

Lys Phe Gln Leu Phe Gly Ser Pro Ser Gly Gln Lys Asp Leu Leu Phe
305                 310                 315                 320

Lys Asp Ser Ala Ile Gly Phe Ser Arg Val Pro Pro Arg Ile Asp Ser
                325                 330                 335

Gly Leu Tyr Leu Gly Ser Gly Tyr Phe Thr Ala Ile Gln Asn Leu Arg
                340                 345                 350

Lys Ser Glu Glu Glu Val Ala Ala Arg Arg Ala Arg Val Val Trp Cys
                355                 360                 365

Ala Val Gly Glu Gln Glu Leu Arg Lys Cys Asn Gln Trp Ser Gly Leu
370                 375                 380

Ser Glu Gly Ser Val Thr Cys Ser Ser Ala Ser Thr Thr Glu Asp Cys
385                 390                 395                 400

Ile Ala Leu Val Leu Lys Gly Glu Ala Asp Ala Met Ser Leu Asp Gly
                405                 410                 415

Gly Tyr Val Tyr Thr Ala Cys Lys Cys Gly Leu Val Pro Val Leu Ala
                420                 425                 430

Glu Asn Tyr Lys Ser Gln Gln Ser Ser Asp Pro Asp Pro Asn Cys Val
                435                 440                 445

Asp Arg Pro Val Glu Gly Tyr Leu Ala Val Ala Val Val Arg Arg Ser
450                 455                 460

Asp Thr Ser Leu Thr Trp Asn Ser Val Lys Gly Lys Lys Ser Cys His
465                 470                 475                 480

Thr Ala Val Asp Arg Thr Ala Gly Trp Asn Ile Pro Met Gly Leu Leu
                485                 490                 495

Phe Asn Gln Thr Gly Ser Cys Lys Phe Asp Glu Tyr Phe Ser Gln Ser
                500                 505                 510

Cys Ala Pro Gly Ser Asp Pro Arg Ser Asn Leu Cys Ala Leu Cys Ile
                515                 520                 525

Gly Asp Glu Gln Gly Glu Asn Lys Cys Val Pro Asn Ser Asn Glu Arg
                530                 535                 540

Tyr Tyr Gly Tyr Thr Gly Ala Phe Arg Cys Leu Ala Glu Asn Ala Gly
545                 550                 555                 560
```

-continued

```
Asp Val Ala Phe Val Lys Asp Val Thr Val Leu Gln Asn Thr Asp Gly
            565                 570                 575

Asn Asn Asn Glu Ala Trp Ala Lys Asp Leu Lys Leu Ala Asp Phe Ala
        580                 585                 590

Leu Leu Cys Leu Asp Gly Lys Arg Lys Pro Val Thr Glu Ala Arg Ser
        595                 600                 605

Cys His Leu Ala Met Ala Pro Asn His Ala Val Ser Arg Met Asp
        610                 615                 620

Lys Val Glu Arg Leu Lys Gln Val Leu Leu His Gln Gln Ala Lys Phe
625                 630                 635                 640

Gly Arg Asn Gly Ser Asp Cys Pro Asp Lys Phe Cys Leu Phe Gln Ser
                645                 650                 655

Glu Thr Lys Asn Leu Leu Phe Asn Asp Asn Thr Glu Cys Leu Ala Arg
                660                 665                 670

Leu His Gly Lys Thr Thr Tyr Glu Lys Tyr Leu Gly Pro Gln Tyr Val
            675                 680                 685

Ala Gly Ile Thr Asn Leu Lys Lys Cys Ser Thr Ser Pro Leu Leu Glu
        690                 695                 700

Ala Cys Glu Phe Leu Arg Lys
705                 710

<210> SEQ ID NO 31
<211> LENGTH: 709
<212> TYPE: PRT
<213> ORGANISM: HUMAN

<400> SEQUENCE: 31

Leu Val Phe Leu Val Leu Leu Phe Leu Gly Ala Leu Gly Leu Cys Leu
1               5                   10                  15

Ala Gly Arg Arg Arg Ser Val Gln Trp Cys Ala Val Ser Gln Pro
            20                  25                  30

Glu Ala Thr Lys Cys Phe Gln Trp Gln Arg Asn Met Arg Lys Val Arg
        35                  40                  45

Gly Pro Pro Val Ser Cys Ile Lys Arg Asp Ser Pro Ile Gln Cys Ile
    50                  55                  60

Gln Ala Ile Ala Glu Asn Arg Ala Asp Ala Val Thr Leu Asp Gly Gly
65                  70                  75                  80

Phe Ile Tyr Glu Ala Gly Leu Ala Pro Tyr Lys Leu Arg Pro Val Ala
                85                  90                  95

Ala Glu Val Tyr Gly Thr Glu Arg Gln Pro Arg Thr His Tyr Tyr Ala
            100                 105                 110

Val Ala Val Val Lys Lys Gly Gly Ser Phe Gln Leu Asn Glu Leu Gln
        115                 120                 125

Gly Leu Lys Ser Cys His Thr Gly Leu Arg Arg Thr Ala Gly Trp Asn
    130                 135                 140

Val Pro Ile Gly Thr Leu Arg Pro Phe Leu Asn Trp Thr Gly Pro Pro
145                 150                 155                 160

Glu Pro Ile Glu Ala Ala Val Ala Arg Phe Phe Ser Ala Ser Cys Val
                165                 170                 175

Pro Gly Ala Asp Lys Gly Gln Phe Pro Asn Leu Cys Arg Leu Cys Ala
            180                 185                 190

Gly Thr Gly Glu Asn Lys Cys Ala Phe Ser Ser Gln Glu Pro Tyr Phe
        195                 200                 205

Ser Tyr Ser Gly Ala Phe Lys Cys Leu Arg Asp Gly Ala Gly Asp Val
```

-continued

```
            210                 215                 220
Ala Phe Ile Arg Glu Ser Thr Val Phe Glu Asp Leu Ser Asp Glu Ala
225                 230                 235                 240

Glu Arg Asp Glu Tyr Glu Leu Leu Cys Pro Asp Asn Thr Arg Lys Pro
                245                 250                 255

Val Asp Lys Phe Lys Asp Cys His Leu Ala Arg Val Pro Ser His Ala
            260                 265                 270

Val Val Ala Arg Ser Val Asn Gly Lys Glu Asp Ala Ile Trp Asn Leu
            275                 280                 285

Leu Arg Gln Ala Gln Glu Lys Phe Gly Lys Asp Lys Ser Pro Lys Phe
290                 295                 300

Gln Leu Phe Gly Ser Pro Ser Gly Gln Lys Asp Leu Leu Phe Lys Asp
305                 310                 315                 320

Ser Ala Ile Gly Phe Ser Arg Val Pro Pro Arg Ile Asp Ser Gly Leu
                325                 330                 335

Tyr Leu Gly Ser Gly Tyr Phe Thr Ala Ile Gln Asn Leu Arg Lys Ser
                340                 345                 350

Glu Glu Glu Val Ala Ala Arg Arg Ala Arg Val Val Trp Cys Ala Val
                355                 360                 365

Gly Glu Gln Glu Leu Arg Lys Cys Asn Gln Trp Ser Gly Leu Ser Glu
370                 375                 380

Gly Ser Val Thr Cys Ser Ser Ala Ser Thr Thr Glu Asp Cys Ile Ala
385                 390                 395                 400

Leu Val Leu Lys Gly Glu Ala Asp Ala Met Ser Leu Asp Gly Gly Tyr
                405                 410                 415

Val Tyr Thr Ala Gly Lys Cys Gly Leu Val Pro Val Leu Ala Glu Asn
                420                 425                 430

Tyr Lys Ser Gln Gln Ser Ser Asp Pro Asp Pro Asn Cys Val Asp Arg
                435                 440                 445

Pro Val Glu Gly Tyr Leu Ala Val Ala Val Val Arg Arg Ser Asp Thr
                450                 455                 460

Ser Leu Thr Trp Asn Ser Val Lys Gly Lys Lys Ser Cys His Thr Ala
465                 470                 475                 480

Val Asp Arg Thr Ala Gly Trp Asn Ile Pro Met Gly Leu Leu Phe Asn
                485                 490                 495

Gln Thr Gly Ser Cys Lys Phe Asp Glu Tyr Phe Ser Gln Ser Cys Ala
                500                 505                 510

Pro Gly Ser Asp Pro Arg Ser Asn Leu Cys Ala Leu Cys Ile Gly Asp
                515                 520                 525

Glu Gln Gly Glu Asn Lys Cys Val Pro Asn Ser Asn Glu Arg Tyr Tyr
                530                 535                 540

Gly Tyr Thr Gly Ala Phe Arg Cys Leu Ala Glu Asn Ala Gly Asp Val
545                 550                 555                 560

Ala Phe Val Lys Asp Val Thr Val Leu Gln Asn Thr Asp Gly Asn Asn
                565                 570                 575

Asn Glu Ala Trp Ala Lys Asp Leu Lys Leu Ala Asp Phe Ala Leu Leu
                580                 585                 590

Cys Leu Asp Gly Lys Arg Lys Pro Val Thr Glu Ala Arg Ser Cys His
                595                 600                 605

Leu Ala Met Ala Pro Asn His Ala Val Val Ser Arg Met Asp Lys Val
                610                 615                 620

Glu Arg Leu Lys Gln Val Leu Leu His Gln Gln Ala Lys Phe Gly Arg
625                 630                 635                 640
```

```
Asn Gly Ser Asp Cys Pro Asp Lys Phe Cys Leu Phe Gln Ser Glu Thr
            645                 650                 655
Lys Asn Leu Leu Phe Asn Asp Asn Thr Glu Cys Leu Ala Arg Leu His
        660                 665                 670
Gly Lys Thr Thr Tyr Glu Lys Tyr Leu Gly Pro Gln Tyr Val Ala Gly
            675                 680                 685
Ile Thr Asn Leu Lys Lys Cys Ser Thr Ser Pro Leu Leu Glu Ala Cys
        690                 695                 700
Glu Phe Leu Arg Lys
705

<210> SEQ ID NO 32
<211> LENGTH: 708
<212> TYPE: PRT
<213> ORGANISM: GOAT

<400> SEQUENCE: 32

Met Lys Leu Phe Val Pro Ala Leu Leu Ser Leu Gly Ala Leu Gly Leu
1               5                   10                  15
Cys Leu Ala Ala Pro Arg Lys Asn Val Arg Trp Cys Ala Ile Ser Leu
            20                  25                  30
Pro Glu Trp Ser Lys Cys Tyr Gln Trp Gln Arg Arg Met Arg Lys Leu
        35                  40                  45
Gly Ala Pro Ser Ile Thr Cys Ile Arg Arg Thr Ser Ala Leu Glu Cys
    50                  55                  60
Ile Arg Ala Ile Ala Gly Lys Asn Ala Asp Ala Val Thr Leu Asp Ser
65                  70                  75                  80
Gly Met Val Phe Glu Ala Gly Leu Asp Pro Tyr Lys Leu Arg Pro Val
                85                  90                  95
Ala Ala Glu Ile Tyr Gly Thr Glu Lys Ser Pro Gln Thr His Tyr Tyr
            100                 105                 110
Ala Val Ala Val Val Lys Lys Gly Ser Asn Phe Gln Leu Asp Gln Leu
        115                 120                 125
Gln Gly Gln Lys Ser Cys His Met Gly Leu Gly Arg Ser Ala Gly Trp
    130                 135                 140
Asn Ile Pro Val Gly Ile Leu Arg Pro Phe Leu Ser Trp Thr Glu Ser
145                 150                 155                 160
Ala Glu Pro Leu Gln Gly Ala Val Ala Arg Phe Phe Ser Ala Ser Cys
                165                 170                 175
Val Pro Cys Val Asp Gly Lys Ala Tyr Pro Asn Leu Cys Gln Leu Cys
            180                 185                 190
Lys Gly Val Gly Glu Asn Lys Cys Ala Cys Ser Ser Gln Glu Pro Tyr
        195                 200                 205
Phe Gly Tyr Ser Gly Ala Phe Lys Cys Leu Gln Asp Gly Ala Gly Asp
    210                 215                 220
Val Ala Phe Val Lys Glu Thr Thr Val Phe Glu Asn Leu Pro Glu Lys
225                 230                 235                 240
Ala Asp Arg Asp Gln Tyr Glu Leu Leu Cys Leu Asn Asn Thr Arg Ala
                245                 250                 255
Pro Val Asp Ala Phe Lys Glu Cys His Leu Ala Gln Val Pro Ser His
            260                 265                 270
Ala Val Val Ala Arg Ser Val Asp Gly Lys Glu Asn Leu Ile Trp Glu
        275                 280                 285
Leu Leu Arg Lys Ala Gln Glu Lys Phe Gly Lys Asn Lys Ser Gln Ser
```

```
              290                 295                 300
Phe Gln Leu Phe Gly Ser Pro Glu Gly Arg Arg Asp Leu Leu Phe Lys
305                 310                 315                 320

Asp Ser Ala Leu Gly Phe Val Arg Ile Pro Ser Lys Val Asp Ser Ala
                325                 330                 335

Leu Tyr Leu Gly Ser Arg Tyr Leu Thr Ala Leu Lys Asn Leu Arg Glu
                340                 345                 350

Thr Ala Glu Glu Leu Lys Ala Arg Cys Thr Arg Val Val Trp Cys Ala
                355                 360                 365

Val Gly Pro Glu Glu Gln Ser Lys Cys Gln Gln Trp Ser Gln Gln Ser
370                 375                 380

Gly Gln Asn Val Thr Cys Ala Thr Ala Ser Thr Thr Asp Asp Cys Ile
385                 390                 395                 400

Ala Leu Val Leu Lys Gly Glu Ala Asp Ala Leu Ser Leu Asp Gly Gly
                405                 410                 415

Tyr Ile Tyr Thr Ala Gly Lys Cys Gly Leu Val Pro Val Met Ala Glu
                420                 425                 430

Asn Arg Lys Ser Ser Lys Tyr Ser Ser Leu Asp Cys Val Leu Arg Pro
                435                 440                 445

Thr Glu Gly Tyr Leu Ala Val Ala Val Val Lys Lys Ala Asn Glu Gly
                450                 455                 460

Leu Thr Trp Asn Ser Leu Lys Gly Lys Lys Ser Cys His Thr Ala Val
465                 470                 475                 480

Asp Arg Thr Ala Gly Trp Asn Ile Pro Met Gly Leu Ile Ala Asn Gln
                485                 490                 495

Thr Gly Ser Cys Ala Phe Asp Glu Phe Phe Ser Gln Ser Cys Ala Pro
                500                 505                 510

Gly Ala Asp Pro Lys Ser Ser Leu Cys Ala Leu Cys Ala Gly Asp Asp
                515                 520                 525

Gln Gly Leu Asp Lys Cys Val Pro Asn Ser Lys Glu Lys Tyr Tyr Gly
                530                 535                 540

Tyr Thr Gly Ala Phe Arg Cys Leu Ala Glu Asp Val Gly Asp Val Ala
545                 550                 555                 560

Phe Val Lys Asn Asp Thr Val Trp Glu Asn Thr Asn Gly Glu Ser Ser
                565                 570                 575

Ala Asp Trp Ala Lys Asn Leu Asn Arg Glu Asp Phe Arg Leu Leu Cys
                580                 585                 590

Leu Asp Gly Thr Thr Lys Pro Val Thr Glu Ala Gln Ser Cys Tyr Leu
                595                 600                 605

Ala Val Ala Pro Asn His Ala Val Val Ser Arg Ser Asp Arg Ala Ala
                610                 615                 620

His Val Glu Gln Val Leu Leu His Gln Gln Ala Leu Phe Gly Lys Asn
625                 630                 635                 640

Gly Lys Asn Cys Pro Asp Gln Phe Cys Leu Phe Lys Ser Glu Thr Lys
                645                 650                 655

Asn Leu Leu Phe Asn Asp Asn Thr Glu Cys Leu Ala Lys Leu Gly Gly
                660                 665                 670

Arg Pro Thr Tyr Glu Lys Tyr Leu Gly Thr Glu Tyr Val Thr Ala Ile
                675                 680                 685

Ala Asn Leu Lys Lys Cys Ser Thr Ser Pro Leu Leu Glu Ala Cys Ala
                690                 695                 700

Phe Leu Thr Arg
705
```

<210> SEQ ID NO 33
<211> LENGTH: 710
<212> TYPE: PRT
<213> ORGANISM: HUMAN

<400> SEQUENCE: 33

```
Met Lys Leu Val Phe Leu Val Leu Leu Phe Leu Gly Ala Leu Gly Leu
1               5                   10                  15

Cys Leu Ala Gly Arg Arg Ser Val Gln Trp Cys Ala Val Ser Gln
            20                  25                  30

Pro Glu Ala Thr Lys Cys Phe Gln Trp Gln Arg Asn Met Arg Lys Val
            35                  40                  45

Arg Gly Pro Pro Val Ser Cys Ile Lys Arg Asp Ser Pro Ile Gln Cys
50                  55                  60

Ile Gln Ala Ile Ala Glu Asn Arg Ala Asp Ala Val Thr Leu Asp Gly
65                  70                  75                  80

Gly Phe Ile Tyr Glu Ala Gly Leu Ala Pro Tyr Lys Leu Arg Pro Val
                85                  90                  95

Ala Ala Glu Val Tyr Gly Thr Glu Arg Gln Pro Arg Thr His Tyr Tyr
            100                 105                 110

Ala Val Ala Val Val Lys Lys Gly Gly Ser Phe Gln Leu Asn Glu Leu
        115                 120                 125

Gln Gly Leu Lys Ser Cys His Thr Gly Leu Arg Arg Thr Ala Gly Trp
130                 135                 140

Asn Val Pro Ile Gly Thr Leu Arg Pro Phe Leu Asn Trp Thr Gly Pro
145                 150                 155                 160

Pro Glu Pro Ile Glu Ala Ala Val Ala Arg Phe Phe Ser Ala Ser Cys
                165                 170                 175

Val Pro Gly Ala Asp Lys Gly Gln Phe Pro Asn Leu Cys Arg Leu Cys
            180                 185                 190

Ala Gly Thr Gly Glu Asn Lys Cys Ala Phe Ser Ser Gln Glu Pro Tyr
        195                 200                 205

Phe Ser Tyr Ser Gly Ala Phe Lys Cys Leu Arg Asp Gly Ala Gly Asp
210                 215                 220

Val Ala Phe Ile Arg Glu Ser Thr Val Phe Glu Asp Leu Ser Asp Glu
225                 230                 235                 240

Ala Glu Arg Asp Glu Tyr Glu Leu Leu Cys Pro Asp Asn Thr Arg Lys
                245                 250                 255

Pro Val Asp Lys Phe Lys Asp Cys His Leu Ala Arg Val Pro Ser His
            260                 265                 270

Ala Val Val Ala Arg Ser Val Asn Gly Lys Glu Asp Ala Ile Trp Asn
        275                 280                 285

Leu Leu Arg Gln Ala Gln Glu Lys Phe Gly Lys Asp Lys Ser Pro Lys
290                 295                 300

Phe Gln Leu Phe Gly Ser Pro Ser Gly Gln Lys Asp Leu Leu Phe Lys
305                 310                 315                 320

Asp Ser Ala Ile Gly Phe Ser Arg Val Pro Pro Arg Ile Asp Ser Gly
                325                 330                 335

Leu Tyr Leu Gly Ser Gly Tyr Phe Thr Ala Ile Gln Asn Leu Arg Lys
            340                 345                 350

Ser Glu Glu Glu Val Ala Ala Arg Arg Ala Arg Val Val Trp Cys Ala
        355                 360                 365

Val Gly Glu Gln Glu Leu Arg Lys Cys Asn Gln Trp Ser Gly Leu Ser
```

```
                    370                 375                 380
Glu Gly Ser Val Thr Cys Ser Ser Ala Ser Thr Thr Glu Asp Cys Ile
385                 390                 395                 400

Ala Leu Val Leu Lys Gly Glu Ala Asp Ala Met Ser Leu Asp Gly Gly
                405                 410                 415

Tyr Val Tyr Thr Ala Gly Lys Cys Gly Leu Val Pro Val Leu Ala Glu
            420                 425                 430

Asn Tyr Lys Ser Gln Gln Ser Ser Asp Pro Asp Pro Asn Cys Val Asp
            435                 440                 445

Arg Pro Val Glu Gly Tyr Leu Ala Val Ala Val Arg Arg Ser Asp
450                 455                 460

Thr Ser Leu Thr Trp Asn Ser Val Lys Gly Lys Lys Ser Cys His Thr
465                 470                 475                 480

Ala Val Asp Arg Thr Ala Gly Trp Asn Ile Pro Met Gly Leu Leu Phe
                485                 490                 495

Asn Gln Thr Gly Ser Cys Lys Phe Asp Glu Tyr Phe Ser Gln Ser Cys
                500                 505                 510

Ala Pro Gly Ser Asp Pro Arg Ser Asn Leu Cys Ala Leu Cys Ile Gly
            515                 520                 525

Asp Glu Gln Gly Glu Asn Lys Cys Val Pro Asn Ser Asn Glu Arg Tyr
530                 535                 540

Tyr Gly Tyr Thr Gly Ala Phe Arg Cys Leu Ala Glu Asn Ala Gly Asp
545                 550                 555                 560

Val Ala Phe Val Lys Asp Val Thr Val Leu Gln Asn Thr Asp Gly Asn
                565                 570                 575

Asn Asn Glu Ala Trp Ala Lys Asp Leu Lys Leu Ala Asp Phe Ala Leu
                580                 585                 590

Leu Cys Leu Asp Gly Lys Arg Lys Pro Val Thr Glu Ala Arg Ser Cys
        595                 600                 605

His Leu Ala Met Ala Pro Asn His Ala Val Val Ser Arg Met Asp Lys
            610                 615                 620

Val Glu Arg Leu Lys Gln Val Leu Leu His Gln Gln Ala Lys Phe Gly
625                 630                 635                 640

Arg Asn Gly Ser Asp Cys Pro Asp Lys Phe Cys Leu Phe Gln Ser Glu
                645                 650                 655

Thr Lys Asn Leu Leu Phe Asn Asp Asn Thr Glu Cys Leu Ala Arg Leu
                660                 665                 670

His Gly Lys Thr Thr Tyr Glu Lys Tyr Leu Gly Pro Gln Tyr Val Ala
            675                 680                 685

Gly Ile Thr Asn Leu Lys Lys Cys Ser Thr Ser Pro Leu Leu Glu Ala
            690                 695                 700

Cys Glu Phe Leu Arg Lys
705                 710

<210> SEQ ID NO 34
<211> LENGTH: 711
<212> TYPE: PRT
<213> ORGANISM: HUMAN

<400> SEQUENCE: 34

Met Lys Leu Val Phe Leu Val Leu Leu Phe Leu Gly Ala Leu Gly Leu
1               5                   10                  15

Cys Leu Ala Gly Arg Arg Arg Ser Val Gln Trp Cys Ala Val Ser
            20                  25                  30
```

```
Gln Pro Glu Ala Thr Lys Cys Phe Gln Trp Gln Arg Asn Met Arg Lys
        35                  40                  45

Val Arg Gly Pro Pro Val Ser Cys Ile Lys Arg Asp Ser Pro Ile Gln
    50                  55                  60

Cys Ile Gln Ala Ile Ala Glu Asn Arg Ala Asp Ala Val Thr Leu Asp
65                  70                  75                  80

Gly Gly Phe Ile Tyr Glu Ala Gly Leu Ala Pro Tyr Lys Leu Arg Pro
                85                  90                  95

Val Ala Ala Glu Val Tyr Gly Thr Glu Arg Gln Pro Arg Thr His Tyr
            100                 105                 110

Tyr Ala Val Ala Val Val Lys Lys Gly Gly Ser Phe Gln Leu Asn Glu
            115                 120                 125

Leu Gln Gly Leu Lys Ser Cys His Thr Gly Leu Arg Arg Thr Ala Gly
130                 135                 140

Trp Asn Val Pro Ile Gly Thr Leu Arg Pro Phe Leu Asn Trp Thr Gly
145                 150                 155                 160

Pro Pro Glu Pro Ile Glu Ala Ala Val Ala Arg Phe Phe Ser Ala Ser
                165                 170                 175

Cys Val Pro Gly Ala Asp Lys Gly Gln Phe Pro Asn Leu Cys Arg Leu
            180                 185                 190

Cys Ala Gly Thr Gly Glu Asn Lys Cys Ala Phe Ser Ser Gln Glu Pro
            195                 200                 205

Tyr Phe Ser Tyr Ser Gly Ala Phe Lys Cys Leu Arg Asp Gly Ala Gly
        210                 215                 220

Asp Val Ala Phe Ile Arg Glu Ser Thr Val Phe Glu Asp Leu Ser Asp
225                 230                 235                 240

Glu Ala Glu Arg Asp Glu Tyr Glu Leu Leu Cys Pro Asp Asn Thr Arg
                245                 250                 255

Lys Pro Val Asp Lys Phe Lys Asp Cys His Leu Ala Arg Val Pro Ser
            260                 265                 270

His Ala Val Val Ala Arg Ser Val Asn Gly Lys Glu Asp Ala Ile Trp
        275                 280                 285

Asn Leu Leu Arg Gln Ala Gln Glu Lys Phe Gly Lys Asp Lys Ser Pro
290                 295                 300

Lys Phe Gln Leu Phe Gly Ser Pro Ser Gly Gln Lys Asp Leu Leu Phe
305                 310                 315                 320

Lys Asp Ser Ala Ile Gly Phe Ser Arg Val Pro Pro Arg Ile Asp Ser
                325                 330                 335

Gly Leu Tyr Leu Gly Ser Gly Tyr Phe Thr Ala Ile Gln Asn Leu Arg
            340                 345                 350

Lys Ser Glu Glu Glu Val Ala Ala Arg Arg Ala Arg Val Val Trp Cys
            355                 360                 365

Ala Val Gly Glu Gln Glu Leu Arg Lys Cys Asn Gln Trp Ser Gly Leu
370                 375                 380

Ser Glu Gly Ser Val Thr Cys Ser Ser Ala Ser Thr Thr Glu Asp Cys
385                 390                 395                 400

Ile Ala Leu Val Leu Lys Gly Glu Ala Asp Ala Met Ser Leu Asp Glu
                405                 410                 415

Gly Tyr Val Tyr Thr Ala Gly Lys Cys Gly Leu Val Pro Val Leu Ala
            420                 425                 430

Glu Asn Tyr Lys Ser Gln Gln Ser Ser Asp Pro Asp Pro Asn Cys Val
            435                 440                 445

Asp Arg Pro Val Glu Gly Tyr Leu Ala Val Ala Val Val Arg Arg Ser
```

```
                450                 455                 460
Asp Thr Ser Leu Thr Trp Asn Ser Val Lys Gly Lys Lys Ser Cys His
465                 470                 475                 480

Thr Ala Val Asp Arg Thr Ala Gly Trp Asn Ile Pro Met Gly Leu Leu
                485                 490                 495

Phe Asn Gln Thr Gly Ser Cys Lys Phe Asp Glu Tyr Phe Ser Gln Ser
            500                 505                 510

Cys Ala Pro Gly Ser Asp Pro Arg Ser Asn Leu Cys Ala Leu Cys Ile
        515                 520                 525

Gly Asp Glu Gln Gly Glu Asn Lys Cys Val Pro Asn Ser Asn Glu Arg
    530                 535                 540

Tyr Tyr Gly Tyr Thr Gly Ala Phe Arg Cys Leu Ala Glu Asn Ala Gly
545                 550                 555                 560

Asp Val Ala Phe Val Lys Asp Val Thr Val Leu Gln Asn Thr Asp Gly
                565                 570                 575

Asn Asn Asn Glu Ala Trp Ala Lys Asp Leu Lys Leu Ala Asp Phe Ala
            580                 585                 590

Leu Leu Cys Leu Asp Gly Lys Arg Lys Pro Val Thr Glu Ala Arg Ser
        595                 600                 605

Cys His Leu Ala Met Ala Pro Asn His Ala Val Val Ser Arg Met Asp
    610                 615                 620

Lys Val Glu Arg Leu Lys Gln Val Leu Leu His Gln Gln Ala Lys Phe
625                 630                 635                 640

Gly Arg Asn Gly Ser Asp Cys Pro Asp Lys Phe Cys Leu Phe Gln Ser
                645                 650                 655

Glu Thr Lys Asn Leu Leu Phe Asn Asp Asn Thr Glu Cys Leu Ala Arg
            660                 665                 670

Leu His Gly Lys Thr Thr Tyr Glu Lys Tyr Leu Gly Pro Gln Tyr Val
        675                 680                 685

Ala Gly Ile Thr Asn Leu Lys Lys Cys Ser Thr Ser Pro Leu Leu Glu
    690                 695                 700

Ala Cys Glu Phe Leu Arg Lys
705                 710

<210> SEQ ID NO 35
<211> LENGTH: 708
<212> TYPE: PRT
<213> ORGANISM: COW

<400> SEQUENCE: 35

Met Lys Leu Phe Val Pro Ala Leu Leu Ser Leu Gly Ala Leu Gly Leu
1               5                   10                  15

Cys Leu Ala Ala Pro Arg Lys Asn Val Arg Trp Cys Thr Ile Ser Gln
                20                  25                  30

Pro Glu Trp Phe Lys Cys Arg Arg Trp Gln Trp Arg Met Lys Lys Leu
            35                  40                  45

Gly Ala Pro Ser Ile Thr Cys Val Arg Arg Ala Phe Ala Leu Glu Cys
        50                  55                  60

Ile Arg Ala Ile Ala Glu Lys Lys Ala Asp Ala Val Thr Leu Asp Gly
65                  70                  75                  80

Gly Met Val Phe Glu Ala Gly Arg Asp Pro Tyr Lys Leu Arg Pro Val
                85                  90                  95

Ala Ala Glu Ile Tyr Gly Thr Lys Glu Ser Pro Gln Thr His Tyr Tyr
            100                 105                 110
```

-continued

```
Ala Val Ala Val Val Lys Lys Gly Ser Asn Phe Gln Leu Asp Gln Leu
            115                 120                 125

Gln Gly Arg Lys Ser Cys His Thr Gly Leu Gly Arg Ser Ala Gly Trp
        130                 135                 140

Val Ile Pro Met Gly Ile Leu Arg Pro Tyr Leu Ser Trp Thr Glu Ser
145                 150                 155                 160

Leu Glu Pro Leu Gln Gly Ala Val Ala Lys Phe Phe Ser Ala Ser Cys
                165                 170                 175

Val Pro Cys Ile Asp Arg Gln Ala Tyr Pro Asn Leu Cys Gln Leu Cys
            180                 185                 190

Lys Gly Glu Gly Glu Asn Gln Cys Ala Cys Ser Ser Arg Glu Pro Tyr
        195                 200                 205

Phe Gly Tyr Ser Gly Ala Phe Lys Cys Leu Gln Asp Gly Ala Gly Asp
    210                 215                 220

Val Ala Phe Val Lys Glu Thr Thr Val Phe Glu Asn Leu Pro Glu Lys
225                 230                 235                 240

Ala Asp Arg Asp Gln Tyr Glu Leu Leu Cys Leu Asn Asn Ser Arg Ala
                245                 250                 255

Pro Val Asp Ala Phe Lys Glu Cys His Leu Ala Gln Val Pro Ser His
            260                 265                 270

Ala Val Val Ala Arg Ser Val Asp Gly Lys Glu Asp Leu Ile Trp Lys
        275                 280                 285

Leu Leu Ser Lys Ala Gln Glu Lys Phe Gly Lys Asn Lys Ser Arg Ser
    290                 295                 300

Phe Gln Leu Phe Gly Ser Pro Pro Gly Gln Arg Asp Leu Leu Phe Lys
305                 310                 315                 320

Asp Ser Ala Leu Gly Phe Leu Arg Ile Pro Ser Lys Val Asp Ser Ala
                325                 330                 335

Leu Tyr Leu Gly Ser Arg Tyr Leu Thr Thr Leu Lys Asn Leu Arg Glu
            340                 345                 350

Thr Ala Glu Glu Val Lys Ala Arg Tyr Thr Arg Val Val Trp Cys Ala
        355                 360                 365

Val Gly Pro Glu Glu Gln Lys Lys Cys Gln Gln Trp Ser Gln Gln Ser
    370                 375                 380

Gly Gln Asn Val Thr Cys Ala Thr Ala Ser Thr Thr Asp Asp Cys Ile
385                 390                 395                 400

Val Leu Val Leu Lys Gly Glu Ala Asp Ala Leu Asn Leu Asp Gly Gly
                405                 410                 415

Tyr Ile Tyr Thr Ala Gly Lys Cys Gly Leu Val Pro Val Leu Ala Glu
            420                 425                 430

Asn Arg Lys Thr Ser Lys Tyr Ser Ser Leu Asp Cys Val Leu Arg Pro
        435                 440                 445

Thr Glu Gly Tyr Leu Ala Val Ala Val Val Lys Lys Ala Asn Glu Gly
    450                 455                 460

Leu Thr Trp Asn Ser Leu Lys Asp Lys Lys Ser Cys His Thr Ala Val
465                 470                 475                 480

Asp Arg Thr Ala Gly Trp Asn Ile Pro Met Gly Leu Ile Val Asn Gln
                485                 490                 495

Thr Gly Ser Cys Ala Phe Asp Glu Phe Phe Ser Gln Ser Cys Ala Pro
            500                 505                 510

Gly Arg Asp Pro Lys Ser Arg Leu Cys Ala Leu Cys Ala Gly Asp Asp
        515                 520                 525

Gln Gly Leu Asp Lys Cys Val Pro Asn Ser Lys Glu Lys Tyr Tyr Gly
```

-continued

```
            530                 535                 540
Tyr Thr Gly Ala Phe Arg Cys Leu Ala Glu Asp Val Gly Asp Val Ala
545                 550                 555                 560

Phe Val Lys Asn Asp Thr Val Trp Glu Asn Thr Asn Gly Glu Ser Thr
                565                 570                 575

Ala Asp Trp Ala Lys Asn Leu Asn Arg Glu Asp Phe Arg Leu Leu Cys
            580                 585                 590

Leu Asp Gly Thr Arg Lys Pro Val Thr Glu Ala Gln Ser Cys His Leu
        595                 600                 605

Ala Val Ala Pro Asn His Ala Val Val Ser Arg Ser Asp Arg Ala Ala
    610                 615                 620

His Val Lys Gln Val Leu Leu His Gln Gln Ala Leu Phe Gly Lys Asn
625                 630                 635                 640

Gly Lys Asn Cys Pro Asp Lys Phe Cys Leu Phe Lys Ser Glu Thr Lys
                645                 650                 655

Asn Leu Leu Phe Asn Asp Asn Thr Glu Cys Leu Ala Lys Leu Gly Gly
            660                 665                 670

Arg Pro Thr Tyr Glu Glu Tyr Leu Gly Thr Glu Tyr Val Thr Ala Ile
        675                 680                 685

Ala Asn Leu Lys Lys Cys Ser Thr Ser Pro Leu Leu Glu Ala Cys Ala
    690                 695                 700

Phe Leu Thr Arg
705

<210> SEQ ID NO 36
<211> LENGTH: 686
<212> TYPE: PRT
<213> ORGANISM: PIG

<400> SEQUENCE: 36

Met Lys Leu Phe Ile Pro Ala Leu Leu Phe Leu Trp Thr Leu Gly Leu
1               5                   10                  15

Cys Leu Ala Ala Pro Lys Lys Gly Val Arg Trp Cys Val Ile Ser Thr
            20                  25                  30

Ala Glu Tyr Ser Lys Cys Arg Gln Trp Gln Ser Lys Ile Arg Arg Thr
        35                  40                  45

Asn Pro Ile Phe Cys Ile Arg Arg Ala Ser Pro Thr Asp Cys Ile Arg
    50                  55                  60

Ala Ile Ala Ala Lys Arg Ala Asp Ala Val Thr Leu Asp Gly Gly Leu
65                  70                  75                  80

Val Phe Glu Ala Gly Gln Tyr Lys Leu Arg Pro Val Ala Ala Glu Ile
                85                  90                  95

Tyr Gly Thr Glu Glu Asn Pro Gln Thr Tyr Tyr Ala Val Ala Val
            100                 105                 110

Val Lys Lys Gly Phe Asn Phe Gln Leu Asn Gln Leu Gln Gly Arg Lys
        115                 120                 125

Ser Cys His Ile Gly Leu Gly Arg Ser Ala Gly Trp Asn Ile Pro Ile
    130                 135                 140

Gly Leu Leu Arg Arg Phe Leu Asp Trp Ala Gly Pro Pro Glu Pro Leu
145                 150                 155                 160

Gln Lys Ala Val Ala Lys Phe Phe Ser Gln Ser Cys Val Pro Cys Ala
                165                 170                 175

Asp Gly Asn Ala Tyr Pro Asn Leu Cys Gln Leu Cys Ile Gly Lys Gly
            180                 185                 190
```

-continued

```
Lys Asp Lys Cys Ala Cys Ser Ser Gln Glu Pro Tyr Phe Gly Tyr Ser
        195                 200                 205

Gly Ala Phe Asn Cys Leu His Lys Gly Ile Gly Asp Val Ala Phe Val
        210                 215                 220

Lys Glu Ser Thr Val Phe Glu Asn Leu Pro Gln Lys Ala Asp Arg Asp
225                 230                 235                 240

Lys Tyr Glu Leu Leu Cys Pro Asp Asn Thr Arg Lys Pro Val Glu Ala
                245                 250                 255

Phe Arg Glu Cys His Leu Ala Arg Val Pro Ser His Ala Val Val Ala
            260                 265                 270

Arg Ser Val Asn Gly Lys Glu Asn Ser Ile Trp Ser Leu Leu Tyr Gln
        275                 280                 285

Ser Gln Lys Lys Phe Gly Lys Ser Asn Pro Gln Glu Phe Gln Leu Phe
    290                 295                 300

Gly Ser Pro Gly Gln Gln Lys Asp Leu Leu Phe Arg Asp Ala Thr Ile
305                 310                 315                 320

Gly Phe Leu Lys Ile Pro Ser Lys Ile Asp Ser Lys Leu Tyr Leu Gly
                325                 330                 335

Leu Pro Tyr Leu Thr Ala Ile Gln Gly Leu Arg Glu Thr Ala Ala Glu
            340                 345                 350

Val Glu Ala Arg Gln Ala Lys Val Val Trp Cys Ala Val Gly Pro Glu
        355                 360                 365

Glu Leu Arg Lys Cys Arg Gln Trp Ser Ser Gln Ser Ser Gln Asn Leu
    370                 375                 380

Asn Cys Ser Leu Ala Ser Thr Thr Glu Asp Cys Ile Val Gln Val Leu
385                 390                 395                 400

Lys Gly Glu Ala Asp Ala Met Ser Leu Asp Gly Gly Phe Ile Tyr Thr
                405                 410                 415

Ala Gly Lys Cys Gly Leu Val Pro Val Leu Ala Glu Asn Gln Lys Ser
            420                 425                 430

Arg Gln Ser Ser Ser Ser Asp Cys Val His Arg Pro Thr Gln Gly Tyr
        435                 440                 445

Phe Ala Val Ala Val Val Arg Lys Ala Asn Gly Gly Ile Thr Trp Asn
    450                 455                 460

Ser Val Arg Gly Thr Lys Ser Cys His Thr Ala Val Asp Arg Thr Ala
465                 470                 475                 480

Gly Trp Asn Ile Pro Met Gly Leu Leu Val Asn Gln Thr Gly Ser Cys
                485                 490                 495

Lys Phe Asp Glu Phe Phe Ser Gln Ser Cys Ala Pro Gly Ser Gln Pro
            500                 505                 510

Gly Ser Asn Leu Cys Ala Leu Cys Val Gly Asn Asp Gln Gly Val Asp
        515                 520                 525

Lys Cys Val Pro Asn Ser Asn Glu Arg Tyr Tyr Gly Tyr Thr Gly Ala
    530                 535                 540

Phe Arg Cys Leu Ala Glu Asn Ala Gly Asp Val Ala Phe Val Lys Asp
545                 550                 555                 560

Val Thr Val Leu Asp Asn Thr Asn Gly Gln Asn Thr Gln Glu Trp Ala
                565                 570                 575

Arg Glu Leu Arg Ser Asp Asp Phe Glu Leu Leu Cys Leu Asn Gly Thr
            580                 585                 590

Arg Lys Pro Val Thr Glu Ala Gln Asn Cys His Leu Ala Val Ala Pro
        595                 600                 605

Ser His Ala Val Val Ser Arg Lys Glu Lys Ala Ala Gln Val Glu Gln
```

```
            610                 615                 620
Met Leu Leu Thr Glu Gln Ala Gln Phe Gly Arg Tyr Gly Lys Asp Cys
625                 630                 635                 640

Pro Asp Lys Phe Cys Leu Phe Arg Ser Glu Thr Lys Asn Leu Leu Phe
                645                 650                 655

Asn Asp Asn Thr Glu Cys Leu Ala Gln Leu Gln Gly Lys Thr Thr Tyr
                660                 665                 670

Glu Lys Tyr Leu Gly Ser Glu Tyr Val Thr Ala Ile Ala Thr
                675                 680                 685

<210> SEQ ID NO 37
<211> LENGTH: 703
<212> TYPE: PRT
<213> ORGANISM: PIG

<400> SEQUENCE: 37

Met Lys Leu Phe Ile Pro Ala Leu Leu Phe Leu Gly Thr Leu Gly Leu
1               5                   10                  15

Cys Leu Ala Ala Pro Lys Lys Gly Val Arg Trp Cys Val Ile Ser Thr
                20                  25                  30

Ala Glu Tyr Ser Lys Cys Arg Gln Trp Gln Ser Lys Ile Arg Arg Thr
                35                  40                  45

Asn Pro Met Phe Cys Ile Arg Arg Ala Ser Pro Thr Asp Cys Ile Arg
50                  55                  60

Ala Ile Ala Ala Lys Arg Ala Asp Ala Val Thr Leu Asp Gly Gly Leu
65                  70                  75                  80

Val Phe Glu Ala Asp Gln Tyr Lys Leu Arg Pro Val Ala Ala Glu Ile
                85                  90                  95

Tyr Gly Thr Glu Glu Asn Pro Gln Thr Tyr Tyr Ala Val Ala Val
                100                 105                 110

Val Lys Lys Gly Phe Asn Phe Gln Asn Gln Leu Gln Gly Arg Lys Ser
                115                 120                 125

Cys His Thr Gly Leu Gly Arg Ser Ala Gly Trp Asn Ile Pro Ile Gly
                130                 135                 140

Leu Leu Arg Arg Phe Leu Asp Trp Ala Gly Pro Pro Glu Pro Leu Gln
145                 150                 155                 160

Lys Ala Val Ala Lys Phe Phe Ser Gln Ser Cys Val Pro Cys Ala Asp
                165                 170                 175

Gly Asn Ala Tyr Pro Asn Leu Cys Gln Leu Cys Ile Gly Lys Gly Lys
                180                 185                 190

Asp Lys Cys Ala Cys Ser Ser Gln Glu Pro Tyr Phe Gly Tyr Ser Gly
                195                 200                 205

Ala Phe Asn Cys Leu His Lys Gly Ile Gly Asp Val Ala Phe Val Lys
                210                 215                 220

Glu Ser Thr Val Phe Glu Asn Leu Pro Gln Lys Ala Asp Arg Asp Lys
225                 230                 235                 240

Tyr Glu Leu Leu Cys Pro Asp Asn Thr Arg Lys Pro Val Glu Ala Phe
                245                 250                 255

Arg Glu Cys His Leu Ala Arg Val Pro Ser His Ala Val Val Ala Arg
                260                 265                 270

Ser Val Asn Gly Lys Glu Asn Ser Ile Trp Glu Leu Leu Tyr Gln Ser
                275                 280                 285

Gln Lys Lys Phe Gly Lys Ser Asn Pro Gln Glu Phe Gln Leu Phe Gly
                290                 295                 300
```

```
Ser Pro Gly Gln Gln Lys Asp Leu Leu Phe Arg Asp Ala Thr Ile Gly
305                 310                 315                 320

Phe Leu Lys Ile Pro Ser Lys Ile Asp Ser Lys Leu Tyr Leu Gly Leu
            325                 330                 335

Pro Tyr Leu Thr Ala Ile Gln Gly Leu Arg Glu Thr Ala Ala Glu Val
        340                 345                 350

Glu Ala Arg Gln Ala Lys Val Val Trp Cys Ala Val Gly Pro Glu Glu
    355                 360                 365

Leu Arg Lys Cys Arg Gln Trp Ser Gln Ser Ser Gln Asn Leu Asn
370                 375                 380

Cys Ser Leu Ala Ser Thr Glu Asp Cys Ile Val Gln Val Leu Lys
385                 390                 395                 400

Gly Glu Ala Asp Ala Met Ser Leu Asp Gly Gly Phe Ile Tyr Thr Ala
                405                 410                 415

Gly Lys Cys Gly Leu Val Pro Val Leu Ala Glu Asn Gln Lys Ser Arg
        420                 425                 430

Gln Ser Ser Ser Asp Cys Val His Arg Pro Thr Gln Gly Tyr Phe
    435                 440                 445

Ala Val Ala Val Val Arg Lys Ala Asn Gly Gly Ile Thr Trp Asn Ser
450                 455                 460

Val Arg Gly Thr Lys Ser Cys His Thr Ala Val Asp Arg Thr Ala Gly
465                 470                 475                 480

Trp Asn Ile Pro Met Gly Leu Leu Val Asn Gln Thr Gly Ser Cys Lys
                485                 490                 495

Phe Asp Glu Phe Phe Ser Gln Ser Cys Ala Pro Gly Ser Gln Pro Gly
                500                 505                 510

Ser Asn Leu Cys Ala Leu Cys Val Gly Asn Asp Gln Gly Val Asp Lys
            515                 520                 525

Cys Val Pro Asn Ser Asn Glu Arg Tyr Tyr Gly Tyr Thr Gly Ala Phe
530                 535                 540

Arg Cys Leu Ala Glu Asn Ala Gly Asp Val Ala Phe Val Lys Asp Val
545                 550                 555                 560

Thr Val Leu Asp Asn Thr Asn Gly Gln Asn Thr Glu Glu Trp Ala Arg
                565                 570                 575

Glu Leu Arg Ser Asp Asp Phe Glu Leu Leu Cys Leu Asp Gly Thr Arg
            580                 585                 590

Lys Pro Val Thr Glu Ala Gln Asn Cys His Leu Ala Val Ala Pro Ser
        595                 600                 605

His Ala Val Val Ser Arg Lys Glu Lys Ala Ala Gln Val Glu Gln Val
    610                 615                 620

Leu Leu Thr Glu Gln Ala Gln Phe Gly Arg Tyr Gly Lys Asp Cys Pro
625                 630                 635                 640

Asp Lys Phe Cys Leu Phe Arg Ser Glu Thr Lys Asn Leu Leu Phe Asn
                645                 650                 655

Asp Asn Thr Glu Val Leu Ala Gln Leu Gln Gly Lys Thr Thr Tyr Glu
            660                 665                 670

Lys Tyr Leu Gly Ser Glu Tyr Val Thr Ala Ile Ala Asn Leu Lys Gln
        675                 680                 685

Cys Ser Val Ser Pro Leu Leu Glu Ala Cys Ala Phe Met Met Arg
    690                 695                 700

<210> SEQ ID NO 38
<211> LENGTH: 708
<212> TYPE: PRT
```

<213> ORGANISM: COW

<400> SEQUENCE: 38

```
Met Lys Leu Phe Val Pro Ala Leu Leu Ser Leu Gly Ala Leu Gly Leu
1               5                   10                  15
Cys Leu Ala Ala Pro Arg Lys Asn Val Arg Trp Cys Thr Ile Ser Gln
            20                  25                  30
Pro Glu Trp Phe Lys Cys Arg Arg Trp Gln Trp Arg Met Lys Lys Leu
        35                  40                  45
Gly Ala Pro Ser Ile Thr Cys Val Arg Arg Ala Phe Ala Leu Glu Cys
    50                  55                  60
Ile Pro Gly Ile Ala Glu Lys Lys Ala Asp Ala Val Thr Leu Asp Gly
65                  70                  75                  80
Gly Met Val Phe Glu Ala Gly Arg Asp Pro Tyr Lys Leu Arg Pro Val
                85                  90                  95
Ala Ala Glu Ile Tyr Gly Thr Lys Glu Ser Pro Gln Thr His Tyr Tyr
            100                 105                 110
Ala Val Ala Val Val Lys Lys Gly Ser Asn Phe Gln Leu Asp Gln Leu
        115                 120                 125
Gln Gly Arg Lys Ser Cys His Thr Gly Leu Gly Arg Ser Ala Gly Trp
    130                 135                 140
Ile Ile Pro Met Gly Ile Leu Arg Pro Tyr Leu Ser Trp Thr Glu Ser
145                 150                 155                 160
Leu Glu Pro Leu Gln Gly Ala Val Ala Lys Phe Phe Ser Ala Ser Cys
                165                 170                 175
Val Pro Cys Ile Asp Arg Gln Ala Tyr Pro Asn Leu Cys Gln Leu Cys
            180                 185                 190
Lys Gly Glu Gly Glu Asn Gln Cys Ala Cys Ser Ser Arg Glu Pro Tyr
        195                 200                 205
Phe Gly Tyr Ser Gly Ala Phe Lys Cys Leu Gln Asp Gly Ala Gly Asp
    210                 215                 220
Val Ala Phe Val Lys Glu Thr Thr Val Phe Glu Asn Leu Pro Glu Lys
225                 230                 235                 240
Ala Asp Arg Asp Gln Tyr Glu Leu Leu Cys Leu Asn Asn Ser Arg Ala
                245                 250                 255
Pro Val Asp Ala Phe Lys Glu Cys His Leu Ala Gln Val Pro Ser His
            260                 265                 270
Ala Val Val Ala Arg Ser Val Asp Gly Lys Glu Asp Leu Ile Trp Lys
        275                 280                 285
Leu Leu Ser Lys Ala Gln Glu Lys Ser Gly Lys Asn Lys Ser Arg Ser
    290                 295                 300
Phe Gln Leu Phe Gly Ser Pro Gly Gln Arg Asp Leu Leu Phe Lys
305                 310                 315                 320
Asp Ser Ala Leu Gly Phe Leu Arg Ile Pro Ser Lys Val Asp Ser Ala
                325                 330                 335
Leu Tyr Leu Gly Ser Arg Tyr Leu Thr Thr Leu Lys Asn Leu Arg Glu
            340                 345                 350
Thr Ala Glu Glu Val Lys Ala Arg Tyr Thr Arg Val Val Trp Cys Ala
        355                 360                 365
Val Gly Pro Glu Glu Gln Lys Lys Cys Gln Gln Trp Ser Gln Gln Ser
    370                 375                 380
Gly Gln Asn Val Thr Cys Ala Thr Ala Ser Thr Thr Asp Asp Cys Ile
385                 390                 395                 400
```

```
Val Leu Val Leu Lys Gly Glu Ala Asp Ala Leu Asn Leu Asp Gly Gly
            405                 410                 415

Tyr Ile Tyr Thr Ala Gly Lys Cys Gly Leu Val Pro Val Leu Ala Glu
            420                 425                 430

Asn Arg Lys Ser Ser Lys His Ser Ser Leu Asp Cys Val Leu Arg Pro
            435                 440                 445

Thr Glu Gly Tyr Leu Ala Val Ala Val Val Lys Lys Ala Asn Glu Gly
            450                 455                 460

Leu Thr Trp Asn Ser Leu Lys Asp Lys Lys Ser Cys His Thr Ala Val
465                 470                 475                 480

Asp Arg Thr Ala Gly Trp Asn Ile Pro Met Gly Leu Ile Val Asn Gln
            485                 490                 495

Thr Gly Ser Cys Ala Phe Asp Glu Phe Phe Ser Gln Ser Cys Ala Pro
            500                 505                 510

Gly Ala Asp Pro Lys Ser Arg Leu Cys Ala Leu Cys Ala Gly Asp Asp
            515                 520                 525

Gln Gly Leu Asp Lys Cys Val Pro Asn Ser Lys Glu Lys Tyr Tyr Gly
            530                 535                 540

Tyr Thr Gly Ala Phe Arg Cys Leu Ala Glu Asp Val Gly Asp Val Ala
545                 550                 555                 560

Phe Val Lys Asn Asp Thr Val Trp Glu Asn Thr Asn Gly Glu Ser Thr
            565                 570                 575

Ala Asp Trp Ala Lys Asn Leu Asn Arg Glu Asp Phe Arg Leu Leu Cys
            580                 585                 590

Leu Asp Gly Thr Arg Lys Pro Val Thr Glu Ala Gln Ser Cys His Leu
            595                 600                 605

Ala Val Ala Pro Asn His Ala Val Val Ser Arg Ser Asp Arg Ala Ala
            610                 615                 620

His Val Lys Gln Val Leu Leu His Gln Gln Ala Leu Phe Gly Lys Asn
625                 630                 635                 640

Gly Lys Asn Cys Pro Asp Lys Phe Cys Leu Phe Lys Ser Glu Thr Lys
            645                 650                 655

Asn Leu Leu Phe Asn Asp Asn Thr Glu Cys Leu Ala Lys Leu Gly Gly
            660                 665                 670

Arg Pro Thr Tyr Glu Glu Tyr Leu Gly Thr Glu Tyr Val Thr Ala Ile
            675                 680                 685

Ala Asn Leu Lys Lys Cys Ser Thr Ser Pro Leu Leu Glu Ala Cys Ala
            690                 695                 700

Phe Leu Thr Arg
705

<210> SEQ ID NO 39
<211> LENGTH: 708
<212> TYPE: PRT
<213> ORGANISM: COW

<400> SEQUENCE: 39

Met Lys Leu Phe Val Pro Ala Leu Leu Ser Leu Gly Ala Leu Gly Leu
1               5                   10                  15

Cys Leu Ala Ala Pro Arg Lys Asn Val Arg Trp Cys Thr Ile Ser Gln
            20                  25                  30

Pro Glu Trp Phe Lys Cys Arg Arg Trp Gln Trp Arg Met Lys Lys Leu
            35                  40                  45

Gly Ala Pro Ser Ile Thr Cys Val Arg Arg Ala Phe Ala Leu Glu Cys
            50                  55                  60
```

-continued

```
Ile Arg Ala Ile Ala Glu Lys Lys Ala Asp Ala Val Thr Leu Asp Gly
 65                  70                  75                  80

Gly Met Val Phe Glu Ala Gly Arg Asp Pro Tyr Lys Leu Arg Pro Val
                 85                  90                  95

Ala Ala Glu Ile Tyr Gly Thr Lys Glu Ser Pro Gln Thr His Tyr Tyr
            100                 105                 110

Ala Val Ala Val Val Lys Lys Gly Ser Asn Phe Gln Leu Asp Gln Leu
        115                 120                 125

Gln Gly Arg Lys Ser Cys His Thr Gly Leu Gly Arg Ser Ala Gly Trp
130                 135                 140

Ile Ile Pro Met Gly Ile Leu Arg Pro Tyr Leu Ser Trp Thr Glu Ser
145                 150                 155                 160

Leu Glu Pro Leu Gln Gly Ala Val Ala Lys Phe Phe Ser Ala Ser Cys
                165                 170                 175

Val Pro Cys Ile Asp Arg Gln Ala Tyr Pro Asn Leu Cys Gln Leu Cys
            180                 185                 190

Lys Gly Glu Gly Glu Asn Gln Cys Ala Cys Ser Ser Arg Glu Pro Tyr
        195                 200                 205

Phe Gly Tyr Ser Gly Ala Phe Lys Cys Leu Gln Asp Gly Ala Gly Asp
210                 215                 220

Val Ala Phe Val Lys Glu Thr Thr Val Phe Glu Asn Leu Pro Glu Lys
225                 230                 235                 240

Ala Asp Arg Asp Gln Tyr Glu Leu Leu Cys Leu Asn Asn Ser Arg Ala
                245                 250                 255

Pro Val Asp Ala Phe Lys Glu Cys His Leu Ala Gln Val Pro Ser His
            260                 265                 270

Ala Val Val Ala Arg Ser Val Asp Gly Lys Glu Asp Leu Ile Trp Lys
        275                 280                 285

Leu Leu Ser Lys Ala Gln Glu Lys Phe Gly Lys Asn Lys Ser Arg Ser
290                 295                 300

Phe Gln Leu Phe Gly Ser Pro Gly Gln Arg Asp Leu Leu Phe Lys
305                 310                 315                 320

Asp Ser Ala Leu Gly Phe Leu Arg Ile Pro Ser Lys Val Asp Ser Ala
                325                 330                 335

Leu Tyr Leu Gly Ser Arg Tyr Leu Thr Thr Leu Lys Asn Leu Arg Glu
            340                 345                 350

Thr Ala Glu Glu Val Lys Ala Arg Tyr Thr Arg Val Val Trp Cys Ala
        355                 360                 365

Val Gly Pro Glu Glu Gln Lys Lys Cys Gln Gln Trp Ser Gln Gln Ser
370                 375                 380

Gly Gln Asn Val Thr Cys Ala Thr Ala Ser Thr Thr Asp Asp Cys Ile
385                 390                 395                 400

Val Leu Val Leu Lys Gly Glu Ala Asp Ala Leu Asn Leu Asp Gly Gly
                405                 410                 415

Tyr Ile Tyr Thr Ala Gly Lys Cys Gly Leu Val Pro Val Leu Ala Glu
            420                 425                 430

Asn Arg Lys Ser Ser Lys His Ser Ser Leu Asp Cys Val Leu Arg Pro
        435                 440                 445

Thr Glu Gly Tyr Leu Ala Val Ala Val Val Lys Lys Ala Asn Glu Gly
450                 455                 460

Leu Thr Trp Asn Ser Leu Lys Asp Lys Lys Ser Cys His Thr Ala Val
465                 470                 475                 480
```

```
Asp Arg Thr Ala Gly Trp Asn Ile Pro Met Gly Leu Ile Val Asn Gln
            485                 490                 495
Thr Gly Ser Cys Ala Phe Asp Glu Phe Phe Ser Gln Ser Cys Ala Pro
            500                 505                 510
Gly Ala Asp Pro Lys Ser Arg Leu Cys Ala Leu Cys Ala Gly Asp Asp
            515                 520                 525
Gln Gly Leu Asp Lys Cys Val Pro Asn Ser Lys Glu Lys Tyr Tyr Gly
            530                 535                 540
Tyr Thr Gly Ala Phe Arg Cys Leu Ala Glu Asp Val Gly Asp Val Ala
545                 550                 555                 560
Phe Val Lys Asn Asp Thr Val Trp Glu Asn Thr Asn Gly Glu Ser Thr
                565                 570                 575
Ala Asp Trp Ala Lys Asn Leu Asn Arg Glu Asp Phe Arg Leu Leu Cys
            580                 585                 590
Leu Asp Gly Thr Arg Lys Pro Val Thr Glu Ala Gln Ser Cys His Leu
            595                 600                 605
Ala Val Ala Pro Asn His Ala Val Val Ser Arg Ser Asp Arg Ala Ala
            610                 615                 620
His Val Lys Gln Val Leu Leu His Gln Gln Ala Leu Phe Gly Lys Asn
625                 630                 635                 640
Gly Lys Asn Cys Pro Asp Lys Phe Cys Leu Phe Lys Ser Glu Thr Lys
                645                 650                 655
Asn Leu Leu Phe Asn Asp Asn Thr Glu Cys Leu Ala Lys Leu Gly Gly
            660                 665                 670
Arg Pro Thr Tyr Glu Glu Tyr Leu Gly Thr Glu Tyr Val Thr Ala Ile
            675                 680                 685
Ala Asn Leu Lys Lys Cys Ser Thr Ser Pro Leu Leu Glu Ala Cys Ala
            690                 695                 700
Phe Leu Thr Arg
705

<210> SEQ ID NO 40
<211> LENGTH: 2360
<212> TYPE: DNA
<213> ORGANISM: HUMAN

<400> SEQUENCE: 40
gaattccgac cgcagacatg aaacttgtct tcctcgtcct gctgttcctc ggggccctcg      60
gactgtgtct ggctggccgt aggagaagga gtgttcagtg gtgcaccgta tcccaacccg     120
aggccacaaa atgcttccaa tggcaaagga atatgagaag agtgcgtggc cctcctgtca     180
gctgcataaa gagagactcc cccatccagt gtatccaggc cattgcggaa acagggccg      240 atgctgtgac ccttgatggt ggtttcatat acgaggcagg cctggccccc tacaaactgc     300
gacctgtagc ggcggaagtc tacgggaccg aaagacagcc acgaactcac tattatgccg     360
tggctgtggt gaagaagggc ggcagctttc agctgaacga actgcaaggt ctgaagtcct     420
gccacacagg ccttcgcagg accgctggat ggaatgtgcc tataggaca cttcgtccat      480 tcttgaattg gacgggtcca cctgagccca ttgaggcagc tgtggccagg ttcttctcag     540
ccagctgtgt tcccggtgca gataaaggac agttccccaa cctgtgtcgc ctgtgtgcgg     600
ggacagggga aaacaaatgt gccttctcct cccaggaacc gtacttcagc tactctggtg     660
ccttcaagtg tctgagagac ggggctggag acgtggcttt tatcagagag agcacagtgt     720 tgaggacct gtcagacgag gctgaaaggg acgagtatga gttactctgc ccagacaaca     780
```

```
ctcggaagcc agtggacaag ttcaaagact gccatctggc ccgggtccct tctcatgccg    840
ttgtggcacg aagtgtgaat ggcaaggagg atgccatctg gaatcttctc cgccaggcac    900
aggaaaagtt tggaaaggac aagtcaccga aattccagct cttggctcc cctagtgggc     960
agaaagatct gctgttcaag gactctgcca ttgggttttc gaggtgccc ccgaggatag    1020
attctgggct gtaccttggc tccggctact tcactgccat ccagaacttg aggaaaagtg   1080
aggaggaagt ggctgcccgg cgtgcgcggg tcgtgtggtg tgcggtgggc gagcaggagc   1140
tgcgcaagtg taaccagtgg agtggcttga gcgaaggcag cgtgacctgc tcctcggcct   1200
ccaccacaga ggactgcatc gccctggtgc tgaaggaga agctgatgcc atgagtttgg    1260
atggaggata tgtgtacact gcaggcaaat gtggtttggt gcctgtcctg cagagaact    1320
acaaatccca caaagcagt gaccctgatc ctaactgtgt ggatagacct gtggaaggat    1380
atcttgctgt ggcggtggtt aggagatcag acactagcct tacctggaac tctgtgaaag   1440
gcaagaagtc ctgccacacc gccgtggaca ggactgcagg ctggaatatc ccatgggcc    1500
tgctcttcaa ccagacgggc tcctgcaaat tgatgaata tttcagtcaa agctgtgccc   1560
ctgggtctga cccgagatct aatctctgtg ctctgtgtat tggcgacgag cagggtgaga   1620
ataagtgcgt gcccaacagc aatgagagat actacggcta cactggggct tccggtgcc   1680
tggctgagaa tgctgagac gttgcatttg tgaaagatgt cactgtcttg cagaacactg    1740
atggaaataa caatgaggca tgggctaagg atttgaagct ggcagacttt gcgctgctgt   1800
gcctcgatgg caaacggaag cctgtgactg aggctagaag ctgccatctt gccatggccc   1860
cgaatcatgc cgtggtgtct cggatggata aggtggaacg cctgaaacag gtgctgctcc   1920
accaacaggc taaatttggg agaaatggat ctgactgccc ggacaagttt tgcttattcc   1980
agtctgaaac caaaaacctt ctgttcaatg acaacactga gtgtctggcc agactccatg   2040
gcaaaacaac atatgaaaaa tatttgggac cacagtatgt cgcaggcatt actaatctga   2100
aaaagtgctc aacctccccc ctcctggaag cctgtgaatt cctcaggaag taaaaccgaa   2160
gaagatggcc cagctcccca agaaagcctc agccattcac tgcccccagc tcttctcccc   2220
aggtgtgttg gggccttggc tcccctgctg aaggtgggga ttgcccatcc atctgcttac   2280
aattccctgc tgtcgtctta gcaagaagta aaatgagaaa ttttgttgaa aaaaaaaaa    2340
aaaaaaaaaa aaaaaaaaa                                                2360
```

<210> SEQ ID NO 41
<211> LENGTH: 2239
<212> TYPE: DNA
<213> ORGANISM: COW

<400> SEQUENCE: 41

```
ggtgtaccat ctcccaacct gagtggttca aatgccgccg atggcagtgg aggatgaaga     60
agctgggtgc tccctctatc acctgtgtga ggagggcctt tgccttggaa tgtatccggg    120
ccatcgcgga gaaaaggcg gatgctgtga ccctggatgg tggcatggtg tttgaggcgt    180
gccgggaccc ctacaaactg cggccagtag cagcagagat ctatgggacg aaagagtctc    240
cccaaaccca ctattatgct gtggccgtcg tgaagaaggg cagcaacttt cagctggacc    300
agctgcaagg ccgaagtcc tgccatacgg gccttggcag gtccgctggg tggatcatcc     360
ctatgggaat ccttcgcccg tacttgagct ggacagagtc actcgagccc tccagggag    420
ctgtggctaa attcttctct gccagctgtg ttccctgcat tgatagacaa gcatacccca   480
acctgtgtca actgtgcaag ggggaggggg agaaccagtg tgcctgctcc tcccgggaac   540
```

```
catacttcgg ttattctggt gccttcaagt gtctgcagga cggggctgga gacgtggctt      600
ttgttaaaga gacgacagtg tttgagaact tgccagagaa ggctgacagg gaccagtatg      660
agcttctctg cctgaacaac agtcgggcgc cagtggatgc gttcaaggag tgccacctgg      720
cccaggtccc ttctcatgct gtcgtggccc gaagtgtgga tggcaaggaa gacttgatct      780
ggaagcttct cagcaaggcg caggagaaat ttggaaaaaa caagtctcgg agcttccagc      840
tctttggctc tccacccggc cagagggacc tgctgttcaa agactctgct cttgggtttt      900
tgaggatccc ctcgaaggta gattcggcgc tgtacctggg ctcccgctac ttgaccacct      960
tgaagaacct cagggaaact gcggaggagg tgaaggcgcg gtacaccagg gtcgtgtggt     1020
gtgccgtggg acctgaggag cagaagaagt gccagcagtg gagccagcag agcggccaga     1080
acgtgacctg tgccacggcg tccaccactg acgactgcat cgtcctggtg ctgaaagggg     1140
aagcagatgc cctgaacttg gatggaggat atatctacac tgcgggcaag tgtggcctgg     1200
tgcctgtcct ggcagagaac cggaaatcct ccaaacacag tagcctagat tgtgtgctga     1260
gaccaacgga agggtacctt gccgtggcag ttgtcaagaa agcaaatgag gggctcacat     1320
ggaattctct gaaagacaag aagtcgtgcc acaccgccgt ggacaggact gcaggctgga     1380
acatccccat gggcctgatc gtcaaccaga caggctcctg cgcatttgat gaattcttta     1440
gtcagagctg tgcccctggg gctgacccga atccagact ctgtgccttg tgtgctggcg      1500
atgaccaggg cctggacaag tgtgtgccca actctaagga agtactat ggctataccg       1560 gggctttcag gtgcctggct gaggacgttg gggacgttgc ctttgtgaaa aacgacacag     1620
tctgggagaa cacgaatgga gagagcactg cagactgggc taagaacttg aatcgtgagg     1680
acttcaggtt gctctgcctc gatggcacca ggaagcctgt gacggaggct cagagctgcc     1740
acctggcggt ggccccgaat cacgctgtgg tgtctcggag cgatagggca gcacacgtga     1800
aacaggtgct gctccaccag caggctctgt ttgggaaaaa tggaaaaaac tgcccggaca     1860
agttttgttt gttcaaatct gaaaccaaaa accttctgtt caatgacaac actgagtgtc     1920
tggccaaact tggaggcaga ccaacgtatg aagaatattt ggggacagag tatgtcacgg     1980
ccattgccaa cctgaaaaaa tgctcaacct ccccgcttct ggaagcctgc gccttcctga     2040
cgaggtaaag cctgcaaaga agctagcctg cctccctggg cctcagctcc tcctgctct     2100 cagccccaat ctccaggcgc gagggacctt cctctccctt cctgaagtcg gattttgcc     2160 aagctcatca gtatttacaa ttccctgctg tcatttagc aagaaataaa attagaaatg      2220
ctgttgattt tcattccct                                                 2239
```

<210> SEQ ID NO 42
<211> LENGTH: 2744
<212> TYPE: DNA
<213> ORGANISM: MOUSE

<400> SEQUENCE: 42

```
gaggcttgtc ctctaggtct cccaagacca cagacatgag gctgctcatc ccttccttga       60
tatttcttga ggcccttgga ctctgtctag ctaaggcaac aactgttcaa tggtgtgctg      120
tgtcaaattc tgaggaagaa aaatgtttaa ggtggcagaa cgagatgaga aaagtgggtg      180
gcccgccgct cagttgtgtc aagaaatcct ccacccgcca gtgcatccag gccattgtga      240
caaacagagc tgatgccatg actcttgatg tggcactat gttcgatgca ggaaagcccc      300
cctacaaact gcgacctgtg gcagctgaag tctacgggac caaagagcag ccccggactc      360
```

-continued

```
actactatgc ggtagcagtc gtgaagaaca gcagtaactt tcatctgaac caactccaag    420
gcctgaggtc ctgccacacc ggcattggca ggagtgcggg gtggaaaatc cctataggga    480
cacttcgtcc atacctgaat tggaatgggc cacctgcatc ccttgaggaa gcggtatcca    540
agttcttctc aaagagctgt gttcccggtg cccaaaagga tagattcccc aacctgtgta    600
gctcgtgtgc agggacagga gccaacaaat gtgcctcttc ccccgaggag ccatactcag    660
gttatgctgg agccttgagg tgtctgagag acaatgctgg agatgtggct tttaccagag    720
gaagcacggt atttgaggag ttaccaaata aagccgaaag ggaccagtac aagctgctct    780
gcccagacaa cacctggaag ccggtgacag aatacaagga gtgccacctg cccaagtcc    840
cttcacatgc tgtcgtatcc cgaagcacga atgacaaaga agaggccatc tgggagcttc    900
tccgccagtc acaggagaag tttgaaaaaa acaagcatc gggattccag ctctttgcct    960
cccctcggg acagaaggac ctgctgttca aggagtctgc cattggcttt gtgagggttc    1020
cccagaaggt agatgtaggg ctctacctga ccttcagcta caccacatcc atacagaacc    1080
tgaataaaaa gcagcaggat gtgatagcct caaaggcccg ggtcacatgg tgtgccgtgg    1140
gcagtgagga gaagcgcaag tgtgatcagt ggaacagagc aagcagaggc agggtcacct    1200
gcatctcatt ccccaccacg gaagactgca ttgtcgcaat catgaaggga gatgctgatg    1260
ccatgagcct ggatggaggc tatatctaca ctgcgggcaa gtgcggttta gttccagtct    1320
tggcagagaa ccagaaatcc tccaaaagca atggcttgga ttgtgtgaac agaccagtgg    1380
aagggtacct tgctgtagca gcagttagaa gagaagatgc tggcttcacc tggagctctt    1440
tgagaggcaa gaagtcctgc cacactgccg tggacaggac cgcaggctgg aacatcccca    1500
tgggcctgct tgctaaccag accagatcct gcaaatttaa tgagttcttt agccaaagct    1560
gtgcccctgg tgctgacccc aaatccaatc tctgtgccct gtgtattggt gatgagaagg    1620
gtgagaacaa gtgtgctccc aacagcaaag agagatacca aggctacact ggggctttaa    1680
ggtgtctggc tgagaaggca ggaaatgttg cattttgaa ggactccact gtcttgcaga    1740
atactgacgg gaagaacact gaagagtggg ctaggaactt aaagctgaag gactttgagc    1800
ttttgtgcct tgatgacacc cggaaacctg tgactgaggc taagaactgc cacctagcca    1860
tagccccaaa ccatgctgta gtgtctcgga cagacaaggt ggaagtcctt cagcaggtgc    1920
tgcttgacca acaggttcag tttgggagaa atggacagag gtgtccagga gagttttgcc    1980
tgttccagtc taaaaccaaa aaccttctgt tcaatgacaa cactgagtgt ctggccaaga    2040
tccccggcaa aaccacatcg gagaagtatc tgggaaagga gtacgtcata gcgaccgagc    2100
gcctgaagca gtgctccagc tccccactcc tggaagcctg cgcttttctt acccagtgaa    2160
aacactgagc aaatagcaga accttcccag gaagtctcat cccggagcca cggtccgggg    2220
gccttcagac catctggtct cctcactccc tgctgtcact ttaggtagaa ataaaatgaa    2280
gtagtgttga gtttctcgtc atatgaggtg tcactcattg ctcctcaaag tttatactgg    2340
aatcctgtgt ctgaccactt gcctgcacac ttggacttgc ttttggagat tctcggtcca    2400
gcccttcctt tatcctgaag tttcaggcat ggtgcccatt gacctggagt ctggggacaa    2460
ccacgtgatg tttctgtccc caggggatct ggtttcttca catagagatc acagtacatg    2520
tgcatctgtg tgcccagat catgcgtgcg tatgggtgac catgtatgcc tcaacataag    2580
tttgcacatg actgtgtgca ctccttgcac tgatgtttgc ataggactgt gtacttgcac    2640
taatgcttat gtgtgtgtgt gcacacacgt gtgaaagcca gaggacaatc tggaatgtca    2700
ccatccacct tttttaaaaa ttaaatttat ttatttacat ccct           2744
```

<210> SEQ ID NO 43
<211> LENGTH: 2619
<212> TYPE: DNA
<213> ORGANISM: HUMAN

<400> SEQUENCE: 43

| | | | | | |
|---|---|---|---|---|---|
| gactcctagg | ggcttgcaga | cctagtggga | gagaaagaac | atcgcagcag | ccaggcagaa | 60 |
| ccaggacagg | tgaggtgcag | gctggctttc | ctctcgcagc | gcggtgtgga | gtcctgtcct | 120 |
| gcctcagggc | ttttcggagc | ctggatcctc | aaggaacaag | tagacctggc | cgcggggagt | 180 |
| ggggagggaa | ggggtgtcta | ttgggcaaca | gggcggcaaa | gccctgaata | aggggcgca | 240 |
| gggcaggcgc | aagtgcagag | ccttcgtttg | ccaagtcgcc | tccagaccgc | agacatgaaa | 300 |
| cttgtcttcc | tcgtcctgct | gttcctcggg | gccctcggac | tgtgtctggc | tggccgtagg | 360 |
| agaaggagtg | ttcagtggtg | cgccgtatcc | aacccgagg | ccacaaaatg | cttccaatgg | 420 |
| caaaggaata | tgagaaaagt | gcgtggccct | cctgtcagct | gcataaagag | agactccccc | 480 |
| atccagtgta | tccaggccat | tgcggaaaac | agggccgatg | ctgtgaccct | tgatggtggt | 540 |
| ttcatatacg | aggcaggcct | ggcccctac | aaactgcgac | ctgtagcggc | ggaagtctac | 600 |
| gggaccgaaa | gacagccacg | aactcactat | tatgccgtgg | ctgtggtgaa | gaagggcggc | 660 |
| agctttcagc | tgaacgaact | gcaaggtctg | aagtcctgcc | acacaggcct | tcgcaggacc | 720 |
| gctggatgga | atgtccctac | agggacactt | cgtccattct | tgaattggac | gggtccacct | 780 |
| gagcccattg | aggcagctgt | ggccaggttc | ttctcagcca | gctgtgttcc | cggtgcagat | 840 |
| aaaggacagt | tccccaacct | gtgtcgcctg | tgtgcgggga | caggggaaaa | caaatgtgcc | 900 |
| ttctcctccc | aggaaccgta | cttcagctac | tctggtgcct | tcaagtgtct | gagagacggg | 960 |
| gctggagacg | tggctttat | cagagagagc | acagtgtttg | aggacctgtc | agacgaggct | 1020 |
| gaaagggacg | agtatgagtt | actctgccca | gacaacactc | ggaagccagt | ggacaagttc | 1080 |
| aaagactgcc | atctggcccg | ggtcccttct | catgccgttg | tggcacgaag | tgtgaatggc | 1140 |
| aaggaggatg | ccatctggaa | tcttctccgc | caggcacagg | aaaagtttgg | aaaggacaag | 1200 |
| tcaccgaaat | tccagctctt | tggctcccct | agtgggcaga | agatctgct | gttcaaggac | 1260 |
| tctgccattg | ggttttcgag | ggtgcccccg | aggatagatt | ctgggctgta | ccttggctcc | 1320 |
| ggctacttca | ctgccatcca | gaacttgagg | aaaagtgagg | aggaagtggc | tgcccggcgt | 1380 |
| gcgcgggtcg | tgtggtgtgc | ggtgggcgag | caggagctgc | gcaagtgtaa | ccagtggagt | 1440 |
| ggcttgagcg | aaggcagcgt | gacctgctcc | tcggcctcca | ccacagagga | ctgcatcgcc | 1500 |
| ctggtgctga | aggagaagc | tgatgccatg | agtttggatg | gaggatatgt | gtacactgca | 1560 |
| tgcaaatgtg | gtttggtgcc | tgtcctggca | gagaactaca | atcccaaca | aagcagtgac | 1620 |
| cctgatccta | actgtgtgga | tagacctgtg | gaaggatatc | ttgctgtggc | ggtggttagg | 1680 |
| agatcagaca | ctagccttac | ctggaactct | gtgaaaggca | agaagtcctg | ccacaccgcc | 1740 |
| gtggacagga | ctgcaggctg | gaatatcccc | atgggcctgc | tcttcaacca | gacgggctcc | 1800 |
| tgcaaatttg | atgaatattt | cagtcaaagc | tgtgcccctg | ggtctgaccc | gagatctaat | 1860 |
| ctctgtgctc | tgtgtattgg | cgacgagcag | ggtgagaata | agtgcgtgcc | caacagcaac | 1920 |
| gagagatact | acggctacac | tggggctttc | cggtgcctgg | ctgagaatgc | tggagacgtt | 1980 |
| gcatttgtga | aagatgtcac | tgtcttgcag | aacactgatg | gaaataacaa | tgaggcatgg | 2040 |
| gctaaggatt | tgaagctggc | agactttgcg | ctgctgtgcc | tcgatggcaa | acggaagcct | 2100 |

```
gtgactgagg ctagaagctg ccatcttgcc atggccccga atcatgccgt ggtgtctcgg    2160
atggataagg tggaacgcct gaaacaggtg ctgctccacc aacaggctaa atttgggaga    2220
aatggatctg actgcccgga caagttttgc ttattccagt ctgaaaccaa aaaccttctg    2280
ttcaatgaca acactgagtg tctggccaga ctccatggca aaacaacata tgaaaaatat    2340 ttggaccac agtatgtcgc aggcattact aatctgaaaa agtgctcaac ctcccccctc     2400
ctggaagcct gtgaattcct caggaagtaa aaccgaagaa gatggcccag ctccccaaga    2460
aagcctcagc cattcactgc ccccagctct tctccccagg tgtgttgggg ccttggctcc    2520
cctgctgaag gtggggattg cccatccatc tgcttacaat tccctgctgt cgtcttagca    2580
agaagtaaaa tgagaaattt tgttgatatt caaaaaaaa                           2619

<210> SEQ ID NO 44
<211> LENGTH: 2457
<212> TYPE: DNA
<213> ORGANISM: COW

<400> SEQUENCE: 44
gggggaggag ggaggctggg gcgcttatag gaccacaggg cggggcaaac ctcgtgaggt      60
caccgagcac tggataaagg gacgcagaac gagcgcaggt ggcagacctt cgttccggag     120
tcgccccagg acgccagcca tgaagctctt cgtccccgcc ctgctgtccc ttggagccct     180
tggactgtgt ctggctgccc cgaggaaaaa cgttcgatgg tgtaccatct cccaacctga     240
gtggttcaaa tgccgccgat ggcagtggag gatgaagaag ctgggtgctc cctctatcac     300
ctgtgtgagg agggcctttg ccttggaatg tatccgggcc atcgcggaga aaaaggcgga    360
tgctgtgacc ctggatggtg gcatggtgtt tgaggcgggc cgggacccct acaaactgcg     420
gccagtagca gcagagatct atgggacgaa agagtctccc caaacccact attatgctgt     480
ggccgtcgtg aagaagggca gcaactttca gctggaccag ctgcaaggcc ggaagtcctg     540
ccatacgggc cttggcaggt ccgctgggtg gatcatccct atgggaatcc ttcgcccgta     600
cttgagctgg acagagtcac tcgagcccct ccagggagct gtggctaaat tcttctctgc     660
cagctgtgtt ccctgcattg atagacaagc ataccccaac ctgtgtcaac tgtgcaaggg    720
ggagggggag aaccagtgtg cctgctcctc ccgggaacca tacttcggtt attctggtgc     780
cttcaagtgt ctgcaggacg gggctggaga cgtggctttt gttaaagaga cgacagtgtt    840
tgagaacttg ccagagaagg ctgacaggga ccagtatgag cttctctgcc tgaacaacag    900
tcgggcgcca gtggatgcgt tcaaggagtg ccacctggcc caggtcccctt ctcatgctgt   960 cgtggcccga agtgtggatg gcaaggaaga cttgatctgg aagcttctca gcaaggcgca   1020
ggagaaattt ggaaaaaaca agtctcggag cttccagctc tttggctctc cacccggcca   1080
gagggacctg ctgttcaaag actctgctct tgggttttttg aggatcccct cgaaggtaga    1140
ttcggcgctg tacctgggct cccgctactt gaccaccttg aagaacctca gggaaactgc   1200
ggaggaggtg aaggcgcggt acaccagggt cgtgtggtgt gccgtgggac ctgaggagca   1260
gaagaagtgc cagcagtgga gccagcagag cggccagaac gtgacctgtg ccacggcgtc    1320
caccactgac gactgcatcg tcctggtgct gaaaggggaa gcagatgccc tgaacttgga    1380
tggaggatat atctcacactg cgggcaagtg tggcctggtg cctgtcctgg cagagaaccg    1440
gaaatcctcc aaaacacagta gcctagattg tgtgctgaga ccaacggaag ggtaccttgc    1500
cgtggcagtt gtcaagaaag caaatgaggg gctcacatgg aattctctga agacaagaa    1560 gtcgtgccac accgccgtgg acaggactgc aggctggaac atccccatgg gcctgatcgt    1620
```

-continued

```
caaccagaca ggctcctgcg catttgatga attctttagt cagagctgtg ccctgggc      1680
tgacccgaaa tccagactct gtgccttgtg tgctggcgat gaccagggcc tggacaagtg    1740
tgtgcccaac tctaaggaga agtactatgg ctataccggg gctttcaggt gcctggctga    1800
ggacgttggg gacgttgcct ttgtgaaaaa cgacacagtc tgggagaaca cgaatggaga    1860
gagcactgca gactgggcta agaacttgaa tcgtgaggac ttcaggttgc tctgcctcga    1920
tggcaccagg aagcctgtga cggaggctca gagctgccac ctggcggtgg ccccgaatca    1980
cgctgtggtg tctcggagcg atagggcagc acacgtgaaa caggtgctgc tccaccagca    2040
ggctctgttt gggaaaaatg gaaaaaactg cccggacaag ttttgtttgt tcaaatctga    2100
aaccaaaaac cttctgttca atgacaacac tgagtgtctg ccaaacttg gaggcagacc     2160
aacgtatgaa gaatatttgg ggacagagta tgtcacggcc attgccaacc tgaaaaaatg    2220
ctcaacctcc ccgcttctgg aagcctgcgc cttcctgacg aggtaaagcc tgcaaagaag    2280
ctagcctgcc tccctgggcc tcagctcctc cctgctctca gccccaatct ccaggcgcga    2340
gggaccttcc tctcccttcc tgaagtcgga ttttgccaa gctcatcagt atttacaatt     2400
ccctgctgtc attttagcaa gaaataaaat tagaaatgct gttgattttc attccct       2457
```

<210> SEQ ID NO 45
<211> LENGTH: 2136
<212> TYPE: DNA
<213> ORGANISM: HUMAN

<400> SEQUENCE: 45

```
atgaaacttg tcttcctcgt cctgctgttc ctcggggccc tcggactgtg tctggctggc     60
cgtaggagaa ggagtgttca gtggtgcacc gtatcccaac ccgaggccac aaaatgcttc    120
caatggcaaa ggaatatgag aagagtgcgt ggccctcctg tcagctgcat aaagagagac    180
tcccccatcc agtgtatcca ggccattgcg gaaaacaggg ccgatgctgt gacccttgat    240
ggtggtttca tatacgaggc aggcctggcc cctacaaaac tgcgacctgt agcggcggaa    300
gtctacggga ccgaaagaca gccacgaact cactattatg ccgtggctgt ggtgaagaag    360
ggcggcagct ttcagctgaa cgaactgcaa ggtctgaagt cctgccacac aggccttcgc    420
aggaccgctg gatggaatgt gcctataggg acacttcgtc cattcttgaa ttggacgggt    480
ccacctgagc ccattgaggc agctgtggcc aggttcttct cagccagctg tgttcccggt    540
gcagataaag gacagttccc caacctgtgt cgcctgtgtg cggggacagg gaaaacaaa    600
tgtgccttct cctcccagga accgtacttc agctactctg gtgccttcaa gtgtctgaga    660
gacggggctg gagacgtggc ttttatcaga gagagcacag tgtttgagga cctgtcagac    720
gaggctgaaa gggacgagta tgagttactc tgcccagaca cactcggaa gccagtggac    780
aagttcaaag actgccatct ggcccgggtc ccttctcatg ccgttgtggc acgaagtgtg    840
aatggcaagg aggatgccat ctggaatctt ctccgccagg cacaggaaaa gtttggaaag    900
gacaagtcac cgaaattcca gctctttggc tcccctagtg ggcagaaaga tctgctgttc    960
aaggactctg ccattgggtt ttcgagggtg ccccgagga tagattctgg gctgtacctt    1020
ggctccggct acttcactgc catccagaac ttgaggaaaa gtgaggagga agtggctgcc    1080
cggcgtgcgc gggtcgtgtg gtgtgcggtg ggcgagcagg agctgcgcaa gtgtaaccag    1140
tggagtggct tgagcgaagg cagcgtgacc tgctcctcgg cctccaccac agaggactgc    1200
atcgccctgg tgctgaaagg agaagctgat gccatgagtt tggatggagg atatgtgtac    1260
```

| | |
|---|---|
| actgcaggca aatgtggttt ggtgcctgtc ctggcagaga actacaaatc ccaacaaagc | 1320 |
| agtgaccctg atcctaactg tgtggataga cctgtggaag gatatcttgc tgtggcggtg | 1380 |
| gttaggagat cagacactag ccttacctgg aactctgtga aaggcaagaa gtcctgccac | 1440 |
| accgccgtgg acaggactgc aggctggaat atccccatgg gcctgctctt caaccagacg | 1500 |
| ggctcctgca aatttgatga atatttcagt caaagctgtg ccctgggtc tgacccgaga | 1560 |
| tctaatctct gtgctctgtg tattggcgac gagcagggtg agaataagtg cgtgcccaac | 1620 |
| agcaatgaga gatactacgg ctacactggg gctttccggt gcctggctga aatgctgga | 1680 |
| gacgttgcat ttgtgaaaga tgtcactgtc ttgcagaaca ctgatggaaa taacaatgag | 1740 |
| gcatgggcta aggatttgaa gctggcagac tttgcgctgc tgtgcctcga tggcaaacgg | 1800 |
| aagcctgtga ctgaggctag aagctgccat cttgccatgg ccccgaatca tgccgtggtg | 1860 |
| tctcggatgg ataaggtgga acgcctgaaa caggtgctgc tccaccaaca ggctaaattt | 1920 |
| gggagaaatg gatctgactg cccggacaag ttttgcttat tccagtctga aaccaaaaac | 1980 |
| cttctgttca atgacaacac tgagtgtctg gccagactcc atggcaaaac aacatatgaa | 2040 |
| aaatatttgg gaccacagta tgtcgcaggc attactaatc tgaaaaagtg ctcaacctcc | 2100 |
| cccctcctgg aagcctgtga attcctcagg aagtaa | 2136 |

```
<210> SEQ ID NO 46
<211> LENGTH: 2136
<212> TYPE: DNA
<213> ORGANISM: HUMAN

<400> SEQUENCE: 46
```

| | |
|---|---|
| atgaaacttg tcttcctcgt cctgctgttc ctcggggccc tcggactgtg tctggctggc | 60 |
| cgtaggagaa ggagtgttca gtggtgcacc gtatcccaac ccgaggccac aaaatgcttc | 120 |
| caatggcaaa ggaatatgag aagagtgcgt ggccctcctg tcagctgcat aaagagagac | 180 |
| tcccccatcc agtgtatcca ggccattgcg gaaaacaggg ccgatgctgt gacccttgat | 240 |
| ggtggtttca tatacgaggc aggcctggcc cctacaaaac tgcgacctgt agcggcggaa | 300 |
| gtctacggga ccgaaagaca gccacgaact cactattatg ccgtggctgt ggtgaagaag | 360 |
| ggcggcagct ttcagctgaa cgaactgcaa ggtctgaagt cctgccacac aggccttcgc | 420 |
| aggaccgctg gatggaatgt ccctataggg acacttcgtc cattcttgaa ttggacgggt | 480 |
| ccacctgagc ccattgaggc agctgtggcc aggttcttct cagccagctg tgttcccggt | 540 |
| gcagataaag gacagttccc caacctgtgt cgcctgtgtg cggggacagg ggaaaacaaa | 600 |
| tgtgccttct cctcccagga accgtacttc agctactctg gtgccttcaa gtgtctgaga | 660 |
| gacggggctg gagacgtggc ttttatcaga gagagcacag tgtttgagga cctgtcagac | 720 |
| gaggctgaaa gggacgagta tgagttactc tgcccagaca cactcggaa gccagtggac | 780 |
| aagttcaaag actgccatct ggcccgggtc ccttctcatg ccgttgtggc acgaagtgtg | 840 |
| aatggcaagg aggatgccat ctggaatctt ctccgccagg cacaggaaaa gtttggaaag | 900 |
| gacaagtcac cgaaattcca gctctttggc tcccctagtg ggcagaaaga tctgctgttc | 960 |
| aaggactctg ccattgggtt ttcgagggtg cccccgagga tagattctgg ctgtaccctt | 1020 |
| ggctccggct acttcactgc catccagaac ttgaggaaaa gtgaggagga agtggctgcc | 1080 |
| cggcgtgcgc gggtcgtgtg gtgtgcggtg ggcgagcagg agctgcgcaa gtgtaaccag | 1140 |
| tggagtggct tgagcgaagg cagcgtgacc tgctcctcgg cctccaccac agaggactgc | 1200 |
| atcgccctgg tgctgaaagg agaagctgat gccatgagtt tggatggagg atatgtgtac | 1260 |

-continued

```
actgcaggca aatgtggttt ggtgcctgtc ctggcagaga actacaaatc ccaacaaagc      1320
agtgaccctg atcctaactg tgtggataga cctgtggaag gatatcttgc tgtggcggtg      1380
gttaggagat cagacactag ccttacctgg aactctgtga aaggcaagaa gtcctgccac      1440
accgccgtgg acaggactgc aggctggaat atccccatgg gcctgctctt caaccagacg      1500
ggctcctgca aatttgatga atatttcagt caaagctgtg ccctgggtc tgaccccgaga      1560 tctaatctct gtgctctgtg tattggcgac gagcagggtg agaataagtg cgtgcccaac      1620
agcaatgaga gatactacgg ctacactggg gctttccggt gcctggctga aatgctgga      1680 gacgttgcat ttgtgaaaga tgtcactgtc ttgcagaaca ctgatggaaa taacaatgac      1740
gcatgggcta aggatttgaa gctggcagac tttcgctgc tgtgcctcga tggcaaacgg      1800
aagcctgtga ctgaggctag aagctgccat cttgccatgg ccccgaatca tgccgtggtg      1860
tctcggatgg ataaggtgga acgcctgaaa caggtgttgc tccaccaaca ggctaaattt      1920
gggagaaatg gatctgactg cccggacaag ttttgcttat tccagtctga aaccaaaaac      1980
cttctgttca atgacaacac tgagtgtctg ccagactcc atggcaaaac acatatgaa      2040 aaatatttgg gaccacagta tgtcgcaggc attactaatc tgaaaagtg ctcaacctcc      2100 cccctcctgg aagcctgtga attcctcagg aagtaa                               2136
```

<210> SEQ ID NO 47
<211> LENGTH: 2307
<212> TYPE: DNA
<213> ORGANISM: WATER BUFFALO

<400> SEQUENCE: 47

```
caggacctca gacatgaagc tcttcgtccc cgccctgctg tcccttggag cccttggact       60
gtgtctggct gccccgagga aaaacgttcg atggtgtacc atctcccaac ccgagtggct      120
caaatgccac cgatggcagt ggaggatgaa gaagctgggt gctccctcta tcacctgtgt      180
gaggagggcc tttgtcttgg aatgtatccg ggccatcacg gaaaaaaagg cagatgctgt      240
gaccctggat ggtggcatgg tgtttgaggc aggcctggac ccctacaaac tgcggccagt      300
agcagcagag atctatggga ccaaagagtc tccccaaacc cactattatg ctgtggctgt      360
cgtcaaaaag gcagcaact tcagctgga ccagctgcaa ggccggaatt cctgccatac      420
gggccttggc aggtctgctg ggtggaacat ccctatggga atccttcgcc cgtacttgag      480
ctggacagag tcactcgagc ccttccaggg agctgtggct aaaattcttct ctgccagctg      540 tgttccctgc gttgatagac aagcgtaccc caacctgtgt caactgtgca aggggagggg      600
ggagaaccag tgtgcctgct cccccgggga accatacttc ggctattctg gtgccttcaa      660
gtgtctgcag gacggggctg gagacgtggc ttttgtcaag gagacgacag tgtttgagaa      720
cttgccagaa aaggctgaca gggaccagta tgagcttctc tgcctaaaca acactcgggc      780
accagtggat gcattcaagg agtgccacct ggcccaggtc ccttctcatg ctgtcgtggc      840
ccgaagtgtg gatggcaagg aagacttgat ctggaagctt tcagcaagg cgcaggagaa      900 gttcggaaaa aacaagtctg ggagcttcca gctctttggc tctccacccg gccagaggga      960
cctgctattc aaagactgtg ctcttgggtt tttgaggatc ccctcgaagg tagattcggc      1020
actgtacctg ggctcccgct acttgaccgc cttgaaaaac ctcagggaaa ctgcggagga      1080
ggtgcaggca cggcgcgcga gggtcgtgtg tgcgcggtg ggacccgagg agcagaaaaa      1140
gtgccagcag tggagccagc agagcggcca gatcgtgacc tgtgccacgg cctccaccac      1200
```

| | |
|---|---|
| cgatgactgc atcgccctgg tgctgaaagg ggaagcggat gccctgagct tggatggagg | 1260 |
| atatatctac actgcgggca agtgtggtct ggtgcctgtc ctggcagaga accggaaatc | 1320 |
| ctccaaacac agtagcctag attgtgtgct gagaccaacg gaagggtacc ttgccgtggc | 1380 |
| agttgtcaag aaagcaaatg aggggctcac ttggaattct ctgaaaggca agaagtcgtg | 1440 |
| ccacaccgcc gtggacagga ctgcaggctg gaacatcccc atgggcctga tcgccaacca | 1500 |
| gacaggctcc tgcgcatttg atgaattctt tagtcagagc tgtgccctg gggctgaccc | 1560 |
| gaaatccaga ctctgtgcat tgtgtgctgg cgatgaccag ggcctggaca agtgtgtgcc | 1620 |
| caactctaag gagaagtact atggctacac cggggctttc aggtgcctgg ctgaggatgt | 1680 |
| tggggacgtt gcctttgtga aaatgacaca gtttgggag aacacgaatg gagagagcac | 1740 |
| tgcagactgg gctaagaact tgaatcgcga ggacttcagg ttgctttgcc tcgatggcac | 1800 |
| caggaagcct gtgacggagg ctcagagctg ccacctggcg gtggccccga atcacgctgt | 1860 |
| ggtgtctttg agcgaaaggg cagctcacgt ggaacaggtg ctgctccacc agcaggctct | 1920 |
| gtttggggaa aatggaaaaa actgcccgga caaattttgt ttgttcaaat ctgaaaccaa | 1980 |
| aaaccttctg ttcaatgaca acactgagtg tctggccaaa cttggaggca gaccaacgta | 2040 |
| tgaagaatat ttggggacag agtatgtcac agccattgcc aacctgaaaa aatgctcaac | 2100 |
| ctccccgctt ctggaagcct gcgccttcct gacgaggtaa agcctgcaaa gaagctagcc | 2160 |
| tgcctccctg ggcctcagct cctccctgct ctcatcccca atctccaggc gcgagggacc | 2220 |
| ctcctctccc ttcctgaagt tggattttg ccaagctcat cagtattcac aattccctgc | 2280 |
| tgtcatctta gcaagaaata aaattag | 2307 |

<210> SEQ ID NO 48
<211> LENGTH: 2178
<212> TYPE: DNA
<213> ORGANISM: MOUSE

<400> SEQUENCE: 48

| | |
|---|---|
| aggcttgtcc tctaggtctc ccaagaccac agacatgagg ctgctcatcc cttccttgat | 60 |
| atttcttgag gcccttggac tctgtctagc taaggcaaca actgttcaat ggtgtgctgt | 120 |
| gtcaaattct gaggaagaaa aatgtttaag gtggcagaac gagatgagaa agtgggtgg | 180 |
| cccgccgctc agttgtgtca agaaatcctc caccgccag tgcatccagg ccattgtgac | 240 |
| aaacagagct gatgccatga ctcttgatgg tggcactttg ttcgatgcag gaaagccccc | 300 |
| ctacaaactg cgacctgtgg cagctgaagt ctacgggacc aaagagcagc cccggactca | 360 |
| ctactatgcg gtagcagtcg tgaagaacag cagtaacttt catctgaacc aactccaagg | 420 |
| cctgaggtcc tgccacaccg gcattggcag gagtgcgggg tggaaaatcc ctatagggac | 480 |
| acttcgtcca tacctgaatt ggaatgggcc acctgcatcc cttgaggaag cggtatccaa | 540 |
| gttcttctca aagagctgtg ttcccggtgc ccaaaaggat agattcccca acctgtgtag | 600 |
| ctcgtgtgca gggacaggag ccaacaaatg tgcctcttcc cccgaggagc atactcagg | 660 |
| ttatgctgga gccttgaggt gtctgagaga caatgctgga gatgtggctt ttaccagagg | 720 |
| aagcacggta tttgaggagt taccaaataa agccgaaagg gaccagtaca agctgctctg | 780 |
| cccagacaac acctggaagc cggtgacaga atacaaggag tgccacctgg cccaagtccc | 840 |
| ttcacatgct gtcgtatccc gaagcacgaa tgacaaagaa gaggccatct gggagcttct | 900 |
| ccgccagtca caggagaagt ttggaaaaaa acaagcatcg ggattccagc tctttgcctc | 960 |
| ccctcggga cagaaggacc tgctgttcaa ggagtctgcc attggctttg tgagggttcc | 1020 |

```
ccagaaggta gatgtagggc tctacctgac cttcagctac accacatcca tacagaacct   1080
gaataaaaag cagcaggatg tgatagccac aaaggcccgg gtcacatggt gtgccgtggg   1140
cagtgaggag aagcgcaagt gtgatcagtg aacagagca agcagaggca gggtcacctg    1200
catctcattc cccaccacgg aagactgcat tgtcgcaatc atgaaggag  atgctgatgc    1260 catgagcctg gatggaggct atatctacac tgcgggcaag tgcggtttag ttccagtctt   1320
ggcagagaac cagaaatcct ccaaaagcaa tggcttggat tgtgtgaaca gaccagtggg   1380
agggtacctt gctgtagcag cagttagaag agaagatgct ggcttcacct ggagctcttt   1440
gagaggcaag aagtcctgcc acactgccgt ggacaggacc gcaggctgga acatccccat   1500
gggcctgctt gctaaccaga ccagatcctg caaatttaat gagttcttta gccaaagctg   1560
tgcccctggt gctgacccca atccaatct  ctgtgccctg tgtattggtg atgagaaggg   1620
tgagaacaag tgtgctccca acagcaaaga gagataccaa ggctacactg ggctttaag   1680 gtgtctggct gagaaggcag gaaatgttgc attttttgaag gactccactg tcttgcagaa   1740
tactgacggg aagaacactg aagagtgggc taggaactta aagctgaagg actttgagct   1800
tttgtgcctt gatgacaccc ggaaacctgt gactgaggct aagaactgcc acctagccat   1860
agccccaaac catgctgtag tgtctcggac agacaaggtg gaagtccttc agcaggtgct   1920
gcttgaccaa caggttcagt ttgggagaaa tggacagagg tgtccaggag agttttgcct   1980
gttccagtct aaaaccaaaa accttctgtt caatgacaac actgagtgtc tggccaagat   2040 cccccggcaaa accacatcgg agaagtatct gggaaaggag tacgtcatag cgaccgagcg   2100
cctgaagcag tgctccagct ccccgctcct ggaagcctgc gcttttctta cccagtgaaa   2160
acactgagca aatagcag                                                 2178

<210> SEQ ID NO 49
<211> LENGTH: 2136
<212> TYPE: DNA
<213> ORGANISM: HUMAN

<400> SEQUENCE: 49
atgaaacttg tcttcctcgt cctgctgttc ctcggggccc tcggactgtg tctggctggc    60
cgtaggagaa ggagtgttca gtggtgcacc gtatcccaac ccgaggccac aaaatgcttc   120
caatggcaaa ggaatatgag aagagtgcgt ggccctcctg tcagctgcat aaagagagac   180
tcccccatcc agtgtatcca ggccattgcg gaaaacaggg ccgatgctgt gacccttgat   240
ggtggtttca tatacgaggc aggcctggcc ccctacaaac tgcgacctgt agcggcggaa   300
gtctacggga ccgaaagaca gccacgaact cactattatg ccgtggctgt ggtgaagaag   360
ggcggcagct ttcagctgaa cgaactgcaa ggtctgaagt cctgccacac aggccttcgc   420
aggaccgctg gatggaatgt ccctataggg acacttcgtc cattcttgaa ttggacgggt   480
ccacctgagc ccattgaggc agctgtggcc aggttcttct cagccagctg tgttcccggt   540
gcagataaag gacagttccc caacctgtgt cgcctgtgtg cggggacagg gaaaacaaa    600 tgtgccttct cctcccagga accgtacttc agctactctg gtgccttcaa gtgtctgaga   660 gacgggggctg gagacgtggc ttttatcaga gagagcacag tgtttgagga cctgtcagac   720
gaggctgaaa gggacgagta tgagttactc tgcccagaca cactcggaa  gccagtggac   780 aagttcaaag actgccatct ggcccgggtc ccttctcatg ccgttgtggc acgaagtgtg   840
aatggcaagg aggatgccat ctggaatctt ctccgccagg cacaggaaaa gtttggaaag   900
```

```
gacaagtcac cgaaattcca gctctttggc tcccctagtg ggcagaaaga tctgctgttc      960
aaggactctg ccattgggtt ttcgagggtg cccccgagga tagattctgg gctgtacctt     1020
ggctccggct acttcactgc catccagaac ttgaggaaaa gtgaggagga agtggctgcc     1080
cggcgtgcgc gggtcgtgtg gtgtgcggtg ggcgagcagg agctgcgcaa gtgtaaccag     1140
tggagtggct tgagcgaagg cagcgtgacc tgctcctcgg cctccaccac agaggactgc     1200
atcgccctgg tgctgaaagg agaagctgat gccatgagtt tggatggagg atatgtgtac     1260
actgcaggca atgtggtttt ggtgcctgtc ctggcagaga actacaaatc ccaacaaagc     1320
agtgaccctg atcctaactg tgtggataga cctgtggaag gatatcttgc tgtggcggtg     1380
gttaggagat cagacactag ccttacctgg aactctgtga aaggcaagaa gtcctgccac     1440
accgccgtgg acaggactgc aggctggaat atccccatgg gcctgctctt caaccagacg     1500
ggctcctgca aatttgatga atatttcagt caaagctgtg cccctgggtc tgacccgaga     1560
tctaatctct gtgctctgtg tattggcgac gagcagggtg agaataagtg cgtgcccaac     1620
agcaatgaga gatactacgg ctacactggg gctttccggt gcctggctga aatgctggaa     1680
gacgttgcat ttgtgaaaga tgtcactgtc ttgcagaaca ctgatggaaa taacaatgac     1740
gcatgggcta aggatctgaa gctggcagac tttgcgctgc tgtgcctcga tggcaaacgg     1800
aagcctgtga ctgaggctag aagctgccat cttgccatgg ccccgaatca tgccgtggtg     1860
tctcggatgg ataaggtgga acgcctgaaa caggtgttgc tccaccaaca ggctaaattt     1920
gggagaaatg gatctgactg cccggacaag ttttgcttat tccagtctga accaaaaac     1980 cttctgttca atgacaacac tgagtgtctg gccagactcc atggcaaaac aacatatgaa     2040
aaatatttgg gaccacagta tgtcgcaggc attactaatc tgaaaaagtg ctcaacctcc     2100
cccctcctgg aagcctgtga attcctcagg aagtaa                               2136

<210> SEQ ID NO 50
<211> LENGTH: 2127
<212> TYPE: DNA
<213> ORGANISM: COW

<400> SEQUENCE: 50
atgaagctct tcgtccccgc cctgctgtcc cttggagccc ttggactgtg tctggctgcc       60
ccgaggaaaa acgttcgatg gtgtaccatc tcccaacctg agtggttcaa atgccgccga      120
tggcagtgga ggatgaagaa gctgggtgct ccctctatca cctgtgtgag gagggccttt      180
gccttggaat gtatccgggc catcgcggag aaaaaggcgg atgctgtgac cctggatggt      240
ggcatggtgt ttgaggcggg ccgggacccc tacaaactgc ggccagtagc agcagagatc      300
tatgggacga aagagtctcc ccaaacccac tattatgctg tggccgtcgt gaagaagggc      360
agcaactttc agctggacca gctgcaaggc cggaagtcct gccatacggg ccttggcagg      420
tccgctgggt ggatcatccc tatgggaatc cttcgcccgt acttgagctg acagagtca      480 ctcgagcccc tccagggagc tgtggctaaa ttcttctctg ccagctgtgt tcctgcatt     540 gatagacaag catacccaa cctgtgtcaa ctgtgcaagg ggagggggga gaaccagtgt      600
gcctgctcct cccgggaacc atacttcggt tattctggtg ccttcaagtg tctgcaggac      660
ggggctggag acgtggcttt tgttaaagag acgacagtgt ttgagaactt gccagagaag      720
gctgacaggg accagtatga gcttctctgc ctgaacaaca gtcgggcgcc agtggatgcg      780
ttcaaggagt gccaccctggc ccaggtccct tctcatgctg tcgtggcccg aagtgtggat      840
ggcaaggaag acttgatctg gaagcttctc agcaaggcgc aggagaaatt tggaaaaaac      900
```

```
aagtctcgga gcttccagct ctttggctct ccacccggcc agagggacct gctgttcaaa    960
gactctgctc ttgggttttt gaggatcccc tcgaaggtag attcggcgct gtacctgggc   1020
tcccgctact tgaccacctt gaagaacctc agggaaactg cggaggaggt gaaggcgcgg   1080
tacaccaggg tcgtgtggtg tgccgtgggc cctgaggagc agaagaagtg ccagcagtgg   1140
agccagcaga gcggccagaa cgtgacctgt gccacggcgt ccaccactga cgactgcatc   1200
gtcctggtgc tgaaagggga agcagatgcc ctgaacttgg atggaggata tatctacact   1260
gcgggcaagt gtggcctggt gcctgtcctg cagagaaacc ggaaatcctc caaacacagt   1320
agcctagatt gtgtgctgag accaacggaa gggtaccttg ccgtggcagt tgtcaagaaa   1380
gcaaatgagg ggctcacatg gaattctctg aaagacaaga agtcgtgcca caccgccgtg   1440
gacaggactg caggctggaa catccccatg ggcctgatcg tcaaccagac aggctcctgc   1500
gcatttgatg aattctttag tcagagctgt gcccctgggg ctgacccgaa atccagactc   1560
tgtgccttgt gtgctggcga tgaccagggc ctggacaagt gtgtgcccaa ctctaaggag   1620
aagtactatg ctataccggg gcttttcagg tgcctggctg aggacgttgg ggacgttgcc   1680
tttgtgaaaa acgacacagt ctgggagaac acgaatggag agagcactgc agactgggct   1740
aagaacttga atcgtgagga cttcaggttg ctctgcctcg atggcaccag gaagcctgtg   1800
acggaggctc agagctgcca cctggcggtg gccccgaatc acgctgtggt gtctcggagc   1860
gatagggcag cacacgtgaa acaggtgctg ctccgccagc aggctctgtt tgggaaaaat   1920
ggaaaaaact gcccggacaa gttttgtttg ttcaaatctg aaaccaaaaa ccttctgttc   1980
aatgacaaca ctgagtgtct ggccaaactt ggaggcagac caacgtatga agaatatttg   2040
gggacagagt atgtcacggc cattgccaac ctgaaaaaat gctcaacctc cccgcttctg   2100
gaagcctgcg ccttcctgac gaggtaa                                       2127
```

<210> SEQ ID NO 51
<211> LENGTH: 2304
<212> TYPE: DNA
<213> ORGANISM: CAMEL

<400> SEQUENCE: 51

```
caggacctca gacatgaagc tcttcttccc cgccctgctg tccctcgggg cccttggact    60
gtgtctggct gcctctaaga aaagtgttcg atggtgcacc acatcaccag cagagtcgtc   120
aaaatgtgcc caatggcaac ggaggatgaa gaaagtgcgt ggtccctctg tcacctgcgt   180
aaagaagaca tctcgctttg aatgcatcca ggccatctcg acagaaaagg cagatgctgt   240
gacccttgac ggtggtttgg tgtatgacgc aggcctggac ccctacaagc tgcggccgat   300
agcggcagag gtctatggga cagaaaacaa tccccaaacc cactattatg ccgttgccat   360
tgccaaaaag gcaccaaact ttcagctgaa ccagctacaa ggtttgaagt cctgccatac   420
cggccttggc aggtctgctg ggtggaacat ccctatgggg ctacttcgtc cattcttgga   480
ctggacaggg cctcctgagc ccctccagaa agctgtggcc aaattcttct ctgccagctg   540
tgttccctgc gtggatggaa aagagtaccc caacctgtgt cagctgtgtg cagggacggg   600
ggaaaataaa tgtgcctgct cctcccagga accatatttt ggctactctg gtgccttcaa   660
gtgtctgcaa gatgggggctg gagatgtggc ttttgtcaag gacagtacag tgtttgagag   720
cctgccagcg aaggcggaca gggaccagta tgagctgctc tgcccaaaca atactcggaa   780
accagtggat gcatcccagg agtgtcatct agcccgggtc ccttctcatg ctgttgtggc   840
```

| | |
|---|---:|
| ccgaagtgtg aatggcaagg aggacttgat ctggaaactt ctcgtcaagg cacaggaaaa | 900 |
| gtttggaaga ggcaagccat cagcattcca gctctttggc tctcctgctg ggcagaagga | 960 |
| cctgctgttc aaagactctg cccttgggtt gttgaggatc ccctcaaaga tagattctgg | 1020 |
| gctgtacctg gctccaact acatcactgc catccgaggc ctgagggaaa cggcggcgga | 1080 |
| ggtggagttg aggcgcgcgc aggtcgtgtg gtgtgccgtg ggctccgacg agcagctcaa | 1140 |
| gtgccaggag tggagccgcc agagcaacca aagcgtggtc tgtgccacgg cctccaccac | 1200 |
| cgaggactgc atcgccctgg tgctgaaagg agaagctgat gctttgagct tggatggagg | 1260 |
| atatatctac attgcgggca agtgtggctt ggtgcctgtc ttggcggaga gccaacaatc | 1320 |
| ccccgaaagc agtggcttag attgtgtgca tcgaccggta aaagggtatc ttgccgtggc | 1380 |
| ggttgtcagg aaagcaaatg acaagatcac ctggaattct ctgagaggca agaagtcctg | 1440 |
| ccacaccgcg gtggacagga ccgcaggctg gaacatcccc atgggccctc tcttcaaaaa | 1500 |
| tacagactcc tgcagatttg atgaattctt cagtcaaagc tgtgccctg gttctgaccc | 1560 |
| aagatccaag ctctgtgctc tgtgtgcagg caacgaggag ggccagaaca agtgtgtgcc | 1620 |
| caacagcagc gagagatact atggctacac tggggctttc aggtgcctgg ctgagaatgt | 1680 |
| tggggatgtt gcgtttgtga agatgtcac cgtcttagac aacactgatg gaaagaacac | 1740 |
| tgagcagtgg gctaaggatt tgaagctggg agactttgag ctgctgtgcc tcaatgcac | 1800 |
| caggaagcct gtgactgagg ctgagagctg ccacctgccc gtggcccaa atcatgctgt | 1860 |
| ggtatctcgg attgataagg tagcacacct ggaacaggtg ctgctccgcc aacaggctca | 1920 |
| ttttggaaga atggacaag actgcccagg caagttttgc ttgttccagt ccaaaaccaa | 1980 |
| aaacctcctg ttcaatgaca acactgagtg tctggccaaa ctccaaggca aaacaacata | 2040 |
| tgaagagtat ttgggaccac agtatgtcac ggccattgct aagctgagac gatgctccac | 2100 |
| ctccccgctt ctggaagcct gcgccttcct gatgaggtaa aactcgaaaa gccgccccgc | 2160 |
| ctccccagaa gcctcagccc ctggctgctc gcaaccctga tcccaggtgt gctgcacctt | 2220 |
| cctctccctt cctgagggcg gagttcgcca agctcatcag ttttcacaat tccctgctgt | 2280 |
| caacttagca agaaataaaa ttag | 2304 |

<210> SEQ ID NO 52
<211> LENGTH: 2337
<212> TYPE: DNA
<213> ORGANISM: CAMEL

<400> SEQUENCE: 52

| | |
|---|---:|
| gagtcgcctc aggaccccag acatgaagct cttcttcccc gccctgctgt ccctcggggc | 60 |
| ccttggactg tgtctggctg cctctaagaa aagtgttcga tggtgcacca catcaccagc | 120 |
| agagtcgtca aaatgtgccc aatggcaacg gaggatgaaa aagtgcgtg gtccctctgt | 180 |
| cacctgcgta aagaagacat ctcgctttga atgcatccag gccatctcga cagaaaaggc | 240 |
| agatgctgtg acccttgacg gtggtttggt gtatgacgca ggcctggacc cctacaagct | 300 |
| gcggccgata gcggcagagg tctatgggac agaaaacaat ccccaaaccc actattatgc | 360 |
| cgttgccatt gccaaaaagg gcaccaactt tcagctgaac cagctacaag gcctgaagtc | 420 |
| ctgccatacc ggccttggca ggtccgctgg gtggaacatc ctatggggc tacttcgtcc | 480 |
| attcttggac tggacagggc ctcctgagcc cctccagaaa gctgtggcca aattcttctc | 540 |
| tgccagctgt gttccctgcg tggatggaaa agagtacccc aacctgtgtc agctgtgtgc | 600 |
| agggacgggg gaaaataaat gtgcctgctc ctcccaggaa ccatatttg gctactctgg | 660 |

| | |
|---|---|
| tgccttcaag tgtctgcaag atggggctgg agatgtggcc tttgtcaagg acagtacagt | 720 |
| gtttgagagc ctgccagcga aggcggacag ggaccagtat gagctgctct gcccaaacaa | 780 |
| tactcggaaa ccagtggatg cattccagga gtgtcatcta gcccgggtcc cttctcatgc | 840 |
| tgttgtggcc cgaagtgtga atggcaagga ggacttgatc tggaaacttc tcgtcaaggc | 900 |
| acaggaaaag tttggaagag gcaagccatc aggattccag ctctttggct ctcctgctgg | 960 |
| gcagaaggac ctgctgttca agactctgcc cttgggttg ttgaggatct cctcaaagat | 1020 |
| agattctggg ctgtacctgg gctccaacta catcactgcc atccgaggcc tgagggaaac | 1080 |
| ggcggcggag gtggagttga ggcgcgcgca ggtcgtgtgg tgcgcggtgg gctccgacga | 1140 |
| gcagctcaag tgccaggagt ggagccgcca gagcaaccaa agcgtggtct gtgccacggc | 1200 |
| ctccaccacc gaggactgca tcgccctggt gctgaaagga gaagctgatg ctttgagctt | 1260 |
| ggatggagga tatatctaca ttgcgggcaa tgtggcttg gtgcctgtct ggcggagag | 1320 |
| ccaacaatcc cccgaaagca gtggcttaga ttgtgtgcat cgaccggtaa aagggtatct | 1380 |
| tgccgtggcg gttgtcagga aagcaaatga caagatcacc tggaattctc tgagaggcaa | 1440 |
| gaagtcctgc cacaccgccg tggacaggac cgcaggctgg aacatcccca tgggcctgct | 1500 |
| ctccaaaaat acagactcct gcagatttga tgaattcctc agtcaaagct gtgcccctgg | 1560 |
| gtctgaccca agatccaagc tctgtgctct gtgtgcaggc aacgaggagg ccagaacaa | 1620 |
| gtgtgtgccc aacagcagcg agagatacta tggctacact ggggctttca ggtgcctggc | 1680 |
| tgagaatgtt ggggatgttg cgtttgtgaa agatgtcacc gtcttagaca acactgatgg | 1740 |
| aaagaacact gagcagtggg ctaaggattt gaagctggga gactttgagc tgctgtgcct | 1800 |
| caatggcacc aggaagcctg tgactgaggc tgagagctgc cacctggccg tggccccaaa | 1860 |
| tcatgctgtg gtatctcgga ttgataaggt agcacacctg aacaggtgc tgctccgcca | 1920 |
| acaggctcat tttggaagaa atggacgaga ctgcccaggc aagttttgct tgttccagtc | 1980 |
| caaaaccaaa aacctcctgt tcaatgacaa cactgagtgt ctggccaaac tccaaggcaa | 2040 |
| aacaacatat gaagagtatt tgggaccaca gtatgtcacg gccattgcta agctgagacg | 2100 |
| atgctccacc tccccgcttc tggaagcctg cgccttcctg atgaggtaaa actcgaaaag | 2160 |
| ccgccccgcc tccccagaag cctcagcccc tggctgctcg caaccctgat cccaggtgtg | 2220 |
| ctgcaccttc ctctcccttc ctgagggcgg agttcgccaa gctcatcagt tttcacaatt | 2280 |
| ccctgctgtc aacttagcaa gaaataaaat tagaaatgct gttggttttc attccct | 2337 |

<210> SEQ ID NO 53
<211> LENGTH: 2293
<212> TYPE: DNA
<213> ORGANISM: RAT

<400> SEQUENCE: 53

| | |
|---|---|
| cgtccgctcc tcgccacaca caccgagagg atgaggttcg ctgtgggtgc cctgctggct | 60 |
| tgtgccgccc tgggactgtg tctggctgtc cctgacaaaa cggtcaaatg gtgcgcagtg | 120 |
| tctgagcatg agaacaccaa gtgtatcagt ttccgtgacc acatgaaaac cgtccttcca | 180 |
| gctgatggcc cccggcttgc ctgtgtgaag aaaacctcct atcaagattg catcaaggcc | 240 |
| atttctggag gtgaagctga tgccattacc ttggatgggg gttgggtgta cgatgcaggc | 300 |
| ctgactccca caacctgaa gcctgtggca gcagagtttt atggatcact tgaacatcca | 360 |
| cagacccact acttggctgt ggccgtggtg aagaagggaa cagacttcca gctgaaccag | 420 |

```
ctccagggca agaagtcctg ccacactggc ctgggcaggt ctgcaggctg gattatcccc      480
attggcttac ttttctgtaa cttgccagag ccccgcaagc tcttgagaa agctgtggcc       540 agtttcttct cgggcagttg tgtccctgt gcagatccag tggccttccc ccagctgtgt       600
caactgtgtc caggctgtgg ctgctccccg actcaaccgt tctttggcta cgtaggcgcc      660
ttcaagtgtc tgagagatgg aggtggagat gtggcctttg tcaagcatac aaccatattt      720
gaggtcttgc cacagaaggc tgacagggat caatatgagc tgctctgcct tgacaatacc      780
cgcaagccag tggatcagta tgaggactgc tacctagccc ggatcccttc tcatgctgtt      840
gtggctcgaa atgagatgg caagaggac ttgatctggg agatcctcaa agtggctcag        900
gaacactttg gcaaaggcaa atcaaaagac ttccaactgt tcggctctcc tcttgggaaa      960
gacctgctgt ttaaggattc tgcctttggc tgttacgggg tgcccccaag gatggactac     1020
aggctgtacc tcggccacag ctatgtcact gccattcgaa atcagcggga aggcgtgtgc     1080
ccggaggcct ccatcgacag cgcgccagtg aaatggtgtg cactgagtca ccaagagaga     1140
gccaagtgtg atgagtggag cgtcacgagc aatgggcaga tagagtgtga gtcagcagag     1200
agcactgagg actgcattga caagattgtg aatggagaag cagatgccat gagcttggat     1260
ggaggtcatg cctacatagc aggccagtgt ggactagtgc ccgtcatggc agagaactat     1320
gatatctctt cgtgtacaaa cccacaatca gatgtctttc ctaaagggta ttatgccgtg     1380
gctgtggtga aggcatcaga ctccagcatc aactggaaca acctgaaagg caagaagtcc     1440
tgccatactg gagtagacag aaccgccggc tggaacatcc ctatgggcct gctgttcagc     1500
aggatcaacc actgcaagtt cgatgaattt ttcagtcaag gctgtgctcc tggctataag     1560
aagaattcca ccctctgtga cctgtgtatt ggcccagcaa atgtgctcc gaacaacaga     1620 gagggatata atggttatac aggggctttc cagtgcctcg ttgagaaggg agacgtagcc     1680
tttgtgaagc accagactgt cctggaaaac acgaacggaa agaacactgc tgcatgggct     1740
aaggatctga gcaggaaga cttccagctg ctgtgccctg atggtaccaa gaagcctgta     1800
accgagttcg ccacctgcca cctggcccaa gctccaaacc atgttgtggt ctcacgaaaa     1860
gagaaggcag cccgggttag cactgtgctg actgcccaga aggatttatt ttggaaaggt     1920
gacaaggact gcactggcaa tttctgtttg ttccggtctt ccaccaagga ccttctgttc     1980
agagatgaca ccaagtgttt gactaaactt ccagaaggta ccacatatga agagtactta     2040
ggagcagagt acttgcaagc tgttggaaac ataaggaagt gttcaacctc acgactccta     2100
gaagcctgca cttttccacaa aagttaaaat ccaagagggt ggtgccactg tggtggagga     2160
ggatgccccc gtgatccatg ggcttctcct ggcctccata gccctgagcg ctggggcta      2220 actgtgtccg tcttactgct tggtgttgtt accacataca cagagcacaa aataaaaaat     2280
gactgttgac ttt                                                      2293
```

<210> SEQ ID NO 54
<211> LENGTH: 2231
<212> TYPE: DNA
<213> ORGANISM: HORSE

<400> SEQUENCE: 54

```
cttggactgt gtctggctgc ccctaggaaa agcgttcgat ggtgcaccat atcaccagca       60
gaggcagcaa aatcgccaa attccaaagg aatatgaaaa aagtgagagg cccctctgtc       120
tcctgcataa ggaaaaccct cagctttgag tgcatccagg ccattgcggc aaacaaggca      180
gatgctgtga ccctcgatgg cggtttggtg tatgaggcag gcttgcaccc ctacaaactg      240
```

-continued

| | |
|---|---|
| cgacctgtgg cagcggaggt ctaccagacc agagggaagc cacaaacccg ctattatgct | 300 |
| gtggccgtag tgaagaaggg cagcggcttt cagctgaacc aactgcaggg cgtgaagtcc | 360 |
| tgccacacag gccttggcag gtccgctggg tggaacatcc ctattgggac acttcgtcca | 420 |
| tacttgaact ggacagggcc acctgagccc cttcagaaag ctgtggccaa cttcttctct | 480 |
| gccagctgtg ttccctgcgc agatggaaaa cagtacccca acctgtgtcg cctgtgtgcg | 540 |
| gggacagagg cagataaatg tgcctgctcc tcccaggaac catactttgg ctactctggt | 600 |
| gccttcaagt gtctggaaaa tggggctgga cacgtggctt ttgtcaagga tagtacagta | 660 |
| tttgagaacc tgccagatga ggctgacagg gataagtatg agctgctctg cccagacaat | 720 |
| actcggaagc cagtggatgc attcaaggag tgccacctgg cccgggttcc ttctcatgct | 780 |
| gttgtggccc gaagtgtgga tggcagggaa gacctgatct ggaggctcct ccaccgggca | 840 |
| caggaggagt ttggaagaaa caagtcatcg gcgttccagc tctttaagtc cactcctgag | 900 |
| aacaaggacc tgctgttcaa agactctgcc ctgggttttg tgaggatccc ctcacagata | 960 |
| gattctgggc tgtacctcgg tgccaactac ctcactgcca cccagaacct gcggaaaacg | 1020 |
| gccgcggaag tggcggcgcg gcgcgagcgg gttgtatggt gcgccgtggg ccccgaggag | 1080 |
| gagcgcaagt gcaagcagtg gagcgacgtg agcaaccgga aagtggcctg cgcctcggcg | 1140 |
| tccaccaccg aggagtgcat cgccctggtc ctgaaaggag aagcggatgc gctgaacttg | 1200 |
| gatggaggat ttatctacgt tgcgggcaag tgtggtttgg tgcctgtcct ggcagagaac | 1260 |
| caaaaatccc agaacagcaa tgccccagat tgtgtgcaca gaccaccaga agggtatctg | 1320 |
| gcagtggcgg ttgtcaggaa atcagatgct gacctcactt ggaattcgct gagtggcaag | 1380 |
| aagtcctgcc ataccggcgt gggcaggacc gcagcttgga acatccccat gggcctgctc | 1440 |
| ttcaaccaga caggctcctg caagtttgat aaattcttta gtcaaagctg tgcccctgga | 1500 |
| gctgacccac aatccagtct ctgtgcacta tgtgttggca caacgagaa tgagaacaag | 1560 |
| tgcatgccca cagcgagga gagatactat ggctacactg gggctttcag gtgcctggct | 1620 |
| gagaaggctg gagacgttgc atttgtgaaa gatgtcactg tcctgcagaa cacagatgga | 1680 |
| aagaacagtg aaccgtgggc taaggatttg aagcaggagg actttgagct actgtgcctt | 1740 |
| gatggcaccc ggaagcctgt ggctgaggct gagagctgcc acctggccag ggccccaaat | 1800 |
| catgctgtgg tatctcagag tgatagggca caacacctga aaaggtgct gttcctccaa | 1860 |
| caggatcagt ttggaggaaa tggacctgac tgcccgggca gtttttgctt attcaagtct | 1920 |
| gaaaccaaaa accttctgtt caacgacaac actgaatgtc tggctgaact ccaaggcaaa | 1980 |
| acaacatatg agcaatattt gggatcagag tatgtcacgt ccatcactaa tctgagacgc | 2040 |
| tgctcgagct ccccgcttct ggaagcctgc gccttcctga gggcataaag tcagagaaga | 2100 |
| cggcccggtg tccctggggg agcctcagcc cctcgccgct cccagccctc accccttcc | 2160 |
| tgagagtgat gctcgccaga ctcatctgct ttcacagttt ccgctgtcat cttagcaaga | 2220 |
| aataaaatta g | 2231 |

<210> SEQ ID NO 55
<211> LENGTH: 2423
<212> TYPE: DNA
<213> ORGANISM: HUMAN

<400> SEQUENCE: 55

| | |
|---|---|
| gaattccggc tagaaatgaa tatgtaagaa agcttatagt agtttaaatc atttgtagaa | 60 |

-continued

```
ccagccgagt ttctcaagtc gcctccagac cgcagacatg aaacttgtct tcctcgtcct      120
gctgttcctc ggggccctcg gactgtgtct ggctggccgt aggagaagga gtgttcagtg      180
gtgcgccgta tcccaacccg aggccacaaa atgcttccaa tggcaaagga atatgagaaa      240
agtgcgtggc cctcctgtca gctgcataaa gagagactcc cccatccagt gtatccaggc      300
cattgcggaa aacagggccg atgctgtgac ccttgatggt ggtttcatat acgaggcagg      360
cctggccccc tacaaactgc gacctgtagc ggcggaagtc tacgggaccg aaagacagcc      420
acgaactcac tattatgccg tggctgtggt gaagaagggc ggcagctttc agctgaacga      480
actgcaaggt ctgaagtcct gccacacagg ccttcgcagg accgctggat ggaatgtccc      540
tatagggaca cttcgtccat tcttgaattg gacgggtcca cctgagccca ttgaggcagc      600
tgtggccagg ttcttctcag ccagctgtgt tcccggtgca gataaaggac agttccccaa      660
cctgtgtcgc ctgtgtgcgg ggacagggga aaacaaatgt gccttctcct cccaggaacc      720
gtacttcagc tactctggtg ccttcaagtg tctgagagac ggggctggag acgtggcttt      780
tatcagagag agcacagtgt ttgaggacct gtcagacgag gctgaaaggg acgagtatga      840
gttactctgc ccagacaaca ctcggaagcc agtggacaag ttcaaagact gccatctggc      900
ccgggtccct tctcatgccg ttgtggcacg aagtgtgaat ggcaaggagg atgccatctg      960
gaatcttctc cgccaggcac aggaaaaagtt tggaaaggac aagtcaccga aattccagct     1020
ctttggctcc cctagtgggc agaaagatct gctgttcaag gactctgcca ttgggttttc     1080
gagggtgccc ccgaggatag attctgggct gtaccttggc tccggctact tcactgccat     1140
ccagaacttg aggaaaagtg aggaggaagt ggctgcccgg cgtgcgcggg tcgtgtggtg     1200
tgcggtgggc gagcaggagc tgcgcaagtg taaccagtgg agtggcttga gcgaaggcag     1260
cgtgacctgc tcctcggcct ccaccacaga ggactgcatc gccctggtgc tgaaaggaga     1320
agctgatgcc atgagtttgg atggaggata tgtgtacact gcaggcaaat gtggtttggt     1380
gcctgtcctg gcagagaact acaaatccca acaaagcagt gaccctgatc ctaactgtgt     1440
ggatagacct gtggaaggat atcttgctgt ggcggtggtt aggagatcag acactagcct     1500
tacctggaac tctgtgaaag gcaagaagtc ctgccacacc gccgtggaca ggactgcagg     1560
ctggaatatc cccatgggcc tgctcttcaa ccagacgggc tcctgcaaat ttgatgaata     1620
tttcagtcaa agctgtgccc ctgggtctga cccgagatct aatctctgtg ctctgtgtat     1680
tggcgacgag cagggtgaga ataagtgcgt gcccaacagc aacgagagat actacggcta     1740 cactgggct ttccggtgcc tggctgagaa tgctggagac gttgcatttg tgaaagatgt     1800
cactgtcttg cagaacactg atggaaataa caatgaggca tgggctaagg atttgaagct     1860
ggcagacttt gcgctgctgt gcctcgatgg caaacggaag cctgtgactg aggctagaag     1920
ctgccatctt gccatggccc cgaatcatgc cgtggtgtct cggatggata aggtggaacg     1980
cctgaaacag gtgttgctcc accaacaggc taaatttggg agaaatggat ctgactgccc     2040
ggacaagttt tgcttattcc agtctgaaac caaaaccctt ctgttcaatg acaacactga     2100
gtgtctggcc agactccatg gcaaacaac atatgaaaaa tatttgggac acagtatgt     2160 cgcaggcatt actaatctga aaagtgctc aacctccccc ctcctggaag cctgtgaatt     2220
cctcaggaag taaaaccgaa gaagatggcc cagctcccca gaaagcctc agccattcac     2280 tgcccccagc tcttctcccc aggtgtgttg ggccttggcc tcccctgctg aaggtgggga     2340
ttgcccatcc atctgcttac aattccctgc tgtcgtctta gcaagaagta aaatgagaaa     2400
ttttgttgta tattctctcc tta                                             2423
```

<210> SEQ ID NO 56
<211> LENGTH: 2411
<212> TYPE: DNA
<213> ORGANISM: GOAT

<400> SEQUENCE: 56

| | | | | | |
|---|---|---|---|---|---|
| agcactggat | aaagggacgc | agaacgaggg | caggtggcag | agcttcgttc | cggagtcgcc | 60 |
| ccaggacccc | agacatgaag | ctcttcgtcc | ccgccctgct | gtcccttgga | gcccttggac | 120 |
| tgtgtctggc | tgccccgagg | aaaaacgttc | gatggtgtgc | catctcactg | ccggagtggt | 180 |
| ccaaatgcta | ccaatggcag | aggaggatga | ggaagctggg | tgctccctct | atcacctgtg | 240 |
| tgaggaggac | ctctgccttg | gaatgtatcc | gggccatcgc | gggaaaaaat | gcggatgctg | 300 |
| tgaccctgga | tagtggcatg | gtgtttgagg | cgggccggga | ccctacaaa | ctgcggccag | 360 |
| tagcggcaga | gatctatggg | acagaaaaat | ctccccaaac | ccactattat | gctgtggccg | 420 |
| tcgtgaagaa | gggcagcaac | tttaagctgg | accagctgca | aggtcagaag | tcctgccaca | 480 |
| tgggcccttgg | caggtccgct | gggtggaaca | tccctgtggg | aatccttcgc | cgcccttga | 540 |
| gctggacaga | gtcggccgag | cccctccagg | gagctgtggc | tagattcttc | tctgccagct | 600 |
| gtgttccctg | cgttgatgga | aaagcgtacc | ccaacctgtg | tcaactgtgc | aaggggtgg | 660 |
| gagagaacaa | gtgtgcctgc | tcctcccagg | aaccatactt | tggttattct | ggtgccttca | 720 |
| agtgcctgca | ggacggggct | ggagacgtgg | cttttgtcaa | ggagacgaca | gtgtttgaga | 780 |
| acttgccaga | gaaggctgac | agggaccagt | atgagcttct | ctgcctaaac | aacactcggg | 840 |
| cgccagtgga | tgcattcaag | gagtgccacc | tggcccaggt | cccttctcat | gctgttgtgg | 900 |
| cccgcagtgt | ggatggcaag | gagaacttga | tctgggagct | tctcaggaag | gcacaggaga | 960 |
| agtttggaaa | aaacaagtct | cagcgcttcc | agctctttgg | ctctccagaa | ggccggaggg | 1020 |
| acctgctatt | caaagactct | gcccttgggt | ttgtgaggat | cccctcaaaa | gtagattcgg | 1080 |
| cgctgtacct | gggctcccgt | tacttgaccg | ccttgaagaa | cctcagggaa | accgcggagg | 1140 |
| agttgaaggc | gcggtgcacg | cgggtcgtgt | ggtgcgcggt | gggacccgag | gagcagagta | 1200 |
| agtgccagca | gtggagcgag | cagagcggcc | agaacgtgac | ctgtgccacg | gcctccacca | 1260 |
| ccgacgactg | catcgccctg | gtgctgaaag | gggaagcgga | cgccctgagc | ttgggtggag | 1320 |
| gatatatcta | cactgccggc | aagtgcggcc | tggtgcctgt | catggcagag | aaccggaaat | 1380 |
| cctccaaata | cagtagccta | gattgtgtgc | tgagaccaac | ggaagggtac | cttgccgtgg | 1440 |
| cagttgtcaa | gaaagcaaat | gaggggctca | cttggaattc | tctgaaaggc | aagaagtcgt | 1500 |
| gccacaccgc | cgtggacagg | actgcaggct | ggaacatccc | catgggcctg | atcgccaacc | 1560 |
| agacaggctc | ctgcgcattt | gatgaattct | ttagtcagag | ctgtgcccct | ggggccgacc | 1620 |
| cgaaatccag | cctctgtgca | ttgtgtgccg | gcgatgacca | gggcctggac | aagtgtgtgc | 1680 |
| ccaactctaa | ggagaagtac | tatggctaca | ccggggcttt | caggtgcctg | gctgaggacg | 1740 |
| ttggggacgt | tgcatttgtg | aaaaacgaca | cagtctggga | gaacacaaat | ggagagagct | 1800 |
| ctgcagactg | ggctaagaac | ttgaatcgcg | aggacttcag | gctgctctgc | ctcgatggca | 1860 |
| ccacgaagcc | tgtgacggag | gctcagagct | gctacctggc | ggtggccccg | aatcacgctg | 1920 |
| tggtgtctcg | gagcgatagg | gcagcgcacg | tggaacaggg | gctgctccac | cagcaggctc | 1980 |
| tgtttgggaa | aaatgaaaaa | aactgcccgg | accagttttg | tttgttcaaa | tctgaaacca | 2040 |
| aaaaccttct | gttcaatgac | aacactgagt | gtctggccaa | acttggaggc | agaccaacgt | 2100 |

```
atgaaaaata tttggggaca gagtatgtca cggccattgc caacctgaaa aaatgctcaa    2160
cctccccgct tctggaagcc tgcgccttcc tgacgaggta aagcctgcaa agaagctagc    2220
ctgcctcccc gggcctcagc tcctccctgc tctcagcccc agtcttcagg cgcgagggac    2280
cttcctctcc cttcctgaag tcggattttt gccaagctca tcagtattca caattccctg    2340
ctgtcatctt agcaagaaat taaattagaa atgctgttga ttttcattcc ctaaaaaaaa    2400
aaaaaaaaaa a                                                         2411
```

<210> SEQ ID NO 57
<211> LENGTH: 2405
<212> TYPE: DNA
<213> ORGANISM: COW

<400> SEQUENCE: 57

```
cttcgttccg gagtcgcccc aggacgccag ccatgaagct cttcgtcccc gccctgctgt     60
cccttggagc ccttggactg tgtctggctg ccccgaggaa aaacgttcga tggtgtacca    120
tctcccaacc cgagtggttc aaatgccgcc gatggcagtg gaggatgaag aagctgggtg    180
ctccctctat cacctgtgtg aggagggcct ttgccttgga atgtatccgg ccatcgcgg     240 agaaaaaggc ggatgctgtg accctggatg gtggcatggt gtttgaggcg ggccgggacc    300
cctacaaact gcggccagta gcagcagaga tctatgggac gaaagagtct ccccaaaccc    360
actattatgc tgtggccgtc gtgaagaagg gcagcaactt tcagctggac cagctgcaag    420
gccggaagtc ctgccatacg ggccttggca ggtccgctgg gtgggtcatc cctatgggaa    480
tccttcgccc gtacttgagc tggacagagt cactcgagcc cctccagga gctgtggcta     540 aattcttctc tgccagctgt gttccctgca ttgatagaca agcataccccc aacctgtgtc    600 aactgtgcaa gggggagggg gagaaccagt gtgcctgctc ctcccgggaa ccatacttcg    660
gttattctgg tgccttcaag tgtctgcagg acggggctgg agacgtggct tttgttaaag    720
agacgacagt gtttgagaac ttgccagaga aggctgacag ggaccagtat gagcttctct    780
gcctgaacaa cagtcgggcg ccagtggatg cgttcaagga gtgccacctg cccaggtcc    840 cttctcatgc tgtcgtggcc cgaagtgtgg atggcaagga agacttgatc tggaagcttc    900
tcagcaaggc gcaggagaaa tttgaaaaaa acaagtctcg gagcttccag ctctttggct    960
ctccacccgg ccagagggac ctgctgttca agactctgc tcttgggttt tgaggatcc     1020 cctcgaaggt agattcggcg ctgtaccttg cgtcccgcta cttgaccacc ttgaagaacc   1080
tcagggaaac tgcggaggag gtgaaggcgc ggtacaccag ggtcgtgtgg tgtgccgtgg   1140 gaccccgagga gcagaagaag tgccagcagt ggagccagca gagcggccag aacgtgacct   1200
gtgccacggc gtccaccacc gacgactgca tcgtcctggt gctgaaaggg gaagcagatg   1260
ccctgaactt ggatggagga tatatctaca ctgcgggcaa gtgtggcctg gtgcctgtcc   1320
tggcagagaa ccggaaatcc tccaaataca gtagcctaga ttgtgtgctg agaccaacag   1380
aagggtacct tgccgtggca gttgtcaaga agcaaatga ggggctcaca tggaattctc    1440
tgaaagacaa gaagtcgtgc cacaccgccg tggacaggac tgcaggctgg aacatcccca   1500
tgggcctgat cgtcaaccag acaggctcct gcgcatttga tgaattcttt agtcagagct   1560
gtgcccctgg gcgtgacccg aaatccagac tctgtgcctt gtgtgctggc gatgaccagg   1620
gcctggacaa gtgtgtgccc aactctaagg agaagtacta tggctatacc ggggctttca   1680
ggtgcctggc tgaggacgtt gggggacgttg ccttttgtgaa aaacgacaca gtctgggaga   1740
acacgaatgg agagagcact gcagactggg ctaagaactt gaatcgtgag gacttcaggt   1800
```

| | |
|---|---|
| tgctctgcct cgatggcacc aggaagcctg tgacggaggc tcagagctgc cacctggcgg | 1860 |
| tcgcccccgaa tcacgctgtg gtgtctcgga gcgatagggc agcacacgtg aaacaggtgc | 1920 |
| tgctccacca gcaggctctg tttgggaaaa atggaaaaaa ctgcccggac aagttttgtt | 1980 |
| tgttcaaatc tgaaaccaaa aaccttctgt tcaatgacaa cactgagtgt ctggccaaac | 2040 |
| ttggaggcag accaacgtat gaagaatatt tggggacaga gtatgtcacg gccattgcca | 2100 |
| acctgaaaaa atgctcaacc tccccgcttc tggaagcctg cgccttcctg acgaggtaaa | 2160 |
| gcctgcaaag aagctagcct gcctcccctgg gcctcagctc ctccctgctc tcagccccaa | 2220 |
| tctccaggcg cgagggacct tcctctccct tcctgaagtc ggattttttgc caagctcatc | 2280 |
| agtatttaca attccctgct gtcatttttag caagaaataa aattagaaat gctgttgatt | 2340 |
| ttcattccct aaaaaaaaaa aaaaaaaaaa aaaaaaaaaa aaaaaaaaaa aaaaaaaaaa | 2400 |
| aaaaa | 2405 |

<210> SEQ ID NO 58
<211> LENGTH: 2619
<212> TYPE: DNA
<213> ORGANISM: HUMAN

<400> SEQUENCE: 58

| | |
|---|---|
| gactcctagg ggcttgcaga cctagtggga gagaaagaac atcgcagcag ccaggcagaa | 60 |
| ccaggacagg tgaggtgcag gctggctttc ctctcgcagc gcggtgtgga gtcctgtcct | 120 |
| gcctcagggc ttttcggagc ctggatcctc aaggaacaag tagacctggc cgcggggagt | 180 |
| ggggagggaa ggggtgtcta ttgggcaaca gggcggcaaa gccctgaata aaggggcgca | 240 |
| gggcaggcgc aagtgcagag ccttcgtttg ccaagtcgcc tccagaccgc agacatgaaa | 300 |
| cttgtcttcc tcgtcctgct gttcctcggg gccctcggac tgtgtctggc tggccgtagg | 360 |
| agaaggagtg ttcagtggtg cgccgtatcc aacccgagg ccacaaaatg cttccaatgg | 420 |
| caaaggaata tgagaaaagt gcgtggccct cctgtcagct gcataaagag agactccccc | 480 |
| atccagtgta tccaggccat tgcggaaaac agggccgatg ctgtgaccct tgatggtggt | 540 |
| tcatatacg aggcaggcct ggccccctac aaactgcgac ctgtagcggc ggaagtctac | 600 |
| gggaccgaaa gacagccacg aactcactat tatgccgtgg ctgtggtgaa gaagggcggc | 660 |
| agctttcagc tgaacgaact gcaaggtctg aagtcctgcc acacaggcct tcgcaggacc | 720 |
| gctggatgga atgtccctac agggacactt cgtccattct tgaattggac gggtccacct | 780 |
| gagcccattg aggcagctgt ggccaggttc ttctcagcca gctgtgttcc cggtgcagat | 840 |
| aaaggacagt tccccaacct gtgtcgcctg tgtgcgggga caggggaaaa caaatgtgcc | 900 |
| ttctcctccc aggaaccgta cttcagctac tctggtgcct tcaagtgtct gagagacggg | 960 |
| gctggagacg tggcttttat cagagagagc acagtgtttg aggacctgtc agacgaggct | 1020 |
| gaaagggacg agtatgagtt actctgccca gacaacactc ggaagccagt ggacaagttc | 1080 |
| aaagactgcc atctggcccg ggtcccttct catgccgttg tggcacgaag tgtgaatggc | 1140 |
| aaggaggatg ccatctggaa tcttctccgc caggcacagg aaaagtttgg aaaggacaag | 1200 |
| tcaccgaaat tccagctctt tggctcccct agtgggcaga agatctgct gttcaaggac | 1260 |
| tctgccattg ggttttcgag ggtgcccccg aggatagatt ctgggctgta ccttggctcc | 1320 |
| ggctacttca ctgccatcca gaacttgagg aaaagtgagg aggaagtggc tgcccggcgt | 1380 |
| gcgcgggtcg tgtggtgtgc ggtgggcgag caggagctgc gcaagtgtaa ccagtggagt | 1440 |

```
ggcttgagcg aaggcagcgt gacctgctcc tcggcctcca ccacagagga ctgcatcgcc    1500
ctggtgctga aggagaagc tgatgccatg agtttggatg gaggatatgt gtacactgca    1560
tgcaaatgtg gtttggtgcc tgtcctggca gagaactaca atcccaaca aagcagtgac    1620 cctgatccta actgtgtgga tagacctgtg aaggatatc ttgctgtggc ggtggttagg    1680
agatcagaca ctagccttac ctggaactct gtgaaaggca agaagtcctg ccacaccgcc    1740
gtggacagga ctgcaggctg aatatcccc atgggcctgc tcttcaacca gacgggctcc    1800
tgcaaatttg atgaatattt cagtcaaagc tgtgcccctg gtctgaccc gagatctaat    1860 ctctgtgctc tgtgtattgg cgacgagcag ggtgagaata agtgcgtgcc caacagcaac    1920
gagagatact acggctacac tggggctttc cggtgcctgg ctgagaatgc tggagacgtt    1980
gcatttgtga agatgtcac tgtcttgcag aacactgatg gaataacaa tgaggcatgg    2040 gctaaggatt tgaagctggc agactttgcg ctgctgtgcc tcgatggcaa acggaagcct    2100
gtgactgagg ctagaagctg ccatcttgcc atggccccga atcatgccgt ggtgtctcgg    2160
atggataagg tggaacgcct gaaacaggtg ctgctccacc aacaggctaa atttgggaga    2220
aatggatctg actgcccgga caagttttgc ttattccagt ctgaaaccaa aaaccttctg    2280
ttcaatgaca acactgagtg tctggccaga ctccatggca aaacaacata tgaaaaatat    2340
ttgggaccac agtatgtcgc aggcattact aatctgaaaa agtgctcaac ctcccccctc    2400
ctggaagcct gtgaattcct caggaagtaa aaccgaagaa gatggcccag ctccccaaga    2460
aagcctcagc cattcactgc ccccagtctct ctccccagg tgtgttgggg ccttggctcc    2520
cctgctgaag gtggggattg cccatccatc tgcttacaat tccctgctgt cgtcttagca    2580
agaagtaaaa tgagaaattt tgttgatatt caaaaaaaa                          2619

<210> SEQ ID NO 59
<211> LENGTH: 2311
<212> TYPE: DNA
<213> ORGANISM: HUMAN

<400> SEQUENCE: 59
cttgtcttcc tcgtcctgct gttcctcggg gccctcggac tgtgtctggc tggccgtagg     60
agaaggagtg ttcagtggtg cgccgtatcc caacccgagg ccacaaaatg cttccaatgg    120
caaaggaata tgagaaaagt gcgtggccct cctgtcagct gcataaagag agactccccc    180
atccagtgta tccaggccat tgcggaaaac agggccgatg ctgtgaccct tgatggtggt    240
ttcatatacg aggcaggcct ggccccctac aaactgcgac ctgtagcggc ggaagtctac    300
gggaccgaaa gacagccacg aactcactat tatgccgtgg ctgtggtgaa gaagggcggc    360
agctttcagc tgaacgaact gcaaggtctg aagtcctgcc acacaggcct tcgcaggacc    420
gctggatgga atgtccctat agggacactt cgtccattct tgaattggac gggtccacct    480
gagcccattg aggcagctgt ggccaggttc ttctcagcca gctgtgttcc cggtgcagat    540
aaaggacagt tccccaacct gtgtcgcctg tgtgcgggga caggggaaaa caaatgtgcc    600
ttctcctccc aggaaccgta cttcagctac tctggtgcct tcaagtgtct gagagacggg    660
gctggagacg tggctttat cagagagagc acagtgtttg aggacctgtc agacgaggct    720
gaaagggacg agtatgagtt actctgccca gacaacactc ggaagccagt ggacaagttc    780
aaagactgcc atctggcccg ggtccttct catgccgttg tggcacgaag tgtgaatgcc    840
aaggaggatg ccatctggaa tcttctccgc caggcacagg aaaagtttgg aaaggacaag    900
tcaccgaaat tccagctctt tggctccccct agtgggcaga aagatctgct gttcaaggac    960
```

```
tctgccattg ggttttcgag ggtgcccccg aggatagatt ctgggctgta ccttggctcc   1020
ggctacttca ctgccatcca gaacttgagg aaaagtgagg aggaagtggc tgcccggcgt   1080
gcgcgggtcg tgtggtgtgc ggtgggcgag caggagctgc gcaagtgtaa ccagtggagt   1140
ggcttgagcg aaggcagcgt gacctgctcc tcggcctcca ccacagagga ctgcatcgcc   1200
ctggtgctga aggagaagc tgatgccatg agtttggatg gaggatatgt gtacactgca    1260
ggcaaatgtg gtttggtgcc tgtcctggca gagaactaca atcccaaca aagcagtgac    1320 cctgatccta actgtgtgga tagacctgtg aaggatatc ttgctgtggc ggtggttagg    1380
agatcagaca ctagccttac ctggaactct gtgaaaggca agaagtcctg ccacaccgcc   1440
gtggacagga ctgcaggctg aatatcccc atgggcctgc tcttcaacca gacgggctcc    1500
tgcaaatttg atgaatattt cagtcaaagc tgtgcccctg ggtctgaccc agatctaat    1560 ctctgtgctc tgtgtattgg cgacgagcag ggtgagaata agtgcgtgcc caacagcaac   1620
gagagatact acggctacac tggggctttc cggtgcctgg ctgagaatgc tggagacgtt   1680
gcatttgtga agatgtcac tgtcttgcag aacactgatg gaaataacaa tgaggcatgg    1740
gctaaggatt tgaagctggc agactttgcg ctgctgtgcc tcgatggcaa acggaagcct   1800
gtgactgagg ctagaagctg ccatcttgcc atggccccga atcatgccgt ggtgtctcgg   1860
atggataagg tggaacgcct gaaacaggtg ttgctccacc aacaggctaa atttgggaga   1920
aatggatctg actgcccgga caagtttttgc ttattccagt ctgaaaccaa aaaccttctg   1980
ttcaatgaca acactgagtg tctggccaga ctccatggca aaacaacata tgaaaaatat   2040
ttgggaccac agtatgtcgc aggcattact aatctgaaaa agtgctcaac ctccccccctc   2100 ctggaagcct gtgaattcct caggaagtaa aaccgaagaa gatggcccag ctccccaaga   2160
aagcctcagc cattcactgc ccccagctct tctccccagg tgtgttgggg ccttggctcc   2220
cctgctgaag gtgggggattg cccatccatc tgcttacaat tccctgctgt cgtcttagca   2280
agaagtaaaa tgagaaattt tgttgatatt c                                  2311

<210> SEQ ID NO 60
<211> LENGTH: 2326
<212> TYPE: DNA
<213> ORGANISM: GOAT

<400> SEQUENCE: 60
ccccagacat gaagctcttc gtcccgccc tgctgtccct ggagcccctt ggactgtgtc     60
tggctgcccc gaggaaaaac gttcgatggt gtgccatctc actgccggag tggtccaaat   120
gctaccaatg gcagaggagg atgaggaagc tgggtgctcc ctctatcacc tgtataagga   180
ggacctctgc cttggaatgt atccgggcca tcgcgggaaa aaatgcggat gctgtgaccc   240
tggatagtgg catggtgttt gaggcgggcc tggaccccta caaactgcgg ccagtagcgg   300
cagagatcta tgggacagaa aaatctcccc aaacccacta ttatgctgtg ccgtcgtga    360 agaagggcag caactttcag ctggaccagc tgcaaggcca gaagtcctgc acatgggcc    420 ttggcaggtc cgctgggtgg aacatccctg tgggaatcct tcgcccgttc ttgagctgga   480
cagagtcggc cgagccctc cagggagctg tggctagatt cttctctgcc agctgtgttc    540
cctgcgttga tggaaaagcg taccccaacc tgtgtcaact gtgcaagggg gtgggagaga   600
acaagtgtgc ctgctcctcc caggaaccat actttggtta ttctggtgcc ttcaagtgcc   660
tgcaggacgg ggctggagac gtggcttttg tcaaggagac gacagtgttt gagaacttgc   720
```

```
cagagaaggc tgacagggac cagtatgagc ttctctgcct aaacaacact cgggcgccag    780
tggatgcatt caaggagtgc cacctggccc aggtcccttc tcatgctgtt gtggcccgca    840
gtgtggatgg caaggagaac ttgatctggg agcttctcag gaaggcacag agaagtttg     900 gaaaaaacaa gtctcagagc ttccagctct ttggctctcc agaaggccgg agggacctgc    960
tattcaaaga ctctgcccttg ggtttgtga ggatcccctc aaaagtagat tcggcgctgt   1020
acctgggctc ccgttacttg accgccttga agaacctcag ggaaaccgcg gaggagttga   1080
aggcgcggtg cacgcgggtc gtgtggtgcg cggtgggacc cgaggagcag agtaagtgcc   1140
agcagtggag cgagcagagc ggccagaacg tgacctgtgc cacggcctcc accaccgacg   1200
actgcatcgc cctggtgctg aaaggggaag cggacgccct gagcttggat ggaggatata   1260
tctacactgc cggcaagtgc ggcctggtgc ctgtcatggc agagaaccgg aaatcctcca   1320
aatacagtag cctagattgt gtgctgagac caacggaagg gtaccttgcc gtggcagttg   1380
tcaagaaagc aaatgagggg ctcacttgga attctctgaa aggcaagaag tcgtgccaca   1440
ccgccgtgga caggactgca ggctggaaca tccccatggg cctgatcgcc aaccagacag   1500
gctcctgcgc atttgatgaa ttctttagtc agagctgtgc ccctggggcc gacccgaaat   1560
ccagcctctg tgcattgtgt gccggcgatg accagggcct ggacaagtgt gtgcccaact   1620
ctaaggagaa gtactatggc tacaccgggg cttttcaggtg cctggctgag gacgttgggg   1680
acgttgcatt tgtgaaaaac gacacagtct gggagaacac gaatggagag agctctgcag   1740
actgggctaa gaacttgaat cgcgaggact tcaggctgct ctgcctcgat ggcaccacga   1800
agcctgtgac ggaggctcag agctgctacc tggcggtggc cccgaatcac gctgtggtgt   1860
ctcggagcga tagggcagcg cacgtggaac aggtgctgct ccaccagcag gctctgttcg   1920
ggaaaaatgg aaaaaactgc ccggaccagt tttgtttgtt caaatctgaa accaaaaacc   1980
ttctgttcaa tgacaacact gagtgtctgg ccaaacttgg aggcagacca acgtatgaaa   2040
aatatttggg gacagagtat gtcacggcca ttgccaacct gaaaaaatgc tcaacctccc   2100
cgcttctgga agcctgcgcc ttcctgacga ggtaaagcct gcaaagaagc tagcctgcct   2160
ccccgggcct cagctcctcc ctgctctcag ccccagtctt cagacgcgag gacccttcct   2220 ctccccttcct gaagtcggat ttttgccaag ctcatcagta ttcacaattc cctgctgtca   2280
tcttagcaag aaataaaatt agaaatgctg ttgattttca ttccct             2326

<210> SEQ ID NO 61
<211> LENGTH: 4896
<212> TYPE: DNA
<213> ORGANISM: HUMAN

<400> SEQUENCE: 61
ggtacccagg ctaatcttct ggagttcttc tggagccctc atgatgggtg ctggtcattc     60
ctcctctggg ccctcacact cacttgcttt atgctgcttg gcctcttctt agggagcctc    120
tgtgatagaa gtgcattcct gtgactgtcc ctcccccata gtgctgtgag ctcctgaggg    180
caaggacaga cccctcttct ctgtctctca tggcatctac cagttctggc atgaatgaat    240
gaatgaatga atgaatgaat gaatgctgtt aatagatcag tgaaacttca ttgttttttg    300
gggcagacta tcccctaca tcagcctcct ctgcaaatgg ccttgagggg ctgctctgcc    360
tgtgtccaga tgctcacatc cctgccctgg gcctgggctg ttccaacagg cacagcagga    420
gaacagtctg ccctgttgcc tacccatgct gccttcaggg cactccttaa gctgagcctc    480
ttggtagtgg ccccaggttc tctgtgttct tgccaacact gtaacatact taagagggcc    540
```

```
cagggcttga cctcccagtc atccttttt aaaatttgga ctcagaaaaa gagacacggt    600
tatgatgttt cttaattctt ttataatgat gaaaaggcaa agtcttgttg ccaatttagg    660
atcaaagatg cttcagcact cctgggaatt agtcaatttt gtatttcttc agtattttg    720
aaagaactta ttgcaattat tgatgatggc aactttaaat ggtgcaatat catgtttcca    780
aacaatgaga gaccttggat ctgtcacccc caaaacccag ctggtgattc tagcaccaaa    840
tcttcagacc ccagtcttca tggcaggcaa gcatgatccc tgattagctc accctgtgct    900
tggcaggatc atgccagaaa tgaggggctc ccagctctta tgcttcacct tgggctgagc    960
tgcttctcca tggctaggtg cccactgcat gctcactctt ggcagagctg gctccctggg   1020
gcattgccta tctgctccag gaaatgcttt ttagtaccaa gtagtctaag cagagtcaag   1080
accagctttt cagaataagc agatttcaga gtcacatatt ggtcagactc acctgccaag   1140
aaggtgttca ggtgacctat tatttccctc actgttagta ccttttttc ttcacttagt   1200
tacccttttt tttttggtg ggggttacag agtcttactc tattgcccag gctgcagtgc   1260
agtgacatga tcatggctca ctgccacctt catctcccag gctcaaatgg tcctcccact   1320
ttagcctccc aagtagctgg gaccataggc ataccacc atgctggcta attttgtat   1380
ttttgtaga gatgggggt ttccctatgt tgcccaggct agtcttgaac tcctgggctc   1440
aagcgatcct cccatcttgg cctcccaaag tgctgggatt acaggcatga ccactgtgc   1500
cctgccctag ttactcttgg gctaagttca catccataca cacaggtctt tctgaggccc   1560
ccaatgtgtc ccacaggtgc catgctgtat gtgacactcc cctagagatg gatgtttagt   1620
ttgcttccaa ctgattaatg gcatgcagtg gtggctggaa acatttgtac ctggggtgct   1680
gtgtgtcatg ggaatgtatt tacgagatgt attcttagaa gctctagctt ttgaattttt   1740
aaatctgaga tttatggcga ttgttaaaat gaggttacca tttcctactg aatactatca   1800
acaccaaaaa agaagaagga ggagatggag aaaaaaaaga caaaaaaaaa agtggtaggg   1860
catcttagcc atagggcatc tttctcattg gcaaataaga acatggaacc agccttgggt   1920
ggtggcattc ccctctgagg tccctgtctg ttttctggga gctgtattgt gggtctcagc   1980
agggcaggga gatacccat gggcagcttg cctgagactc tgggcagcct gctctttct   2040
ctgtcagctg tccctaggct gctgctgggg gtggtcgggt catcttttcc aactctcagc   2100
tcactgctga gacaaggtga agctaaaac ccacctgccc taactggctc ctaggcacct   2160
tcaaggtcat ctgctgaaga agatagcagt ctcacaggtc aaggcgatct tcaagtaaag   2220
accctctgct ctgtgtcctg ccctctagaa ggcactgaga ccagagactg gacagggct   2280
caggggcttt gcgagactcc tagggcttg cagactagtg ggagagaaag aacatcgcag   2340
cagccaggca gaaccaggac aggtgaggtg caggctggct ttcctctcgc agcgcggtgt   2400
ggagtcctgt cctgcctcag ggcttttcgg agcctggatc ctcaaggaac aagtagacct   2460
ggccgcgggg agtggggagg gaagggggtgt ctattgggca cagggcggc aaagccctga   2520
ataaagggc gcaggcagg cgcaagtggc agagccttcg tttgccaagt cgcctccaga   2580
ccgcagacat gaaacttgtc ttcctcgtcc tgctgttcct cggggccctc ggactgtgtc   2640
tggctggccg taggaggagt gttcagtggt gcgccgtatc ccaacccgag ccacaaaat   2700
gcttccaatg gcaaaggaat atgagaaaag tgcgtggccc tcctgtcagc tgcataaaga   2760
gagactcccc catccagtgt atccaggcca ttgcggaaaa cagggccgat gctgtgaccc   2820
ttgatggtgg tttcatatac gaggcaggcc tggccccta caaactgcga cctgtagcgg   2880
```

| | |
|---|---:|
| cggaagtcta cgggaccgaa agacagccac gaactcacta ttatgccgtg gctgtggtga | 2940 |
| agaagggcgg cagctttcag ctgaacgaac tgcaaggtct gaagtcctgc cacacaggcc | 3000 |
| ttcgcaggac cgctggatgg aatgtcccta taggaacact tcgtccattc ttgaattgga | 3060 |
| cgggtccacc tgagcccatt gaggcagctg tggccaggtt cttctcagcc agctgtgttc | 3120 |
| ccggtgcaga taaaggacag ttccccaacc tgtgtcgcct gtgtgcgggg acagggaaa | 3180 |
| acaaatgtgc cttctcctcc caggaaccgt acttcagcta ctctggtgcc ttcaagtgtc | 3240 |
| tgagagacgg ggctggagac gtggctttta tcagagagag cacagtgttt gaggacctgt | 3300 |
| cagacgaggc tgaaagggac gagtatgagt tactctgccc agacaacact cggaagccag | 3360 |
| tggacaagtt caaagactgc catctggccc gggtccctta tcatgccgtt gtggcacgaa | 3420 |
| gtgtgaatgg caaggaggat gccatctgga atcttctccg ccaggcacag aaaagtttg | 3480 |
| gaaaggacaa gtcaccgaaa ttccagctct ttggctcccc tagtgggcag aaagatctgc | 3540 |
| tgttcaagga ctctgccatt gggttttcga ggtgccccc gaggatagat tctgggctgt | 3600 |
| accttggctc cggctacttc actgccatcc agaacttgag gaaaagtgag gaggaagtgg | 3660 |
| ctgcccggcg tgcgcgggtc gtgtggtgtg cggtgggcga gcaggagctg cgcaagtgta | 3720 |
| accagtggag tggcttgagc gaaggcagcg tgacctgctc ctcggcctcc accacagagg | 3780 |
| actgcatcgc cctggtgctg aaaggagaag ctgatgccat gagtttggat ggaggatatg | 3840 |
| tgtacactgc aggcaaatgt ggtttggtgc ctgtcctggc agagaactac aaatcccaac | 3900 |
| aaagcagtga ccctgatcct aactgtgtgg atagacctgt ggaaggatat cttgctgtgg | 3960 |
| cggtggttag gagatcagac actagcctta cctggaactc tgtgaaaggc aagaagtcct | 4020 |
| gccacaccgc cgtggacagg actgcaggct ggaatatccc catgggcctg ctcttcaacc | 4080 |
| agacgggctc ctgcaaattt gatgaatatt tcagtcaaag ctgtgcccct gggtctgacc | 4140 |
| cgagatctaa tctctgtgct ctgtgtattg gcgacgagca gggtgagaat aagtgcgtgc | 4200 |
| ccaacagcaa tgagagatac tacggctaca ctggggcttt ccggtgcctg gctgagaatg | 4260 |
| ctggagacgt tgcatttgtg aaagatgtca ctgtcttgca gaacactgat ggaaataaca | 4320 |
| atgaggcatg ggctaaggat ttgaagctgg cagactttgc gctgctgtgc ctcgatggca | 4380 |
| aacggaagcc tgtgactgag gctagaagct gccatcttgc catggccccg aatcatgccg | 4440 |
| tggtgtctcg gatggataag gtggaacgcc tgaaacaggt gctgctccac caacaggcta | 4500 |
| aatttgggag aaatggatct gactgcccgg acaagttttg cttattccag tctgaaacca | 4560 |
| aaaaccttct gttcaatgac aacactgagt gtctggccag actccatggc aaaacaacat | 4620 |
| atgaaaaata tttgggacca cagtatgtcg caggcattac taatctgaaa aagtgctcaa | 4680 |
| cctccccct cctggaagcc tgtgaattcc tcaggaagta aaaccgaaga agatgggccca | 4740 |
| gctccccaag aaagcctcag ccattcactg cccccagctc ttctcccag gtgtgttggg | 4800 |
| gccttggctc ccctgctgaa ggtggggatt gcccatccat ctgcttacaa ttccctgctg | 4860 |
| tcgtcttagc aagaagtaaa atgagaaatt ttgttg | 4896 |

<210> SEQ ID NO 62
<211> LENGTH: 2331
<212> TYPE: DNA
<213> ORGANISM: HUMAN

<400> SEQUENCE: 62

| | |
|---|---:|
| cgcagacatg aaacttgtct tcctcgtcct gctgttcctc ggggcccctcg gactgtgtct | 60 |
| ggctggccgt aggagaagga gtgttcagtg gtgcgccgta tcccaacccg aggccacaaa | 120 |

-continued

| | |
|---|---|
| atgcttccaa tggcaaagga atatgagaaa agtgcgtggc cctcctgtca gctgcataaa | 180 |
| gagagactcc cccatccagt gtatccaggc cattgcggaa acagggccg atgctgtgac | 240 |
| ccttgatggt ggtttcatat acgaggcagg cctggccccc tacaaactgc gacctgtagc | 300 |
| ggcggaagtc tacgggaccg aaagacagcc acgaactcac tattatgccg tggctgtggt | 360 |
| gaagaagggc ggcagctttc agctgaacga actgcaaggt ctgaagtcct gccacacagg | 420 |
| ccttcgcagg accgctggat ggaatgtccc tatagggaca cttcgtccat tcttgaattg | 480 |
| gacgggtcca cctgagccca ttgaggcagc tgtggccagg ttcttctcag ccagctgtgt | 540 |
| tcccggtgca gataaaggac agttccccaa cctgtgtcgc ctgtgtgcgg ggacagggga | 600 |
| aaacaaatgt gccttctcct cccaggaacc gtacttcagc tactctggtg ccttcaagtg | 660 |
| tctgagagac ggggctggag acgtggcttt tatcagagag agcacagtgt ttgaggacct | 720 |
| gtcagacgag gctgaaaggg acgagtatga gttactctgc ccagacaaca ctcggaagcc | 780 |
| agtggacaag ttcaaagact gccatctggc ccgggtccct tctcatgccg ttgtggcacg | 840 |
| aagtgtgaat ggcaaggagg atgccatctg gaatcttctc cgccaggcac aggaaaagtt | 900 |
| tggaaaggac aagtcaccga attccagctc tttggctcc cctagtgggc agaaagatct | 960 |
| gctgttcaag gactctgcca ttgggttttc gagggtgccc ccgaggatag attctgggct | 1020 |
| gtaccttggc tccggctact tcactgccat ccagaacttg aggaaaagtg aggaggaagt | 1080 |
| ggctgcccgg cgtgcgcggg tcgtgtggtg tgcggtgggc gagcaggagc tgcgcaagtg | 1140 |
| taaccagtgg agtggcttga gcgaaggcag cgtgacctgc tcctcggcct ccaccacaga | 1200 |
| ggactgcatc gccctggtgc tgaaaggaga agctgatgcc atgagtttgg atgaaggata | 1260 |
| tgtgtacact gcaggcaaat gtggtttggt gcctgtcctg gcagagaact acaaatccca | 1320 |
| acaaagcagt gaccctgatc ctaactgtgt ggatagacct gtggaaggat atcttgctgt | 1380 |
| ggcggtggtt aggagatcag acactagcct tacctggaac tctgtgaaag caagaagtc | 1440 |
| ctgccacacc gccgtggaca ggactgcagg ctggaatatc cccatgggcc tgctcttcaa | 1500 |
| ccagacgggc tcctgcaaat ttgatgaata tttcagtcaa agctgtgccc ctgggtctga | 1560 |
| cccgagatct aatctctgtg ctctgtgtat tggcgacgag cagggtgaga ataagtgcgt | 1620 |
| gcccaacagc aacgagagat actacggcta cactgggggct ttccggtgcc tggctgagaa | 1680 |
| tgctggagac gttgcatttg tgaaagatgt cactgtcttg cagaacactg atggaaataa | 1740 |
| caatgaggca tggctaagg atttgaagct ggcagacttt cgctgctgt gcctcgatgg | 1800 |
| caaacggaag cctgtgactg aggctagaag ctgccatctt gccatggccc cgaatcatgc | 1860 |
| cgtggtgtct cggatggata agtggaacg cctgaaacag gtgttgctcc accaacaggc | 1920 |
| taaatttggg agaaatggat ctgactgccc ggacaagttt tgcttattcc agtctgaaac | 1980 |
| caaaaccttt ctgttcaatg acaacactga gtgtctggcc agactccatg gcaaacaac | 2040 |
| atatgaaaaa tatttgggac cacagtatgt cgcaggcatt actaatctga aaagtgctc | 2100 |
| aacctcccc ctcctggaag cctgtgaatt cctcaggaag taaaaccgaa gaagatggcc | 2160 |
| cagctcccca agaaagcctc agccattcac tgccccagc tcttctcccc aggtgtgttg | 2220 |
| ggccttggcc tccctgctg aaggtgggga ttgcccatcc atctgcttac aattccctgc | 2280 |
| tgtcgtctta gcaagaagta aaatgagaaa ttttgttgat attctctcct t | 2331 |

<210> SEQ ID NO 63
<211> LENGTH: 2357
<212> TYPE: DNA

<213> ORGANISM: COW

<400> SEQUENCE: 63

```
gcagagcctt cgttccggag tcgccccagg accccagcca tgaagctctt cgtccccgcc      60
ctgctgtccc ttggagccct tggactgtgt ctggctgccc cgaggaaaaa cgttcgatgg     120
tgtaccatct cccaacccga gtggttcaaa tgccgccgat ggcagtggag gatgaagaag     180
ctgggtgctc cctctatcac ctgtgtgagg agggcctttg ccttggaatg tatccgggcc     240
atcgcggaga aaaaggcgga tgctgtgacc ctggatggtg gcatggtgtt tgaggcgggc     300
cgggacccct acaaactgcg gccagtagca gcagagatct atgggacgaa agagtctccc     360
caaacccact attatgctgt ggccgtcgtg aagaagggca gcaactttca gctggaccag     420
ctgcaaggcc ggaagtcctg ccatacgggc cttggcaggt ccgctgggtg ggtcatccct     480
atgggaatcc ttcgcccgta cttgagctgg acagagtcac tcgagcccct ccagggagct     540
gtggctaaat tcttctctgc cagctgtgtt ccctgcattg atagacaagc ataccccaac     600
ctgtgtcaac tgtgcaaggg ggaggggag aaccagtgtg cctgctcctc ccgggaacca     660
tacttcggtt attctggtgc cttcaagtgt ctgcaggacg gggctggaga cgtggctttt     720
gttaaagaga cgacagtgtt tgagaacttg ccagagaagg ctgacaggga ccagtatgag     780
cttctctgcc tgaacaacag tcgggcgcca gtggatgcgt tcaaggagtg ccacctggcc     840
caggtccctt ctcatgctgt cgtggcccga agtgtggatg caaggaaga cttgatctgg     900
aagcttctca gcaaggcgca ggagaaattt ggaaaaaaca gtctcggag cttccagctc     960
tttggctctc caccggcca gagggacctg ctgttcaaag actctgctct tgggtttttg    1020
aggatcccct cgaaggtaga ttcggcgctg taccttggct cccgctactt gaccaccttg    1080
aagaacctca gggaaactgc ggaggaggtg aaggcgcggt acaccaggt cgtgtggtgt    1140
gccgtgggac ccgaggagca aagaagtgc cagcagtgga gccagcagag cggcagaac     1200
gtgacctgtg ccacggcgtc caccaccgac gactgcatcg tcctggtgct gaaaggggaa    1260
gcagatgccc tgaacttgga tggaggatat atctacactg cgggcaagtg tggcctggtg    1320
cctgtcctgg cagagaaccg gaaaacctcc aaatacagta gcctagattg tgtgctgaga    1380
ccaacagaag ggtaccttgc cgtggcagtt gtcaagaaag caaatgaggg gctcacatgg    1440
aattctctga agacaagaa gtcgtgccac accgccgtgg acaggactgc aggctggaac    1500
atccccatgg gcctgatcgt caaccagaca ggctcctgcg catttgatga attctttagt    1560
cagagctgtg cccctgggcg tgacccgaaa tccagactct gtgccttgtg tgctggcgat    1620
gaccagggcc tggacaagtg tgtgcccaac tctaaggaga agtactatgg ctataccggg    1680
gctttcaggt gcctggctga ggacgttggg acgttgcct tgtgaaaaa cgacacagtc    1740
tgggagaaca cgaatggaga gagcactgca gactgggcta agaacttgaa tcgtgaggac    1800
ttcaggttgc tctgcctcga tggcaccagg aagcctgtga cggaggctca gagctgccac    1860
ctggcggtgg ccccgaatca cgctgtggtg tctcggagcg atagggcagc acacgtgaaa    1920
caggtgctgc tccaccagca ggctctgttt gggaaaaatg gaaaaaactg cccggacaag    1980
ttttgtttgt tcaaatctga aaccaaaaac cttctgttca atgacaacac tgagtgtctg    2040
gccaaacttg gaggcagacc aacgtatgaa gaatatttgg ggacagagta tgtcacggcc    2100
attgccaacc tgaaaaaatg ctcaacctcc ccgcttctgg aagcctgcgc cttcctgacg    2160
aggtaaagcc tgcaaagaag ctagcctgcc tccctgggcc tcagctcctc cctgctctca    2220
gccccaatct ccaggcgcga gggaccttcc tctcccttcc tgaagtcgga ttttgccaa     2280
```

```
gctcatcagt atttacaatt ccctgctgtc attttagcaa gaaataaaat tagaaatgct    2340
gttgattttc attccct                                                   2357

<210> SEQ ID NO 64
<211> LENGTH: 2578
<212> TYPE: DNA
<213> ORGANISM: PIG

<400> SEQUENCE: 64
tttcactggt ttatgctttt attgctgaag gaggaagggc ccagagcagg agatgccagg      60
cgggtcccag gggtccgggt cccagaaggg gtgacctggg tcccaggccc tcctgattcc     120
ggctgatggg gaggtggggt gatatcttgt ctcccagagg gaaccccccg gaggtgatgg     180
ccgggactcc cctagacgcg gcactgctct tcagctgggc tgcaggatcc gcatgggcac     240
agacagcgtc ttgagggcag tcgcctcagg acctcagaca tgaagctctt catccccgcc     300
ctgctgttcc tctggacact tggactgtgt ctggctgccc taagaaaggg ggttcgatgg     360
tgtgtcatat ccacagcaga gtattcaaaa tgccgccagt ggcaatcaaa gataagaaga     420
actaatccca tcttctgcat aaggagggct tctcccactg actgtatccg ggccatcgcg     480
gcaaaaaggg cagatgctgt gacccttgat ggtggtttgg tgtttgaagc aggccagtac     540
aaactgcggc cggtagcagc ggagatctac gggacagaag agaatcccca aacctactat     600
tatgctgtgg ctgtagtgaa gaaaggtttc aactttcagc tgaaccagct acaaggtcga     660
aagtcctgcc acataggcct tggcaggtct gccgggtgga atatccctat agggttactt     720
cgccggttct tggactgggc agggccacct gagcccctcc agaaagctgt ggccaaattc     780
ttctctcaga gctgtgtgcc ctgcgcagat ggaaatgcgt atcccaacct gtgtcagctg     840
tgcatagggc aagggaaaga taaatgtgct tgttcctccc aggaaccgta ttttggctat     900
tccggtgcct tcaactgtct gcacaaaggg attggagatg tggcttttgt caaggagagt     960
acagtgtttg agaacctgcc acagaaggct gaccgggaca atacgagct actctgccca    1020 gacaatactc gaaagccagt ggaagcattc agggagtgcc accttgcccg ggtcccttct    1080
catgctgttg tggcccgaag tgtgaatggc aaggagaact ccatctggag ccttctctac    1140
cagtcacaga aaaagtttgg aaaaagcaat ccacaggagt tccagctctt tggctctcct    1200
ggtcagcaga aggacctcct gtttagagac gctaccatcg ggttttttgaa gatcccctca    1260 aagatagatt ctaagctgta cctgggcctc ccgtacctta ctgccatcca gggcctgagg    1320
gaaacggcag cggaggtgga ggcgcggcag gcgaaggtcg tgtggtgcgc cgtgggtcca    1380
gaggagctgc gcaagtgccg gcagtggagc agccagagca gccagaacct gaactgcagc    1440
ctggcctcca ccaccgagga ctgcatcgtc caggtgctga aggagaagc tgatgctatg    1500 agcttggatg gaggatttat ctacactgcg ggcaagtgtg gtttggtgcc tgtcctggca    1560
gagaaccaaa atctcgccaa agcagtagc tcagactgtg tgcatagacc aacacaaggg    1620
tattttgccg tggcggttgt caggaaagca aatggtggta tcacctggaa ttctgtgaga    1680
ggcacgaagt cctgccacac tgctgtggac aggacagcag gctggaacat ccccatgggc    1740
ctgcttgtca accagacagg ctcctgcaaa tttgacgaat tctttagtca aagctgtgct    1800
cctgggtctc agccgggatc caatctctgt gcactgtgtg ttggcaatga ccagggcgtg    1860
gacaagtgtg tgcccaacag taatgagaga tactatggtt acaccggggc tttcaggtgc    1920
ctggctgaga atgctgggga tgtggcgttt gtgaaagatg tcactgtctt ggacaacacg    1980
```

-continued

```
aatggacaga acactcaaga gtgggccagg gaattgaggt cagacgactt tgagctgctg    2040
tgccttaatg gcaccaggaa gcctgtgact gaggctcaga actgtcacct ggctgtggcc    2100
cccagtcatg ctgtggtctc tcggaaggaa aaggcagcac aggtagaaca gatgctgctc    2160
actgagcagg ctcagtttgg aagatacgga aaagactgcc cagacaagtt ttgcttgttc    2220
cggtctgaga ccaaaaacct tctgttcaac gacaacacgg agtgtctggc ccaactccaa    2280
ggcaaaacaa catacgaaaa atatttggga tcagagtatg tcacagccat cgctacctga    2340
aacatgctgc agcctcccct cagtctggaa gcctgtgcct tcatgatgag gtaaaaccgg    2400
aaaagaagct gccccgcctc cccaggggcc tcagcttttcc ctcctcccgt cttgattccc    2460
agctgccctg ggcctgcctc tctcccttcc tgagggcaga cttttgttcag ctcatccgtt    2520 ttcacaattc cctgctggcc tcttagcaag aaataaaatt agaaattctg ccgaattc     2578

<210> SEQ ID NO 65
<211> LENGTH: 2259
<212> TYPE: DNA
<213> ORGANISM: PIG

<400> SEQUENCE: 65
acatgaagct cttcatcccc gccctgctgt tcctcgggac acttggactg tgtctggctg      60
cccctaagaa aggggttcga tggtgtgtca tatccacagc agagtattca aaatgccgcc     120
agtggcaatc aaagataaga agaactaatc ccatgttctg cataaggagg gcttctccca     180
ctgactgtat ccgggccatc gcggcaaaaa gggcagatgc tgtgacccct gatggtggtt     240
tggtgtttga agcagaccag tacaaactgc ggccggtagc agcggagatc tacgggacag     300
aagagaatcc ccaaacctac tattatgctg tggctgtagt gaagaaaggt ttcaactttc     360
agaaccagct acaaggtcga aagtcctgcc acacaggcct tggcaggtct gccgggtgga     420
atatccctat agggttactt cgccggttct tggactgggc agggccacct gagcccctcc     480
agaaagctgt ggccaaattc ttctctcaga gctgtgtgcc ctgcgcagat ggaaatgcgt     540
atcccaacct gtgtcagctg tgcataggga aagggaaaga taatgtgct tgttcctccc     600 aggaaccgta ttttggctat tccggtgcct tcaactgtct gcacaaaggg attggagatg     660
tggcttttgt caaggagagt acagtgtttg agaacctgcc acagaaggct gaccgggaca     720
aatacgagct actctgccca gacaatactc gaaagccagt ggaagcattc agggagtgcc     780
accttgcccg ggtcccttct catgctgttg tggcccgaag tgtgaatggc aaggagaact     840
ccatctggga gcttctctac cagtcacaga aaaagtttgg aaaaagcaat ccacaggagt     900
tccagctctt tggctctcct ggtcagcaga aggacctcct gtttagagat gctaccatcg     960
ggtttttgaa gatcccctca aagatagatt ctaagctgta cctgggcctc ccgtaccttla    1020 ctgccatcca gggcctgagg gaaacggcag cggaggtgga ggcgcggcag gcgaaggtcg    1080 tgtggtcgc cgtgggtcca gaggagctgc gcaagtgccg gcagtggagc agccagagca    1140
gccagaacct gaactgcagc ctggcctcca ccaccgagga ctgcatcgtc caggtgctga    1200
aaggagaagc tgatgctatg agcttggatg gaggatttat ctacactgcg ggcaagtgtg    1260
gtttggtgcc tgtcctggca gagaaccaaa aatctcgcca aagcagtagc tcagactgtg    1320
tgcatagacc aacacaaggg tatttgccg tggcggttgt caggaaagca aatggtggta    1380
tcacctggaa ctctgtgaga ggcacgaagt cctgccacac tgctgtggac aggacagcag    1440
gctgaaacat ccccatgggc ctgcttgtca accagacagg ctcctgcaaa tttgacgaat    1500
tctttagtca aagctgtgct cctgggtctc agccgggatc caatctctgt gcactgtgtg    1560
```

```
ttggcaatga ccagggcgtg gacaagtgtg tgcccaacag taatgagaga tactatggtt      1620
acaccggggc tttcaggtgc ctggctgaga atgctgggga tgtggcgttt gtgaaagatg      1680
tcactgtctt ggacaacacg aatggacaga acacagaaga gtgggccagg gaattgaggt      1740
cagatgactt tgagctgctg tgccttgatg gcaccaggaa gcctgtgact gaggctcaga      1800
actgtcacct ggctgtggcc cccagtcatg ctgtggtctc tcggaaggaa aaggcagcac      1860
aggtggaaca ggtgctactc actgagcagg ctcagtttgg aagatacgga aaagactgcc      1920
cggacaagtt tgcttgttc cggtctgaga ccaaaaacct tctgttcaac gacaacacgg        1980
aggttctggc ccaactccaa ggcaaaacaa catacgaaaa atatttggga tcagagtatg      2040
tcacagccat cgctaacctg aaacagtgct cagtctcccc gcttctggaa gcctgtgcct      2100
tcatgatgag gtaaaaccgg aaaagaagct gcccgcctcc ccaggggcct cagctttccc     2160
tcctcccgtc ttgattccca gctgccctgg gcctgcctct ctcccttcct gagggcagac      2220
tttgttcagc tcatccgttt tcacaattcc ctcgtgccg                              2259

<210> SEQ ID NO 66
<211> LENGTH: 2351
<212> TYPE: DNA
<213> ORGANISM: COW
<220> FEATURE:
<221> NAME/KEY: misc_feature
<222> LOCATION: (1)..(4)
<223> OTHER INFORMATION: n is a, c, g, or t

<400> SEQUENCE: 66
nnnngagcct tcgttccgga gtcgccccag gacgccagcc catgaagctc ttcgtccccg       60
ccctcctgtc ccttggagcc cttggactgt gtctggctgc cccgaggaaa aacgttcgat      120
ggtgtaccat ctcccaacct gagtggttca aatgccgcag atggcagtgg aggatgaaga      180
agctgggtgc tccctctatc acctgtgtga ggcgggcctt tgccttggaa tgtattccgg      240
gcatcgcgga gaaaaaggcg gatgctgtga ccctggatgg tggcatggtg tttgaggcgg      300
gccgggaccc ctacaaactg cggccagtag cagcagagat ctatgggacg aaagagtctc      360
cccaaaccca ctattatgct gtggccgtcg tgaagaaggg cagcaacttt cagctggacc      420
agctgcaagg ccggaagtcc tgccatacgg gccttggcag gtccgctggg tggatcatcc      480
ctatgggaat ccttcgcccg tacttgagct ggacagagtc actcgagccc tccagggag     540 ctgtggctaa attcttctct gccagctgtg ttccctgcat tgatagacaa gcataccccca    600 acctgtgtca actgtgcaag gggagggggg agaaccagtg tgcctgctcc tcccgggaac    660
catacttcgg ttattctggt gccttcaagt gtctgcagga cggggctgga gacgtggctt    720
ttgttaaaga gacgacagtg tttgagaact tgccagagaa ggctgacagg gaccagtatg    780
agcttctctg cctgaacaac agtcgggcgc cagtggatgc gttcaaggag tgccacctgg    840
cccaggtccc ttctcatgct gtcgtggccc gaagtgtgga tggcaaggaa gacttgatct    900
ggaagcttct cagcaaggcg caggagaaat ctggaaaaaa caagtctcgg agcttccagc    960
tctttggctc tccacccggc cagagggacc tgctgttcaa agactctgct cttgggtttt    1020
tgaggatccc ctcgaaggta gattcggcgc tgtacctggg ctcccgctac ttgaccacct    1080
tgaagaacct cagggaaact gcggaggagg tgaaggcgcg gtacaccagg gtcgtgtggt    1140
gtgccgtggg acctgaggag cagaagaagt gccagcagtg gagccagcag agcggccaga    1200 acgtgaccctg tgccacggcg tccaccactg acgactgcat cgtcctggtg ctgaaagggg    1260
```

-continued

```
aagcagatgc cctgaacttg gatggaggat atatctacac tgcgggcaag tgtggcctgg    1320
tgcctgtcct ggcagagaac cggaaatcct ccaaacacag tagcctagat tgtgtgctga    1380
gaccaacgga agggtacctt gccgtggcag ttgtcaagaa agcaaatgag gggctcacat    1440
ggaattctct gaaagacaag aagtcgtgcc acaccgccgt ggacaggact gcaggctgga    1500
acatccccat gggcctgatc gtcaaccaga caggctcctg cgcatttgat gaattcttta    1560
gtcagagctg tgcccctggg gctgaccgga atccagact ctgtgccttg tgtgctggcg     1620
atgaccaggg cctggacaag tgtgtgccca actctaagga aagtactat ggctataccg     1680 gggctttcag gtgcctggct gaggacgttg ggacgttgc ctttgtgaaa aacgacacag     1740
tctgggagaa cacgaatgga gagagcactg cagactgggc taagaacttg aatcgtgagg    1800
acttcaggtt gctctgcctc gatggcacca ggaagcctgt gacggaggct cagagctgcc    1860
acctggcggt ggccccgaat cacgctgtgg tgtctcggag cgatagggca gcacacgtga    1920
aacaggtgct gctccaccag caggctctgt ttgggaaaaa tggaaaaaac tgcccggaca    1980
agttttgttt gttcaaatct gaaaccaaaa accttctgtt caatgacaac actgagtgtc    2040
tggccaaact tggaggcaga ccaacgtatg aagaatattt ggggacagag tatgtcacgg    2100
ccattgccaa cctgaaaaaa tgctcaacct ccccgcttct ggaagcctgc gccttcctga    2160
cgaggtaaag cctgcaaaga agctagcctg cctccctggg cctcagctcc tccctgctct    2220
cagccccaat ctccaggcgc gagggacctt cctctccctt cctgaagtcg attttttgcc    2280
aagctcatca gtatttacaa ttccctgctg tcattttagc aagaaataaa attagaaatg    2340
ctgttgaaaa a                                                         2351
```

<210> SEQ ID NO 67
<211> LENGTH: 2457
<212> TYPE: DNA
<213> ORGANISM: COW

<400> SEQUENCE: 67

```
gggggaggag ggaggctggg gcgcttatag gaccacaggg cggggcaaac ctcgtgaggt      60
caccgagcac tggataaagg gacgcagaac gagcgcaggt ggcagacctt cgttccggag    120
tcgccccagg acgccagcca tgaagctctt cgtccccgcc ctgctgtccc ttggagccct    180
tggactgtgt ctggctgccc cgaggaaaaa cgttcgatgg tgtaccatct cccaacctga    240
gtggttcaaa tgccgccgat ggcagtggag gatgaagaag ctgggtgctc cctctatcac    300
ctgtgtgagg agggcctttg ccttggaatg tatccgggcc atcgcggaga aaaaggcgga    360
tgctgtgacc ctggatggtg gcatggtgtt tgaggcgggc cgggaccccct acaaactgcg    420 gccagtagca gcagagatct atgggacgaa agagtctccc caaacccact attatgctgt    480
ggccgtcgtg aagaagggca gcaactttca gctggaccag ctgcaaggcc ggaagtcctg    540
ccatacgggc cttggcaggt ccgctgggtg gatcatccct atgggaatcc ttcgcccgta    600
cttgagctgg acagagtcac tcgagcccct ccagggagct gtggctaaat tcttctctgc    660
cagctgtgtt ccctgcattg atagacaagc ataccccaac ctgtgtcaac tgtgcaaggg    720
ggagggggag aaccagtgtg cctgctcctc ccgggaacca tacttcggtt attctggtgc    780
cttcaagtgt ctgcaggacg gggctggaga cgtggctttt gttaaagaga cgacagtgtt    840
tgagaacttg ccagagaagg ctgacaggga ccagtatgag cttctctgcc tgaacaacag    900
tcggcgccca gtggatgcgt tcaaggagtg ccacctggcc caggtccctt ctcatgctgt    960
cgtggcccga agtgtggatg gcaaggaaga cttgatctgg aagcttctca gcaaggcgca    1020
```

-continued

```
ggagaaattt ggaaaaaaca agtctcggag cttccagctc tttggctctc cacccggcca  1080
gagggacctg ctgttcaaag actctgctct tgggttttg aggatcccct cgaaggtaga   1140
ttcggcgctg tacctgggct cccgctactt gaccaccttg aagaacctca gggaaactgc  1200
ggaggaggtg aaggcgcggt acaccagggt cgtgtggtgt gccgtgggac ctgaggagca  1260
gaagaagtgc cagcagtgga gccagcagag cggccagaac gtgacctgtg ccacggcgtc  1320
caccactgac gactgcatcg tcctggtgct gaaaggggaa gcagatgccc tgaacttgga  1380
tggaggatat atctacactg cgggcaagtg tggcctggtg cctgtcctgg cagagaaccg  1440
gaaatcctcc aaacacagta gcctagattg tgtgctgaga ccaacggaag ggtaccttgc  1500
cgtggcagtt gtcaagaaag caaatgaggg gctcacatgg aattctctga aagacaagaa  1560
gtcgtgccac accgccgtgg acaggactgc aggctggaac atccccatgg gcctgatcgt  1620
caaccagaca ggctcctgcg catttgatga attctttagt cagagctgtg cccctggggc  1680
tgacccgaaa tccagactct gtgccttgtg tgctggcgat gaccagggcc tggacaagtg  1740
tgtgcccaac tctaaggaga agtactatgg ctataccggg gctttcaggt gcctggctga  1800
ggacgttggg gacgttgcct ttgtgaaaaa cgacacagtc tgggagaaca cgaatggaga  1860
gagcactgca gactgggcta agaacttgaa tcgtgaggac ttcaggttgc tctgcctcga  1920
tggcaccagg aagcctgtga cggaggctca gagctgccac ctggcggtgg ccccgaatca  1980
cgctgtggtg tctcggagcg ataggggcagc acacgtgaaa caggtgctgc tccaccagca  2040
ggctctgttt gggaaaaatg gaaaaaactg cccggacaag ttttgtttgt tcaaatctga  2100
aaccaaaaac cttctgttca atgacaacac tgagtgtctg gccaaacttg gaggcagacc  2160
aacgtatgaa gaatatttgg ggacagagta tgtcacggcc attgccaacc tgaaaaaatg  2220
ctcaacctcc ccgcttctgg aagcctgcgc cttcctgacg aggtaaagcc tgcaagaag   2280
ctagcctgcc tccctgggcc tcagctcctc cctgctctca gccccaatct ccaggcgcga  2340
gggaccttcc tctcccttcc tgaagtcgga ttttttgccaa gctcatcagt atttacaatt  2400
ccctgctgtc attttagcaa gaaataaaat tagaaatgct gttgattttc attccct     2457
```